US007569660B1

(12) United States Patent
Lindquist et al.

(10) Patent No.: US 7,569,660 B1
(45) Date of Patent: Aug. 4, 2009

(54) RECOMBINANT PRION-LIKE PROTEINS AND MATERIALS COMPRISING SAME

(75) Inventors: Susan Lindquist, Chicago, IL (US); Liming Li, Chicago, IL (US); Jiyan Ma, Chicago, IL (US); Jia-Jia Liu, Chicago, IL (US); Neal Sondheimer, Chicago, IL (US); Thomas Scheibel, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 09/591,632

(22) Filed: Jun. 9, 2000

Related U.S. Application Data

(60) Provisional application No. 60/138,833, filed on Jun. 9, 1999.

(51) Int. Cl.
*A61K 38/00* (2006.01)
*C07K 14/00* (2006.01)
*C07K 16/00* (2006.01)
*C07K 17/00* (2006.01)

(52) U.S. Cl. .................. 530/300; 530/324; 530/323; 530/332; 530/335; 930/20

(58) Field of Classification Search ................ 530/350, 530/388.21, 802, 806, 823, 824; 536/23.5; 435/325, 7.31, 69.1; 436/501; 519/2
See application file for complete search history.

(56) References Cited

U.S. PATENT DOCUMENTS

| | | | |
|---|---|---|---|
| 5,670,483 A | 9/1997 | Zhang et al. | 514/14 |
| 5,679,530 A | 10/1997 | Brentani et al. | 435/7.1 |
| 5,698,763 A | 12/1997 | Weissmann et al. | 800/2 |
| 5,750,361 A * | 5/1998 | Prusiner et al. | |
| 5,750,374 A | 5/1998 | Dobeli et al. | 435/69.7 |
| 5,763,740 A | 6/1998 | Prusiner et al. | 800/2 |
| 5,770,697 A | 6/1998 | Ferrari et al. | 530/353 |
| 5,773,572 A | 6/1998 | Fishleigh et al. | 530/324 |
| 5,789,655 A | 8/1998 | Prusiner et al. | 800/2 |
| 5,792,901 A | 8/1998 | Prusiner et al. | 800/2 |
| 5,804,417 A | 9/1998 | Martens et al. | 435/69.1 |
| 5,811,633 A | 9/1998 | Wadsworth et al. | 800/2 |
| 5,854,204 A | 12/1998 | Findeis et al. | 514/2 |
| 5,900,360 A | 5/1999 | Welch et al. | 435/29 |
| 5,962,669 A * | 10/1999 | Prusiner et al. | 536/23.5 |
| 6,277,970 B1 * | 8/2001 | Prusiner et al. | 536/23.1 |
| 6,600,017 B1 * | 7/2003 | Glabe et al. | 530/345 |

FOREIGN PATENT DOCUMENTS

| | | |
|---|---|---|
| EP | 653154 | 5/1995 |
| WO | WO 93/04194 | 3/1993 |
| WO | WO 93/10227 | 5/1993 |
| WO | WO 94/28412 | 12/1994 |
| WO | WO 95/12815 | 5/1995 |
| WO | WO 95/20979 | 8/1995 |
| WO | WO 96/28471 * | 9/1996 |
| WO | WO 97/45746 | 12/1997 |
| WO | WO 98/33815 | 8/1998 |
| WO | WO 99/06545 | 2/1999 |
| WO | WO 99/29891 | 6/1999 |
| WO | WO 00/75324 | 12/2000 |

OTHER PUBLICATIONS

Gregori et al., J. Biol. Chem. 272:1(58(62)1997.*
Paushkin et al., Science 277(381-383)1997.*
King et al. PNAS 94(6618-6622)1997.*
Stayton et al. J. Biol. Chem. 263(27)1344-13548, 1988.*
Alberts ed. Molecular Biology of the Cell, p. 114, 1994.*
Wei et al., J. of Biol. Chem., 273(19):11806-814, 1998.*
Levy et al., J. Exp. Med., 169:1771-78, May 1989.*
Kushnirov et al., 1988, Gene, 66, pp. 45-54.*
Altschul et al., "Gapped Blast and PSI_Blast: a new generation od protein database search programs", *Nucleic Acids Res.*, 25(17): 3389-3402 (1997).
Anraku, Y., "Protein splicing: its chemistry and biology", *Genes to Cells*, 2:359-397(1997).
Balter, M., "Generating New Yeast Prions", *Science*, 287:562-563 (2000).
Barinaga, M., "Protective Role for Prion Protein?", *Science*, 5342:1404-1405(1997).
Brewer, "Engineering proteins to enable their isolation in a biologically active form", *Bioprocess. Technol.*, 2:239-266 (1991).
Brizzard et al., "Immunoaffinity purification of Flag epitope-tagged bacterial alkaline phophatase using novel monoclonal antibody and peptide elution", *Biotechniques* 16:730-735 (1994).
Chernoff et al., "Role of Chaperone Protein Hsp104 in Propagation of the Yeast Prion-Like Factor [psi+]", *Science*, 268:880-883 (1995).
Chernoff et al., *Mol. Microbiol.*, 35:865-876(2000).
Chong et al., "Single-column purification of free recombinant proteins using a self-cleavable affinity tag derived from a protein splicing element", *Gene*, 192:27-281(1997).
Cox et al., "The psi factor of yeast: a problem in inheritance," *Yeast*, 4(3):159-178(1988).
Cubitt et al., "Understanding, improving and using green fluorescent proteins," *Trends Biochem. Sci.*, 20:448-455(1995).
Dagkesamanskaia et al., "Fusion of Glutathione S-transferase with the N-terminus of Yeast Sup35 Protein Inhibits Its Prion-like Properties", *Genetika*, 5:610-615(1997). abstract only.
DeArmond et al., "Prion Protein Transgenes and the Neuropathology in Prion Diseases", *Brain Pathol.*, 1:77-89(1995).
DebBurman et al., "Chaperone-supervised Conversion of Prion Protein to its Protease-resistant form", *Proc. Natl. Acad. Sci.* USA, 94: 13938-13943 (1997).

(Continued)

*Primary Examiner*—Olga N Chernyshev
(74) *Attorney, Agent, or Firm*—Marshall, Gerstein & Borun LLP

(57) ABSTRACT

The present invention provides novel polypeptides comprising a prion-aggregation domain and a second domain; novel polynucleotides encoding such polypeptides; host cells transformed or transfected with such polynucleotides; and methods of making and using the foregoing.

40 Claims, 9 Drawing Sheets

OTHER PUBLICATIONS

DePace et al., "A Critical Role for Amino-Terminal Glutamine/Asparagine Repeats in the Formation and Propagation of a Yeast Prion", *Cell*, 93:1241-1252(1998).

Derkatch et al., "Genesis and Variability of [PSI] Prion Factors in *Saccharomyces cerevisiae*," *Genetics*, 144:1375-1386(1996).

Edskes, et al., "The [URE3] prion is an aggregated form of Ure20 that can be cured by overexpression of Ure2p fragments", *Proc. Natl. Acad. Sci. USA*, 96:1498-1503(1999).

Elgersma et al., "An efficient positive selection procedure for the isolation of peroxisomal import and peroxisome assembly mutants of *Saccharomyces cerevisiae*", *Genetics*, 135: 731-740 (1993).

GenBank Accession No. AF003087, "*Felis catus* prion protein (Prp) gene, complete cds.", Rohwer et al., 1997.

Genbank Accession No. AF 020554, "*Candida albicans* translation release factor 3 (SUP35) gene, complete cds", Resende et al., 1997.

GenBank Accession No. AJ223072, "*Ovis aries* PrP gene, complete cds.", Goldmann et al., 1998.

GenBank Accession No. D10612 or D90545, "Bovine mRNA for prion protein", Yoshimoto et al., 1993.

GenBank Accession No. D79214, "*Schizocaccharomyces pombe* DNA for omnipotent nonsense suppressor SUP35/eRF-3, complete cds.", Ito et al., 1998.

GenBank Accession No. K02234, "Syrian golden hamster scrapie (prion) protein PrP 27-30 mRNA", Oesch et al., 1993.

Genbank Accession No. M13807, "Yeast (*S. cerevisiae*) glyceraldehyde-3-phosphate dehydrogenase gene, promoter gene", Musti et al., 1993.

GenBank Accession No. M13899, "Human prion protein (PrP) mRNA, complete cds.", Kretzschmar et al., 1995.

GenBank Accession No. M14053, "Rat glucocorticoid receptor mRNA, complete cds.", Miesfield et al., 1993.

Genbank Accession No. M15077, "*P. pyralis* (firefly) luciferase gene, complete cds.", de Wet et al., 1993.

Genbank Accession No. M21129, "Yeast (*S. cerevisiae*) omnipotent suppressor (SUP2) gene, complete cds", Kushnirov et al., 1989.

Genbank Accession No. M35268, "*Saccharomyces cerevisiae* URE2", Coschigano et al., 1991.

GenBank Accession No. M15683, "*S. cerevisiae* KAR1 gene, complete cds", Rose et al., 1993.

Genbank Accession No. NP009572, "Ybr016WP, *S. cerevisiae*", Feldmann et al., 2001.

Genbank Accession No. NP009902, "Transferable Epigenetic Modifier; Rnq1p, *S. cerevisiae*", Oliver et al., 2001.

Genbank Accession No. NP014518, "Putative Polyadenylated-RNA-binding protein; Hrp1p, *S. cerevisiae*", Goffeau et al., 2001.

GenBank Accession No. P00722, "Beta-glactosidase (lactase)", Kalnins et al., 2000.

GenBank Accession No. P25367, "Ubiquitin-conjugating enzyme E2-17 KDA (Ubiquitin-Protein Ligase) (Ubiquitin Carrier Protein) (HR6B)", Schneider et al., 2000.

GenBank Accession No. P27476, "Nuclear localization sequence binding protein(P67)", Lee et al., 2000.

GenBank Accession No. P36168, "Hypothetical 137.5 KD Protein in MPL1-PPC1 Intergenic Region", Baladron et al., 1995.

GenBank Accession No. P38216, "Hypothetical 14.6 KD Protein in TTP1-KAP104 Intergenic Region", Entian et al., 1997.

GenBank Accession No. P40002, "Hypothetical 72.5KD protein in GCN4-WBP1 Intergenic Region", Dietrich et al., 1995.

GenBank Accession No. P40467, "Putative 108.8 KD Transcriptional Regulatory Protein in FKH1-STH1 Intergenic Region", Barrell et al., 1995.

GenBank Accession No. P40957, "Spindle Assembly Checkpoint Component MAD1 (Mitotic MAD1 Protein", Hardwick et al., 2000.

GenBank Accession No. U03438, "Yeast integrative pRS306 with URA3 marker, complete sequence", Sikorski et al., 1995.

GenBank Accession No. U30442, "Human isolate M88 T-cell receptor alpha V-J junction (TCR Valpha 5'J Alpha 4) mRNA, partial cds.", Dave et al., 1995.

GenBank Accession No. U33077, "*Lentinula boryana* isolate R39, 5.8S rRNA gene, complete sequence, 18S rRNA amd 25S rRNA genes, partial sequence", Hibbett et al., 1995.

GenBank Accession No. U35737, "*Saccharomyces cerevisiae* nuclear polyadenylated RNA-binding protein (NAB4) gene, complete cds", Oberdorf et al., 1995.

GenBank Accession No. U38535, "*Saccharomyces cerevisiae* heterogenous nuclear ribonucleoprotein (HRP1) gene, complete cds. ", Henry et al., 1996.

GenBank Accession No. U73901, "*Aequorea victoria* green fluorescent proetin mutant 3 (GFP) gene, complete cds.", Cormack et al., 1996.

GenBank Accession No. X07163, "Yeast SUF12+ gene for suppressor protein", Wilson et al., 1993.

GenBank Accession No. X14187, "Yeast MCM1 gene, protein involved in replication of ARS and expression of mating-type alpha-specific genes", Passmore et al., 1993.

GenBank Accession No. X55882, "Bovine PrP gene for a prion-protein", Goldmann, W., 1991.

Genbank Accession Nos. X56910, "*P. pinus* SUP2 gene for an EF-1-alpha-like protein factor", Kushnirov et al., 1991.

GenBank Accession No. X99021, "*S. pombe* hrp1+ gene", Jin et al., 1998.

Genbank Accession No. Z71255, "*S. cerevisiae* chromosome XVI 165536 bp sequence, cen rightwards", Badcock et al., 1996.

Genbank Accession No. Z73582, "*S. cerevisiae* chromosome XVI reading frame ORF YPL226w", Urrestarazu et al., 1997.

Glover et al., "Hsp104, Hsp70, and Hsp40: A Novel Chaperone System that Rescues Previously Aggregated Proteins," *Cell*, 94:73-82 (1998).

Glover, et al., "Self-Seeded Fibers Formed by Sup35, the Protein Determinant of [PSI+], a Heritable Prion-like Factor of S. cerevisiae," Cell, 89:811-819 (1997).

Guthrie & Fink, "Guide to Yeast Genetics and Molecular Biology" in *Methods of Enzymology*, vol. 194, pp. 389-398 (1981).

Harper et al., "Models of Amyloid Seeding In Alzheimer's Disease and Scrapie: Mechanistic Truths and Physiological Consequences of the Time-Dependent Solubility of Amyloid Proteins", *Annu. Rev. Biochem*, 66: 385-407 (1997).

Hedge et al., "A Transmembrane Form of the Prion Protein in Neurodegenerative Disease", *Science*, 279:827-834(1998).

Hollenbach, et al., "Aggregation of truncated GST-HD exon 1 fusion proteins containing normal range and expanded glutamine repeats", *Phil. Trans. R. Soc. Lond.* B:354, 991-994(1999).

Horwich et al., "Deadly Conformations-Protein Misfolding in Prion Disease," *Cell*, 89: 499-510(1997).

Horworka et al., "Improved Protocol for High-Throughput Cysteine Scanning Mutagenesis", *Biotechniques*, 25:764-772(1998).

Jackson et al., "Reversible conversion of monomeric human prion protein between native and fibrilogenic conformations", *Science*, 283:1935-1937(1999).

Jaegly et al., "Search for a Nuclear Localization Signal in the Prion Protein", *Mol. Cell. Neurosci.*, 11(3):127-133(1998).

Jean-Jean et al., "Is there a human [psi]?", *C R Acad Sci III*, 319(6):487-492(1996). abstract only.

Jones et al., "Replacing the Complementarity-Determining Regions In a Human Antibody With Those From a Mouse", *Nature*, 321:522-525 (1986).

Kain et al., "Green Fluorescent Protein as a Reporter of Gene Expression and Protein Localization", *Biotechniques*, 19:650-655 (1995).

Kelly, J.W., "Alternative conformations of amyloidogenic proteins govern their behavior," *Curr. Opin. Struct. Biol.*, 6:11-17(1996).

Kenward et al., "Heat shock proteins, molecular chaperones and the prion encephalopathies", *Cell Stress and Chaperones*, 1(1) 18-22(1996).

King, et al., "Prion-inducing domain 2-114 of yeast Sup35 protein transforms in vitro into amyloid-like filaments", *Proc. Natl. Acad. Sci. USA*, 94:6618-6622(1997).

Klunk et al., "Two simple methods for quantiftying low-affinity dye-substrate binding", *J. Histochem. Cytochem.*, 37: 1293-1297 (1989).

Kunz, "The Human Leukocyte Platelet-activating Factor Receptor", *J. Biol. Chem.*, 267:9101-9106 (1992).

Kushnirov et al., "Structure and Replication of Yeast Prions," *Cell*, 94:13-16(1998).

Kushnirov et al., "Prion properties of the Sup35 protein of yeast *Pichia methanolica*", *Embo. J.*, 19:324-331(2000).
Kushnirov et al., "Divergence and Conservation of SUP2(SUP35) Gene of Yeast *Pichia pinus* and *Saccharomyces cerevisiae*", Yeast, 6:461-472(1990).
Lanzetta et al., "An improved assay for nanomole amounts of inorganic phosphate", *Analyt. Biochem.*, 100: 95-97 (1979).
Lewin, B., "The Mystique of Epigenetics", *Cell*, 93:301-303(1998).
Li et al., "Creating a Protein-Based Element of Inheritance," *Science*, 287:661-664 (2000).
Lindquist, "Mad Cows Meet Psi-chotic Yeast: The Expansion of the Prion Hypothesis," *Cell*, 89: 495-498(1997).
Lindquist et al., "Amyloid Fibres of Sup35 Support a Prion-like Mechanism of Inheritance in Yeast", *Biochem. Soc. Trans*, 26:486-90(1998).
Manstein et al., "Clongin vectors for the production of proteins in Dictyostelium discoideum", *Gene*, 162: 126-134 (1995).
Masison et al., "Prion-Inducing Domain of Yeast Ure2p and Protease Resistance of Ure2p in Prion-Containing Cells", *Science*, 270: 93-95 (1995).
Meeker et al., "A Fusion Protein Between Serum Amyloid A and *Staphylococcal* Nuclease-Synthesis, Purification, and Structural Studies", *Proteins: Structure, Function, and Genetics*, 30: 381-387 (1998).
Mestel, R., "Putting Prions to the Test", *Science*, 273:184-189(1996).
Morrison et al, "Genetically Engineered Antibody Molecules", *Adv. Immunol.*, 44:65-92 (1989).
Murray et al., "Epitope Tagging of the Human ENdoplasmic Reticulum HSP70 Protein, BiP, to Facilitate Analysis of BiP-Substrate Interactions", *Anal. Biochem.*, 229: 170-179 (1995).
Newnam et al., "Antagonistic Interactions between Yeast Chaperones Hsp 104 and Hsp70 in Prion Curing", *Mol. Cell. Biol.*, 19:1325-1333(1999).
Parsell et al., "Protein Disaggregation Mediated by Heat-Shock Protein Hsp104," *Nature*, 372:475-478(1994).
Patino, et al., "Support for the Prion Hypothesis for Inheritance of a Phenotypic Trait in Yeast", *Science*, 273:622-626(1996).
Paushkin et al., "Propagation of the yeast prion-like [psi+] determinant is mediated bi oligomerization of the SUP35-encoded polypeptide chain release factor", *EMBO J.*, 15(12): 3127-3134 (1996).
Paushkin et al., "In vitro Propagation of the Prion-Like State of Yeast Sup35 Protein", *Science*, 277:381-383(1997).
Paushkin et al., "Interaction between Yeast Sup35p (eRF1) and Sup35p (eRF3) Polypeptide Chain Release Factors: Implications for Prion-Dependent Regulation", *Molecular and Cellular Biology*, 17(5):2798-2805(1997).
Prusiner et al., "Prion Protein Biology", *Cell*, 93: 337-348 (1998).
Prusiner, "Prion Diseases and the BSE Crisis", *Science*, 278:245-251(1997).
Riechmann et al., "Reshaping human antibodies for therapy", *Nature*, 332:323-327 (1988).
Sanchez et al., "HSP104 Required for Induced Thermotolerance", *Science*, 248:1112-1115(1990).
Santoso et al., "Molecular Basis of a Yeast Prion Species Barrier", *Cell*, 100:277-288(2000).
Schafer, *Biochem. Biophys. Res. Commun.*, 207: 708-714 (1995).
Schena et al., "Mammalian Clucocorticoid Receptor Derivatives Enhance Transcription in Yeast", *Science*, 241:965-967 (1988).
Schirmer et al., "Purification and Properties of Hsp104 From Yeast", *Meth. Enzymol.*, 290: 430-444 (1998).
Schirmer and S. Lindquist, "Interactions of the Chaperone Hsp104 with Yeast Sup35 and Mammalian PrP", *Proc. Natl. Acad. Sci. USA*, 94: 13932-13937 (1997).
Schirmer et al., "HSP100/Clp proteins: a common mechanism explains diverse functions", *TIBS*, 21: 289-296 (1996).
Schlumpberger, et al., "The prion domain of yeast Ure2p induces autocatalytic formation of amyloid fibers by a recombinant fusion protein", *Protein Science* 9:440-451(2000).
Schmidt, "One-step Affinity Purification of Bacterially Produced Proteins By Means Of The "Strep tag" and Immobilized Recombinant Core Streptavidin", *J. Chromatography*, 676: 337-345 (1994).
Schreiber et al., "Immunophilins, Ligands, and the Control of Signal Transduction", *Harvey Lectures*, Wiley-Liss, Inc. pp. 99-114, 1997.
Scott et al., Propagation of Prions with Artificial Properties in Transgenic Mice Expressing Chimeric PrP Genes, *Cell*, 73:979-988(1993).
Shinoda, et al., "Modulation of Fibrillogenicity of Aβ and its Fusion Proteins", *Neurobiology of Aging*, 17:6(1993).
Speiss et al., *Electon Microscopy and Molecular Biology: A Practical Approach*, Oxford Press, pp. 146-166(1987).
Taylor et al., "Prion Domain Initiation of Amyloid Formation in Vitro from Native Ure2p", *Science*, 283:1339-1343(1999).
Telling et al., "Prion Propagation in Mice Expressing Human and Chimeric PrP Transgenes Implicates the Interaction of Cellular PrP with Another Protein", *Cell*, 83:79-90(1995).
Tempest et al., "Reshaping a human monoclonal antibody to inhibit human respiratory syncytial virus infaction in vivo", *Bio/Technology*, 9:266-271 (1991).
Ter-Avanesyan, et al., "Deletion analysis of the SUP35 gene of the yeast *Saccharomyces cerevisiae* revealse two-non-overlapping functional regions in the encoded protein", *Mol. Micro.*, 7(5)683-692(1993).
Thiele, D.J., "ACE1 Regulated Expression of *Saccharomyces cerevisiae* Methallothionen Gene", *Mol. Cell. Biol.*, 8: 2745-2752 (1988).
Tuite et al., "Maintenance and inheritance of yeast prions", *TIG*, 12(11):467-471(1996).
Verhoeyen et al., "Reshaping Human Antibodies: Grafting an Autilysozyme Activity", *Science*, 239:1534-1536 (1988).
Vogel et al., "Large-scale production, purification and refolding of the full-length cellular prion protein from Syrian golden hamster in *Escherichia coli* using the glutathione S-transferase-fusion system", *Eur. J. Biochem.*, 251(1-2):462-471(1998).
Vogel, G., "Yeast Protein Acting Alone Triggers Prion-Like Process", *Science*, 277(5324):314(1998).
Vogel et al., "Heat-shock proteins Hap104 and Hap70 reactivate mRNA splicing after heat inactivation", *Current Biology*, 5(3):306-317(1995).
Volkel et al., "Large-scale Production, Purification and Refolding of the Full-length Cellular Prion Portein from the Syrian Golden Hamster in *Escherichia coli* Using the Glutathione S-transferase-fusion System", *Eur. J. Biochem*, 251:462-471 (1998).
Weiss, et al., "Overexpression of Active Syrian Golden Hamster Prion Protein PrP$^c$ as a Glutathione S-Transferase Fusion in Heterologous Systems", *Journal of Virology*, 69:4776-4783 (1995).
Weiss et al., "Recombinant prion protein rPrP27-30 from Syrian golden hamster reveals proteinase K sensitivity", *Biochem. Biophys. Res. Commun.*, 219(1): 173-179(1996).
Wickner, R., "Prions and RNA Viruses of *Saccharomyces cerevisiae*", *Annu. Rev. Genet.*, 30:109-139 (1996).
Wickner, R., "[URE3] as an Altered *URE2* Protein: Evidence for a Prion Analog in *Saccharomyces cerevisiae*", Science, 264:566-569(1994).
Zahn, et al., "Human prion proteins in *Escherichia coli* and purified by high-affinity column refolding", *FEBS*, 417:400-404 (1997).
Genbank Accession No. S54522, "Hypothetical Protein YMR164c, *S. cerevisiae*", Hunt et al., 1999.

* cited by examiner

Sup35 →
```
   1 ATGTCGGATTCAAACCAAGGCAACAATCAGCAAAACTACCAGCAATACAGCCAGAACGGTAACCAACAACAAGGTAAC
   1▶ M  S  D  S  N  Q  G  N  N  Q  Q  N  Y  Q  Q  Y  S  Q  N  G  N  Q  Q  Q  G  N
  79 AACAGATACCAAGGTTATCAAGCTTACAATGCTCAAGCCCAACCTGCAGGTGGGTACTACCAAAATTACCAAGGTTAT
  27▶ N  R  Y  Q  G  Y  Q  A  Y  N  A  Q  A  Q  P  A  G  G  Y  Y  Q  N  Y  Q  G  Y
 157 TCTGGGTACCAACAAGGTGGCTATCAACAGTACAATCCCGACGCCGGTTACCAGCAACAGTATAATCCTCAAGGAGGC
  53▶ S  G  Y  Q  Q  G  G  Y  Q  Q  Y  N  P  D  A  G  Y  Q  Q  Q  Y  N  P  Q  G  G
 235 TATCAACAGTACAATCCTCAAGGCGGTTATCAGCAGCAATTCAATCCACAAGGTGGCCGTGGAAATTACAAAAACTTC
  79▶ Y  Q  Q  Y  N  P  Q  G  G  Y  Q  Q  Q  F  N  P  Q  G  G  R  G  N  Y  K  N  F
 313 AACTACAATAACAATTTGCAAGGATATCAAGCTGGTTTCCAACCACAGTCTCAAGGTATGTCTTTGAACGACTTTCAA
 105▶ N  Y  N  N  N  L  Q  G  Y  Q  A  G  F  Q  P  Q  S  Q  G  M  S  L  N  D  F  Q
 391 AAGCAACAAAAGCAGGCCGCTCCCAAACCAAAGAAGACTTTGAAGCTTGTCTCCAGTTCCGGTATCAAGTTGGCCAAT
 131▶ K  Q  Q  K  Q  A  A  P  K  P  K  K  T  L  K  L  V  S  S  S  G  I  K  L  A  N
 469 GCTACCAAGAAGGTTGGCACAAAACCTGCCGAATCTGATAAGAAAGAGGAAGAGAAGTCTGCTGAAACCAAAGAACCA
 157▶ A  T  K  K  V  G  T  K  P  A  E  S  D  K  K  E  E  E  K  S  A  E  T  K  E  P
 547 ACTAAAGAGCCAACAAAGGTCGAAGAACCAGTTAAAAAGGAGGAGAAACCAGTCCAGACTGAAGAAAAGACGGAGGAA
 183▶ T  K  E  P  T  K  V  E  E  P  V  K  K  E  E  K  P  V  Q  T  E  E  K  T  E  E
 625 AAATCGGAACTTCCAAAGGTAGAAGACCTTAAAATCTCTGAATCAACACATAATACCAACAATGCCAATGTTACCAGT
 209▶ K  S  E  L  P  K  V  E  D  L  K  I  S  E  S  T  H  N  T  N  N  A  N  V  T  S
                                             ← Sup35     GR →
 703 GCTGATGCCTTGATCAAGGAACAGGAAGAAGAAGTGGATGACGAAGTTGTTAACGATCCGCGGATGGACTCCAAAGA
 235▶ A  D  A  L  I  K  E  Q  E  E  E  V  D  D  E  V  V  N  D  P  R  M  D  S  K  E
 780 ATCCTTAGCTCCCCCTGGTAGAGACGAAGTCCCTGGCAGTTTGCTTGGCCAAGGGAGGGGGAGCGTAATGGACTTTTA
 260▶ S  L  A  P  P  G  R  D  E  V  P  G  S  L  L  G  Q  G  R  G  S  V  M  D  F  Y
 858 TAAAAGCCTGAGGGGAGGAGCTACAGTCAAGGTTTCTGCATCTTCGCCCTCAGTGGCTGCTGCTTCTCAGGCAGATTC
 286▶ K  S  L  R  G  G  A  T  V  K  V  S  A  S  S  P  S  V  A  A  A  S  Q  A  D  S
 936 CAAGCAGCAGAGGATTCTCCTTGATTTCTCGAAAGGCTCCACAAGCAATGTGCAGCAGCGACAGCAGCAGCAGCAGCA
 312▶ K  Q  Q  R  I  L  L  D  F  S  K  G  S  T  S  N  V  Q  Q  R  Q  Q  Q  Q  Q  Q
1014 GCAGCAGCAGCAGCAGCAGCAGCAGCAGCAGCAGCAGCCAGGCTTATCCAAAGCCGTTTCACTGTCCATGGGGCT
 338▶ Q  Q  Q  Q  Q  Q  Q  Q  Q  Q  Q  Q  Q  P  G  L  S  K  A  V  S  L  S  M  G  L
1092 GTATATGGGAGAGACAGAAACAAAAGTGATGGGGAATGACTTGGGCTACCCACAGCAGGGCCAACTTGGCCTTTCCTC
 364▶ Y  M  G  E  T  E  T  K  V  M  G  N  D  L  G  Y  P  Q  Q  G  Q  L  G  L  S  S
1170 TGGGGAAACAGACTTTCGGCTTCTGGAAGAAAGCATTGCAAACCTCAATAGGTCGACCAGCGTTCCAGAGAACCCCAA
 390▶ G  E  T  D  F  R  L  L  E  E  S  I  A  N  L  N  R  S  T  S  V  P  E  N  P  K
1248 GAGTTCAACGTCTGCAACTGGGTGTGCTACCCCGACAGAGAAGGAGTTTCCCAAAACTCACTCGGATGCATCTTCAGA
 416▶ S  S  T  S  A  T  G  C  A  T  P  T  E  K  E  F  P  K  T  H  S  D  A  S  S  E
1326 ACAGCAAAATCGAAAAAGCCAGACCGGCACCAACGGAGGCAGTGTGAAATTGTATCCCACAGACCAAAGCACCTTTGA
 442▶ Q  Q  N  R  K  S  Q  T  G  T  N  G  G  S  V  K  L  Y  P  T  D  Q  S  T  F  D
1404 CCTCTTGAAGGATTTGGAGTTTTCCGCTGGGTCCCCAAGTAAAGACACAAACGAGAGTCCCTGGAGATCAGATCTGTT
 468▶ L  L  K  D  L  E  F  S  A  G  S  P  S  K  D  T  N  E  S  P  W  R  S  D  L  L
1482 GATAGATGAAAACTTGCTTTCTCCTTTGGCGGGAGAAGATGATCCATTCCTTCTCGAAGGGAACACGAATGAGGATTG
 494▶ I  D  E  N  L  L  S  P  L  A  G  E  D  D  P  F  L  L  E  G  N  T  E  D  C
1560 TAAGCCTCTTATTTTACCGGACACTAAACCTAAAATTAAGGATACTGGAGATACAATCTTATCAAGTCCCAGCAGTGT
 520▶ K  P  L  I  L  P  D  T  K  P  K  I  K  D  T  G  D  T  I  L  S  S  P  S  S  V
1638 GGCACTACCCCAAGTGAAAACAGAAAAAGATGATTTCATTGAACTTTGCACCCCGGGGTAATTAAGCAAGAGAAACT
 546▶ A  L  P  Q  V  K  T  E  K  D  D  F  I  E  L  C  T  P  G  V  I  K  Q  E  K  L
1716 GGGCCCAGTTTATTGTCAGGCAAGCTTTTCTGGGACAAATATAATTGGTAATAAAATGTCTGCCATTTCTGTTCATGG
 572▶ G  P  V  Y  C  Q  A  S  F  S  G  T  N  I  I  G  N  K  M  S  A  I  S  V  H  G
1794 TGTGAGTACCTCTGGAGGACAGATGTACCACTATGACATGAATACAGCATCCCTTTCTCAGCAGCAGGATCAGAAGCC
 598▶ V  S  T  S  G  G  Q  M  Y  H  Y  D  M  N  T  A  S  L  S  Q  Q  Q  D  Q  K  P
1872 TGTTTTTAATGTCATTCCACCAATTCCTGTTGGTTCTGAAAACTGGAATAGGTGCCAAGGCTCCGGAGAGGACAGCCT
 624▶ V  F  N  V  I  P  P  I  P  V  G  S  E  N  W  N  R  C  Q  G  S  G  E  D  S  L
1950 GACTTCCTTGGGGGCTCTGAACTTCCCAGGCCGGTCAGTGTTTTCTAATGGGTACTCAAGCCCTGGAATGAGACCAGA
 650▶ T  S  L  G  A  L  N  F  P  G  R  S  V  F  S  N  G  Y  S  S  P  G  M  R  P  D
2028 TGTAAGCTCTCCTCCATCCAGCTCGTCAGCAGCCACGGGACCACCTCCCAAGCTCTGCCTGGTGTGCTCCGATGAAGC
 676▶ V  S  S  P  P  S  S  S  S  A  A  T  G  P  P  P  K  L  C  L  V  C  S  D  E  A
2106 TTCAGGATGTCATTACGGGGTGCTGACATGTGGAAGCTGCAAAGTATTCTTTAAAAGAGCAGTGGAAGGACAGCACAA
 702▶ S  G  C  H  Y  G  V  L  T  C  G  S  C  K  V  F  F  K  R  A  V  E  G  Q  H  N
```

FIG. 1A

```
2184 TTACCTTTGTGCTGGAAGAAACGATTGCATCATTGATAAAATTCGAAGGAAAAACTGCCCAGCATGCCGCTATCGGAA
 728▶  Y  L  C  A  G  R  N  D  C  I  I  D  K  I  R  R  K  N  C  P  A  C  R  Y  R  K
2262 ATGTCTTCAGGCTGGAATGAACCTTGAAGCTCGAAAAACAAAGAAAAAAATCAAAGGGATTCAGCAAGCCACTGCAGG
 754▶  C  L  Q  A  G  M  N  E  A  R  K  T  K  K  K  I  K  G  I  Q  Q  A  T  A  G
      2341(GR526)
2340 AGTCTCACAAGACACTTCGGAAAATCCTAACAAAACAATAGTTCCTGCAGCATTACCACAGCTCACCCCTACCTTGGT
 780▶  V  S  Q  D  T  S  E  N  P  N  K  T  I  V  P  A  A  L  P  Q  L  T  P  T  L  V
2418 GTCACTGCTGGAGGTGATTGAACCCGAGGTGTTGTATGCAGGATATGATAGCTCTGTTCCAGATTCAGCATGGAGAAT
 806▶  S  L  L  E  V  I  E  P  E  V  L  Y  A  G  Y  D  S  S  V  P  D  S  A  W  R  I
2496 TATGACCACACTCAACATGTTAGGTGGGCGTCAAGTGATTGCAGCAGTGAAATGGGCAAAGGCGATACTAGGCTTGAG
 832▶  M  T  T  L  N  M  L  G  G  R  Q  V  I  A  A  V  K  W  A  K  A  I  L  G  L  R
2574 AAACTTACACCTCGATGACCAAATGACCCTGCTACAGTACTCATGGATGTTTCTCATGGCATTTGCCTTGGGTTGGAG
 858▶  N  L  H  L  D  D  Q  M  T  L  L  Q  Y  S  W  M  F  L  M  A  F  A  L  G  W  R
2652 ATCATACAGACAATCAAGCGGAAACCTGCTCTGCTTTGCTCCTGATCTGATTATTAATGAGCAGAGAATGTCTCTACC
 884▶  S  Y  R  Q  S  S  G  N  L  L  C  F  A  P  D  L  I  I  N  E  Q  R  M  S  L  P
2730 CTGCATGTATGACCAATGTAAACACATGCTGTTTGTCTCCTCTGAATTACAAAGATTGCAGGTATCCTATGAAGAGTA
 910▶  C  M  Y  D  Q  C  K  H  M  L  F  V  S  S  E  L  Q  R  L  Q  V  S  Y  E  E  Y
2808 TCTCTGTATGAAAACCTTACTGCTTCTCTCCTCAGTTCCTAAGGAAGGTCTGAAGAGCCAAGAGTTATTTGATGAGAT
 936▶  L  C  M  K  T  L  L  L  L  S  S  V  P  K  E  G  L  K  S  Q  E  L  F  D  E  I
2886 TCGAATGACTTATATCAAAGAGCTAGGAAAAGCCATCGTCAAAAGGGAAGGGAACTCCAGTCAGAACTGGCAACGGTT
 962▶  R  M  T  Y  I  K  E  L  G  K  A  I  V  K  R  E  G  N  S  S  Q  N  W  Q  R  F
2964 TTACCAACTGACAAAGCTTCTGGACTCCATGCATGAGGTGGTTGAGAATCTCCTTACCTACTGCTTCCAGACATTTTT
 988▶  Y  Q  L  T  K  L  L  D  S  M  H  E  V  V  E  N  L  L  T  Y  C  F  Q  T  F  L
3042 GGATAAGACCATGAGTATTGAATTCCCAGAGATGTTAGCTGAAATCATCACTAATCAGATACCAAAATATTCAAATGG
1014▶  D  K  T  M  S  I  E  F  P  E  M  L  A  E  I  I  T  N  Q  I  P  K  Y  S  N  G
3120 AAATATCAAAAAGCTTCTGTTTCATCAAAAATGA
1040▶  N  I  K  K  L  L  F  H  Q  K  •
```

```
1201  GATCCGGCCA GCAAAACTAA AAAAACTGTAT TATAAGTAAA TGCATGTATA CTAAACTCAC AAATTAGAGC TTCAATTTAA AAATTAGAGC TTATATCAGT TATTACCCTA
      ▸ R   C   G   Q   Q   N
 262
1301  TGCGGTGTGA AATACCCCAC AGATGCGTAA GGAGAAAATA CCCGCATCAGG AAATTGTAAA CGTTAATATT TTGTTAAAAT TCGCGTTAAA TTTTTGTTAA
1401  ATCAGCTCAT TTTTTAACCA ATAGGCCGAA ATCGGCAAAA TCCCCTTATAA ATCAAAAGAA TAGACCGAGA TAGGGTTGAG TGTTGTTCCA GTTTCGAACA
1501  AGAGTCCACT ATTAAAGAAC GTTGACTCCA ACGTTCAAAGG GCGAAAAACC GTCTATCGGT GCCATGGCCC ACTACGTGAA CCATCACCCT AATCAACTTT
                                                                                          Nael (1676)
1601  TTTTGGGTCG AGGTGCCGTA AAGCACTAAA TCGGAACCCT AAAGGGAGCC CCCGATTTAG AGCTTGACGG GGAAAGCCGG CGAACGTGGC GAGAAAGAA
1701  GGGAAGAAAG CGAAAGGAGC GGGCGCTAGG GCGCGTCGCAA GTGTAGCGGT CACGCTGCGC GTAACCACCA CACCCGCCGC GCTTAATGCG CCGCTACAGG
                                                                                          ▼
                                                                                         PvuII
1801  GCGCGTCGCG CCATTCGCCA TTCAGGGCTGC GCAACTGTTG GGAAGGGCGA TCGGTGCGGG CCTCTTCGCT ATTACGCCAG CTGGCGAAAG GGGGATCTGC
1901  TGCAAGGCGA TTAAGTTGGG TAACGCCAGG GTTTTCCCAG TCACGACGTT GTAAAACGAC GGCCAGTGAA TTGTAATACG ACTCACTATA GGGCGAATTG
      SacI    SacII
2001  GAGCTCCACC GC GGTGAAAAGAGT CAGTGAGACGA CGACGACTTC AGGATCTCTT TGGGTTTCAG GATATATGTG CATGAAAATA CAGAAAATCC CTCTGTCGTC TGAATCAGCTTT
2111  CGCTCGAATA TTTACGAAGA AGCAGACAGT CATTATATCT TTATAAACAA TGTATGGTCG TTCAAGAACC GATCAAAATG TTTCAGATGC AATTGAACTT TATTTAA
2223  CAATCCTCAT CTGTCGGATG CGAGAAAGCA TCAACTGAAG AAACATTTTG AAAAGAAGAT TCAGTGTTT TATAATAACAT TATGCTAGAA GAAGTTAGAA TGATATCAAGT
2335  AGTCTTTTGT TTATTGTTAT TACGAAGGAT GGGAATTACA CTATAAGATC GATGATTCTT TGAGTTCCAT GTCTTCTTTGA ATAGAGATT TTGCACATTC TGAAATA
2447  ATGATGATGA TGATGCCGAG GGGAAGGACC AGCAAGGACG AAGAACAACT GGTCGTCTTT TGAGTTCTTT TGAGTTCCAT GTCACTAATAG AGATTTTGCA CATTCTGAAATA
                                                                                          XbaI
2559  GCCCGGGAAG GGTTATGATG AATGATGAAA CTGATTGAAG GAGTTGAAAT TCTAGATATT TTATGAAATTC TAGATATAT GAGAGGTGAA GTTTACCTTG TTTTAATGGT ATAT
2671  GGTACAAAAG AACTAAACTAA TTATACGTCT ATATATAATA TATATATATA CAGCTTATT TAATAAACCT TGTTTTTTTAA TAATAGAAGA AAATGCTTAT GATCGGTATT AT
      junction marker
      BamHI
2783  TGTGTTTGCA TTTACTTATG TTTGCAAAGA AATGGATCCT TACTCGGCAA TTTTACCAAT TGCTATTGTG GTACCCTGAT CTCTCAAAGT GAATCTACCT AATT
2895  GAGGGTAATC TTGGTAAGTT TCCACACAAA CTGAGCTTCA GTTTCTAAAAA CAGCGATGAC CTTCATACCC TTCTTACCAA AAGCAGGTGG TTCTTTGACT TACGGTTGGT
```

```
7196 GTAAGTAGTT CGCCAGTTAA TAGTTTGCGC AACGTTGTTG CCATTGCTAC AGGCATGCTG GTGTCACGCT CGTCGTTTGG TATGGCTTCA TTCAGCTCCG
         T  L  L  E  G  T  L     L  K  R  L  T  T  A     M  A  V  P  M  T  T  D  R  E     D  N  P  I  A  E  N  L  E  P
197◀                                                                                    PvuI (7368)
7296 GTTCCCAACG ATCAAGGCGA GTTACATGAT CCCCCATGTT GTGCAAAAAA GCGGTTAGCT CCTTCGGTCC TCCGATCGTT GTCAGAAGTA AGTTGGCCGC
         E  W  R  D  L  R     T  V  H  D     G  M  N     H  L  F  A  T  L  E     K  P  G     G  I  T     T  L  L  L  N  A  A
164◀
7396 AGTGTTATCA CTCGTGGTTA TGGCAGGCACT GCATAATTCT CTTACTGTCA TGCCATCCGT AAGATGCTTT TCTGTGACTG GTGAGTACTC AACCAAGTCA
         T  N  D  S  M  T  I     A  A  S     C  L  E     R  V  T  M     G  D  T     L  H  K     E  T  V  P     S  Y  E     V  L  D
131◀
7496 TTCTGAGAAT AGTGTATGCG GCGACCGAGT TGCTCTTGCC CGGCGTCAAT ACGGGATAAT ACCGGCGCCAC ATAGCAGAAC TTTAAAAGTG CTCATCATTG
         N  Q  S  Y  H  I  R     R  G  L     Q  E  Q  G     A  D  I     R  S  L     V  A  G  C     L  L  V     K  F  T     S  M  M  P
97◀
7596 GAAAACGTTC TTCGGGGCGA AAACTCTCAA GGATCTTACC TGTGTTGAGA TCCAGTTCGA TGTAACCCAC TCGTGCACCC AACTGATCTT CAGCATCTTT
         F  R  E     E  P  R     F  S  E  L     I  K  G     S  N  L     D  L  E  I     Y  G  V     R  A  G     L  Q  D  E     A  D  K
64◀
7696 TACTTTCACC AGCGTTTCTG GGTGAGCAAA AACAGGAAGG CAAAAAAGGG ACACGGAAAT GTTGAATACT CATACTCTTC
         V  K  V     L  T  E  P     H  A  F     V  P  L     C  F  A  A     F  F  P     I  L  A     V  R  F  H     Q  I  S     M
31◀
7796 CTTTTTCAAT ATTATTGAAG CATTTATCAG GGTTATTGTC TCATGAGCCG ATACATATTT GAATGTATTT AGAAAAATAA ACAAATAGGG GTTCCGCGCA
                                                                                                            junction marker
7896 CATTTCCCCG AAAAGTGCCA CCTGACGTCT AAGAAACCAT TATTATCATG ACATTAACCT ATAAAAATAG GGGTATCACG AGGCCCTTTC GTC
```

FIG. 3E

Spontaneous conversion of Sup35 repeat mutants

SEQUENCE LISTING

```
<160> NUMBER OF SEQ ID NOS: 70

<210> SEQ ID NO 1
<211> LENGTH: 3321
<212> TYPE: DNA
<213> ORGANISM: Saccharomyces cerevisiae
<220> FEATURE:
<221> NAME/KEY: CDS
<222> LOCATION: (739)..(2796)

<400> SEQUENCE: 1
agaaattaaa gctacttaca acaacggtct actacaaatt aaggtgccta aaattgtcaa      60
tgacactgaa aagccgaagc caaaaaagag gatcgccatt gaggaaatac ccgacgaaga     120
attggagttt gaagaaaatc ccaaccctac ggtagaaaat tgaatatcgt atctgtttat     180
acacacatac atacatttat atttataata agcgttaaaa tttcggcaga atatctgtca     240
accacacaaa aatcatacaa cgaatggtat atgcttcatt tctttgtttc gcattagctg     300
cgctatttga ctcaaattat tattttttac taagacgacg cgtcacagtg ttcgagtctg     360
tgtcatttct tttgtaattc tcttaaacca cttcataaag ttgtgaagtt catagcaaaa     420
ttcttccgca aaaagatgaa tcttagttct cagcccacca aaagaggtac atgctaagat     480
catacagaag ttattgtcac ttcttacctt gctcttaaat gtacattaca accgggtatt     540
atatcttaca tcatcgtata atatgatctt tctttatgga gaaattttt ttttcactcg      600 accaaagctc ccattgcttc tgaagagtgt agtgtatatt ggtacatctt ctcttgaaag     660
actccattgt actgtaacaa aaagcggttt cttcatcgac ttgctcggaa taacatctat     720
atctgcccac tagcaaca atg tcg gat tca aac caa ggc aac aat cag caa       771
                       Met Ser Asp Ser Asn Gln Gly Asn Asn Gln Gln
                       1               5                   10 aac tac cag caa tac agc cag aac ggt aac caa caa caa ggt aac aac       819
Asn Tyr Gln Gln Tyr Ser Gln Asn Gly Asn Gln Gln Gln Gly Asn Asn
            15                  20                  25 aga tac caa ggt tat caa gct tac aat gct caa gcc caa cct gca ggt       867
Arg Tyr Gln Gly Tyr Gln Ala Tyr Asn Ala Gln Ala Gln Pro Ala Gly
        30                  35                  40 ggg tac tac caa aat tac caa ggt tat tct ggg tac caa caa ggt ggc       915
Gly Tyr Tyr Gln Asn Tyr Gln Gly Tyr Ser Gly Tyr Gln Gln Gly Gly
    45                  50                  55 tat caa cag tac aat ccc gac gcc ggt tac cag caa cag tat aat cct       963
Tyr Gln Gln Tyr Asn Pro Asp Ala Gly Tyr Gln Gln Gln Tyr Asn Pro
60                  65                  70                  75 caa gga ggc tat caa cag tac aat cct caa ggc ggt tat cag cag caa      1011
Gln Gly Gly Tyr Gln Gln Tyr Asn Pro Gln Gly Gly Tyr Gln Gln Gln
                80                  85                  90 ttc aat cca caa ggt ggc cgt gga aat tac aaa aac ttc aac tac aat      1059
Phe Asn Pro Gln Gly Gly Arg Gly Asn Tyr Lys Asn Phe Asn Tyr Asn
                95                  100                 105
```

```
aac aat ttg caa gga tat caa gct ggt ttc caa cca cag tct caa ggt    1107
Asn Asn Leu Gln Gly Tyr Gln Ala Gly Phe Gln Pro Gln Ser Gln Gly
        110             115             120 atg tct ttg aac gac ttt caa aag caa caa aag cag gcc gct ccc aaa    1155
Met Ser Leu Asn Asp Phe Gln Lys Gln Gln Lys Gln Ala Ala Pro Lys
125             130             135 cca aag aag act ttg aag ctt gtc tcc agt tcc ggt atc aag ttg gcc    1203
Pro Lys Lys Thr Leu Lys Leu Val Ser Ser Ser Gly Ile Lys Leu Ala
140             145             150             155 aat gct acc aag aag gtt ggc aca aaa cct gcc gaa tct gat aag aaa    1251
Asn Ala Thr Lys Lys Val Gly Thr Lys Pro Ala Glu Ser Asp Lys Lys
                160             165             170 gag gaa gag aag tct gct gaa acc aaa gaa cca act aaa gag cca aca    1299
Glu Glu Glu Lys Ser Ala Glu Thr Lys Glu Pro Thr Lys Glu Pro Thr
            175             180             185 aag gtc gaa gaa cca gtt aaa aag gag gag aaa cca gtc cag act gaa    1347
Lys Val Glu Glu Pro Val Lys Lys Glu Glu Lys Pro Val Gln Thr Glu
        190             195             200 gaa aag acg gag gaa aaa tcg gaa ctt cca aag gta gaa gac ctt aaa    1395
Glu Lys Thr Glu Glu Lys Ser Glu Leu Pro Lys Val Glu Asp Leu Lys
    205             210             215 atc tct gaa tca aca cat aat acc aac aat gcc aat gtt acc agt gct    1443
Ile Ser Glu Ser Thr His Asn Thr Asn Asn Ala Asn Val Thr Ser Ala
220             225             230             235 gat gcc ttg atc aag gaa cag gaa gaa gaa gtg gat gac gaa gtt gtt    1491
Asp Ala Leu Ile Lys Glu Gln Glu Glu Glu Val Asp Asp Glu Val Val
                240             245             250 aac gat atg ttt ggt ggt aaa gat cac gtt tct tta att ttc atg ggt    1539
Asn Asp Met Phe Gly Gly Lys Asp His Val Ser Leu Ile Phe Met Gly
            255             260             265 cat gtt gat gcc ggt aaa tct act atg ggt ggt aat cta cta tac ttg    1587
His Val Asp Ala Gly Lys Ser Thr Met Gly Gly Asn Leu Leu Tyr Leu
        270             275             280 act ggc tct gtg gat aag aga act att gag aaa tat gaa aga gaa gcc    1635
Thr Gly Ser Val Asp Lys Arg Thr Ile Glu Lys Tyr Glu Arg Glu Ala
    285             290             295 aag gat gca ggc aga caa ggt tgg tac ttg tca tgg gtc atg gat acc    1683
Lys Asp Ala Gly Arg Gln Gly Trp Tyr Leu Ser Trp Val Met Asp Thr
300             305             310             315 aac aaa gaa gaa aga aat gat ggt aag act atc gaa gtt ggt aag gcc    1731
Asn Lys Glu Glu Arg Asn Asp Gly Lys Thr Ile Glu Val Gly Lys Ala
                320             325             330 tac ttt gaa act gaa aaa agg cgt tat acc ata ttg gat gct cct ggt    1779
Tyr Phe Glu Thr Glu Lys Arg Arg Tyr Thr Ile Leu Asp Ala Pro Gly
            335             340             345 cat aaa atg tac gtt tcc gag atg atc ggt ggt gct tct caa gct gat    1827
His Lys Met Tyr Val Ser Glu Met Ile Gly Gly Ala Ser Gln Ala Asp
        350             355             360 gtt ggt gtt ttg gtc att tcc gcc aga aag ggt gag tac gaa acc ggt    1875
Val Gly Val Leu Val Ile Ser Ala Arg Lys Gly Glu Tyr Glu Thr Gly
    365             370             375 ttt gag aga ggt ggt caa act cgt gaa cac gcc cta ttg gcc aag acc    1923
Phe Glu Arg Gly Gly Gln Thr Arg Glu His Ala Leu Leu Ala Lys Thr
380             385             390             395 caa ggt gtt aat aag atg gtt gtc gtc gta aat aag atg gat gac cca    1971
Gln Gly Val Asn Lys Met Val Val Val Asn Lys Met Asp Asp Pro
                400             405             410 acc gtt aac tgg tct aag gaa cgt tac gac caa tgt gtg agt aat gtc    2019
Thr Val Asn Trp Ser Lys Glu Arg Tyr Asp Gln Cys Val Ser Asn Val
            415             420             425
```

```
agc aat ttc ttg aga gca att ggt tac aac att aag aca gac gtt gta      2067
Ser Asn Phe Leu Arg Ala Ile Gly Tyr Asn Ile Lys Thr Asp Val Val
        430                 435                 440 ttt atg cca gta tcc ggc tac agt ggt gca aat ttg aaa gat cac gta      2115
Phe Met Pro Val Ser Gly Tyr Ser Gly Ala Asn Leu Lys Asp His Val
    445                 450                 455 gat cca aaa gaa tgc cca tgg tac acc ggc cca act ctg tta gaa tat      2163
Asp Pro Lys Glu Cys Pro Trp Tyr Thr Gly Pro Thr Leu Leu Glu Tyr
460                 465                 470                 475 ctg gat aca atg aac cac gtc gac cgt cac atc aat gct cca ttc atg      2211
Leu Asp Thr Met Asn His Val Asp Arg His Ile Asn Ala Pro Phe Met
                480                 485                 490 ttg cct att gcc gct aag atg aag gat cta ggt acc atc gtt gaa ggt      2259
Leu Pro Ile Ala Ala Lys Met Lys Asp Leu Gly Thr Ile Val Glu Gly
        495                 500                 505 aaa att gaa tcc ggt cat atc aaa aag ggt caa tcc acc cta ctg atg      2307
Lys Ile Glu Ser Gly His Ile Lys Lys Gly Gln Ser Thr Leu Leu Met
    510                 515                 520 cct aac aaa acc gct gtg gaa att caa aat att tac aac gaa act gaa      2355
Pro Asn Lys Thr Ala Val Glu Ile Gln Asn Ile Tyr Asn Glu Thr Glu
525                 530                 535 aat gaa gtt gat atg gct atg tgt ggt gag caa gtt aaa cta aga atc      2403
Asn Glu Val Asp Met Ala Met Cys Gly Glu Gln Val Lys Leu Arg Ile
540                 545                 550                 555 aaa ggt gtt gaa gaa gaa gac att tca cca ggt ttt gta cta aca tcg      2451
Lys Gly Val Glu Glu Glu Asp Ile Ser Pro Gly Phe Val Leu Thr Ser
                560                 565                 570 cca aag aac cct atc aag agt gtt acc aag ttt gta gct caa att gct      2499
Pro Lys Asn Pro Ile Lys Ser Val Thr Lys Phe Val Ala Gln Ile Ala
        575                 580                 585 att gta gaa tta aaa tct atc ata gca gcc ggt ttt tca tgt gtt atg      2547
Ile Val Glu Leu Lys Ser Ile Ile Ala Ala Gly Phe Ser Cys Val Met
    590                 595                 600 cat gtt cat aca gca att gaa gag gta cat att gtt aag tta ttg cac      2595
His Val His Thr Ala Ile Glu Glu Val His Ile Val Lys Leu Leu His
605                 610                 615 aaa tta gaa aag ggt acc aac cgt aag tca aag aaa cca cct gct ttt      2643
Lys Leu Glu Lys Gly Thr Asn Arg Lys Ser Lys Lys Pro Pro Ala Phe
620                 625                 630                 635 gct aag aag ggt atg aag gtc atc gct gtt tta gaa act gaa gct cca      2691
Ala Lys Lys Gly Met Lys Val Ile Ala Val Leu Glu Thr Glu Ala Pro
                640                 645                 650 gtt tgt gtg gaa act tac caa gat tac cct caa tta ggt aga ttc act      2739
Val Cys Val Glu Thr Tyr Gln Asp Tyr Pro Gln Leu Gly Arg Phe Thr
        655                 660                 665 ttg aga gat caa ggt acc aca ata gca att ggt aaa att gtt aaa att      2787
Leu Arg Asp Gln Gly Thr Thr Ile Ala Ile Gly Lys Ile Val Lys Ile
    670                 675                 680 gcc gag taa atttcttgca aacataagta aatgcaaaca caataatacc              2836
Ala Glu
    685 gatcataaag cattttcttc tatattaaaa aacaaggttt aataaagctg ttatatatat    2896 atatatatat atagacgtat aattagttta gttcttttg taccatatac cataaacaag     2956 gtaaacttca cctctcaata tatctagaat ttcataaaaa tatctagcaa ggtttcaact    3016 ccttcaatca cgttttcatc ataacccttc cccggcgtta tttcagaatg tgcaaaatct    3076 attagtgaca tggaactcaa agaaccagtt gttttttgt cctttggtcc ttcgctgctt     3136
```

-continued

```
ccctcggcat catcatcatc atcatcatca ttatcatcat cgtcgtcatc atcgtctata      3196
aaatcatctc gcataagttt gtcaacatca tttagtaatt cccatcgctc cgggtctcct      3256
tcgtaaataa acaaaagact acttgatatc attctaactt cttcttctag catagtatta      3316
taaaa                                                                  3321
```

<210> SEQ ID NO 2
<211> LENGTH: 685
<212> TYPE: PRT
<213> ORGANISM: Saccharomyces cerevisiae

<400> SEQUENCE: 2

```
Met Ser Asp Ser Asn Gln Gly Asn Asn Gln Gln Asn Tyr Gln Gln Tyr
1               5                   10                  15

Ser Gln Asn Gly Asn Gln Gln Gln Gly Asn Asn Arg Tyr Gln Gly Tyr
                20                  25                  30

Gln Ala Tyr Asn Ala Gln Ala Gln Pro Ala Gly Gly Tyr Tyr Gln Asn
            35                  40                  45

Tyr Gln Gly Tyr Ser Gly Tyr Gln Gln Gly Gly Tyr Gln Gln Tyr Asn
        50                  55                  60

Pro Asp Ala Gly Tyr Gln Gln Gln Tyr Asn Pro Gln Gly Gly Tyr Gln
65                  70                  75                  80

Gln Tyr Asn Pro Gln Gly Gly Tyr Gln Gln Phe Asn Pro Gln Gly
                85                  90                  95

Gly Arg Gly Asn Tyr Lys Asn Phe Asn Tyr Asn Asn Asn Leu Gln Gly
            100                 105                 110

Tyr Gln Ala Gly Phe Gln Pro Gln Ser Gln Gly Met Ser Leu Asn Asp
        115                 120                 125

Phe Gln Lys Gln Gln Lys Gln Ala Ala Pro Lys Pro Lys Lys Thr Leu
130                 135                 140

Lys Leu Val Ser Ser Gly Ile Lys Leu Ala Asn Ala Thr Lys Lys
145                 150                 155                 160

Val Gly Thr Lys Pro Ala Glu Ser Asp Lys Lys Glu Glu Lys Ser
                165                 170                 175

Ala Glu Thr Lys Glu Pro Thr Lys Glu Pro Thr Lys Val Glu Glu Pro
            180                 185                 190

Val Lys Lys Glu Glu Lys Pro Val Gln Thr Glu Glu Lys Thr Glu Glu
        195                 200                 205

Lys Ser Glu Leu Pro Lys Val Glu Asp Leu Lys Ile Ser Glu Ser Thr
210                 215                 220

His Asn Thr Asn Asn Ala Asn Val Thr Ser Ala Asp Ala Leu Ile Lys
225                 230                 235                 240

Glu Gln Glu Glu Glu Val Asp Asp Glu Val Asn Asp Met Phe Gly
                245                 250                 255

Gly Lys Asp His Val Ser Leu Ile Phe Met Gly His Val Asp Ala Gly
            260                 265                 270

Lys Ser Thr Met Gly Gly Asn Leu Leu Tyr Leu Thr Gly Ser Val Asp
        275                 280                 285

Lys Arg Thr Ile Glu Lys Tyr Glu Arg Glu Ala Lys Asp Ala Gly Arg
290                 295                 300

Gln Gly Trp Tyr Leu Ser Trp Val Met Asp Thr Asn Lys Glu Glu Arg
305                 310                 315                 320

Asn Asp Gly Lys Thr Ile Glu Val Gly Lys Ala Tyr Phe Glu Thr Glu
                325                 330                 335
```

```
Lys Arg Arg Tyr Thr Ile Leu Asp Ala Pro Gly His Lys Met Tyr Val
                340                 345                 350

Ser Glu Met Ile Gly Gly Ala Ser Gln Ala Asp Val Gly Val Leu Val
            355                 360                 365

Ile Ser Ala Arg Lys Gly Glu Tyr Glu Thr Gly Phe Glu Arg Gly Gly
        370                 375                 380

Gln Thr Arg Glu His Ala Leu Leu Ala Lys Thr Gln Gly Val Asn Lys
385                 390                 395                 400

Met Val Val Val Asn Lys Met Asp Asp Pro Thr Val Asn Trp Ser
                405                 410                 415

Lys Glu Arg Tyr Asp Gln Cys Val Ser Asn Val Ser Asn Phe Leu Arg
            420                 425                 430

Ala Ile Gly Tyr Asn Ile Lys Thr Asp Val Val Phe Met Pro Val Ser
        435                 440                 445

Gly Tyr Ser Gly Ala Asn Leu Lys Asp His Val Asp Pro Lys Glu Cys
    450                 455                 460

Pro Trp Tyr Thr Gly Pro Thr Leu Leu Glu Tyr Leu Asp Thr Met Asn
465                 470                 475                 480

His Val Asp Arg His Ile Asn Ala Pro Phe Met Leu Pro Ile Ala Ala
                485                 490                 495

Lys Met Lys Asp Leu Gly Thr Ile Val Glu Gly Lys Ile Glu Ser Gly
            500                 505                 510

His Ile Lys Lys Gly Gln Ser Thr Leu Leu Met Pro Asn Lys Thr Ala
        515                 520                 525

Val Glu Ile Gln Asn Ile Tyr Asn Glu Thr Glu Asn Glu Val Asp Met
    530                 535                 540

Ala Met Cys Gly Glu Gln Val Lys Leu Arg Ile Lys Gly Val Glu Glu
545                 550                 555                 560

Glu Asp Ile Ser Pro Gly Phe Val Leu Thr Ser Pro Lys Asn Pro Ile
                565                 570                 575

Lys Ser Val Thr Lys Phe Val Ala Gln Ile Ala Ile Val Glu Leu Lys
            580                 585                 590

Ser Ile Ile Ala Ala Gly Phe Ser Cys Val Met His Val His Thr Ala
        595                 600                 605

Ile Glu Glu Val His Ile Val Lys Leu Leu His Lys Leu Glu Lys Gly
    610                 615                 620

Thr Asn Arg Lys Ser Lys Lys Pro Pro Ala Phe Ala Lys Lys Gly Met
625                 630                 635                 640

Lys Val Ile Ala Val Leu Glu Thr Glu Ala Pro Val Cys Val Glu Thr
                645                 650                 655

Tyr Gln Asp Tyr Pro Gln Leu Gly Arg Phe Thr Leu Arg Asp Gln Gly
            660                 665                 670

Thr Thr Ile Ala Ile Gly Lys Ile Val Lys Ile Ala Glu
        675                 680                 685

<210> SEQ ID NO 3
<211> LENGTH: 1427
<212> TYPE: DNA
<213> ORGANISM: Saccharomyces cerevisiae
<220> FEATURE:
<221> NAME/KEY: CDS
<222> LOCATION: (182)..(1246)

<400> SEQUENCE: 3
ctcgaggttg aaaagaatag caaaaatctt tccttttcaa acagctcatt tggaattgtt      60
```

| | |
|---|---:|
| tatagcactg aattgaatcg aagaggaata aagatccccc gtacgaactt ctttatttt | 120 |
| agtttttcat tttttgttat tagtcatatt gttttaagct gcaaattaag ttgtacacca | 180 |

```
a atg atg aat aac aac ggc aac caa gtg tcg aat ctc tcc aat gcg ctc      229
  Met Met Asn Asn Asn Gly Asn Gln Val Ser Asn Leu Ser Asn Ala Leu
  1               5                  10                  15 cgt caa gta aac ata gga aac agg aac agt aat aca acc acc gat caa         277
Arg Gln Val Asn Ile Gly Asn Arg Asn Ser Asn Thr Thr Thr Asp Gln
                20                  25                  30 agt aat ata aat ttt gaa ttt tca aca ggt gta aat aat aat aat aat         325
Ser Asn Ile Asn Phe Glu Phe Ser Thr Gly Val Asn Asn Asn Asn Asn
            35                  40                  45 aac aat agc agt agt aat aac aat aat gtt caa aac aat aac agc ggc         373
Asn Asn Ser Ser Ser Asn Asn Asn Asn Val Gln Asn Asn Asn Ser Gly
        50                  55                  60 cgc aat ggt agc caa aat aat gat aac gag aat aat atc aag aat acc         421
Arg Asn Gly Ser Gln Asn Asn Asp Asn Glu Asn Asn Ile Lys Asn Thr
65                  70                  75                  80 tta gaa caa cat cga caa caa caa cag gca ttt tcg gat atg agt cac         469
Leu Glu Gln His Arg Gln Gln Gln Gln Ala Phe Ser Asp Met Ser His
                85                  90                  95 gtg gag tat tcc aga att aca aaa ttt ttt caa gaa caa cca ctg gag         517
Val Glu Tyr Ser Arg Ile Thr Lys Phe Phe Gln Glu Gln Pro Leu Glu
            100                 105                 110 gga tat acc ctt ttc tct cac agg tct gcg cct aat gga ttc aaa gtt         565
Gly Tyr Thr Leu Phe Ser His Arg Ser Ala Pro Asn Gly Phe Lys Val
        115                 120                 125 gct ata gta cta agt gaa ctt gga ttt cat tat aac aca atc ttc cta         613
Ala Ile Val Leu Ser Glu Leu Gly Phe His Tyr Asn Thr Ile Phe Leu
130                 135                 140 gat ttc aat ctt ggc gaa cat agg gcc ccc gaa ttt gtg tct gtg aac         661
Asp Phe Asn Leu Gly Glu His Arg Ala Pro Glu Phe Val Ser Val Asn
145                 150                 155                 160 cct aat gca aga gtt cca gct tta atc gat cat ggt atg gac aac ttg         709
Pro Asn Ala Arg Val Pro Ala Leu Ile Asp His Gly Met Asp Asn Leu
                165                 170                 175 tct att tgg gaa tca ggg gcg att tta tta cat ttg gta aat aaa tat         757
Ser Ile Trp Glu Ser Gly Ala Ile Leu Leu His Leu Val Asn Lys Tyr
            180                 185                 190 tac aaa gag act ggt aat cca tta ctc tgg tcc gat gat tta gct gac         805
Tyr Lys Glu Thr Gly Asn Pro Leu Leu Trp Ser Asp Asp Leu Ala Asp
        195                 200                 205 caa tca caa atc aac gca tgg ttg ttc ttc caa acg tca ggg cat gcg         853
Gln Ser Gln Ile Asn Ala Trp Leu Phe Phe Gln Thr Ser Gly His Ala
210                 215                 220 cca atg att gga caa gct tta cat ttc aga tac ttc cat tca caa aag         901
Pro Met Ile Gly Gln Ala Leu His Phe Arg Tyr Phe His Ser Gln Lys
225                 230                 235                 240 ata gca agt gct gta gaa aga tat acg gat gag gtt aga aga gtt tac         949
Ile Ala Ser Ala Val Glu Arg Tyr Thr Asp Glu Val Arg Arg Val Tyr
                245                 250                 255 ggt gta gtg gag atg gcc ttg gct gaa cgt aga gaa gcg ctg gtg atg         997
Gly Val Val Glu Met Ala Leu Ala Glu Arg Arg Glu Ala Leu Val Met
            260                 265                 270 gaa tta gac acg gaa aat gcg gct gca tac tca gct ggt aca aca cca         1045
Glu Leu Asp Thr Glu Asn Ala Ala Ala Tyr Ser Ala Gly Thr Thr Pro
        275                 280                 285 atg tca caa agt cgt ttc ttt gat tat ccc gta tgg ctt gta gga gat         1093
Met Ser Gln Ser Arg Phe Phe Asp Tyr Pro Val Trp Leu Val Gly Asp
290                 295                 300
```

-continued

```
aaa tta act ata gca gat ttg gcc ttt gtc cca tgg aat aat gtc gtg    1141
Lys Leu Thr Ile Ala Asp Leu Ala Phe Val Pro Trp Asn Asn Val Val
305                 310                 315                 320 gat aga att ggc att aat atc aaa att gaa ttt cca gaa gtt tac aaa    1189
Asp Arg Ile Gly Ile Asn Ile Lys Ile Glu Phe Pro Glu Val Tyr Lys
                325                 330                 335 tgg acg aag cat atg atg aga aga ccc gcg gtc atc aag gca ttg cgt    1237
Trp Thr Lys His Met Met Arg Arg Pro Ala Val Ile Lys Ala Leu Arg
            340                 345                 350 ggt gaa tga aggctgcttt aaaaacaaga agaaagaag aaggaggaaa             1286
Gly Glu agaaggttat aagggtatgt atataggcag acaaaaagga aaattaagtg caaatataaa  1346
caaaaatgtc atagaagtat ataatagttt tgaaatttct gttgcttcta tttattcttt  1406
gttaccccaa ccacagaatt c                                            1427

<210> SEQ ID NO 4
<211> LENGTH: 354
<212> TYPE: PRT
<213> ORGANISM: Saccharomyces cerevisiae

<400> SEQUENCE: 4

Met Met Asn Asn Gly Asn Gln Val Ser Asn Leu Ser Asn Ala Leu
1               5                   10                  15

Arg Gln Val Asn Ile Gly Asn Arg Asn Ser Asn Thr Thr Thr Asp Gln
            20                  25                  30

Ser Asn Ile Asn Phe Glu Phe Ser Thr Gly Val Asn Asn Asn Asn
        35                  40                  45

Asn Asn Ser Ser Asn Asn Asn Val Gln Asn Asn Asn Ser Gly
    50                  55                  60

Arg Asn Gly Ser Gln Asn Asn Asp Asn Glu Asn Asn Ile Lys Asn Thr
65                  70                  75                  80

Leu Glu Gln His Arg Gln Gln Gln Ala Phe Ser Asp Met Ser His
                85                  90                  95

Val Glu Tyr Ser Arg Ile Thr Lys Phe Phe Gln Glu Gln Pro Leu Glu
            100                 105                 110

Gly Tyr Thr Leu Phe Ser His Arg Ser Ala Pro Asn Gly Phe Lys Val
        115                 120                 125

Ala Ile Val Leu Ser Glu Leu Gly Phe His Tyr Asn Thr Ile Phe Leu
    130                 135                 140

Asp Phe Asn Leu Gly Glu His Arg Ala Pro Glu Phe Val Ser Val Asn
145                 150                 155                 160

Pro Asn Ala Arg Val Pro Ala Leu Ile Asp His Gly Met Asp Asn Leu
                165                 170                 175

Ser Ile Trp Glu Ser Gly Ala Ile Leu Leu His Leu Val Asn Lys Tyr
            180                 185                 190

Tyr Lys Glu Thr Gly Asn Pro Leu Leu Trp Ser Asp Leu Ala Asp
        195                 200                 205

Gln Ser Gln Ile Asn Ala Trp Leu Phe Phe Gln Thr Ser Gly His Ala
    210                 215                 220

Pro Met Ile Gly Gln Ala Leu His Phe Arg Tyr Phe His Ser Gln Lys
225                 230                 235                 240

Ile Ala Ser Ala Val Glu Arg Tyr Thr Asp Glu Val Arg Arg Val Tyr
                245                 250                 255
```

```
Gly Val Val Glu Met Ala Leu Ala Glu Arg Arg Glu Ala Leu Val Met
                260                 265                 270

Glu Leu Asp Thr Glu Asn Ala Ala Ala Tyr Ser Ala Gly Thr Thr Pro
            275                 280                 285

Met Ser Gln Ser Arg Phe Phe Asp Tyr Pro Val Trp Leu Val Gly Asp
        290                 295                 300

Lys Leu Thr Ile Ala Asp Leu Ala Phe Val Pro Trp Asn Asn Val Val
305                 310                 315                 320

Asp Arg Ile Gly Ile Asn Ile Lys Ile Glu Phe Pro Glu Val Tyr Lys
                325                 330                 335

Trp Thr Lys His Met Met Arg Arg Pro Ala Val Ile Lys Ala Leu Arg
                340                 345                 350

Gly Glu

<210> SEQ ID NO 5
<211> LENGTH: 8
<212> TYPE: PRT
<213> ORGANISM: Artificial sequence
<220> FEATURE:
<223> OTHER INFORMATION: FLAG peptide

<400> SEQUENCE: 5

Asp Tyr Lys Asp Asp Asp Asp Lys
1               5

<210> SEQ ID NO 6
<211> LENGTH: 8
<212> TYPE: PRT
<213> ORGANISM: Artificial sequence
<220> FEATURE:
<223> OTHER INFORMATION: FLAG peptide

<400> SEQUENCE: 6

Asp Tyr Lys Asp Glu Asp Asp Lys
1               5

<210> SEQ ID NO 7
<211> LENGTH: 9
<212> TYPE: PRT
<213> ORGANISM: Artificial sequence
<220> FEATURE:
<223> OTHER INFORMATION: Strep epitope

<400> SEQUENCE: 7

Ala Trp Arg His Pro Gln Phe Gly Gly
1               5

<210> SEQ ID NO 8
<211> LENGTH: 13
<212> TYPE: PRT
<213> ORGANISM: Artificial sequence
<220> FEATURE:
<223> OTHER INFORMATION: Hemagglutinin epitope

<400> SEQUENCE: 8

Tyr Pro Tyr Asp Val Pro Asp Tyr Ala Ile Glu Gly Arg
1               5                   10

<210> SEQ ID NO 9
<211> LENGTH: 11
<212> TYPE: PRT
<213> ORGANISM: Artificial sequence
<220> FEATURE:
<223> OTHER INFORMATION: Myc epitope
```

```
<400> SEQUENCE: 9

Glu Gln Lys Leu Leu Ser Glu Glu Asp Leu Asn
1               5                   10

<210> SEQ ID NO 10
<211> LENGTH: 9
<212> TYPE: PRT
<213> ORGANISM: Saccharomyces cerevisiae

<400> SEQUENCE: 10

Pro Gln Gly Gly Tyr Gln Gln Tyr Asn
1               5

<210> SEQ ID NO 11
<211> LENGTH: 445
<212> TYPE: DNA
<213> ORGANISM: Artificial sequence
<220> FEATURE:
<223> OTHER INFORMATION: CUP1 promoter

<400> SEQUENCE: 11
ccattaccga catttgggcg ctatacgtgc atatgttcat gtatgtatct gtatttaaaa      60 cactttgta ttattttcc tcatatatgt gtataggttt atacggatga tttaattatt      120
acttcaccac cctttatttc aggctgatat cttagccttg ttactagtta gaaaaagaca    180 ttttttgctgt cagtcactgt caagagattc ttttgctggc atttcttcta gaagcaaaaa    240
gagcgatgcg tcttttccgc tgaaccgttc agcaaaaaa gactaccaac gcaatatgga     300
ttgtcagaat catataaaag agaagcaaat aactccttgt cttgtatcaa ttgcattata    360
atatcttctt gttagtgcaa tatcatatag aagtcatcga aatagatatt aagaaaaaca    420
aactgtacaa tcaatcaatc aatca                                          445

<210> SEQ ID NO 12
<211> LENGTH: 717
<212> TYPE: DNA
<213> ORGANISM: Aequorea victoria

<400> SEQUENCE: 12
atgtctaaag gtgaagaatt attcactggt gttgtcccaa ttttggttga attagatggt    60
gatgttaatg gtcacaaatt ttctgtctcc ggtgaaggtg aaggtgatgc tacttacggt    120
aaattgacct aaaatttat ttgtactact ggtaaattgc cagttccatg gccaacctta    180
gtcactactt tcggttatgg tgttcaatgt tttgctagat acccagatca tatgaaacaa    240
catgactttt tcaagtctgc catgccagaa ggttatgttc aagaaagaac tatttttttc    300
aaagatgacg gtaactacaa gaccagagct gaagtcaagt ttgaaggtga taccttagtt    360
aatagaatcg aattaaaagg tattgatttt aagaagatg gtaacatttt aggtcacaaa    420
ttggaataca actataactc tcacaatgtt tacatcatgg ctgacaaaca aaagaatggt    480
atcaaagtta acttcaaaat tagacacaac attgaagatg gttctgttca attagctgac    540
cattatcaac aaaatactcc aattggtgat ggtccagtct tgttaccaga caaccattac    600
ttatccactc aatctgcctt atccaaagat ccaaacgaaa agagagacca catggtcttg    660
ttagaatttg ttactgctgc tggtattacc catggtatgg atgaattgta caaataa      717

<210> SEQ ID NO 13
<211> LENGTH: 27
<212> TYPE: DNA
```

<213> ORGANISM: Artificial sequence
<220> FEATURE:
<223> OTHER INFORMATION: HA tag-encoding sequence

<400> SEQUENCE: 13
tacccatacg acgtcccaga ctacgct                                               27

<210> SEQ ID NO 14
<211> LENGTH: 645
<212> TYPE: DNA
<213> ORGANISM: Artificial sequence
<220> FEATURE:
<223> OTHER INFORMATION: Yeast Sup35Rdelta2-5 encoding sequence
<220> FEATURE:
<221> NAME/KEY: CDS
<222> LOCATION: (1)..(645)

<400> SEQUENCE: 14

| | | | | | | | | | | | | | | | | |
|---|---|---|---|---|---|---|---|---|---|---|---|---|---|---|---|---|
| atg | tcg | gat | tca | aac | caa | ggc | aac | aat | cag | caa | aac | tac | cag | caa | tac | 48 |
| Met | Ser | Asp | Ser | Asn | Gln | Gly | Asn | Asn | Gln | Gln | Asn | Tyr | Gln | Gln | Tyr | |
| 1 | | | | 5 | | | | | 10 | | | | | 15 | | |
| agc | cag | aac | ggt | aac | caa | caa | caa | ggt | aac | aac | aga | tac | caa | ggt | tat | 96 |
| Ser | Gln | Asn | Gly | Asn | Gln | Gln | Gln | Gly | Asn | Asn | Arg | Tyr | Gln | Gly | Tyr | |
| | | | 20 | | | | | 25 | | | | | 30 | | | |
| caa | gct | tac | aat | gct | caa | gcc | caa | cct | gca | ggt | ggg | tac | tac | caa | aat | 144 |
| Gln | Ala | Tyr | Asn | Ala | Gln | Ala | Gln | Pro | Ala | Gly | Gly | Tyr | Tyr | Gln | Asn | |
| | 35 | | | | | 40 | | | | | 45 | | | | | |
| tac | caa | ggt | tat | tct | ggg | tac | cca | caa | ggt | ggc | cgt | gga | aat | tac | aaa | 192 |
| Tyr | Gln | Gly | Tyr | Ser | Gly | Tyr | Pro | Gln | Gly | Gly | Arg | Gly | Asn | Tyr | Lys | |
| 50 | | | | | 55 | | | | | 60 | | | | | | |
| aac | ttc | aac | tac | aat | aac | aat | ttg | caa | gga | tat | caa | gct | ggt | ttc | caa | 240 |
| Asn | Phe | Asn | Tyr | Asn | Asn | Asn | Leu | Gln | Gly | Tyr | Gln | Ala | Gly | Phe | Gln | |
| 65 | | | | | 70 | | | | | 75 | | | | | 80 | |
| cca | cag | tct | caa | ggt | atg | tct | ttg | aac | gac | ttt | caa | aag | caa | caa | aag | 288 |
| Pro | Gln | Ser | Gln | Gly | Met | Ser | Leu | Asn | Asp | Phe | Gln | Lys | Gln | Gln | Lys | |
| | | | | 85 | | | | | 90 | | | | | 95 | | |
| cag | gcc | gct | ccc | aaa | cca | aag | aag | act | ttg | aag | ctt | gtc | tcc | agt | tcc | 336 |
| Gln | Ala | Ala | Pro | Lys | Pro | Lys | Lys | Thr | Leu | Lys | Leu | Val | Ser | Ser | Ser | |
| | | 100 | | | | | 105 | | | | | 110 | | | | |
| ggt | atc | aag | ttg | gcc | aat | gct | acc | aag | aag | gtt | ggc | aca | aaa | cct | gcc | 384 |
| Gly | Ile | Lys | Leu | Ala | Asn | Ala | Thr | Lys | Lys | Val | Gly | Thr | Lys | Pro | Ala | |
| | | 115 | | | | | 120 | | | | | 125 | | | | |
| gaa | tct | gat | aag | aaa | gag | gaa | gag | aag | tct | gct | gaa | acc | aaa | gaa | cca | 432 |
| Glu | Ser | Asp | Lys | Lys | Glu | Glu | Glu | Lys | Ser | Ala | Glu | Thr | Lys | Glu | Pro | |
| | 130 | | | | | 135 | | | | | 140 | | | | | |
| act | aaa | gag | cca | aca | aag | gtc | gaa | gaa | cca | gtt | aaa | aag | gag | gag | aaa | 480 |
| Thr | Lys | Glu | Pro | Thr | Lys | Val | Glu | Glu | Pro | Val | Lys | Lys | Glu | Glu | Lys | |
| 145 | | | | | 150 | | | | | 155 | | | | | 160 | |
| cca | gtc | cag | act | gaa | gaa | aag | acg | gag | gaa | aaa | tcg | gaa | ctt | cca | aag | 528 |
| Pro | Val | Gln | Thr | Glu | Glu | Lys | Thr | Glu | Glu | Lys | Ser | Glu | Leu | Pro | Lys | |
| | | | | 165 | | | | | 170 | | | | | 175 | | |
| gta | gaa | gac | ctt | aaa | atc | tct | gaa | tca | aca | cat | aat | acc | aac | aat | gcc | 576 |
| Val | Glu | Asp | Leu | Lys | Ile | Ser | Glu | Ser | Thr | His | Asn | Thr | Asn | Asn | Ala | |
| | | | | 180 | | | | | 185 | | | | | 190 | | |
| aat | gtt | acc | agt | gct | gat | gcc | ttg | atc | aag | gaa | cag | gaa | gaa | gaa | gtg | 624 |
| Asn | Val | Thr | Ser | Ala | Asp | Ala | Leu | Ile | Lys | Glu | Gln | Glu | Glu | Glu | Val | |
| | | | 195 | | | | | 200 | | | | | 205 | | | |
| gat | gac | gaa | gtt | gtt | aac | gat | | | | | | | | | | 645 |
| Asp | Asp | Glu | Val | Val | Asn | Asp | | | | | | | | | | |
| | 210 | | | | | 215 | | | | | | | | | | |

<210> SEQ ID NO 15

```
<211> LENGTH: 215
<212> TYPE: PRT
<213> ORGANISM: Artificial sequence
<220> FEATURE:
<223> OTHER INFORMATION: Synthetic Peptide

<400> SEQUENCE: 15

Met Ser Asp Ser Asn Gln Gly Asn Asn Gln Gln Asn Tyr Gln Gln Tyr
1               5                   10                  15

Ser Gln Asn Gly Asn Gln Gln Gly Asn Asn Arg Tyr Gln Gly Tyr
            20                  25                  30

Gln Ala Tyr Asn Ala Gln Ala Gln Pro Ala Gly Gly Tyr Tyr Gln Asn
        35                  40                  45

Tyr Gln Gly Tyr Ser Gly Tyr Pro Gln Gly Gly Arg Gly Asn Tyr Lys
    50                  55                  60

Asn Phe Asn Tyr Asn Asn Asn Leu Gln Gly Tyr Gln Ala Gly Phe Gln
65                  70                  75                  80

Pro Gln Ser Gln Gly Met Ser Leu Asn Asp Phe Gln Lys Gln Gln Lys
                85                  90                  95

Gln Ala Ala Pro Lys Pro Lys Lys Thr Leu Lys Leu Val Ser Ser Ser
            100                 105                 110

Gly Ile Lys Leu Ala Asn Ala Thr Lys Lys Val Gly Thr Lys Pro Ala
        115                 120                 125

Glu Ser Asp Lys Lys Glu Glu Glu Lys Ser Ala Glu Thr Lys Glu Pro
    130                 135                 140

Thr Lys Glu Pro Thr Lys Val Glu Glu Pro Val Lys Lys Glu Glu Lys
145                 150                 155                 160

Pro Val Gln Thr Glu Glu Lys Thr Glu Glu Lys Ser Glu Leu Pro Lys
                165                 170                 175

Val Glu Asp Leu Lys Ile Ser Glu Ser Thr His Asn Thr Asn Asn Ala
            180                 185                 190

Asn Val Thr Ser Ala Asp Ala Leu Ile Lys Glu Gln Glu Glu Glu Val
        195                 200                 205

Asp Asp Glu Val Val Asn Asp
    210                 215

<210> SEQ ID NO 16
<211> LENGTH: 813
<212> TYPE: DNA
<213> ORGANISM: Artificial sequence
<220> FEATURE:
<223> OTHER INFORMATION: Yeast Sup35R2E2 encoding sequence
<220> FEATURE:
<221> NAME/KEY: CDS
<222> LOCATION: (1)..(813)

<400> SEQUENCE: 16 atg tcg gat tca aac caa ggc aac aat cag caa aac tac cag caa tac     48
Met Ser Asp Ser Asn Gln Gly Asn Asn Gln Gln Asn Tyr Gln Gln Tyr
1               5                   10                  15 agc cag aac ggt aac caa caa caa ggt aac aac aga tac caa ggt tat     96
Ser Gln Asn Gly Asn Gln Gln Gln Gly Asn Asn Arg Tyr Gln Gly Tyr
            20                  25                  30 caa gct tac aat gct caa gcc caa cct gca ggt ggg tac tac caa aat    144
Gln Ala Tyr Asn Ala Gln Ala Gln Pro Ala Gly Gly Tyr Tyr Gln Asn
        35                  40                  45 tac caa ggt tat tct ggg tac caa caa ggt ggc tat caa cag tac aat    192
Tyr Gln Gly Tyr Ser Gly Tyr Gln Gln Gly Gly Tyr Gln Gln Tyr Asn
    50                  55                  60
```

-continued

| | |
|---|---|
| ccc caa ggt ggc tat caa cag tac aat ccc caa ggt ggc tat caa cag<br>Pro Gln Gly Gly Tyr Gln Gln Tyr Asn Pro Gln Gly Gly Tyr Gln Gln<br>65                70                  75                  80 | 240 |
| tac aat ccc gac gcc ggt tac cag caa cag tat aat cct caa gga ggc<br>Tyr Asn Pro Asp Ala Gly Tyr Gln Gln Gln Tyr Asn Pro Gln Gly Gly<br>                 85                  90                  95 | 288 |
| tat caa cag tac aat cct caa ggc ggt tat cag cag caa ttc aat cca<br>Tyr Gln Gln Tyr Asn Pro Gln Gly Gly Tyr Gln Gln Gln Phe Asn Pro<br>               100               105               110 | 336 |
| caa ggt ggc cgt gga aat tac aaa aac ttc aac tac aat aac aat ttg<br>Gln Gly Gly Arg Gly Asn Tyr Lys Asn Phe Asn Tyr Asn Asn Asn Leu<br>              115               120               125 | 384 |
| caa gga tat caa gct ggt ttc caa cca cag tct caa ggt atg tct ttg<br>Gln Gly Tyr Gln Ala Gly Phe Gln Pro Gln Ser Gln Gly Met Ser Leu<br>    130               135               140 | 432 |
| aac gac ttt caa aag caa caa aag cag gcc gct ccc aaa cca aag aag<br>Asn Asp Phe Gln Lys Gln Gln Lys Gln Ala Ala Pro Lys Pro Lys Lys<br>145                 150               155               160 | 480 |
| act ttg aag ctt gtc tcc agt tcc ggt atc aag ttg gcc aat gct acc<br>Thr Leu Lys Leu Val Ser Ser Ser Gly Ile Lys Leu Ala Asn Ala Thr<br>                  165               170               175 | 528 |
| aag aag gtt ggc aca aaa cct gcc gaa tct gat aag aaa gag gaa gag<br>Lys Lys Val Gly Thr Lys Pro Ala Glu Ser Asp Lys Lys Glu Glu Glu<br>             180               185               190 | 576 |
| aag tct gct gaa acc aaa gaa cca act aaa gag cca aca aag gtc gaa<br>Lys Ser Ala Glu Thr Lys Glu Pro Thr Lys Glu Pro Thr Lys Val Glu<br>               195               200               205 | 624 |
| gaa cca gtt aaa aag gag gag aaa cca gtc cag act gaa gaa aag acg<br>Glu Pro Val Lys Lys Glu Glu Lys Pro Val Gln Thr Glu Glu Lys Thr<br>    210               215               220 | 672 |
| gag gaa aaa tcg gaa ctt cca aag gta gaa gac ctt aaa atc tct gaa<br>Glu Glu Lys Ser Glu Leu Pro Lys Val Glu Asp Leu Lys Ile Ser Glu<br>225                 230               235               240 | 720 |
| tca aca cat aat acc aac aat gcc aat gtt acc agt gct gat gcc ttg<br>Ser Thr His Asn Thr Asn Asn Ala Asn Val Thr Ser Ala Asp Ala Leu<br>                  245               250               255 | 768 |
| atc aag gaa cag gaa gaa gaa gtg gat gac gaa gtt gtt aac gat<br>Ile Lys Glu Gln Glu Glu Glu Val Asp Asp Glu Val Val Asn Asp<br>             260               265               270 | 813 |

<210> SEQ ID NO 17
<211> LENGTH: 271
<212> TYPE: PRT
<213> ORGANISM: Artificial sequence
<220> FEATURE:
<223> OTHER INFORMATION: Synthetic Peptide

<400> SEQUENCE: 17

Met Ser Asp Ser Asn Gln Gly Asn Asn Gln Gln Asn Tyr Gln Gln Tyr
1                 5                     10                 15

Ser Gln Asn Gly Asn Gln Gln Gly Asn Asn Arg Tyr Gln Gly Tyr
                20               25               30

Gln Ala Tyr Asn Ala Gln Ala Gln Pro Ala Gly Gly Tyr Tyr Gln Asn
           35                   40               45

Tyr Gln Gly Tyr Ser Gly Tyr Gln Gln Gly Gly Tyr Gln Gln Tyr Asn
    50               55               60

Pro Gln Gly Gly Tyr Gln Gln Tyr Asn Pro Gln Gly Gly Tyr Gln Gln
65               70                 75               80

Tyr Asn Pro Asp Ala Gly Tyr Gln Gln Gln Tyr Asn Pro Gln Gly Gly
               85               90               95

Tyr Gln Gln Tyr Asn Pro Gln Gly Gly Tyr Gln Gln Gln Phe Asn Pro
            100                 105                 110

Gln Gly Gly Arg Gly Asn Tyr Lys Asn Phe Asn Tyr Asn Asn Asn Leu
        115                 120                 125

Gln Gly Tyr Gln Ala Gly Phe Gln Pro Gln Ser Gln Gly Met Ser Leu
    130                 135                 140

Asn Asp Phe Gln Lys Gln Lys Gln Ala Ala Pro Lys Pro Lys Lys
145                 150                 155                 160

Thr Leu Lys Leu Val Ser Ser Gly Ile Lys Leu Ala Asn Ala Thr
                165                 170                 175

Lys Lys Val Gly Thr Lys Pro Ala Glu Ser Asp Lys Lys Glu Glu
            180                 185                 190

Lys Ser Ala Glu Thr Lys Glu Pro Thr Lys Glu Pro Thr Lys Val Glu
        195                 200                 205

Glu Pro Val Lys Lys Glu Glu Lys Pro Val Gln Thr Glu Glu Lys Thr
    210                 215                 220

Glu Glu Lys Ser Glu Leu Pro Lys Val Glu Asp Leu Lys Ile Ser Glu
225                 230                 235                 240

Ser Thr His Asn Thr Asn Asn Ala Asn Val Thr Ser Ala Asp Ala Leu
                245                 250                 255

Ile Lys Glu Gln Glu Glu Val Asp Asp Glu Val Val Asn Asp
            260                 265                 270

<210> SEQ ID NO 18
<211> LENGTH: 641
<212> TYPE: DNA
<213> ORGANISM: Mouse
<220> FEATURE:
<221> NAME/KEY: CDS
<222> LOCATION: (1)..(633)

<400> SEQUENCE: 18

| | | | | | | | | | | | | | | | | |
|---|---|---|---|---|---|---|---|---|---|---|---|---|---|---|---|---|---|
| atg | tct | aaa | aag | cgg | cca | aag | cct | gga | ggg | tgg | aac | acc | ggt | gga | agc | | 48 |
| Met | Ser | Lys | Lys | Arg | Pro | Lys | Pro | Gly | Gly | Trp | Asn | Thr | Gly | Gly | Ser | | |
| 1 | | | | 5 | | | | | 10 | | | | | 15 | | | |

| cgg | tat | ccc | ggg | cag | gga | agc | cct | gga | ggc | aac | cgt | tac | cca | cct | cag | | 96 |
|---|---|---|---|---|---|---|---|---|---|---|---|---|---|---|---|---|---|
| Arg | Tyr | Pro | Gly | Gln | Gly | Ser | Pro | Gly | Gly | Asn | Arg | Tyr | Pro | Pro | Gln | | |
| | | | 20 | | | | | 25 | | | | | 30 | | | | |

| ggt | ggc | acc | tgg | ggg | cag | ccc | cac | ggt | ggt | ggc | tgg | gga | caa | ccc | cat | | 144 |
|---|---|---|---|---|---|---|---|---|---|---|---|---|---|---|---|---|---|
| Gly | Gly | Thr | Trp | Gly | Gln | Pro | His | Gly | Gly | Gly | Trp | Gly | Gln | Pro | His | | |
| | | | | 35 | | | | | 40 | | | | | 45 | | | |

| ggg | ggc | agc | tgg | gga | caa | cct | cat | ggt | ggt | agt | tgg | ggt | cag | ccc | cat | | 192 |
|---|---|---|---|---|---|---|---|---|---|---|---|---|---|---|---|---|---|
| Gly | Gly | Ser | Trp | Gly | Gln | Pro | His | Gly | Gly | Ser | Trp | Gly | Gln | Pro | His | | |
| 50 | | | | | 55 | | | | | 60 | | | | | | | |

| ggc | ggt | gga | tgg | ggc | caa | gga | ggg | ggt | acc | cat | aat | cag | tgg | aac | aag | | 240 |
|---|---|---|---|---|---|---|---|---|---|---|---|---|---|---|---|---|---|
| Gly | Gly | Gly | Trp | Gly | Gln | Gly | Gly | Gly | Thr | His | Asn | Gln | Trp | Asn | Lys | | |
| 65 | | | | | 70 | | | | | 75 | | | | | 80 | | |

| ccc | agc | aaa | cca | aaa | acc | aac | ctc | aag | cat | gtg | gca | ggg | gct | gcg | gca | | 288 |
|---|---|---|---|---|---|---|---|---|---|---|---|---|---|---|---|---|---|
| Pro | Ser | Lys | Pro | Lys | Thr | Asn | Leu | Lys | His | Val | Ala | Gly | Ala | Ala | Ala | | |
| | | | | 85 | | | | | 90 | | | | | 95 | | | |

| gct | ggg | gca | gta | gtg | ggg | ggc | ctt | ggt | ggc | tac | atg | ctg | ggg | agc | gcc | | 336 |
|---|---|---|---|---|---|---|---|---|---|---|---|---|---|---|---|---|---|
| Ala | Gly | Ala | Val | Val | Gly | Gly | Leu | Gly | Gly | Tyr | Met | Leu | Gly | Ser | Ala | | |
| | | | | 100 | | | | | 105 | | | | | 110 | | | |

| gtg | agc | agg | ccc | atg | atc | cat | ttt | ggc | aac | gac | tgg | gag | gac | cgc | tac | | 384 |
|---|---|---|---|---|---|---|---|---|---|---|---|---|---|---|---|---|---|
| Val | Ser | Arg | Pro | Met | Ile | His | Phe | Gly | Asn | Asp | Trp | Glu | Asp | Arg | Tyr | | |
| | | | | 115 | | | | | 120 | | | | | 125 | | | |

```
tac cgt gaa aac atg tac cgc tac cct aac caa gtg tac tac agg cca       432
Tyr Arg Glu Asn Met Tyr Arg Tyr Pro Asn Gln Val Tyr Tyr Arg Pro
    130                 135                 140 gtg gat cag tac agc aac cag aac aac ttc gtg cac gac tgc gtc aat       480
Val Asp Gln Tyr Ser Asn Gln Asn Asn Phe Val His Asp Cys Val Asn
145                 150                 155                 160 atc acc atc aag cag cac acg gtc acc acc acc aag ggg gag aac           528
Ile Thr Ile Lys Gln His Thr Val Thr Thr Thr Lys Gly Glu Asn
                165                 170                 175 ttc acc gag acc gat gtg aag atg atg gag cgc gtg gtg gag cag atg       576
Phe Thr Glu Thr Asp Val Lys Met Met Glu Arg Val Val Glu Gln Met
            180                 185                 190 tgc gtc acc cag tac cag aag gag tcc cag gcc tat tac gac ggg aga       624
Cys Val Thr Gln Tyr Gln Lys Glu Ser Gln Ala Tyr Tyr Asp Gly Arg
        195                 200                 205 aga tcc agc tgataacc                                                  641
Arg Ser Ser
    210

<210> SEQ ID NO 19
<211> LENGTH: 211
<212> TYPE: PRT
<213> ORGANISM: Mouse

<400> SEQUENCE: 19

Met Ser Lys Lys Arg Pro Lys Pro Gly Gly Trp Asn Thr Gly Gly Ser
1               5                   10                  15

Arg Tyr Pro Gly Gln Gly Ser Pro Gly Gly Asn Arg Tyr Pro Pro Gln
            20                  25                  30

Gly Gly Thr Trp Gly Gln Pro His Gly Gly Gly Trp Gly Gln Pro His
        35                  40                  45

Gly Gly Ser Trp Gly Gln Pro His Gly Gly Ser Trp Gly Gln Pro His
    50                  55                  60

Gly Gly Gly Trp Gly Gln Gly Gly Thr His Asn Gln Trp Asn Lys
65                  70                  75                  80

Pro Ser Lys Pro Lys Thr Asn Leu Lys His Val Ala Gly Ala Ala
            85                  90                  95

Ala Gly Ala Val Val Gly Gly Leu Gly Gly Tyr Met Leu Gly Ser Ala
        100                 105                 110

Val Ser Arg Pro Met Ile His Phe Gly Asn Asp Trp Glu Asp Arg Tyr
    115                 120                 125

Tyr Arg Glu Asn Met Tyr Arg Tyr Pro Asn Gln Val Tyr Tyr Arg Pro
130                 135                 140

Val Asp Gln Tyr Ser Asn Gln Asn Asn Phe Val His Asp Cys Val Asn
145                 150                 155                 160

Ile Thr Ile Lys Gln His Thr Val Thr Thr Thr Lys Gly Glu Asn
                165                 170                 175

Phe Thr Glu Thr Asp Val Lys Met Met Glu Arg Val Val Glu Gln Met
            180                 185                 190

Cys Val Thr Gln Tyr Gln Lys Glu Ser Gln Ala Tyr Tyr Asp Gly Arg
        195                 200                 205

Arg Ser Ser
    210

<210> SEQ ID NO 20
<211> LENGTH: 644
<212> TYPE: DNA
<213> ORGANISM: Mesocricetus auratus
```

```
<220> FEATURE:
<221> NAME/KEY: CDS
<222> LOCATION: (1)..(636)

<400> SEQUENCE: 20 atg tct aag aag cgg cca aag cct gga ggg tgg aac act ggc gga agc      48
Met Ser Lys Lys Arg Pro Lys Pro Gly Gly Trp Asn Thr Gly Gly Ser
1               5                   10                  15 cga tac cct ggg cag ggc agc cct gga ggc aac cgt tac cca cct cag      96
Arg Tyr Pro Gly Gln Gly Ser Pro Gly Gly Asn Arg Tyr Pro Pro Gln
            20                  25                  30 ggt ggc ggc aca tgg ggg caa ccc cat ggt ggt ggc tgg gga cag ccc     144
Gly Gly Gly Thr Trp Gly Gln Pro His Gly Gly Gly Trp Gly Gln Pro
        35                  40                  45 cat ggt ggt ggc tgg gga cag ccc cat ggt ggt ggc tgg ggt cag ccc     192
His Gly Gly Gly Trp Gly Gln Pro His Gly Gly Gly Trp Gly Gln Pro
    50                  55                  60 cat ggt ggt ggc tgg ggt caa gga ggt ggc acc cac aat cag tgg aac     240
His Gly Gly Gly Trp Gly Gln Gly Gly Gly Thr His Asn Gln Trp Asn
65                  70                  75                  80 aag ccc agt aag cca aaa acc aac atg aag cac atg gcc ggc gct gct     288
Lys Pro Ser Lys Pro Lys Thr Asn Met Lys His Met Ala Gly Ala Ala
                85                  90                  95 gcg gca ggg gcc gtg gtg ggg ggc ctt ggt ggc tac atg ctg ggg agt     336
Ala Ala Gly Ala Val Val Gly Gly Leu Gly Gly Tyr Met Leu Gly Ser
            100                 105                 110 gcc atg agc agg ccc atg atg cat ttt ggc aat gac tgg gag gac cgc     384
Ala Met Ser Arg Pro Met Met His Phe Gly Asn Asp Trp Glu Asp Arg
        115                 120                 125 tac tac cgt gaa aac atg aac cgc tac cct aac caa gtg tat tac cgg     432
Tyr Tyr Arg Glu Asn Met Asn Arg Tyr Pro Asn Gln Val Tyr Tyr Arg
    130                 135                 140 cca gtg gac cag tac aac aac cag aac aac ttt gtg cac gat tgt gtc     480
Pro Val Asp Gln Tyr Asn Asn Gln Asn Asn Phe Val His Asp Cys Val
145                 150                 155                 160 aac atc acc atc aag cag cac aca gtc acc acc acc aag ggg gag         528
Asn Ile Thr Ile Lys Gln His Thr Val Thr Thr Thr Lys Gly Glu
                165                 170                 175 aac ttc acg gag acc gac atc aag ata atg gag cgc gtg gtg gag cag     576
Asn Phe Thr Glu Thr Asp Ile Lys Ile Met Glu Arg Val Val Glu Gln
            180                 185                 190 atg tgt acc acc cag tat cag aag gag tcc cag gcc tac tac gat gga     624
Met Cys Thr Thr Gln Tyr Gln Lys Glu Ser Gln Ala Tyr Tyr Asp Gly
        195                 200                 205 aga agg tcc agc tgataacc                                            644
Arg Arg Ser Ser
    210

<210> SEQ ID NO 21
<211> LENGTH: 212
<212> TYPE: PRT
<213> ORGANISM: Mesocricetus auratus

<400> SEQUENCE: 21

Met Ser Lys Lys Arg Pro Lys Pro Gly Gly Trp Asn Thr Gly Gly Ser
1               5                   10                  15

Arg Tyr Pro Gly Gln Gly Ser Pro Gly Gly Asn Arg Tyr Pro Pro Gln
            20                  25                  30

Gly Gly Gly Thr Trp Gly Gln Pro His Gly Gly Gly Trp Gly Gln Pro
        35                  40                  45
```

His Gly Gly Gly Trp Gly Gln Pro His Gly Gly Trp Gly Gln Pro
50              55                  60

His Gly Gly Gly Trp Gly Gln Gly Gly Gly Thr His Asn Gln Trp Asn
65              70                  75                  80

Lys Pro Ser Lys Pro Lys Thr Asn Met Lys His Met Ala Gly Ala Ala
                85                  90                  95

Ala Ala Gly Ala Val Val Gly Gly Leu Gly Gly Tyr Met Leu Gly Ser
            100                 105                 110

Ala Met Ser Arg Pro Met Met His Phe Gly Asn Asp Trp Glu Asp Arg
            115                 120                 125

Tyr Tyr Arg Glu Asn Met Asn Arg Tyr Pro Asn Gln Val Tyr Tyr Arg
            130                 135                 140

Pro Val Asp Gln Tyr Asn Asn Gln Asn Phe Val His Asp Cys Val
145                 150                 155                 160

Asn Ile Thr Ile Lys Gln His Thr Val Thr Thr Thr Lys Gly Glu
                165                 170                 175

Asn Phe Thr Glu Thr Asp Ile Lys Ile Met Glu Arg Val Val Glu Gln
            180                 185                 190

Met Cys Thr Thr Gln Tyr Gln Lys Glu Ser Gln Ala Tyr Tyr Asp Gly
            195                 200                 205

Arg Arg Ser Ser
    210

<210> SEQ ID NO 22
<211> LENGTH: 780
<212> TYPE: PRT
<213> ORGANISM: Saccharomyces cerevisiae

<400> SEQUENCE: 22

Met Lys Lys Lys Asp Asn Ser Asp Asp Lys Asp Asn Val Ala Ser Gly
1               5                   10                  15

Gly Tyr Lys Asn Ala Ala Asp Ala Gly Ser Asn Asn Ala Ser Lys Lys
            20                  25                  30

Ser Ser Tyr Arg Asn Trp Lys Gly Gly Asn Tyr Gly Gly Tyr Ser Tyr
            35                  40                  45

Asn Ser Asn Tyr Asn Asn Tyr Asn Asn Tyr Asn Asn Tyr Asn Asn Tyr
50                  55                  60

Asn Asn Tyr Asn Asn Tyr Asn Lys Tyr Asn Gly Gly Tyr Lys Ser Thr
65              70                  75                  80

Tyr Lys Ser Ala Val Thr Asn Ser Gly Thr Thr Ser Ala Ser Thr Thr
                85                  90                  95

Ser Thr Ser Asn Lys Ser Asn Thr Ser Ser Lys Cys Ser Thr Asp Cys
            100                 105                 110

Lys Asn Lys Gly Lys Gly Asn Ser Thr Gly Lys Trp Lys Val Asp Val
            115                 120                 125

Ser Lys Lys Lys Asn Ser Val Arg Ser Ala Met Ser Asn Ala Ser Gly
130                 135                 140

Lys Ala Tyr Asn Val Ala Asp Cys Ser Asp Lys Asn Thr Val Lys Arg
145                 150                 155                 160

Ala Ala His Ala Asp Ser Asn Cys Met Ala Thr Cys Val Thr Asp Tyr
                165                 170                 175

Ser Ser Gly Ala Lys Trp Ala Lys Met Ala Ala Ser Val Val Asp Arg
            180                 185                 190

Arg Asp Ser Ala Asn Asp Thr Lys Asp Ala Val Val Thr Asp Val Ala
            195                 200                 205

-continued

```
Thr Asp Lys Ala Lys Gly Tyr Lys Thr Asp Tyr Val Ser Asp Asn Asp
    210                 215                 220

Ser Arg Tyr Lys Val Asp Thr Asp Ser Lys Val Ser Val Lys Ser Ser
225                 230                 235                 240

Ser Val Thr Val Ala Val Thr Ser Ser Val Asn Arg Ser Asn Ser Ser
                245                 250                 255

Ser Ser Arg Thr Val Val Asn Thr Arg Val Asn Asn Arg Asn Ser
        260                 265                 270

Gly Lys Val Val Asp Thr Ala Ser Val Arg Ala Lys Ala Asn Val Lys
        275                 280                 285

Asp Asp Ala Asp Lys Asn Lys Ser Gly Arg Thr Gly Arg Asp Asp His
    290                 295                 300

Lys Asp Lys Ala Asp Asp Ser Cys Val Lys Tyr Met Asn Asp Thr Val
305                 310                 315                 320

Lys Tyr Met Ser Lys Thr Val Asp Ser Asn Val Asn Asp Trp Lys Arg
                325                 330                 335

Asp Thr Ala Val Gly Gly Ser Asp Ser Arg Val Lys Asp His Asn Arg
            340                 345                 350

Ala Tyr Lys Arg Ala Asp Asp Gly Val Asn Thr Asp Ser Ala Tyr Gly
        355                 360                 365

Ser Arg Met Asn Lys Thr Asn Arg Lys Gly His Arg Tyr Gly Cys Gly
    370                 375                 380

Arg Asn Gly Ala Gly Lys Ser Thr Met Arg Ala Ala Asn Gly Asp Gly
385                 390                 395                 400

Asp Lys Asp Thr Arg Thr Cys Val His Lys Gly Gly Asp Asp Val Ser
                405                 410                 415

Ala Asp Ser Thr Ser Arg Ala Ala Ala Ser Val Gly Asp Arg Arg Ala
            420                 425                 430

Thr Val Gly Ser Ser Gly Gly Trp Lys Met Lys Ala Arg Ala Met Lys
        435                 440                 445

Ala Asp Asp Thr Asn His Asp Val Ser Asn Val Lys Trp Tyr His Thr
    450                 455                 460

Asp Thr Ser Val Ser His Asp Ser Gly Asp Thr Val Cys Thr Asp His
465                 470                 475                 480

Tyr Asn Lys Lys Ala Tyr Tyr Lys Gly Asn Ala Ala Val Lys Ala Lys
                485                 490                 495

Ser Tyr Tyr Thr Thr Asp Ser Asn Ala Met Arg Gly Thr Gly Val Lys
            500                 505                 510

Ser Asn Thr Arg Ala Val Ala Lys Met Thr Asp Val Thr Ser Tyr Gly
        515                 520                 525

Ala Lys Ser Ser His Val Ser Cys Ser Ser Ser Arg Val Ala Cys
    530                 535                 540

Gly Asn Gly Ala Gly Lys Ser Thr Lys Thr Gly Val Asn Gly Lys Val
545                 550                 555                 560

Lys His Asn Arg Gly Tyr Ala His Ala His Val Asn His Lys Lys Thr
                565                 570                 575

Ala Asn Tyr Trp Arg Tyr Gly Asp Asp Arg Val Lys Ser Arg Lys Ser
            580                 585                 590

Asp Lys Met Met Thr Lys Asp Asp Gly Arg Gly Lys Arg Ala Ala
        595                 600                 605

Val Gly Arg Lys Lys Lys Ser Tyr Val Lys Trp Lys Tyr Trp Lys Lys
610                 615                 620
```

```
Tyr Asn Ser Trp Val Lys Asp Val His Gly Lys Val Lys Asp Asp
625                 630                 635                 640

His Ala Ser Arg Gly Tyr Arg Ser Val Thr Lys His Asp Val Gly
            645                 650                 655

Asp Ser Ala Asn His Thr Gly Ser Ser Gly Val Lys Val Val Ala
                660                 665                 670

Gly Ala Met Trp Asn Asn His Val Asp Thr Asn Tyr Asp Arg Asp Ser
            675                 680                 685

Gly Ala Ala Val Ala Arg Asp Trp Ser Gly Gly Val Val Met Ser His
690                 695                 700

Asn Asn Val Gly Ala Cys Trp Val Asn Gly Lys Met Val Lys Gly Ser
705                 710                 715                 720

Ala Val Asp Ser Lys Asp Gly Gly Asn Ala Asp Ala Val Gly Lys Ala
                725                 730                 735

Ser Asn Ala Lys Ser Val Asp Asp Asp Ser Ala Asn Lys Val Lys
            740                 745                 750

Arg Lys Lys Arg Thr Arg Asn Lys Lys Ala Arg Arg Arg Tyr Trp
        755                 760                 765

Ser Ser Lys Gly Thr Lys Val Asp Thr Asp Asp
    770                 775                 780

<210> SEQ ID NO 23
<211> LENGTH: 1075
<212> TYPE: PRT
<213> ORGANISM: Saccharomyces cerevisiae

<400> SEQUENCE: 23

Met Asp Asn Lys Arg Leu Tyr Asn Gly Asn Leu Ser Asn Ile Pro Glu
1               5                   10                  15

Val Ile Asp Pro Gly Ile Thr Ile Pro Ile Tyr Glu Glu Asp Ile Arg
                20                  25                  30

Asn Asp Thr Arg Met Asn Thr Asn Ala Arg Ser Val Arg Val Ser Asp
            35                  40                  45

Lys Arg Gly Arg Ser Ser Thr Ser Pro Gln Lys Ile Gly Ser Tyr
    50                  55                  60

Arg Thr Arg Ala Gly Arg Phe Ser Asp Thr Leu Thr Asn Leu Leu Pro
65                  70                  75                  80

Ser Ile Ser Ala Lys Leu His His Ser Lys Lys Ser Thr Pro Val Val
                85                  90                  95

Val Val Pro Pro Thr Ser Ser Thr Pro Asp Ser Leu Asn Ser Thr Thr
            100                 105                 110

Tyr Ala Pro Arg Val Ser Ser Asp Ser Phe Thr Val Ala Thr Pro Leu
            115                 120                 125

Ser Leu Gln Ser Thr Thr Thr Arg Thr Arg Thr Arg Asn Asn Thr Val
130                 135                 140

Ser Ser Gln Ile Thr Ala Ser Ser Ser Leu Thr Thr Asp Val Gly Asn
145                 150                 155                 160

Ala Thr Ser Ala Asn Ile Trp Ser Ala Asn Ala Glu Ser Asn Thr Ser
                165                 170                 175

Ser Ser Pro Leu Phe Asp Tyr Pro Leu Ala Thr Ser Tyr Phe Glu Pro
            180                 185                 190

Leu Thr Arg Phe Lys Ser Thr Asp Asn Tyr Thr Leu Pro Gln Thr Ala
            195                 200                 205

Gln Leu Asn Ser Phe Leu Glu Lys Asn Gly Asn Pro Asn Ile Trp Ser
210                 215                 220
```

-continued

```
Ser Ala Gly Asn Ser Asn Thr Asp His Leu Asn Thr Pro Ile Val Asn
225                 230                 235                 240

Arg Gln Arg Ser Gln Ser Gln Ser Thr Thr Asn Arg Val Tyr Thr Asp
            245                 250                 255

Ala Pro Tyr Tyr Gln Gln Pro Ala Gln Asn Tyr Gln Val Gln Val Pro
            260                 265                 270

Pro Arg Val Pro Lys Ser Thr Ser Ile Ser Pro Val Ile Leu Asp Asp
            275                 280                 285

Val Asp Pro Ala Ser Ile Asn Trp Ile Thr Ala Asn Gln Lys Val Pro
290                 295                 300

Leu Val Asn Gln Ile Ser Ala Leu Leu Pro Thr Asn Thr Ile Ser Ile
305                 310                 315                 320

Ser Asn Val Phe Pro Leu Gln Pro Thr Gln Gln His Gln Gln Asn Ala
                325                 330                 335

Val Asn Leu Thr Ser Thr Ser Leu Ala Thr Leu Cys Ser Gln Tyr Gly
                340                 345                 350

Lys Val Leu Ser Ala Arg Thr Leu Arg Gly Leu Asn Met Ala Leu Val
                355                 360                 365

Glu Phe Ser Thr Val Glu Ser Ala Ile Cys Ala Leu Glu Ala Leu Gln
370                 375                 380

Gly Lys Glu Leu Ser Lys Val Gly Ala Pro Ser Thr Val Ser Phe Ala
385                 390                 395                 400

Arg Val Leu Pro Met Tyr Glu Gln Pro Leu Asn Val Asn Gly Phe Asn
                405                 410                 415

Asn Thr Pro Lys Gln Pro Leu Leu Gln Glu Gln Leu Asn His Gly Val
                420                 425                 430

Leu Asn Tyr Gln Leu Gln Gln Ser Leu Gln Gln Pro Glu Leu Gln Gln
                435                 440                 445

Gln Pro Thr Ser Phe Asn Gln Pro Asn Leu Thr Tyr Cys Asn Pro Thr
450                 455                 460

Gln Asn Leu Ser His Leu Gln Leu Ser Ser Asn Glu Asn Glu Pro Tyr
465                 470                 475                 480

Pro Phe Pro Leu Pro Pro Ser Leu Ser Asp Ser Lys Lys Asp Ile
                485                 490                 495

Leu His Thr Ile Ser Ser Phe Lys Leu Glu Tyr Asp His Leu Glu Leu
                500                 505                 510

Asn His Leu Leu Gln Asn Ala Leu Lys Asn Lys Gly Val Ser Asp Thr
                515                 520                 525

Asn Tyr Phe Gly Pro Leu Pro Glu His Asn Ser Lys Val Pro Lys Arg
                530                 535                 540

Lys Asp Thr Phe Asp Ala Pro Lys Leu Arg Glu Leu Arg Lys Gln Phe
545                 550                 555                 560

Asp Ser Asn Ser Leu Ser Thr Ile Glu Met Glu Gln Leu Ala Ile Val
                565                 570                 575

Met Leu Asp Gln Leu Pro Glu Leu Ser Ser Asp Tyr Leu Gly Asn Thr
                580                 585                 590

Val Ile Gln Lys Leu Phe Glu Asn Ser Ser Asn Ile Ile Arg Asp Ile
                595                 600                 605

Met Leu Arg Lys Cys Asn Lys Tyr Leu Thr Ser Met Gly Val His Lys
                610                 615                 620

Asn Gly Thr Trp Val Cys Gln Lys Ile Ile Lys Met Ala Asn Thr Pro
625                 630                 635                 640
```

-continued

```
Arg Gln Ile Asn Leu Val Thr Ser Gly Val Ser Asp Tyr Cys Thr Pro
            645                 650                 655

Leu Phe Asn Asp Gln Phe Gly Asn Tyr Val Ile Gln Gly Ile Leu Lys
        660                 665                 670

Phe Gly Phe Pro Trp Asn Ser Phe Ile Phe Glu Ser Val Leu Ser His
            675                 680                 685

Phe Trp Thr Ile Val Gln Asn Arg Tyr Gly Ser Arg Ala Val Arg Ala
690                 695                 700

Cys Leu Glu Ala Asp Ser Ile Ile Thr Gln Cys Gln Leu Leu Thr Ile
705                 710                 715                 720

Thr Ser Leu Ile Ile Val Leu Ser Pro Tyr Leu Ala Thr Asp Thr Asn
                725                 730                 735

Gly Thr Leu Leu Ile Thr Trp Leu Leu Asp Thr Cys Thr Leu Pro Asn
            740                 745                 750

Lys Asn Leu Ile Leu Cys Asp Lys Leu Val Asn Lys Asn Leu Val Lys
        755                 760                 765

Leu Cys Cys His Lys Leu Gly Ser Leu Thr Val Leu Lys Ile Leu Asn
    770                 775                 780

Leu Arg Gly Gly Glu Glu Ala Leu Ser Lys Asn Lys Ile Ile His
785                 790                 795                 800

Ala Ile Phe Asp Gly Pro Ile Ser Ser Asp Ser Ile Leu Phe Gln Ile
                805                 810                 815

Leu Asp Glu Gly Asn Tyr Gly Pro Thr Phe Ile Tyr Lys Val Leu Thr
            820                 825                 830

Ser Arg Ile Leu Asp Asn Ser Val Arg Asp Glu Ala Ile Thr Lys Ile
        835                 840                 845

Arg Gln Leu Ile Leu Asn Ser Asn Ile Asn Leu Gln Ser Arg Gln Leu
    850                 855                 860

Leu Glu Glu Val Gly Leu Ser Ser Ala Gly Ile Ser Pro Lys Gln Ser
865                 870                 875                 880

Ser Lys Asn His Arg Lys Gln His Pro Gln Gly Phe His Ser Pro Gly
                885                 890                 895

Arg Ala Arg Gly Val Ser Val Ser Ser Val Arg Ser Ser Asn Ser Arg
            900                 905                 910

His Asn Ser Val Ile Gln Met Asn Asn Ala Gly Pro Thr Pro Ala Leu
        915                 920                 925

Asn Phe Asn Pro Ala Pro Met Ser Glu Ile Asn Ser Tyr Phe Asn Asn
    930                 935                 940

Gln Gln Val Val Tyr Ser Gly Asn Gln Asn Gln Asn Gly Asn
945                 950                 955                 960

Ser Asn Gly Leu Asp Glu Leu Asn Ser Gln Phe Asp Ser Phe Arg Ile
                965                 970                 975

Ala Asn Gly Thr Asn Leu Ser Leu Pro Ile Val Asn Leu Pro Asn Val
            980                 985                 990

Ser Asn Asn Asn Asn Tyr Asn Asn Ser Gly Tyr Ser Ser Gln Met
        995                 1000                1005

Asn Pro Leu Ser Arg Ser Val Ser His Asn Asn Asn Asn Thr Asn
    1010                1015                1020

Asn Tyr Asn Asn Asn Asp Asn Asp Asn Asn Asn Asn Asn Asn Asn
1025                1030                1035                1040

Asn Asn Asn Asn Asn Asn Asn Asn Asn Asn Asn Ser Asn Asn
                1045                1050                1055
```

```
Ser Asn Asn Asn  Asn Asn Asn Asp Thr Ser Leu Tyr Arg Tyr Arg Ser
            1060            1065                1070

Tyr Gly Tyr
        1075

<210> SEQ ID NO 24
<211> LENGTH: 76
<212> TYPE: PRT
<213> ORGANISM: Saccharomyces cerevisiae

<400> SEQUENCE: 24

Met Ser Ala Asn Asp Tyr Tyr Gly Gly Thr Ala Gly Lys Ser Tyr Ser
1               5                   10                  15

Arg Ser Asn Ser Ser Ala His Asn Lys Thr Arg Gly Tyr Tyr Tyr His
            20                  25                  30

Gly Tyr Tyr Asn Gly Tyr Asn Gly Tyr Asn Gly Tyr Asn Gly Tyr Asn
        35                  40                  45

Gly Tyr Asn Gly Tyr Asn Gly His Val Tyr Val Arg Gly Asn Gly Cys
    50                  55                  60

Ala Ala Cys Ala Ala Cys Cys Cys Thr Met Asp Met
65                  70                  75

<210> SEQ ID NO 25
<211> LENGTH: 380
<212> TYPE: PRT
<213> ORGANISM: Saccharomyces cerevisiae

<400> SEQUENCE: 25

Met Ser Ser Asp Asp Asn Asp Tyr Gly Asp Asp Lys Thr Thr Thr Val
1               5                   10                  15

Lys Lys Asn Lys Ala Gly Ser Gly Thr Ser Asp Ala Ala Ser Ser
            20                  25                  30

Ser Asn Lys Asn Asn Ser Asn Asn Ser Ser Asn Asn Ser Asn
        35                  40                  45

Asp Thr Ser Ser Lys Asp Gly Thr Ala Asn Asp Lys Gly Ser Asn
    50                  55                  60

Asp Thr Lys Asn Lys Lys Ser Ala Thr Ser Ala Asn Ala Asn Ala Asn
65                  70                  75                  80

Ala Ser Ser Ala Gly Ser Gly Trp Thr Met Ser Ser Ser Val Thr
            85                  90                  95

Thr Lys Arg Ser Lys Ala Asp Ser Lys Ser Cys Lys Met Gly Gly Asn
        100                 105                 110

Trp Asp Thr Thr Asp Asn Arg Tyr Gly Lys Tyr Gly Thr Val Thr Asp
    115                 120                 125

Lys Met Lys Asp Ala Thr Gly Arg Ser Arg Gly Gly Ser Lys Ser Ser
    130                 135                 140

Val Asp Val Val Lys Thr His Asp Gly Lys Val Asp Lys Arg Ala Arg
145                 150                 155                 160

Asp Asp Lys Thr Gly Lys Val Gly Gly Asp Val Arg Lys Ser Trp
            165                 170                 175

Gly Thr Asp Ala Met Asp Lys Asp Thr Gly Ser Arg Gly Val Thr
        180                 185                 190

Tyr Asp Ser Ala Asp Ala Val Asp Arg Val Cys Asn Lys Asp Lys Asp
    195                 200                 205

Arg Lys Lys Arg Ala Arg His Met Lys Ser Ser Asn Asn Gly Gly Asn
    210                 215                 220
```

```
Asn Gly Gly Asn Asn Met Asn Arg Arg Gly Gly Asn Gly Asn Gly Asp
225                 230                 235                 240

Asn Met Tyr Asn Met Met Gly Gly Tyr Asn Met Met Asn Ala Met Thr
            245                 250                 255

Asp Tyr Tyr Lys Met Tyr Tyr Met Lys Thr Gly Met Asp Tyr Thr Met
            260                 265                 270

Tyr Met Met Ala Met Met Met Gly Ala Met Asn Ala Met Thr Asn Asp
        275                 280                 285

Ser Asn Ala Thr Gly Ser Ala Ser Asp Ser Asp Asn Asn Lys Ser Asn
    290                 295                 300

Asp Val Thr Gly Asn Thr Ser Asn Thr Asp Ser Gly Ser Asn Asn Gly
305                 310                 315                 320

Lys Gly Ser Tyr Asn Asp Asp His Asn Ser Gly Tyr Gly Tyr Asn Arg
                325                 330                 335

Asp Arg Gly Asp Arg Asp Arg Asn Asp Arg Asp Arg Asp Tyr Asn His
                340                 345                 350

Arg Ser Gly Gly Asn His Arg Arg Asn Gly Arg Gly Gly Arg Gly Gly
            355                 360                 365

Tyr Asn Arg Arg Asn Asn Gly Tyr His Tyr Asn Arg
            370                 375                 380

<210> SEQ ID NO 26
<211> LENGTH: 256
<212> TYPE: PRT
<213> ORGANISM: Saccharomyces cerevisiae

<400> SEQUENCE: 26

Met Ser Ala Thr His Val Ser Val Val Asp Ala Val His Ala Asp Ala
1               5                   10                  15

Val Ser Ala Ser Ala Ala Asn Asp Val Ser Asn Ala Tyr Gly Ser His
            20                  25                  30

Ser Val Asp Tyr Ala His His His Tyr Tyr Gly His Met His Gly Arg
        35                  40                  45

Met His His Arg Gly Ser Asn Thr Arg Val Arg Asp Val Ser Asn Gly
    50                  55                  60

Gly Met Lys Val Lys Asn Gly Ala Val Ala Ser Ala Ala Lys Ala Val
65                  70                  75                  80

His Gly Lys Ser Ala Asn Val Val Tyr Ser Lys Ala Lys Arg Tyr Arg
                85                  90                  95

Thr Met Lys Asn Gly Cys Ser Trp Asp Lys Asp Ala Arg Asn Ser Thr
            100                 105                 110

Thr Ser Ser Val Asn Thr Arg Asp Asp Gly Thr Gly Ala Ser Val Ala
        115                 120                 125

Arg Asn Asn Arg Gly Ser Val Thr Val Arg Asp Asp Asn Arg Arg Ser
    130                 135                 140

Asn Arg Gly Gly Arg Gly Arg Gly Gly Arg Gly Arg Gly Gly Gly Arg
145                 150                 155                 160

Gly Gly Ser Arg Gly Gly Gly Arg Gly Gly Gly Arg Gly Gly Arg Gly
                165                 170                 175

Tyr Gly Gly Tyr Ser Arg Gly Gly Tyr Gly Gly Tyr Ser Arg Gly Gly
            180                 185                 190

Tyr Gly Gly Ser Arg Gly Gly Tyr Asp Ser Arg Gly Gly Tyr Asp Ser
        195                 200                 205

Arg Gly Gly Tyr Ser Arg Gly Gly Tyr Gly Gly Arg Asn Asp Tyr Gly
    210                 215                 220
```

```
Arg Gly Ser Tyr Gly Gly Ser Arg Gly Gly Tyr Asp Gly Arg Gly Asp
225                 230                 235                 240

Tyr Gly Arg Asp Ala Tyr Arg Thr Arg Asp Ala Arg Arg Ser Thr Arg
            245                 250                 255
```

<210> SEQ ID NO 27
<211> LENGTH: 286
<212> TYPE: PRT
<213> ORGANISM: Saccharomyces cerevisiae

<400> SEQUENCE: 27

```
Met Ser Asp Ile Glu Glu Gly Thr Pro Thr Asn Asn Gly Gln Gln Lys
1               5                   10                  15

Glu Arg Arg Lys Ile Glu Ile Lys Phe Ile Glu Asn Lys Thr Arg Arg
                20                  25                  30

His Val Thr Phe Ser Lys Arg Lys His Gly Ile Met Lys Lys Ala Phe
            35                  40                  45

Glu Leu Ser Val Leu Thr Gly Thr Gln Val Leu Leu Leu Val Val Ser
    50                  55                  60

Glu Thr Gly Leu Val Tyr Thr Phe Ser Thr Pro Lys Phe Glu Pro Ile
65                  70                  75                  80

Val Thr Gln Gln Glu Gly Arg Asn Leu Ile Gln Ala Cys Leu Asn Ala
                85                  90                  95

Pro Asp Asp Glu Glu Asp Glu Glu Asp Gly Asp Asp Asp Asp
            100                 105                 110

Asp Asp Asp Asp Asp Gly Asn Asp Met Gln Arg Gln Gln Pro Gln Gln
            115                 120                 125

Gln Gln Pro Gln Gln Gln Gln Val Leu Asn Ala His Ala Asn Ser
    130                 135                 140

Leu Gly His Leu Asn Gln Asp Gln Val Pro Ala Gly Ala Leu Lys Gln
145                 150                 155                 160

Glu Val Lys Ser Gln Leu Leu Gly Gly Ala Asn Pro Asn Gln Asn Ser
                165                 170                 175

Met Ile Gln Gln Gln Gln His His Thr Gln Asn Ser Gln Pro Gln Gln
            180                 185                 190

Gln Gln Gln Gln Pro Gln Gln Gln Met Ser Gln Gln Gln Met Ser
    195                 200                 205

Gln His Pro Arg Pro Gln Gln Gly Ile Pro His Pro Gln Gln Ser Gln
            210                 215                 220

Pro Gln Gln Gln Gln Gln Gln Gln Leu Gln Gln Gln Gln Gln
225                 230                 235                 240

Gln Gln Gln Gln Gln Pro Leu Thr Gly Ile His Gln Pro His Gln Gln
                245                 250                 255

Ala Phe Ala Asn Ala Ala Ser Pro Tyr Leu Asn Ala Glu Gln Asn Ala
            260                 265                 270

Ala Tyr Gln Gln Tyr Phe Gln Glu Pro Gln Gln Gly Gln Tyr
    275                 280                 285
```

<210> SEQ ID NO 28
<211> LENGTH: 414
<212> TYPE: PRT
<213> ORGANISM: Saccharomyces cerevisiae

<400> SEQUENCE: 28

```
Met Ala Lys Thr Thr Lys Val Lys Gly Asn Lys Lys Glu Val Lys Ala
1               5                   10                  15
```

```
Ser Lys Gln Ala Lys Glu Glu Lys Ala Lys Val Ser Ser Ser Ser
                20                  25                  30

Ser Glu Ser Ser Ser Ser Ser Ser Ser Glu Ser Glu Ser Glu
            35                  40                  45

Ser Glu Ser Glu Ser Glu Ser Ser Ser Ser Ser Ser Asp Ser
    50                  55                  60

Glu Ser Ser Ser Ser Ser Ser Asp Ser Glu Ser Glu Ala Glu Thr
65                  70                  75                  80

Lys Lys Glu Glu Ser Lys Asp Ser Ser Ser Ser Ser Asp Ser Ser
                85                  90                  95

Ser Asp Glu Glu Glu Glu Glu Glu Lys Glu Glu Thr Lys Lys Glu Glu
                100                 105                 110

Ser Lys Glu Ser Ser Ser Ser Asp Ser Ser Ser Ser Ser Ser Asp
            115                 120                 125

Ser Glu Ser Glu Lys Glu Glu Ser Asn Asp Lys Lys Arg Lys Ser Glu
            130                 135                 140

Asp Ala Glu Glu Glu Glu Asp Glu Glu Ser Ser Asn Lys Lys Gln Lys
145                 150                 155                 160

Asn Glu Glu Thr Glu Glu Pro Ala Thr Ile Phe Val Gly Arg Leu Ser
                165                 170                 175

Trp Ser Ile Asp Asp Glu Trp Leu Lys Lys Glu Phe Glu His Ile Gly
            180                 185                 190

Gly Val Ile Gly Ala Arg Val Ile Tyr Glu Arg Gly Thr Asp Arg Ser
            195                 200                 205

Arg Gly Tyr Gly Tyr Val Asp Phe Glu Asn Lys Ser Tyr Ala Glu Lys
        210                 215                 220

Ala Ile Gln Glu Met Gln Gly Lys Glu Ile Asp Gly Arg Pro Ile Asn
225                 230                 235                 240

Cys Asp Met Ser Thr Ser Lys Pro Ala Gly Asn Asn Asp Arg Ala Lys
                245                 250                 255

Lys Phe Gly Asp Thr Pro Ser Glu Pro Ser Asp Thr Leu Phe Leu Gly
            260                 265                 270

Asn Leu Ser Phe Asn Ala Asp Arg Asp Ala Ile Phe Glu Leu Phe Ala
        275                 280                 285

Lys His Gly Glu Val Val Ser Val Arg Ile Pro Thr His Pro Glu Thr
    290                 295                 300

Glu Gln Pro Lys Gly Phe Gly Tyr Val Gln Phe Ser Asn Met Glu Asp
305                 310                 315                 320

Ala Lys Lys Ala Leu Asp Ala Leu Gln Gly Glu Tyr Ile Asp Asn Arg
                325                 330                 335

Pro Val Arg Leu Asp Phe Ser Ser Pro Arg Pro Asn Asn Asp Gly Gly
            340                 345                 350

Arg Gly Gly Ser Arg Gly Phe Gly Gly Arg Gly Gly Arg Gly Gly
            355                 360                 365

Asn Arg Gly Phe Gly Gly Arg Gly Gly Ala Arg Gly Gly Arg Gly Gly
    370                 375                 380

Phe Arg Pro Ser Gly Ser Gly Ala Asn Thr Ala Pro Leu Gly Arg Ser
385                 390                 395                 400

Arg Asn Thr Ala Ser Phe Ala Gly Ser Lys Lys Thr Phe Asp
                405                 410

<210> SEQ ID NO 29
<211> LENGTH: 405
```

```
<212> TYPE: PRT
<213> ORGANISM: Saccharomyces cerevisiae

<400> SEQUENCE: 29

Met Asp Thr Asp Lys Leu Ile Ser Glu Ala Glu Ser His Phe Ser Gln
1               5                   10                  15

Gly Asn His Ala Glu Ala Val Ala Lys Leu Thr Ser Ala Ala Gln Ser
            20                  25                  30

Asn Pro Asn Asp Glu Gln Met Ser Thr Ile Glu Ser Leu Ile Gln Lys
        35                  40                  45

Ile Ala Gly Tyr Val Met Asp Asn Arg Ser Gly Gly Ser Asp Ala Ser
50                  55                  60

Gln Asp Arg Ala Ala Gly Gly Ser Ser Phe Met Asn Thr Leu Met
65                  70                  75                  80

Ala Asp Ser Lys Gly Ser Ser Gln Thr Gln Leu Gly Lys Leu Ala Leu
                85                  90                  95

Leu Ala Thr Val Met Thr His Ser Ser Asn Lys Gly Ser Ser Asn Arg
            100                 105                 110

Gly Phe Asp Val Gly Thr Val Met Ser Met Leu Ser Gly Ser Gly Gly
        115                 120                 125

Gly Ser Gln Ser Met Gly Ala Ser Gly Leu Ala Ala Leu Ala Ser Gln
    130                 135                 140

Phe Phe Lys Ser Gly Asn Asn Ser Gln Gly Gln Gly Gln Gly Gln Gly
145                 150                 155                 160

Gln Gly Gln Gly Gln Gly Gln Gly Gln Gly Gln Gly Ser Phe Thr Ala
                165                 170                 175

Leu Ala Ser Leu Ala Ser Ser Phe Met Asn Ser Asn Asn Asn Asn Gln
            180                 185                 190

Gln Gly Gln Asn Gln Ser Ser Gly Gly Ser Ser Phe Gly Ala Leu Ala
        195                 200                 205

Ser Met Ala Ser Ser Phe Met His Ser Asn Asn Asn Gln Asn Ser Asn
    210                 215                 220

Asn Ser Gln Gln Gly Tyr Asn Gln Ser Tyr Gln Asn Gly Asn Gln Asn
225                 230                 235                 240

Ser Gln Gly Tyr Asn Asn Gln Gln Tyr Gln Gly Gly Asn Gly Gly Tyr
                245                 250                 255

Gln Gln Gln Gln Gly Gln Ser Gly Gly Ala Phe Ser Ser Leu Ala Ser
            260                 265                 270

Met Ala Gln Ser Tyr Leu Gly Gly Gly Gln Thr Gln Ser Asn Gln Gln
        275                 280                 285

Gln Tyr Asn Gln Gln Gly Gln Asn Asn Gln Gln Tyr Gln Gln Gln
    290                 295                 300

Gly Gln Asn Tyr Gln His Gln Gln Gly Gln Gln Gln Gln Gly
305                 310                 315                 320

His Ser Ser Ser Phe Ser Ala Leu Ala Ser Met Ala Ser Ser Tyr Leu
                325                 330                 335

Gly Asn Asn Ser Asn Ser Asn Ser Ser Tyr Gly Gly Gln Gln Gln Ala
            340                 345                 350

Asn Glu Tyr Gly Arg Pro Gln His Asn Gly Gln Gln Ser Asn Glu
        355                 360                 365

Tyr Gly Arg Pro Gln Tyr Gly Gly Asn Gln Asn Ser Asn Gly Gln His
    370                 375                 380

Glu Ser Phe Asn Phe Ser Gly Asn Phe Ser Gln Gln Asn Asn Asn Gly
385                 390                 395                 400
```

Asn Gln Asn Arg Tyr
                405

<210> SEQ ID NO 30
<211> LENGTH: 964
<212> TYPE: PRT
<213> ORGANISM: Saccharomyces cerevisiae

<400> SEQUENCE: 30

Met Pro Glu Gln Ala Gln Gln Gly Glu Gln Ser Val Lys Arg Arg
1               5                   10                  15

Val Thr Arg Ala Cys Asp Glu Cys Arg Lys Lys Val Lys Cys Asp
                20                  25                  30

Gly Gln Gln Pro Cys Ile His Cys Thr Val Tyr Ser Tyr Glu Cys Thr
                35                  40                  45

Tyr Lys Lys Pro Thr Lys Arg Thr Gln Asn Ser Gly Asn Ser Gly Val
            50                  55                  60

Leu Thr Leu Gly Asn Val Thr Thr Gly Pro Ser Ser Thr Val Val
65              70                  75                  80

Ala Ala Ala Ala Ser Asn Pro Asn Lys Leu Leu Ser Asn Ile Lys Thr
                85                  90                  95

Glu Arg Ala Ile Leu Pro Gly Ala Ser Thr Ile Pro Ala Ser Asn Asn
                100                 105                 110

Pro Ser Lys Pro Arg Lys Tyr Lys Thr Lys Ser Thr Arg Leu Gln Ser
            115                 120                 125

Lys Ile Asp Arg Tyr Lys Gln Ile Phe Asp Glu Val Phe Pro Gln Leu
    130                 135                 140

Pro Asp Ile Asp Asn Leu Asp Ile Pro Val Phe Leu Gln Ile Phe His
145                 150                 155                 160

Asn Phe Lys Arg Asp Ser Gln Ser Phe Leu Asp Asp Thr Val Lys Glu
                165                 170                 175

Tyr Thr Leu Ile Val Asn Asp Ser Ser Ser Pro Ile Gln Pro Val Leu
            180                 185                 190

Ser Ser Asn Ser Lys Asn Ser Thr Pro Asp Glu Phe Leu Pro Asn Met
    195                 200                 205

Lys Ser Asp Ser Asn Ser Ala Ser Ser Asn Arg Glu Gln Asp Ser Val
210                 215                 220

Asp Thr Tyr Ser Asn Ile Pro Val Gly Arg Glu Ile Lys Ile Leu
225                 230                 235                 240

Pro Pro Lys Ala Ile Ala Leu Gln Phe Val Lys Ser Thr Trp Glu His
                245                 250                 255

Cys Cys Val Leu Leu Arg Phe Tyr His Arg Pro Ser Phe Ile Arg Gln
            260                 265                 270

Leu Asp Glu Leu Tyr Glu Thr Asp Pro Asn Asn Tyr Thr Ser Lys Gln
    275                 280                 285

Met Gln Phe Leu Pro Leu Cys Tyr Ala Ala Ile Ala Val Gly Ala Leu
290                 295                 300

Phe Ser Lys Ser Ile Val Ser Asn Asp Ser Ser Arg Glu Lys Phe Leu
305                 310                 315                 320

Gln Asp Glu Gly Tyr Lys Tyr Phe Ile Ala Ala Arg Lys Leu Ile Asp
                325                 330                 335

Ile Thr Asn Ala Arg Asp Leu Asn Ser Ile Gln Ala Ile Leu Met Leu
            340                 345                 350

-continued

```
Ile Ile Phe Leu Gln Cys Ser Ala Arg Leu Ser Thr Cys Tyr Thr Tyr
        355                 360                 365

Ile Gly Val Ala Met Arg Ser Ala Leu Arg Ala Gly Phe His Arg Lys
        370                 375                 380

Leu Ser Pro Asn Ser Gly Phe Ser Pro Ile Glu Ile Glu Met Arg Lys
385                 390                 395                 400

Arg Leu Phe Tyr Thr Ile Tyr Lys Leu Asp Val Tyr Ile Asn Ala Met
                405                 410                 415

Leu Gly Leu Pro Arg Ser Ile Ser Pro Asp Phe Asp Gln Thr Leu
                420                 425                 430

Pro Leu Asp Leu Ser Asp Glu Asn Ile Thr Glu Val Ala Tyr Leu Pro
                435                 440                 445

Glu Asn Gln His Ser Val Leu Ser Ser Thr Gly Ile Ser Asn Glu His
        450                 455                 460

Thr Lys Leu Phe Leu Ile Leu Asn Glu Ile Ile Ser Glu Leu Tyr Pro
465                 470                 475                 480

Ile Lys Lys Thr Ser Asn Ile Ile Ser His Glu Thr Val Thr Ser Leu
                485                 490                 495

Glu Leu Lys Leu Arg Asn Trp Leu Asp Ser Leu Pro Lys Glu Leu Ile
                500                 505                 510

Pro Asn Ala Glu Asn Ile Asp Pro Glu Tyr Glu Arg Ala Asn Arg Leu
        515                 520                 525

Leu His Leu Ser Phe Leu His Val Gln Ile Ile Leu Tyr Arg Pro Phe
        530                 535                 540

Ile His Tyr Leu Ser Arg Asn Met Asn Ala Glu Asn Val Asp Pro Leu
545                 550                 555                 560

Cys Tyr Arg Arg Ala Arg Asn Ser Ile Ala Val Ala Arg Thr Val Ile
                565                 570                 575

Lys Leu Ala Lys Glu Met Val Ser Asn Asn Leu Leu Thr Gly Ser Tyr
                580                 585                 590

Trp Tyr Ala Cys Tyr Thr Ile Phe Tyr Ser Val Ala Gly Leu Leu Phe
        595                 600                 605

Tyr Ile His Glu Ala Gln Leu Pro Asp Lys Asp Ser Ala Arg Glu Tyr
        610                 615                 620

Tyr Asp Ile Leu Lys Asp Ala Glu Thr Gly Arg Ser Val Leu Ile Gln
625                 630                 635                 640

Leu Lys Asp Ser Ser Met Ala Ala Ser Arg Thr Tyr Asn Leu Leu Asn
                645                 650                 655

Gln Ile Phe Glu Lys Leu Asn Ser Lys Thr Ile Gln Leu Thr Ala Leu
                660                 665                 670

His Ser Ser Pro Ser Asn Glu Ser Ala Phe Leu Val Thr Asn Asn Ser
        675                 680                 685

Ser Ala Leu Lys Pro His Leu Gly Asp Ser Leu Gln Pro Pro Val Phe
        690                 695                 700

Phe Ser Ser Gln Asp Thr Lys Asn Ser Phe Ser Leu Ala Lys Ser Glu
705                 710                 715                 720

Glu Ser Thr Asn Asp Tyr Ala Met Ala Asn Tyr Leu Asn Asn Thr Pro
                725                 730                 735

Ile Ser Glu Asn Pro Leu Asn Glu Ala Gln Gln Asp Gln Val Ser
                740                 745                 750

Gln Gly Thr Thr Asn Met Ser Asn Glu Arg Asp Pro Asn Asn Phe Leu
        755                 760                 765
```

Ser Ile Asp Ile Arg Leu Asp Asn Asn Gly Gln Ser Asn Ile Leu Asp
770                 775                 780

Ala Thr Asp Asp Val Phe Ile Arg Asn Asp Gly Asp Ile Pro Thr Asn
785                 790                 795                 800

Ser Ala Phe Asp Phe Ser Ser Lys Ser Asn Ala Ser Asn Asn Ser
            805                 810                 815

Asn Pro Asp Thr Ile Asn Asn Asn Tyr Asn Asn Val Ser Gly Lys Asn
        820                 825                 830

Asn Asn Asn Asn Asn Ile Thr Asn Asn Ser Asn Asn His Asn Asn
    835                 840                 845

Asn Asn Asn Asp Asn Asn Asn Asn Asn Asn Asn Asn Asn Asn Asn
850                 855                 860

Asn Asn Asn Asn Asn Ser Gly Asn Ser Ser Asn Asn Asn Asn Asn
865                 870                 875                 880

Asn Asn Asn Lys Asn Asn Asn Asp Phe Gly Ile Lys Ile Asp Asn Asn
            885                 890                 895

Ser Pro Ser Tyr Glu Gly Phe Pro Gln Leu Gln Ile Pro Leu Ser Gln
            900                 905                 910

Asp Asn Leu Asn Ile Glu Asp Lys Glu Glu Met Ser Pro Asn Ile Glu
            915                 920                 925

Ile Lys Asn Glu Gln Asn Met Thr Asp Ser Asn Asp Ile Leu Gly Val
        930                 935                 940

Phe Asp Gln Leu Asp Ala Gln Leu Phe Gly Lys Tyr Leu Pro Leu Asn
945                 950                 955                 960

Tyr Pro Ser Glu

<210> SEQ ID NO 31
<211> LENGTH: 758
<212> TYPE: PRT
<213> ORGANISM: Saccharomyces cerevisiae

<400> SEQUENCE: 31

Met Asp Asn Thr Thr Asn Ile Asn Thr Asn Glu Arg Ser Ser Asn Thr
1               5                   10                  15

Asp Phe Ser Ser Ala Pro Asn Ile Lys Gly Leu Asn Ser His Thr Gln
            20                  25                  30

Leu Gln Phe Asp Ala Asp Ser Arg Val Phe Val Ser Asp Val Met Ala
        35                  40                  45

Lys Asn Ser Lys Gln Leu Leu Tyr Ala His Ile Tyr Asn Tyr Leu Ile
50                  55                  60

Lys Asn Asn Tyr Trp Asn Ser Ala Ala Lys Phe Leu Ser Glu Ala Asp
65                  70                  75                  80

Leu Pro Leu Ser Arg Ile Asn Gly Ser Ala Ser Gly Gly Lys Thr Ser
            85                  90                  95

Leu Asn Ala Ser Leu Lys Gln Gly Leu Met Asp Ile Ala Ser Lys Gly
        100                 105                 110

Asp Ile Val Ser Glu Asp Gly Leu Leu Pro Ser Lys Met Leu Met Asp
    115                 120                 125

Ala Asn Asp Thr Phe Leu Leu Glu Trp Trp Glu Ile Phe Gln Ser Leu
130                 135                 140

Phe Asn Gly Asp Leu Glu Ser Gly Tyr Gln Gln Asp His Asn Pro Leu
145                 150                 155                 160

Arg Glu Arg Ile Ile Pro Ile Leu Pro Ala Asn Ser Lys Ser Asn Met
            165                 170                 175

-continued

```
Pro Ser His Phe Ser Asn Leu Pro Pro Asn Val Ile Pro Pro Thr Gln
            180                 185                 190

Asn Ser Phe Pro Val Ser Glu Glu Ser Phe Arg Pro Asn Gly Asp Gly
            195                 200                 205

Ser Asn Phe Asn Leu Asn Asp Pro Thr Asn Arg Asn Val Ser Glu Arg
210                 215                 220

Phe Leu Ser Arg Thr Ser Gly Val Tyr Asp Lys Gln Asn Ser Ala Asn
225                 230                 235                 240

Phe Ala Pro Asp Thr Ala Ile Asn Ser Asp Ile Ala Gly Gln Gln Tyr
                245                 250                 255

Ala Thr Ile Asn Leu His Lys His Phe Asn Asp Leu Gln Ser Pro Ala
            260                 265                 270

Gln Pro Gln Gln Ser Ser Gln Gln Ile Gln Gln Pro Gln His Gln
            275                 280                 285

Pro Gln His Gln Pro Gln Gln Gln Gln Gln Gln Gln Gln Gln Gln
290                 295                 300

Gln Gln Gln Gln Gln Gln Gln Gln Gln Gln Gln Gln Gln Gln Gln Gln
305                 310                 315                 320

Gln Gln Gln His Gln Gln Gln Gln Thr Pro Tyr Pro Ile Val Asn
                325                 330                 335

Pro Gln Met Val Pro His Ile Pro Ser Glu Asn Ser His Ser Thr Gly
            340                 345                 350

Leu Met Pro Ser Val Pro Pro Thr Asn Gln Gln Phe Asn Ala Gln Thr
            355                 360                 365

Gln Ser Ser Met Phe Ser Asp Gln Gln Arg Phe Phe Gln Tyr Gln Leu
            370                 375                 380

His His Gln Asn Gln Gly Gln Ala Pro Ser Phe Gln Gln Ser Gln Ser
385                 390                 395                 400

Gly Arg Phe Asp Asp Met Asn Ala Met Lys Met Phe Phe Gln Gln Gln
                405                 410                 415

Ala Leu Gln Gln Asn Ser Leu Gln Gln Asn Leu Gly Asn Gln Asn Tyr
            420                 425                 430

Gln Ser Asn Thr Arg Asn Asn Thr Ala Glu Thr Thr Pro Thr Asn
            435                 440                 445

Asp Asn Asn Ala Asn Gly Asn Ser Leu Leu Gln Glu His Ile Arg Ala
450                 455                 460

Arg Phe Asn Lys Met Lys Thr Ile Pro Gln Gln Met Lys Asn Gln Ser
465                 470                 475                 480

Thr Val Ala Asn Pro Val Val Ser Asp Ile Thr Ser Gln Gln Gln Tyr
                485                 490                 495

Met His Met Met Met Gln Arg Met Ala Ala Asn Gln Gln Leu Gln Asn
            500                 505                 510

Ser Ala Phe Pro Pro Asp Thr Asn Arg Ile Ala Pro Ala Asn Asn Thr
            515                 520                 525

Met Pro Leu Gln Pro Gly Asn Met Gly Ser Pro Val Ile Glu Asn Pro
            530                 535                 540

Gly Met Arg Gln Thr Asn Pro Ser Gly Gln Asn Pro Met Ile Asn Met
545                 550                 555                 560

Gln Pro Leu Tyr Gln Asn Val Ser Ser Ala Met His Ala Phe Ala Pro
                565                 570                 575

Gln Gln Gln Phe His Leu Pro Gln His Tyr Lys Thr Asn Thr Ser Val
            580                 585                 590
```

-continued

```
Pro Gln Asn Asp Ser Thr Ser Val Phe Pro Leu Pro Asn Asn Asn
            595                 600                 605

Asn Asn Asn Asn Asn Asn Asn Asn Asn Asn Asn Ser Asn Asn
610                 615                 620

Ser Asn Asn Asn Asn Asn Asn Asn Asn Asn Asn Ser Asn Asn
625                 630                 635                 640

Thr Pro Thr Val Ser Gln Pro Ser Ser Lys Cys Thr Ser Ser Ser
                645                 650                 655

Thr Thr Pro Asn Ile Thr Thr Ile Gln Pro Lys Arg Lys Gln Arg
            660                 665                 670

Val Gly Lys Thr Lys Thr Lys Glu Ser Arg Lys Val Ala Ala Gln
            675                 680                 685

Lys Val Met Lys Ser Lys Lys Leu Glu Gln Asn Gly Asp Ser Ala Ala
            690                 695                 700

Thr Asn Phe Ile Asn Val Thr Pro Lys Asp Ser Gly Gly Lys Gly Thr
705                 710                 715                 720

Val Lys Val Gln Asn Ser Asn Ser Gln Gln Gln Leu Asn Gly Ser Phe
                725                 730                 735

Ser Met Asp Thr Glu Thr Phe Asp Ile Phe Asn Ile Gly Asp Phe Ser
            740                 745                 750

Pro Asp Leu Met Asp Ser
        755
```

<210> SEQ ID NO 32
<211> LENGTH: 750
<212> TYPE: PRT
<213> ORGANISM: Saccharomyces cerevisiae

<400> SEQUENCE: 32

```
Met Thr Ser Val Asn Arg Ser Asn Asn Thr Arg Ser Met Ser Ala Ser
1               5                   10                  15

Arg Ser Ala Thr Ser Arg Val Arg Asn Thr Thr Ala Asn Ser Ser Asp
            20                  25                  30

Val Asn Ser Ser Lys Arg Asn Ser Asn Ser Val Tyr Asp Asp Asn Ser
        35                  40                  45

Ser Lys Arg Arg Ser Arg Arg Ser Asp Gly Lys Asn Asn Asp His Thr
    50                  55                  60

Tyr Arg Thr Thr Val Lys Ser Lys Asn Ser Arg Tyr Val Ser Ser Ser
65                  70                  75                  80

Lys Arg Ala Lys Arg Asn Ser Val Gly Thr Ser Ser Ala Ser Lys Ser
                85                  90                  95

Ser Asn Gly Gly Ser Ala His Lys Trp Ser Asn Met Lys Asn Val Ser
            100                 105                 110

Asn Ser Ala Val Asp Ala Gly Ser Asp Ser Lys Ser Val Gly Gly Arg
        115                 120                 125

Lys Ser Asn Asn Ser Asn Asp Lys Asp Asn Ser Ala Arg Asp Asp Asn
    130                 135                 140

Asn Ser Gly Asn Asn Asn Asn Asn His Ser Ser Asn Asn Asn
145                 150                 155                 160

Asp Asn Asn Asn Asn Asn Asp Asp Asn Asn Asn Asn Asn Ser
                165                 170                 175

Asn Ser Arg Asp Asn Asn Asn Ser Asp Asp Ser Asn Arg Asn Asp
            180                 185                 190

Ser Cys Lys Ala Ser Asn Lys Arg Ser Gly Ala Lys Tyr Lys Val Val
        195                 200                 205
```

-continued

```
Lys Arg Cys Ser Thr Asn Ser Thr Thr Lys Ser Trp Thr Tyr Lys Asn
    210                 215                 220
Thr Asp Val Asn Asn Tyr Val Thr Thr Ala Ser His Asp Val Gly
225                 230                 235                 240
Val Tyr Arg Arg Arg Trp Val Tyr Gly Thr Thr Asp Val Lys Asn Ser
                245                 250                 255
Asn Met Asp Val Cys Cys Thr His Val Val Ser Ser Thr Met Ser Asp
            260                 265                 270
Ser Lys Tyr Ser Thr Trp Arg Gly Asp Ser Arg Met Ala Ala Tyr Ser
        275                 280                 285
Ser Asp Trp Lys Ser Ala His Trp Tyr Thr Ala Met Lys Tyr Tyr Asn
    290                 295                 300
His Gly Lys Tyr Tyr His Met Ser Thr Val Asn Thr Ala Val Asn Gly
305                 310                 315                 320
Lys Ser Val Cys Thr Thr Ser Tyr Met Val Asp Asn Tyr Arg Ala Val
                325                 330                 335
Arg Asn Asn Gly Asn Arg Asn Ser Tyr Lys His Ser Ala Met Ser Ser
            340                 345                 350
Asp Asn Val Val Ser Tyr Lys Gly Asp Ala Asn Gly Cys Asn Asn Ala
        355                 360                 365
Asp Met Val Asn Asp Lys Tyr Arg His Gly Ser Ala Ser His Val Gly
    370                 375                 380
Gly Lys Asn Ala Lys Tyr Lys Arg Lys Asp Lys Lys Arg Lys Lys Ser
385                 390                 395                 400
Ser Asn Asn Asp Ser Ser Val Thr Ser Ser Thr Gly Asn Ser Arg Asn
                405                 410                 415
Asp Asn Asp Asp Asp Met Ser Ser Thr Thr Ser Ser Asp His Asp Ala
            420                 425                 430
Asn Asp Asp Thr Arg Arg Ser Met Thr Asn Ala Trp Thr Lys Asn Met
        435                 440                 445
Thr Ser Lys Cys Gly Val Arg Lys His Gly Gly Ala His Trp Tyr Ser
    450                 455                 460
Cys Lys Ser Ser Ser Asp Val Ser Lys Trp Met Val Lys Arg Ala Trp
465                 470                 475                 480
Asp Thr Met Val Thr Met Asn Val Val Tyr Asp Asn Thr Ser Asn Ser
                485                 490                 495
Gly Asp Cys Asp Asp Tyr Asp Lys Ser Ser Asn Gly Gly Cys Trp Gly
            500                 505                 510
Thr Trp Asp Thr Cys Lys Asn Thr His Ser Ser Ser Asp Asn Gly Lys
        515                 520                 525
Asp Tyr Met Ala Asp Ser Thr Asp Gly Asp Lys Asp Asn Gly Lys Trp
    530                 535                 540
Lys Arg Ala Cys Arg Thr Arg Ser Arg Ser Gly Val Arg Asn Asp Tyr
545                 550                 555                 560
Arg Ser Ser Asn Thr Asn Gly Ser Val Lys Cys Asn His Asn Asn Val
                565                 570                 575
Gly Ala Ser Asp Ser Ala Arg Ser Asn Asn Thr Asp His Ala Val Ser
            580                 585                 590
Val Asn Gly Asp Asn His Tyr Val Gly Tyr Lys Lys Arg Ala Asp Tyr
        595                 600                 605
Thr Cys Asp Lys Asn Gly Ser Ala Ser Tyr Thr Thr Trp Tyr Val Asn
    610                 615                 620
```

```
Ser Asn Asn Thr Asn Asp Asn Tyr Asn Ser Lys Asn Gly Cys Lys
625                 630                 635                 640

Ser Asp Tyr Asp Lys Thr Thr Tyr Val Asp Ala Ser Trp Arg His
            645                 650                 655

Ser Ala Arg Lys Ala Asn Arg Arg Ala Cys Thr Thr Arg Lys Ser
            660                 665                 670

Lys Asp Asn Val Met Ala Ala Thr Arg Gly Thr Arg Tyr Tyr Asn Lys
            675                 680                 685

Val Arg Thr Gly Asn Val Ala Thr His Asn Thr Trp Arg Thr His Val
690                 695                 700

Asp Val Ser Val Met Lys Ala Lys Ser Ala Ser Arg Ser Arg Arg Asn
705                 710                 715                 720

Tyr Val Val Ser Asp Asp Ala Met Lys Lys Ala Lys Lys Thr
            725                 730                 735

Ser Thr Arg Val Ser Cys Thr Lys Gly Arg His Cys Thr Asp
            740                 745                 750

<210> SEQ ID NO 33
<211> LENGTH: 710
<212> TYPE: PRT
<213> ORGANISM: Saccharomyces cerevisiae

<400> SEQUENCE: 33

Met Asp Asn Lys Arg Tyr Asn Gly Asn Ser Asn Val Asp Gly Thr Tyr
1               5                   10                  15

Asp Arg Asn Asp Thr Arg Met Asn Thr Asn Ala Arg Ser Val Arg Val
            20                  25                  30

Ser Asp Lys Arg Gly Arg Ser Ser Thr Ser Lys Gly Ser Tyr Arg
            35                  40                  45

Thr Arg Ala Gly Arg Ser Asp Thr Thr Asn Ser Ser Ala Lys His His
50                  55                  60

Ser Lys Lys Ser Thr Val Val Val Thr Ser Ser Thr Asp Ser Asn
65                  70                  75                  80

Ser Thr Thr Tyr Ala Arg Val Ser Ser Asp Ser Thr Val Ala Thr Ser
                85                  90                  95

Ser Thr Thr Thr Arg Thr Arg Thr Arg Asn Asn Thr Val Ser Ser Thr
            100                 105                 110

Ala Ser Ser Ser Thr Thr Asp Val Gly Asn Ala Thr Ser Ala Asn Trp
        115                 120                 125

Ser Ala Asn Ala Ser Asn Thr Ser Ser Ser Asp Tyr Ala Thr Ser Tyr
    130                 135                 140

Thr Arg Lys Ser Thr Asp Asn Tyr Thr Thr Ala Asn Ser Lys Asn Gly
145                 150                 155                 160

Asn Asn Trp Ser Ser Ala Gly Asn Ser Asn Thr Asp His Asn Thr Val
                165                 170                 175

Asn Arg Arg Ser Ser Ser Thr Thr Asn Arg Val Tyr Thr Asp Ala Tyr
            180                 185                 190

Tyr Ala Asn Tyr Val Val Arg Val Lys Ser Thr Ser Ser Val Asp Asp
        195                 200                 205

Val Asp Ala Ser Asn Trp Thr Ala Asn Lys Val Val Asn Ser Ala Thr
    210                 215                 220

Asn Thr Ser Ser Asn Val Thr His Asn Ala Val Asn Thr Ser Thr Ser
225                 230                 235                 240

Ala Thr Cys Ser Tyr Gly Lys Val Ser Ala Arg Thr Arg Gly Asn Met
                245                 250                 255
```

```
Ala Val Ser Thr Val Ser Ala Cys Ala Ala Gly Lys Ser Lys Val Gly
            260                 265                 270

Ala Ser Thr Val Ser Ala Arg Val Met Tyr Asn Val Asn Gly Asn Asn
            275                 280                 285

Thr Lys Asn His Gly Val Asn Tyr Ser Thr Ser Asn Asn Thr Tyr Cys
            290                 295                 300

Asn Thr Asn Ser His Ser Ser Asn Asn Tyr Ser Ser Asp Ser Lys Lys
305                 310                 315                 320

Asp His Thr Ser Ser Lys Tyr Asp His Asn His Asn Ala Lys Asn Lys
                325                 330                 335

Gly Val Ser Asp Thr Asn Tyr Gly His Asn Ser Lys Val Lys Arg Lys
            340                 345                 350

Asp Thr Asp Ala Lys Arg Arg Lys Asp Ser Asn Ser Ser Thr Met Ala
            355                 360                 365

Val Met Asp Ser Ser Asp Tyr Gly Asn Thr Val Lys Asn Ser Ser Asn
            370                 375                 380

Arg Asp Met Arg Lys Cys Asn Lys Tyr Thr Ser Met Gly Val His Lys
385                 390                 395                 400

Asn Gly Thr Trp Val Cys Lys Lys Met Ala Asn Thr Arg Asn Val Thr
                405                 410                 415

Ser Gly Val Ser Asp Tyr Cys Thr Asn Asp Gly Asn Tyr Val Gly Lys
            420                 425                 430

Gly Trp Asn Ser Ser Val Ser His Trp Thr Val Asn Arg Tyr Gly Ser
                435                 440                 445

Arg Ala Val Arg Ala Cys Ala Asp Ser Thr Cys Thr Thr Ser Val Ser
            450                 455                 460

Tyr Ala Thr Asp Thr Asn Gly Thr Thr Trp Asp Thr Cys Thr Asn Lys
465                 470                 475                 480

Asn Cys Asp Lys Val Asn Lys Asn Val Lys Cys Cys His Lys Gly Ser
                485                 490                 495

Thr Val Lys Asn Arg Gly Gly Ala Ser Lys Asn Lys His Ala Asp Gly
            500                 505                 510

Ser Ser Asp Ser Asp Gly Asn Tyr Gly Thr Tyr Lys Val Thr Ser Arg
            515                 520                 525

Asp Asn Ser Val Arg Asp Ala Thr Lys Arg Asn Ser Asn Asn Ser Arg
530                 535                 540

Val Gly Ser Ser Ala Gly Ser Lys Ser Ser Lys Asn His Arg Lys His
545                 550                 555                 560

Gly His Ser Gly Arg Ala Arg Gly Val Ser Val Ser Ser Val Arg Ser
                565                 570                 575

Ser Asn Ser Arg His Asn Ser Val Met Asn Asn Ala Gly Thr Ala Asn
            580                 585                 590

Asn Ala Met Ser Asn Ser Tyr Asn Asn Val Val Tyr Ser Gly Asn Asn
            595                 600                 605

Asn Asn Gly Asn Ser Asn Gly Asp Asn Ser Asp Ser Arg Ala Asn Gly
            610                 615                 620

Thr Asn Ser Val Asn Asn Val Ser Asn Asn Asn Asn Tyr Asn Asn Asn
625                 630                 635                 640

Ser Gly Tyr Ser Ser Met Asn Ser Arg Ser Val Ser His Asn Asn Asn
                645                 650                 655

Asn Asn Thr Asn Asn Tyr Asn Asn Asn Asp Asn Asp Asn Asn Asn Asn
            660                 665                 670
```

```
Asn Asn Asn Asn Asn Asn Asn Asn Asn Asn Asn Asn Asn Asn
        675                 680                 685

Asn Ser Asn Asn Ser Asn Asn Asn Asn Asn Asp Thr Ser Tyr Arg
    690                 695                 700

Tyr Arg Ser Tyr Gly Tyr
705                 710

<210> SEQ ID NO 34
<211> LENGTH: 477
<212> TYPE: PRT
<213> ORGANISM: Saccharomyces cerevisiae

<400> SEQUENCE: 34

Asp Thr Lys Gly Tyr Asp Asp Ala Ala Thr Asp Gly Lys Lys His
1               5                   10                  15

Arg Arg Tyr Arg Tyr Val Ser Gly Val Ser Gly Lys Arg Trp Thr
                20                  25                  30

Asp Gly Val Ser Trp Ser Ser Arg Ser Gly Lys Tyr Lys Asp Lys Asn
                35                  40                  45

Ala Gly Ser Asn Ala Asn Ala Thr Ser Ser Gly Ser Thr Asp Ser Ala
        50                  55                  60

Val Thr Asp Gly Thr Ser Gly Ala Arg Asn Asn Ser Ser Ser Lys Lys
65                  70                  75                  80

Lys Asn His Asp Thr Met Gly His Ser Ser Asp Thr Ser Ser Ser
                    85                  90                  95

Asn Arg Ser Asn Lys Tyr Thr Gly Val Lys Lys Thr Ser Val Lys Lys
                100                 105                 110

Arg Asn Ser Asn His Val Ser Tyr Tyr Ser Val Lys Asp Lys Asn Cys
                115                 120                 125

Val Thr Lys Ala Ser Lys Asp Val Arg Ser Val Ala Met Gly Asn Thr
        130                 135                 140

Thr Gly Asn Val Lys Asn Asn Ser Thr Thr Thr Gly Asn Gly Asn Asn
145                 150                 155                 160

Asn Asn Lys Ser Asn Ser Ser Thr Asn Thr Val Ser Thr Asn Asn Asn
                165                 170                 175

Ser Ala Asn Asn Ala Ala Gly Ser Asn Thr Ser Ala Asn Lys Asn Tyr
                180                 185                 190

Tyr Tyr Lys Asn Asp Ser Ser Gly Tyr Thr Ala Ala Ser Thr Thr Met
                195                 200                 205

Tyr Thr Ala Asn Tyr Thr Ser Asp Asn Thr Asn Ala Thr Gly Met Asn
        210                 215                 220

Thr His Val Asn Asn Asn Asn Asn Ser Asn Asn Ser Ser Asn Ser
225                 230                 235                 240

Asn Asn Ser Asn Asn Asn Asn Asn Asn Asn Asn Asn Asn Asn
                245                 250                 255

Asn Asn Asn Asn Asn Asn Asn Val Asn Thr Asn Ala Gly Asn Gly
                260                 265                 270

Asn Asn Asn Arg His Asn Ala Ser Ala Tyr Asn Thr Thr Gly Asp Asn
                275                 280                 285

Gly Ser Tyr Tyr Tyr Thr Thr Asn Asn Asn Tyr Tyr Thr Thr Asn Val
        290                 295                 300

Thr Asn Ala Ser Thr Asn Asn Gly Tyr Ser Thr Ser Ser Thr His Tyr
305                 310                 315                 320

Tyr Gly His Thr Ser Ser Ala Ser Ala Ala Ala Gly Thr Gly Thr
                325                 330                 335
```

```
Gly Thr Ala Asn Val Val Ser Ser Met His Ala Asn Asn Ser Ala
            340                 345                 350
Ser Ser Ala Thr Ser Thr Ala Tyr Val Tyr Ser Met Asn Val Asn Val
        355                 360                 365
Tyr Tyr Asn Ser Ser Ala Ser Ala Tyr Lys Arg Ala Asn Thr Thr Ser
370                 375                 380
Asn Thr Asn Ala Ser Gly Ala Thr Ser Thr Asn Ser Gly Thr Met Ser
385                 390                 395                 400
Asn Ala Tyr Ala Asn Ser Tyr Thr Ser Val Tyr Tyr Gly Tyr Ala Met
                405                 410                 415
Ala Ser Ala Asn Ser Met Tyr His His His Thr Val Tyr Ala Thr Asn
            420                 425                 430
Met Ser Ser Gly His Thr Ser Thr Gly Ser Asp His His His Tyr Asn
        435                 440                 445
Asp His Lys Asn Ala Met Gly His Ala Asn Asn Asn Thr Asn Asn
450                 455                 460
Asp Thr Met Asn Asn Asn Thr Asn Thr Ser Thr Thr Thr
465                 470                 475

<210> SEQ ID NO 35
<211> LENGTH: 454
<212> TYPE: PRT
<213> ORGANISM: Saccharomyces cerevisiae

<400> SEQUENCE: 35

Met Asp Val Arg Ala Ala Cys Ser Ala Ser Gly Arg Thr Gly Lys Lys
1               5                   10                  15
Gly Tyr Ser Tyr Lys Met Ser Asn Ser Gly Ser Ser Ser Gly Gly
            20                  25                  30
Ser Asp Val Gly Ser Thr Asn Gly Ser Asn Arg Ala Lys Asn Thr Asn
        35                  40                  45
Tyr Lys Lys Thr Asn Lys Lys Tyr Lys Ala Thr Asp Lys Ala Asn Asp
    50                  55                  60
Thr Lys Tyr Tyr Ser Asn Asp Lys Lys Ser Lys Arg Ser Ala Asn Ser
65                  70                  75                  80
Met Asn Asp Lys Asp Lys Cys Arg Thr Thr Asn Lys Asp Met Thr Arg
                85                  90                  95
Tyr Asp Ser Lys Ser Lys Val Thr Asn Cys Asp His Lys Ala Ser Ser
            100                 105                 110
His Ser Met Lys Tyr Lys Lys Arg Ser Val Asp Lys Asp His Val Met
        115                 120                 125
Lys Asp Asp Ser Ser Val Lys Ala Ser Lys Met Asn Ser His Asn Tyr
    130                 135                 140
Ser Thr Asn Thr Met Asn Lys Met Asp Val Tyr Thr Lys Ala Asn Met
145                 150                 155                 160
Ala Asn Lys Lys Lys Ser Asp Thr Ser Thr Trp Lys Asn Lys Asn Lys
                165                 170                 175
Ser His Val Ser Tyr Asn Asn Asp Lys Ser Lys Thr Lys Trp Tyr Asn
            180                 185                 190
Asp Ser Asp Asp Asp Asp Asp Asn Asn Val Asn Asn Asn Asp Asn Asn
        195                 200                 205
Asn Asn Asn Lys Asn Asp Asn Asn Asn Asp Asn Asn Asn Asp Thr Ser
    210                 215                 220
```

```
Asn Asn Asn Asn Asn Asn Asn Arg Thr Lys Asn Arg Asn Asn
225                 230                 235                 240

Arg Asp Trp Lys Thr Lys Cys Thr Asp Met Asn Asp Lys Arg Asp
            245                 250                 255

Asn Asn Asn Lys Asn Asp Met Ala Arg Asn Asp Asn Lys Asn Tyr Asn
        260                 265                 270

Asn Val Asn Lys Arg Asn His Lys Ser Ser Cys Arg Arg Asp Gly Tyr
            275                 280                 285

Ser Ala Asn Asn Ala Val Asn Ser Thr His Ala Ser Asn Lys Asn Val
        290                 295                 300

Asn Asp Met Asn Asn Asp Thr Tyr Lys Asn Lys Thr Asp Thr Asn Lys
305                 310                 315                 320

Lys Asn Asp Ser Asn Ser Asn Asp Val Thr Arg Lys Lys Arg Lys Thr
                325                 330                 335

Ser Asp Gly Asn Tyr Ser Arg Asn Asn Val Ser Val Ser Arg Ser Lys
            340                 345                 350

Ala Thr Thr Lys Lys Thr Lys Lys Lys Arg Arg Asp Gly Lys Asp
        355                 360                 365

Lys Lys Asn Lys Lys Asn Ala Asp Asn Lys Lys Asn Asn Ala Val Thr
370                 375                 380

Val Ser Val Tyr Asp Ser Asn Lys Val Lys Ser Asn Lys Arg Ser Arg
385                 390                 395                 400

Lys Val Asn Asn Lys Ser Asp Val Val Asn Ser Gly Lys Asp Ser Arg
                405                 410                 415

Val Lys Ser Cys Lys Lys Tyr Ala Asp Asn Asn Thr Lys Ser Asn Asp
            420                 425                 430

Ala Asp Gly Trp Asp Asp Met Asn Trp Val Asp Arg Gly Cys Ala Thr
        435                 440                 445

Thr Arg Trp Arg Ala Lys
    450

<210> SEQ ID NO 36
<211> LENGTH: 284
<212> TYPE: PRT
<213> ORGANISM: Saccharomyces cerevisiae

<400> SEQUENCE: 36

Met Asn Val Thr Ser Lys Asp Gly Asn His Ser Ser Lys Lys Asn Arg
1               5                   10                  15

Asn Thr Asn Lys Arg His Lys Asn Ala Ser Asn Asp Arg Asp Ser Val
            20                  25                  30

Ser Ser Asn Thr Thr Ser Met Thr Asp Asp Ala Asp Tyr Asn Gly Ala
        35                  40                  45

Ser Arg Thr Lys Asn Asn Ser Asp Ser Asp Arg Ser Asn Asp Thr Lys
    50                  55                  60

Asn Asn Tyr Asn Lys Arg Thr Gly Tyr Asn Tyr Asn Gly Ser Gly Asn
65                  70                  75                  80

Arg Tyr Thr Arg Lys Arg Thr Ala Asn Lys Ala Tyr Ser Asp Asp Asn
            85                  90                  95

Val Lys Asp Asp Asn Asn Thr Lys Lys Ala Ser Arg Ser Ser Gly Arg
        100                 105                 110

Asn Val Asn Thr Arg Asn Lys Ser Lys Ser His Lys Val Lys Asn Asn
    115                 120                 125

Lys Ser Ser Ser Arg Lys Ser Ser Ala Ala Arg Lys Gly Lys Tyr Asn
130                 135                 140
```

```
Ser Asn Ser Asp Ser Thr Thr Arg Lys Val Thr Asp Val Lys Lys Arg
145                 150                 155                 160

Ser Lys Trp His Arg His Asp Lys Lys Met Val Lys Lys Ser Arg Tyr
            165                 170                 175

Arg Lys Arg Met Arg Gly Thr Asp Val Ser Ser Asp Asn Ser Lys
        180                 185                 190

Ser Thr Thr Lys Ser Tyr Val Ser Lys Asn Ser Ala Met Asn Asn
        195                 200                 205

Asp Val Thr Asp Asn Lys Lys Thr Asn Asn Lys Ala Arg Asp Ser
    210                 215                 220

Met His Thr Lys Lys Asp Thr Lys Asp Asp Thr Asp Ser Lys Lys Arg
225                 230                 235                 240

Lys Val Val Thr Asn Asp Ala Ala Met Val Asn Lys Gly Trp Arg
                245                 250                 255

Lys Asn Val Met Met Tyr Lys Lys Ser Gly Asn Met Lys Lys Tyr Arg
                260                 265                 270

Tyr Trp Thr Cys Tyr Cys Asn Tyr Val Tyr Tyr Arg
        275                 280

<210> SEQ ID NO 37
<211> LENGTH: 29
<212> TYPE: DNA
<213> ORGANISM: Artificial sequence
<220> FEATURE:
<223> OTHER INFORMATION: Synthetic primer

<400> SEQUENCE: 37
gggaattccc attaccgaca tttgggcgc                                       29

<210> SEQ ID NO 38
<211> LENGTH: 29
<212> TYPE: DNA
<213> ORGANISM: Artificial sequence
<220> FEATURE:
<223> OTHER INFORMATION: Synthetic primer

<400> SEQUENCE: 38
ggggattctg attgattgat tgattgtac                                       29

<210> SEQ ID NO 39
<211> LENGTH: 720
<212> TYPE: DNA
<213> ORGANISM: Artificial sequence
<220> FEATURE:
<223> OTHER INFORMATION: Superbright GFP encoding sequence
<220> FEATURE:
<221> NAME/KEY: CDS
<222> LOCATION: (1)..(720)

<400> SEQUENCE: 39 atg gct agc aaa gga gaa gaa ctc ttc act gga gtt gtc cca att ctt     48
Met Ala Ser Lys Gly Glu Glu Leu Phe Thr Gly Val Val Pro Ile Leu
1               5                   10                  15 gtt gaa tta gat ggt gat gtt aat ggg cac aaa ttt tct gtc agt gga     96
Val Glu Leu Asp Gly Asp Val Asn Gly His Lys Phe Ser Val Ser Gly
                20                  25                  30 gag ggt gaa ggt gat gca aca tac gga aaa ctt acc ctt aaa ttt att    144
Glu Gly Glu Gly Asp Ala Thr Tyr Gly Lys Leu Thr Leu Lys Phe Ile
            35                  40                  45
```

```
tgc act act gga aaa cta cct gtt cca tgg cca aca ctt gtc act act        192
Cys Thr Thr Gly Lys Leu Pro Val Pro Trp Pro Thr Leu Val Thr Thr
 50                  55                  60 ttc act tat ggt gtt cag tgc ttt tca aga tac ccg gat cat atg aaa        240
Phe Thr Tyr Gly Val Gln Cys Phe Ser Arg Tyr Pro Asp His Met Lys
 65                  70                  75                  80 cgg cat gac ttt ttc aag agt gcc atg ccc gaa ggt tat gta cag gaa        288
Arg His Asp Phe Phe Lys Ser Ala Met Pro Glu Gly Tyr Val Gln Glu
                 85                  90                  95 aga act ata ttt ttc aaa gat gac ggg aac tac aag aca cgt gct gaa        336
Arg Thr Ile Phe Phe Lys Asp Asp Gly Asn Tyr Lys Thr Arg Ala Glu
            100                 105                 110 gtc aag ttt gaa ggt gat acc ctt gtt aat aga atc gag tta aaa ggt        384
Val Lys Phe Glu Gly Asp Thr Leu Val Asn Arg Ile Glu Leu Lys Gly
        115                 120                 125 att gat ttt aaa gaa gat gga aac att ctt ggg cac aaa ttg gaa tac        432
Ile Asp Phe Lys Glu Asp Gly Asn Ile Leu Gly His Lys Leu Glu Tyr
130                 135                 140 aac tat aac tca cac aat gta tac atc atg gca gac aaa caa aag aat        480
Asn Tyr Asn Ser His Asn Val Tyr Ile Met Ala Asp Lys Gln Lys Asn
145                 150                 155                 160 gga atc aaa gct aac ttc aaa att aga cac aac att gaa gat gga agc        528
Gly Ile Lys Ala Asn Phe Lys Ile Arg His Asn Ile Glu Asp Gly Ser
                165                 170                 175 gtt caa cta gca gac cat tat caa caa aat act cca att ggc gat ggc        576
Val Gln Leu Ala Asp His Tyr Gln Gln Asn Thr Pro Ile Gly Asp Gly
            180                 185                 190 cct gtc ctt tta cca gac aac cat tac ctg tcc aca caa tct gcc ctt        624
Pro Val Leu Leu Pro Asp Asn His Tyr Leu Ser Thr Gln Ser Ala Leu
        195                 200                 205 tcg aaa gat ccc aac gaa aag aga gac cac atg gtc ctt ctt gag ttt        672
Ser Lys Asp Pro Asn Glu Lys Arg Asp His Met Val Leu Leu Glu Phe
210                 215                 220 gta aca gct gct ggg att aca cat ggc atg gat gaa cta tac aaa tga       720
Val Thr Ala Ala Gly Ile Thr His Gly Met Asp Glu Leu Tyr Lys
225                 230                 235
```

<210> SEQ ID NO 40
<211> LENGTH: 239
<212> TYPE: PRT
<213> ORGANISM: Artificial sequence
<220> FEATURE:
<223> OTHER INFORMATION: Synthetic Peptide

<400> SEQUENCE: 40

```
Met Ala Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
 50                  55                  60

Phe Thr Tyr Gly Val Gln Cys Phe Ser Arg Tyr Pro Asp His Met Lys
 65                  70                  75                  80

Arg His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys
225                 230                 235

<210> SEQ ID NO 41
<211> LENGTH: 27
<212> TYPE: DNA
<213> ORGANISM: Artificial sequence
<220> FEATURE:
<223> OTHER INFORMATION: Synthetic primer

<400> SEQUENCE: 41
gaccgcggat ggctagcaaa ggagaag                                        27

<210> SEQ ID NO 42
<211> LENGTH: 28
<212> TYPE: DNA
<213> ORGANISM: Artificial sequence
<220> FEATURE:
<223> OTHER INFORMATION: Synthetic primer

<400> SEQUENCE: 42
cctgagctct catttgtata gttcatcc                                       28

<210> SEQ ID NO 43
<211> LENGTH: 34
<212> TYPE: DNA
<213> ORGANISM: Artificial sequence
<220> FEATURE:
<223> OTHER INFORMATION: Synthetic primer

<400> SEQUENCE: 43
ggaggatcca tggatacgga taagttaatc tcag                                34

<210> SEQ ID NO 44
<211> LENGTH: 36
<212> TYPE: DNA
<213> ORGANISM: Artificial sequence
<220> FEATURE:
<223> OTHER INFORMATION: Synthetic primer

<400> SEQUENCE: 44
ggaccgcggg tagcggttct gttgagaaaa gttgcc                              36

<210> SEQ ID NO 45
<211> LENGTH: 7239
<212> TYPE: DNA
<213> ORGANISM: Artificial sequence
<220> FEATURE:
<223> OTHER INFORMATION: Vector containing chimeric gene
```

```
<400> SEQUENCE: 45
gacgaaaggg cctcgtgata cgcctatttt tataggttaa tgtcatgata ataatggttt      60
cttaggacgg atcgcttgcc tgtaacttac acgcgcctcg tatcttttaa tgatggaata    120
atttgggaat ttactctgtg tttatttatt tttatgtttt gtatttggat tttagaaagt    180
aaataaagaa ggtagaagag ttacggaatg aagaaaaaaa aataaacaaa ggtttaaaaa    240
atttcaacaa aaagcgtact ttacatatat atttattaga caagaaaagc agattaaata    300
gatatacatt cgattaacga taagtaaaat gtaaaatcac aggattttcg tgtgtggtct    360
tctacacaga caagatgaaa caattcggca ttaatacctg agagcaggaa gagcaagata    420
aaaggtagta tttgttggcg atcccccctag agtcttttac atcttcggaa aacaaaaact    480
attttttctt taatttcttt ttttactttc tattttttaat ttatatattt atattaaaaa    540
atttaaatta taattatttt tatagcacgt gatgaaaagg acccaggtgg cacttttcgg    600
ggaaatgtgc gcggaacccc tatttgttta tttttctaaa tacattcaaa tatgtatccg    660
ctcatgagac aataaccctg ataaatgctt caataatatt gaaaaaggaa gagtatgagt    720
attcaacatt tccgtgtcgc ccttattccc tttttttgcgg cattttgcct tcctgttttt    780
gctcacccag aaacgctggt gaaagtaaaa gatgctgaag atcagttggg tgcacgagtg    840
ggttacatcg aactggatct caacagcggt aagatccttg agagttttcg ccccgaagaa    900
cgttttccaa tgatgagcac ttttaaagtt ctgctatgtg cgcggtatt atcccgtatt    960
gacgccgggc aagagcaact cggtcgccgc atacactatt ctcagaatga cttggttgag   1020
tactcaccag tcacagaaaa gcatcttacg gatggcatga cagtaagaga attatgcagt   1080
gctgccataa ccatgagtga taacactgcg gccaacttac ttctgacaac gatcggagga   1140
ccgaaggagc taaccgcttt tttgcacaac atggggggatc atgtaactcg ccttgatcgt   1200
tgggaaccgg agctgaatga agccatacca aacgacgagc gtgacaccac gatgcctgta   1260
gcaatggcaa caacgttgcg caaactatta actggcgaac tacttactct agcttcccgg   1320
caacaattaa tagactggat ggaggcggat aaagttgcag gaccacttct gcgctcggcc   1380
cttccggctg gctggtttat tgctgataaa tctggagccg gtgagcgtgg gtctcgcggt   1440
atcattgcag cactggggcc agatggtaag ccctcccgta tcgtagttat ctacacgacg   1500
gggagtcagg caactatgga tgaacgaaat agacagatcg ctgagatagg tgcctcactg   1560
attaagcatt ggtaactgtc agaccaagtt tactcatata tactttagat tgatttaaaa   1620
cttcattttt aatttaaaag gatctaggtg aagatccttt ttgataatct catgaccaaa   1680
atcccttaac gtgagttttc gttccactga gcgtcagacc ccgtagaaaa gatcaaagga   1740
tcttcttgag atcctttttt tctgcgcgta atctgctgct tgcaaacaaa aaaaccaccg   1800
ctaccagcgg tggtttgttt gccggatcaa gagctaccaa ctctttttcc gaaggtaact   1860
ggcttcagca gagcgcagat accaaatact gtccttctag tgtagccgta gttaggccac   1920
cacttcaaga actctgtagc accgcctaca tacctcgctc tgctaatcct gttaccagtg   1980
gctgctgcca gtggcgataa gtcgtgtctt accgggttgg actcaagacg atagttaccg   2040
gataaggcgc agcggtcggg ctgaacgggg ggttcgtgca cacagcccag cttggagcga   2100
acgacctaca ccgaactgag atacctacag cgtgagctat gagaaagcgc cacgcttccc   2160
gaagggagaa aggcggacag gtatccggta agcggcaggg tcggaacagg agagcgcacg   2220
agggagcttc caggggggaaa cgcctggtat ctttatagtc ctgtcgggtt tcgccacctc   2280
```

```
tgacttgagc gtcgattttt gtgatgctcg tcagggggc ggagcctatg gaaaaacgcc    2340
agcaacgcgg cctttttacg gttcctggcc ttttgctggc cttttgctca catgttcttt    2400
cctgcgttat cccctgattc tgtggataac cgtattaccg cctttgagtg agctgatacc    2460
gctcgccgca gccgaacgac cgagcgcagc gagtcagtga gcgaggaagc ggaagagcgc    2520
ccaatacgca aaccgcctct ccccgcgcgt tggccgattc attaatgcag ctggcacgac    2580
aggtttcccg actggaaagc gggcagtgag cgcaacgcaa ttaatgtgag ttacctcact    2640
cattaggcac cccaggcttt acactttatg cttccggctc gtatgttgtg tggaattgtg    2700
agcggataac aatttcacac aggaaacagc tatgaccatg attacgccaa gctcggaatt    2760
aaccctcact aaagggaaca aaagctgggt accgggcccc ccctcgaggt cgacggtatc    2820
gataagcttg atatcgaatt cccattaccg acatttgggc gctatacgtg catatgttca    2880
tgtatgtatc tgtatttaaa acactttgt attattttc ctcatatatg tgtataggtt    2940
tatacggatg atttaattat tacttcacca ccctttattt caggctgata tcttagcctt    3000
gttactagtt agaaaagac attttgctg tcagtcactg tcaagagatt cttttgctgg    3060
catttcttct agaagcaaaa agagcgatgc gtcttttccg ctgaaccgtt ccagcaaaaa    3120
agactaccaa cgcaatatgg attgtcagaa tcatataaaa gagaagcaaa taactccttg    3180
tcttgtatca attgcattat aatatcttct tgttagtgca atatcatata gaagtcatcg    3240
aaatagatat taagaaaaac aaactgtaca atcaatcaat caatcaggat ccatggatac    3300
ggataagtta atctcagagg ctgagtctca tttttctcaa ggaaaccatg cagaagctgt    3360
tgcgaagttg acatccgcag ctcagtcgaa ccccaatgac gagcaaatgt caactattga    3420
atcattaatt caaaaaatcg caggatacgt catggacaac cgtagtggtg gtagtgacgc    3480
ctcgcaagat cgtgctgctg gtggtggttc atcttttatg aacactttaa tggcagactc    3540
taagggttct tcccaaacgc aactaggaaa actagctttg ttagccacag tgatgacaca    3600
ctcatcaaat aaaggttctt ctaacagagg gtttgacgta gggactgtca tgtcaatgct    3660
aagtggttct ggcggcggga gccaaagtat gggtgcttcc ggcctggctg ccttggcttc    3720
tcaattcttt aagtcaggta acaattccca aggtcaggga caaggtcaag gtcaaggtca    3780
aggtcaagga caaggtcaag gtcaaggttc ttttactgct ttggcgtctt tggcttcatc    3840
tttcatgaat tccaacaaca ataatcagca aggtcaaaat caaagctccg gtggttcctc    3900
ctttggagca ctagcttcta tggcaagttc ttttatgcat tccaataata atcagaactc    3960
caacaatagt caacagggtt ataaccaatc ctatcaaaac ggtaaccaaa atagtcaagg    4020
ttacaataat caacagtacc aaggtggcaa cggtggttac caacaacaac agggacaatc    4080
tggtggtgct ttttcctcat tggcctccat ggctcaatct tacttaggtg gtggacaaac    4140
tcaatccaac caacagcaat acaatcaaca aggccaaaac aaccagcagc aataccagca    4200
acaaggccaa aactatcagc accaacaaca gggtcagcag cagcaacaag gccactccag    4260
ttcattctca gctttggctt ccatggcaag ttcctacctg ggcaataact ccaattcaaa    4320
ttcgagttat gggggccagc aacaggctaa tgagtatggt agaccacaac acaatggtca    4380
acaacaatct aatgagtacg gaagaccgca atacggcgga aaccagaact ccaatggaca    4440
gcacgaatcc tttaattttt ctggcaactt ttctcaacag aacaataacg caaccagaa    4500 ccgctacccg cggatggcta gcaaaggaga agaactcttc actggagttg tcccaattct    4560
tgttgaatta gatggtgatg ttaatgggca caaattttct gtcagtggag agggtgaagg    4620
tgatgcaaca tacggaaaac ttacccttaa atttatttgc actactggaa aactacctgt    4680
```

-continued

```
tccatggcca acacttgtca ctactttcac ttatggtgtt cagtgctttt caagataccc    4740
ggatcatatg aaacggcatg acttttttcaa gagtgccatg cccgaaggtt atgtacagga    4800
aagaactata ttttttcaaag atgacgggaa ctacaagaca cgtgctgaag tcaagtttga    4860
aggtgatacc cttgttaata gaatcgagtt aaaaggtatt gattttaaag aagatggaaa    4920
cattcttggg cacaaattgg aatacaacta taactcacac aatgtataca tcatggcaga    4980
caaacaaaag aatggaatca aagctaactt caaaattaga cacaacattg aagatggaag    5040
cgttcaacta gcagaccatt atcaacaaaa tactccaatt ggcgatggcc ctgtcctttt    5100
accagacaac cattacctgt ccacacaatc tgccctttcg aaagatccca acgaaaagag    5160
agaccacatg gtccttcttg agtttgtaac agctgctggg attacacatg gcatggatga    5220
actatacaaa tgagagctcc aattcgccct atagtgagtc gtattacaat tcactggccg    5280
tcgttttaca acgtcgtgac tgggaaaacc ctggcgttac ccaacttaat cgccttgcag    5340
cacatccccc tttcgccagc tggcgtaata gcgaagaggc ccgcaccgat cgcccttccc    5400
aacagttgcg cagcctgaat ggcgaatggc gcgacgcgcc ctgtagcggc gcattaagcg    5460
cggcgggtgt ggtggttacg cgcagcgtga ccgctacact tgccagcgcc ctagcgcccg    5520
ctcctttcgc tttcttccct tcctttctcg ccacgttcgc cggctttccc cgtcaagctc    5580
taaatcgggg gctcccttta gggttccgat ttagtgcttt acggcacctc gaccccaaaa    5640
aacttgatta gggtgatggt tcacgtagtg ggccatcgcc ctgatagacg ttttttcgcc    5700
ctttgacgtt ggagtccacg ttctttaata gtggactctt gttccaaact ggaacaacac    5760
tcaaccctat ctcggtctat tcttttgatt tataagggat tttgccgatt tcggcctatt    5820
ggttaaaaaa tgagctgatt taacaaaaat ttaacgcgaa ttttaacaaa atattaacgt    5880
ttacaatttc ctgatgcggt attttctcct tacgcatctg tgcggtattt cacaccgcat    5940
agggtaataa ctgatataat taaattgaag ctctaatttg tgagtttagt atacatgcat    6000
ttacttataa tacagttttt tagttttgct ggccgcatct tctcaaatat gcttcccagc    6060
ctgcttttct gtaacgttca ccctctacct tagcatccct tccctttgca atagtcctc    6120
ttccaacaat aataatgtca gatcctgtag agaccacatc atccacggtt ctatactgtt    6180
gacccaatgc gtctcccttg tcatctaaac ccacaccggg tgtcataatc aaccaatcgt    6240
aaccttcatc tcttccaccc atgtctcttt gagcaataaa gccgataaca aaatctttgt    6300
cgctcttcgc aatgtcaaca gtaccccttag tatattctcc agtagatagg gagcccttgc    6360
atgacaattc tgctaacatc aaaaggcctc taggttcctt tgttacttct tctgccgcct    6420
gcttcaaacc gctaacaata cctgggccca ccacaccgtg tgcattcgta atgtctgccc    6480
attctgctat tctgtataca cccgcagagt actgcaattt gactgtatta ccaatgtcag    6540
caaatttttct gtcttcgaag agtaaaaaaat tgtacttggc ggataatgcc tttagcggct    6600
taactgtgcc ctccatggaa aaatcagtca agatatccac atgtgttttt agtaaacaaa    6660
ttttgggacc taatgcttca actaactcca gtaattcctt ggtggtacga acatccaatg    6720
aagcacacaa gtttgtttgc ttttcgtgca tgatattaaa tagcttggca gcaacaggac    6780
taggatgagt agcagcacgt tccttatatg tagctttcga catgatttat cttcgtttcc    6840
tgcaggtttt tgttctgtgc agttgggtta agaatactgg gcaatttcat gtttcttcaa    6900
cactacatat gcgtatatat accaatctaa gtctgtgctc cttccttcgt tcttccttct    6960
gttcggagat taccgaatca aaaaaatttc aagaaaccg aaatcaaaaa aaagaataaa    7020
```

```
aaaaaaatga tgaattgaat tgaaaagctg tggtatggtg cactctcagt acaatctgct      7080
ctgatgccgc atagttaagc cagccccgac acccgccaac acccgctgac gcgccctgac      7140
gggcttgtct gctcccggca tccgcttaca gacaagctgt gaccgtctcc gggagctgca      7200
tgtgtcagag gttttcaccg tcatcaccga aacgcgcga                             7239

<210> SEQ ID NO 46
<211> LENGTH: 741
<212> TYPE: PRT
<213> ORGANISM: Pichia pinus

<400> SEQUENCE: 46

Met Ser Gln Asp Gln Gln Gln Gln Gln Phe Asn Ala Asn Asn Leu
1               5                  10                  15

Ala Gly Asn Val Gln Asn Ile Asn Leu Asn Ala Pro Ala Tyr Asp Pro
            20                  25                  30

Ala Val Gln Ser Tyr Ile Pro Asn Thr Ala Gln Ala Phe Val Pro Ser
        35                  40                  45

Ala Gln Pro Tyr Ile Pro Gly Gln Gln Glu Gln Gln Phe Gly Gln Tyr
    50                  55                  60

Gly Gln Gln Gln Gln Asn Tyr Asn Gln Gly Gly Tyr Asn Asn Tyr Asn
65                  70                  75                  80

Asn Arg Gly Gly Tyr Ser Asn Asn Arg Gly Gly Tyr Asn Ser Asn
                85                  90                  95

Arg Gly Gly Tyr Ser Asn Tyr Asn Ser Tyr Asn Thr Asn Ser Asn Gln
            100                 105                 110

Gly Gly Tyr Ser Asn Tyr Asn Asn Tyr Ala Asn Asn Ser Tyr Asn
        115                 120                 125

Asn Asn Asn Tyr Asn Asn Asn Tyr Asn Gln Gly Tyr Asn Asn Tyr
    130                 135                 140

Asn Ser Gln Pro Gln Gly Gln Asp Gln Gln Glu Thr Gly Ser Gly
145                 150                 155                 160

Gln Met Ser Leu Glu Asp Tyr Gln Lys Gln Gln Lys Glu Ser Leu Asn
                165                 170                 175

Lys Leu Asn Thr Lys Pro Lys Lys Val Leu Lys Leu Asn Leu Asn Ser
            180                 185                 190

Ser Thr Val Lys Ala Pro Ile Val Thr Lys Lys Glu Glu Glu Pro
        195                 200                 205

Val Asn Gln Glu Ser Lys Thr Glu Gly Pro Ala Lys Glu Glu Ile Lys
    210                 215                 220

Asn Gln Glu Pro Ala Glu Ala Glu Asn Lys Val Glu Glu Ser Lys
225                 230                 235                 240

Val Glu Ala Pro Thr Ala Ala Lys Pro Val Ser Glu Ser Glu Phe Pro
                245                 250                 255

Ala Ser Thr Pro Lys Thr Glu Ala Lys Ala Ser Lys Glu Val Ala Ala
            260                 265                 270

Ala Ala Ala Ala Leu Lys Lys Glu Val Ser Gln Ala Lys Lys Glu Ser
        275                 280                 285

Asn Val Thr Asn Ala Asp Ala Leu Val Lys Glu Gln Glu Glu Gln Ile
    290                 295                 300

Asp Ala Ser Ile Val Asn Asp Met Phe Gly Gly Lys Asp His Met Ser
305                 310                 315                 320

Ile Ile Phe Met Gly His Val Asp Ala Gly Lys Ser Thr Met Gly Gly
                325                 330                 335
```

```
Asn Leu Leu Phe Leu Thr Gly Ala Val Asp Lys Arg Thr Val Glu Lys
            340                 345                 350

Tyr Glu Arg Glu Ala Lys Asp Ala Gly Arg Gln Gly Trp Tyr Leu Ser
            355                 360                 365

Trp Ile Met Asp Thr Asn Lys Glu Glu Arg Asn Asp Gly Lys Thr Ile
            370                 375                 380

Glu Val Gly Lys Ser Tyr Phe Glu Thr Asp Lys Arg Arg Tyr Thr Ile
385                 390                 395                 400

Leu Asp Ala Pro Gly His Lys Leu Tyr Ile Ser Glu Met Ile Gly Gly
                405                 410                 415

Ala Ser Gln Ala Asp Val Gly Val Leu Val Ile Ser Ser Arg Lys Gly
            420                 425                 430

Glu Tyr Glu Ala Gly Phe Glu Arg Gly Gly Gln Ser Arg Glu His Ala
            435                 440                 445

Ile Leu Ala Lys Thr Gln Gly Val Asn Lys Leu Val Val Ile Asn
450                 455                 460

Lys Met Asp Asp Pro Thr Val Asn Trp Ser Lys Glu Arg Tyr Glu Glu
465                 470                 475                 480

Cys Thr Thr Lys Leu Ala Met Tyr Leu Lys Gly Val Gly Tyr Gln Lys
            485                 490                 495

Gly Asp Val Leu Phe Met Pro Val Ser Gly Tyr Thr Gly Ala Gly Leu
            500                 505                 510

Lys Glu Arg Val Ser Gln Lys Asp Ala Pro Trp Tyr Asn Gly Pro Ser
            515                 520                 525

Leu Leu Glu Tyr Leu Asp Ser Met Pro Leu Ala Val Arg Lys Ile Asn
            530                 535                 540

Asp Pro Phe Met Leu Pro Ile Ser Ser Lys Met Lys Asp Leu Gly Thr
545                 550                 555                 560

Val Ile Glu Gly Lys Ile Glu Ser Gly His Val Lys Lys Gly Gln Asn
                565                 570                 575

Leu Leu Val Met Pro Asn Lys Thr Gln Val Glu Val Thr Thr Ile Tyr
            580                 585                 590

Asn Glu Thr Glu Ala Glu Ala Asp Ser Ala Phe Cys Gly Glu Gln Val
            595                 600                 605

Arg Leu Arg Leu Arg Gly Ile Glu Glu Glu Asp Leu Ser Ala Gly Tyr
            610                 615                 620

Val Leu Ser Ser Ile Asn His Pro Val Lys Thr Val Thr Arg Phe Glu
625                 630                 635                 640

Ala Gln Ile Ala Ile Val Glu Leu Lys Ser Ile Leu Ser Thr Gly Phe
                645                 650                 655

Ser Cys Val Met His Val His Thr Ala Ile Glu Glu Val Thr Phe Thr
                660                 665                 670

Gln Leu Leu His Asn Leu Gln Lys Gly Thr Asn Arg Arg Ser Lys Lys
            675                 680                 685

Ala Pro Ala Phe Ala Lys Gln Gly Met Lys Ile Ile Ala Val Leu Glu
            690                 695                 700

Thr Thr Glu Pro Val Cys Ile Glu Ser Tyr Asp Asp Tyr Pro Gln Leu
705                 710                 715                 720

Gly Arg Phe Thr Leu Arg Asp Gln Gly Gln Thr Ile Ala Ile Gly Lys
                725                 730                 735

Val Thr Lys Leu Leu
            740
```

<210> SEQ ID NO 47
<211> LENGTH: 715
<212> TYPE: PRT
<213> ORGANISM: Candida albicans

<400> SEQUENCE: 47

```
Met Ala Asn Ala Ser Leu Asn Gly Asp Gln Ser Lys Gln Gln Gln Gln
1               5                   10                  15

Gln Gln Gln Gln Gln Gln Gln Gln Asn Tyr Tyr Asn Pro Asn Ala
            20                  25                  30

Ala Gln Ser Phe Val Pro Gln Gly Tyr Gln Gln Phe Gln Gln Phe
        35                  40                  45

Gln Pro Gln Gln Gln Gln Gln Tyr Gly Gly Tyr Asn Gln Tyr Asn
    50                  55                  60

Gln Tyr Gln Gly Gly Tyr Gln Gln Asn Tyr Asn Arg Gly Gly Tyr
65                  70                  75                  80

Gln Gln Gly Tyr Asn Asn Arg Gly Gly Tyr Gln Gln Asn Tyr Asn Asn
                85                  90                  95

Arg Gly Gly Tyr Gln Gly Tyr Asn Gln Asn Gln Gln Tyr Gly Gly Tyr
            100                 105                 110

Gln Gln Tyr Asn Ser Gln Pro Gln Gln Gln Gln Gln Gln Ser Gln
        115                 120                 125

Gly Met Ser Leu Ala Asp Phe Gln Lys Gln Lys Thr Glu Gln Gln Ala
    130                 135                 140

Ser Leu Asn Lys Pro Ala Val Lys Lys Thr Leu Lys Leu Ala Gly Ser
145                 150                 155                 160

Ser Gly Ile Lys Leu Ala Asn Ala Thr Lys Lys Val Asp Thr Thr Ser
                165                 170                 175

Lys Pro Gln Ser Lys Glu Ser Ser Pro Ala Pro Ala Pro Ala Ala Ser
            180                 185                 190

Ala Ser Ala Ser Ala Pro Gln Glu Glu Lys Lys Glu Glu Lys Glu Ala
        195                 200                 205

Ala Ala Ala Thr Pro Ala Ala Ala Pro Glu Thr Lys Lys Glu Thr Ser
    210                 215                 220

Ala Pro Ala Glu Thr Lys Lys Glu Ala Thr Pro Thr Pro Ala Ala Lys
225                 230                 235                 240

Asn Glu Ser Thr Pro Ile Pro Ala Ala Ala Lys Lys Glu Ser Thr
                245                 250                 255

Pro Val Ser Asn Ser Ala Ser Val Ala Thr Ala Asp Ala Leu Val Lys
            260                 265                 270

Glu Gln Glu Asp Glu Ile Asp Glu Glu Val Val Lys Asp Met Phe Gly
        275                 280                 285

Gly Lys Asp His Val Ser Ile Ile Phe Met Gly His Val Asp Ala Gly
    290                 295                 300

Lys Ser Thr Met Gly Gly Asn Ile Leu Tyr Leu Thr Gly Ser Val Asp
305                 310                 315                 320

Lys Arg Thr Val Glu Lys Tyr Glu Arg Glu Ala Lys Asp Ala Gly Arg
                325                 330                 335

Gln Gly Trp Tyr Leu Ser Trp Val Met Asp Thr Asn Lys Glu Glu Arg
            340                 345                 350

Asn Asp Gly Lys Thr Ile Glu Val Gly Lys Ala Tyr Phe Glu Thr Asp
        355                 360                 365

Lys Arg Arg Tyr Thr Ile Leu Asp Ala Pro Gly His Lys Met Tyr Val
    370                 375                 380
```

```
Ser Glu Met Ile Gly Gly Ala Ser Gln Ala Asp Val Gly Ile Leu Val
385                 390                 395                 400

Ile Ser Ala Arg Lys Gly Tyr Glu Thr Gly Phe Glu Lys Gly Gly
            405                 410                 415

Gln Thr Arg Glu His Ala Leu Leu Ala Lys Thr Gln Gly Val Asn Lys
            420                 425                 430

Ile Ile Val Val Val Asn Lys Met Asp Asp Ser Thr Val Gly Trp Ser
                435                 440                 445

Lys Glu Arg Tyr Gln Glu Cys Thr Thr Lys Leu Gly Ala Phe Leu Lys
        450                 455                 460

Gly Ile Gly Tyr Ala Lys Asp Asp Ile Ile Tyr Met Pro Val Ser Gly
465                 470                 475                 480

Tyr Thr Gly Ala Gly Leu Lys Asp Arg Val Asp Pro Lys Asp Cys Pro
                485                 490                 495

Trp Tyr Asp Gly Pro Ser Leu Leu Glu Tyr Leu Asp Asn Met Asp Thr
            500                 505                 510

Met Asn Arg Lys Ile Asn Gly Pro Phe Met Met Pro Val Ser Gly Lys
        515                 520                 525

Met Lys Asp Leu Gly Thr Ile Val Glu Gly Lys Ile Glu Ser Gly His
530                 535                 540

Val Lys Lys Gly Thr Asn Leu Ile Met Met Pro Asn Lys Thr Pro Ile
545                 550                 555                 560

Glu Val Leu Thr Ile Phe Asn Glu Thr Glu Gln Glu Cys Asp Thr Ala
                565                 570                 575

Phe Ser Gly Glu Gln Val Arg Leu Lys Ile Lys Gly Ile Glu Glu Glu
            580                 585                 590

Asp Leu Gln Pro Gly Tyr Val Leu Thr Ser Pro Lys Asn Pro Val Lys
        595                 600                 605

Thr Val Thr Arg Phe Glu Ala Gln Ile Ala Ile Val Glu Leu Lys Ser
610                 615                 620

Ile Leu Ser Asn Gly Phe Ser Cys Val Met His Leu His Thr Ala Ile
625                 630                 635                 640

Glu Glu Val Lys Phe Ile Glu Leu Lys His Lys Leu Glu Lys Gly Thr
                645                 650                 655

Asn Arg Lys Ser Lys Lys Pro Pro Ala Phe Ala Lys Lys Gly Met Lys
            660                 665                 670

Ile Ile Ala Ile Leu Glu Val Gly Glu Leu Val Cys Ala Glu Thr Tyr
        675                 680                 685

Lys Asp Tyr Pro Gln Leu Gly Arg Phe Thr Leu Arg Asp Gln Gly Thr
        690                 695                 700

Thr Ile Ala Ile Gly Lys Ile Thr Lys Leu Leu
705                 710                 715

<210> SEQ ID NO 48
<211> LENGTH: 653
<212> TYPE: DNA
<213> ORGANISM: Saccharomyces cerevisiae

<400> SEQUENCE: 48
tcgagtttat cattatcaat actcgccatt tcaaagaata cgtaaataat taatagtagt      60
gattttccta actttatttta gtcaaaaaat tagccttta attctgctgt aacccgtaca     120
tgccaaaata gggggcgggt tacacagaat atataacact gatggtgctt gggtgaacag     180
gtttattcct ggcatccact aaatataatg gagcccgctt tttaagctgg catccagaaa     240
```

```
aaaaaagaat cccagcacca aaatattgtt ttcttcacca accatcagtt cataggtcca      300
ttctcttagc gcaactacag agaacagggc acaaacaggc aaaaaacggg cacaacctca      360
atggagtgat gcaacctgcc tggagtaaat gatgacacaa ggcaattgac ccacgcatgt      420
atctatctca ttttcttaca ccttctatta ccttctgctc tctctgattt ggaaaaagct      480
gaaaaaaaag gtttaaacca gttccctgaa attattcccc tacttgacta ataagtatat      540
aaagacggta ggtattgatt gtaattctgt aaatctattt cttaaacttc ttaaattcta      600
cttttatagt tagtcttttt tttagtttta aaacaccaag aacttagttt cga             653
```

<210> SEQ ID NO 49
<211> LENGTH: 7988
<212> TYPE: DNA
<213> ORGANISM: Artificial sequence
<220> FEATURE:
<223> OTHER INFORMATION: Ure2N-Sup35C integration plasmid

<400> SEQUENCE: 49

```
tcgcgcgttt cggtgatgac ggtgaaaacc tctgacacat gcagctcccg gagacggtca       60
cagcttgtct gtaagcggat gccgggagca gacaagcccg tcaggcgcg tcagcgggtg      120 ttggcgggtg tcggggctgg cttaactatg cggcatcaga gcagattgta ctgagagtgc      180
accataccac agcttttcaa ttcaattcat catttttttt ttattctttt ttttgatttc      240
ggtttctttg aaatttttt gattcggtaa tctccgaaca aaggaagaa cgaaggaagg      300 agcacagact tagattggta tatatacgca tatgtagtgt tgaagaaaca tgaaattgcc      360
cagtattctt aacccaactg cacagaacaa aaacctgcag gaaacgaaga taaatcatgt      420
cgaaagctac atataaggaa cgtgctgcta ctcatcctag tcctgttgct gccaagctat      480
ttaatatcat gcacgaaaag caaacaaact tgtgtgcttc attggatgtt cgtaccacca      540
aggaattact ggagttagtt gaagcattag gtcccaaaat tgtttacta aaacacatg       600 tggatatctt gactgatttt tccatggagg gcacagttaa gccgctaaag gcattatccg      660
ccaagtacaa tttttactc ttcgaagaca gaaaatttgc tgacattggt aatacagtca      720
aattgcagta ctctgcgggt gtatacagaa tagcagaatg gcagacatt acgaatgcac      780 acggtgtggt gggcccaggt attgttagcg gtttgaagca ggcggcagaa gaagtaacaa      840
aggaacctag aggccttttg atgttagcag aattgtcatg caagggctcc ctatctactg      900
gagaatatac taagggtact gttgacattg cgaagagcga caagatttt gttatcggct      960 ttattgctca aagagacatg ggtggaagag atgaaggtta cgattggttg attatgacac     1020
ccggtgtggg tttagatgac aagggagacg cattgggtca acagtataga accgtggatg     1080
atgtggtctc tacaggatct gacattatta ttgttgaag aggactattt gcaaagggaa     1140
gggatgctaa ggtagagggt gaacgttaca gaaaagcagg ctgggaagca tatttgagaa     1200
gatgcggcca gcaaaactaa aaactgtat tataagtaaa tgcatgtata ctaaactcac     1260
aaattagagc ttcaatttaa ttatatcagt tattacccta tgcggtgtga aataccgcac     1320
agatgcgtaa ggagaaaata ccgcatcagg aaattgtaaa cgttaatatt tgttaaaat     1380 tcgcgttaaa ttttgttaa atcagctcat tttttaacca ataggccgaa atcggcaaaa     1440
tcccttataa atcaaaagaa tagaccgaga tagggttgag tgttgttcca gtttggaaca     1500
agagtccact attaaagaac gtggactcca acgtcaaagg gcgaaaaacc gtctatcagg     1560
gcgatggccc actacgtgaa ccatcaccct aatcaagttt ttggggtcg aggtgccgta     1620 aagcactaaa tcggaaccct aaagggagcc ccgatttag agcttgacgg ggaaagccgg     1680
```

```
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtcgcg ccattcgcca ttcaggctgc gcaactgttg ggaagggcga tcggtgcggg    1860
cctcttcgct attacgccag ctggcgaaag ggggatgtgc tgcaaggcga ttaagtttggg   1920
taacgccagg gttttcccag tcacgacgtt gtaaaacgac ggccagtgaa ttgtaatacg    1980
actcactata gggcgaattg gagctccacc gcggtgaaaa gagtcagtga gacgacgact    2040
tcaggatctt tgggtttcag gatatgtggc atgaaaatac agaaaaatcc ctctgtgctg    2100
aatcagcttt cgctcgaata ttacgaagaa gaagcagaca gtgattatat ctttataaac    2160
aaattgtatg gtcgttcaag aaccgatcaa aatgtttcag atgcaattga actttatttt    2220
aacaatcctc atctgtcgga tgcgagaaag catcaactga agaaaacatt tttgaaaaga    2280
ttgcagttgt tttataatac tatgctagaa gaagaagtta gaatgatatc aagtagtctt    2340
ttgtttatttt acgaaggaga cccggagcga tgggaattac taaatgatgt tgacaaactt    2400
atgcgagatg atttttataga cgatgatgac gacgatgatg ataatgatga tgatgatgat    2460
gatgatgccg agggaagcag cgaaggacca aaggacaaaa aaacaactgg ttctttgagt    2520
tccatgtcac taatagattt tgcacattct gaaataacgc cggggaaggg ttatgatgaa    2580
aacgtgattg aaggagttga aaccttgcta gatatttttta tgaaattcta gatatattga    2640
gaggtgaagt ttaccttgtt tatggtatat ggtacaaaaa gaactaaact aattatacgt    2700
ctatatatat atatatatat ataacagctt tattaaacct tgttttttaa tatagaagaa    2760
aatgctttat gatcggtatt attgtgtttg catttactta tgtttgcaag aaatggatcc    2820
ttactcggca atttttaacaa ttttaccaat tgctattgtg gtaccttgat ctctcaaagt    2880
gaatctacct aattgagggt aatcttggta agtttccaca caaactggag cttcagtttc    2940
taaaacagcg atgaccttca taccccttctt agcaaaagca ggtggttctct ttgacttacg    3000
gttggtaccc ttttctaatt tgtgcaataa cttaacaata tgtacctctt caattgctgt    3060
atgaacatgc ataacacatg aaaaaccggc tgctatgata gattttaatt ctacaatagc    3120
aatttgagct acaaacttgg taacactctt gatagggttc tttggcgatg ttagtacaaa    3180
acctggtgaa atgtcttctt cttcaacacc tttgattctt agtttaactt gctcaccaca    3240
catagccata tcaacttcat tttcagtttc gttgtaaata ttttgaattt ccacagcggt    3300
tttgttaggc atcagtaggg tggattgacc cttttttgata tgaccggatt caattttacc    3360
ttcaacgatg gtacctagat ccttcatctt agcggcaata ggcaacatga atggagcatt    3420
gatgtgacgc tcgacgtggt tcattgtatc cagatattct aacagagttg ggccggtgta    3480
ccatgggcat tcttttggat ctacgtgatc tttcaaattt gcaccactgt agccggatac    3540
tggcataaat acaacgtctg tcttaatgtt gtaccaatt gctctcaaga aattgctgac    3600
attactcaca cattggtcgt aacgttcctt agaccagtta acggttgggt catccatctt    3660
atttacgacg acaaccatct tattaacacc ttgggtcttg gccaataggg cgtgttcacg    3720
agtttgacca cctctctcaa aaccggtttc gtactcaccc tttctggcgg aaatgaccaa    3780
aacaccaaca tcagcttgag aagcaccacc gatcatctcg gaaacgtaca ttttatgacc    3840
aggagcatcc aatatggtat aacgcctttt ttcagtttca aagtaggcct taccaacttc    3900
gatagtctta ccatcatttc tttcttcttt gttggtatcc atgacccatg acaagtacca    3960
accttgtctg cctgcatcct tggcttctct ttcatatttc tcaatagttc tcttatccac    4020
```

```
agagccagtc aagtatagta gattaccacc catagtagat ttaccggcat caacatgacc    4080
catgaaaatt aaagaaacgt gatctttacc accaaacata gcgtagtctg ggacgtcgta    4140
tgggtagcgg ccgctgttat tgttttgaac attattgtta ttactactgc tattgttatt    4200
attattatta tttacacctg ttgaaaattc aaaatttata ttactttgat cggtggttgt    4260
attactgttc ctgtttccta tgtttacttg acggagcgca ttggagagat tcgacacttg    4320
gttgccgttg ttattcatca tgaattctgt tgctagtggg cagatataga tgttattccg    4380
agcaagtcga tgaagaaacc gcttttgtt acagtacaat ggagtctttc aagagaagat     4440
gtaccaatat acactacact cttcagaagc aatgggagct ttggtcgagt gaaaaaaaaa    4500
tttctccat aaagaaagat catattatac gatgatgtaa gatataatac ccggttgtaa     4560
tgtacattta agagcaaggt aagaagtgac aataacttct gtatgatctt agcatgtacc    4620
tcttttggtg ggctgagaac taagattcat ctttttgcgg aagaattttg ctatgaactt    4680
cacaacttta tgaagtggtt taagagaatt acaaagaaa tgacacagac tcgaacactg     4740
tgacgcgtcg tcttagtaaa aataataat ttgagtcaaa tagcgcagct aatgcgaaac     4800
aaagaaatga agcatatacc attcgttgta tgattttgt gtggttgaca gatattctgc     4860
cgaaattta acgcttatta taaatataaa tgtatgtatg tgtgtataaa cagatacgat     4920
attcaatttt ctaccgtagg gttgggattt tcttcaaact ccaattcttc gtcgggtatt    4980
tcctcaatgg cgatcctctt ttttggcttc ggcttttcag tgtcattgac aattttaggc    5040
accttaattt gtagtagacc gttgttgtaa gtagctttaa ttcttcgtc cttaatgcgt      5100
ggcagcacgg ggaatttaac ggttctctca aacgcaccat attttagttc cgtgatcttc    5160
aagaattttt catcaatgcc cactctgtct tcgatcttac ccttgatgag catctcatga    5220
gaagatggat ggtaatcaat gtggaaagcc ctagagttag cacctggtaa cgcaagaaca    5280
actacgtaag tgtcctcggt atcatagaca ttcacttctg gtgaaaatgg taagtccatt    5340
ctcgtttcag gcttggatac ttgtaacggg tcaggtattg gggaaggcgc ttgtaggtga    5400
gcgaacgatg aagattttt ggctaatggt ggtctcgacg attcctccag ctgattcaaa     5460
ggttttctt tgttggtttc gccagcttcc tctttgggtg cttcagactt atccttctta     5520
tccttttctt ctcccttttc gccctcctgt tcggtatttg cttcaatttc tggttcagtg    5580
ccttcatatg gtggaacacc tattaacgcg gttaataagt cgtttaaact gtttgcctgt    5640
tggttggtcc tattattcct ggcagtatta caatggtaat atgatggata tcttctcgag    5700
gggggggcccg gtacccagct tttgttccct ttagtgaggg ttaattccga gcttggcgta    5760
atcatggtca tagctgtttc ctgtgtgaaa ttgttatccg ctcacaattc cacacaacat    5820
acgagccgga agcataaagt gtaaagcctg gggtgcctaa tgagtgaggt aactcacatt    5880
aattgcgttg cgctcactgc ccgctttcca gtcgggaaac ctgtcgtgcc agctgcatta    5940
atgaatcggc caacgcgcgg ggagaggcgg tttgcgtatt gggcgctctt ccgcttcctc    6000
gctcactgac tcgctgcgct cggtcgttcg gctgcggcga gcggtatcag ctcactcaaa    6060
ggcggtaata cggttatcca cagaatcagg ggataacgca ggaaagaaca tgtgagcaaa    6120
aggccagcaa aaggccagga accgtaaaaa ggccgcgttg ctggcgtttt tccataggct    6180
ccgcccccct gacgagcatc acaaaaatcg acgctcaagt cagaggtggc gaaacccgac    6240
aggactataa agataccagg cgtttccccc tggaagctcc ctcgtgcgct ctcctgttcc    6300
gaccctgccg cttaccggat acctgtccgc ctttctccct tcgggaagcg tggcgctttc    6360
tcatagctca cgctgtaggt atctcagttc ggtgtaggtc gttcgctcca agctgggctg    6420
```

-continued

```
tgtgcacgaa ccccccgttc agcccgaccg ctgcgcctta tccggtaact atcgtcttga    6480
gtccaacccg gtaagacacg acttatcgcc actggcagca gccactggta acaggattag    6540
cagagcgagg tatgtaggcg gtgctacaga gttcttgaag tggtggccta actacggcta    6600
cactagaagg acagtatttg gtatctgcgc tctgctgaag ccagttacct tcggaaaaag    6660
agttggtagc tcttgatccg gcaaacaaac caccgctggt agcggtggtt ttttgtttg    6720 caagcagcag attacgcgca gaaaaaaagg atctcaagaa gatcctttga tcttttctac    6780
ggggtctgac gctcagtgga acgaaaactc acgttaaggg attttggtca tgagattatc    6840
aaaaaggatc ttcacctaga tccttttaaa ttaaaaatga agttttaaat caatctaaag    6900
tatatatgag taaacttggt ctgacagtta ccaatgctta atcagtgagg cacctatctc    6960
agcgatctgt ctatttcgtt catccatagt tgcctgactc cccgtcgtgt agataactac    7020
gatacgggag ggcttaccat ctggccccag tgctgcaatg ataccgcgag acccacgctc    7080
accggctcca gatttatcag caataaacca gccagccgga agggccgagc gcagaagtgg    7140
tcctgcaact ttatccgcct ccatccagtc tattaattgt tgccgggaag ctagagtaag    7200
tagttcgcca gttaatagtt tgcgcaacgt tgttgccatt gctacaggca tcgtggtgtc    7260
acgctcgtcg tttggtatgg cttcattcag ctccggttcc caacgatcaa ggcgagttac    7320
atgatccccc atgttgtgca aaaaagcggt tagctccttc ggtcctccga tcgttgtcag    7380
aagtaagttg gccgcagtgt tatcactcat ggttatggca gcactgcata attctcttac    7440
tgtcatgcca tccgtaagat gcttttctgt gactggtgag tactcaacca agtcattctg    7500
agaatagtgt atgcggcgac cgagttgctc ttgcccggcg tcaatacggg ataataccgc    7560
gccacatagc agaactttaa aagtgctcat cattggaaaa cgttcttcgg ggcgaaaact    7620
ctcaaggatc ttaccgctgt tgagatccag ttcgatgtaa cccactcgtg cacccaactg    7680
atcttcagca tctttactt tcaccagcgt ttctgggtga gcaaaaacag gaaggcaaaa    7740
tgccgcaaaa aagggaataa gggcgacacg gaaatgttga atactcatac tcttcctttt    7800
tcaatattat tgaagcattt atcagggtta ttgtctcatg agcggataca tatttgaatg    7860
tatttagaaa aataaacaaa tagggggttcc gcgcacattt ccccgaaaag tgccacctga    7920
cgtctaagaa accattatta tcatgacatt aacctataaa aataggcgta tcacgaggcc    7980
ctttcgtc                                                             7988
```

<210> SEQ ID NO 50
<211> LENGTH: 405
<212> TYPE: PRT
<213> ORGANISM: Saccharomyces cerevisiae

<400> SEQUENCE: 50

```
Met Asp Thr Asp Lys Leu Ile Ser Glu Ala Glu Ser His Phe Ser Gln
1               5                   10                  15

Gly Asn His Ala Glu Ala Val Ala Lys Leu Thr Ser Ala Ala Gln Ser
            20                  25                  30

Asn Pro Asn Asp Glu Gln Met Ser Thr Ile Glu Ser Leu Ile Gln Lys
        35                  40                  45

Ile Ala Gly Tyr Val Met Asp Asn Arg Ser Gly Gly Ser Asp Ala Ser
    50                  55                  60

Gln Asp Arg Ala Ala Gly Gly Gly Ser Ser Phe Met Asn Thr Leu Met
65                  70                  75                  80
```

-continued

```
Ala Asp Ser Lys Gly Ser Ser Gln Thr Gln Leu Gly Lys Leu Ala Leu
             85                  90                  95
Leu Ala Thr Val Met Thr His Ser Ser Asn Lys Gly Ser Ser Asn Arg
            100                 105                 110
Gly Phe Asp Val Gly Thr Val Met Ser Met Leu Ser Ser Gly Gly
            115                 120                 125
Gly Ser Gln Ser Met Gly Ala Ser Gly Leu Ala Ala Leu Ala Ser Gln
            130                 135                 140
Phe Phe Lys Ser Gly Asn Asn Ser Gln Gly Gln Gly Gln Gly
145                 150                 155                 160
Gln Gly Gln Gly Gln Gly Gln Gly Gln Gly Ser Phe Thr Ala
                165                 170                 175
Leu Ala Ser Leu Ala Ser Ser Phe Met Asn Ser Asn Asn Asn Gln
            180                 185                 190
Gln Gly Gln Asn Gln Ser Ser Gly Gly Ser Ser Phe Gly Ala Leu Ala
            195                 200                 205
Ser Met Ala Ser Ser Phe Met His Ser Asn Asn Asn Gln Asn Ser Asn
            210                 215                 220
Asn Ser Gln Gln Gly Tyr Asn Gln Ser Tyr Gln Asn Gly Asn Gln Asn
225                 230                 235                 240
Ser Gln Gly Tyr Asn Asn Gln Gln Tyr Gln Gly Gly Asn Gly Gly Tyr
                245                 250                 255
Gln Gln Gln Gln Gly Gln Ser Gly Gly Ala Phe Ser Ser Leu Ala Ser
                260                 265                 270
Met Ala Gln Ser Tyr Leu Gly Gly Gly Gln Thr Gln Ser Asn Gln Gln
            275                 280                 285
Gln Tyr Asn Gln Gln Gly Gln Asn Asn Gln Gln Tyr Gln Gln Gln
            290                 295                 300
Gly Gln Asn Tyr Gln His Gln Gln Gly Gln Gln Gln Gln Gln Gly
305                 310                 315                 320
His Ser Ser Ser Phe Ser Ala Leu Ala Ser Met Ala Ser Ser Tyr Leu
                325                 330                 335
Gly Asn Asn Ser Asn Ser Asn Ser Ser Tyr Gly Gly Gln Gln Gln Ala
            340                 345                 350
Asn Glu Tyr Gly Arg Pro Gln His Asn Gly Gln Gln Gln Ser Asn Glu
            355                 360                 365
Tyr Gly Arg Pro Gln Tyr Gly Gly Asn Gln Asn Ser Asn Gly Gln His
            370                 375                 380
Glu Ser Phe Asn Phe Ser Gly Asn Phe Ser Gln Gln Asn Asn Gly
385                 390                 395                 400
Asn Gln Asn Arg Tyr
                405

<210> SEQ ID NO 51
<211> LENGTH: 128
<212> TYPE: PRT
<213> ORGANISM: Saccharomyces cerevisiae

<400> SEQUENCE: 51

Met Ser Ala Asn Asp Tyr Tyr Gly Gly Thr Ala Gly Glu Lys Ser Gln
1               5                   10                  15
Tyr Ser Arg Pro Ser Asn Pro Pro Ser Ser Ala His Gln Asn Lys
                20                  25                  30
Thr Gln Glu Arg Gly Tyr Pro Pro Gln Gln Gln Gln Tyr Tyr Gln
            35                  40                  45
```

```
Gln Gln Gln Gln His Pro Gly Tyr Tyr Asn Gln Gly Tyr Asn Gln
         50                  55                  60

Gln Gly Tyr Asn Gln Gln Gly Tyr Asn Gln Gln Gly Tyr Asn Gln Gln
 65                  70                  75                  80

Gly Tyr Asn Gln Gln Gly Tyr Asn Gln Gln Gly His Gln Gln Pro Val
             85                  90                  95

Tyr Val Gln Gln Gln Pro Pro Gln Arg Gly Asn Glu Gly Cys Leu Ala
            100                 105                 110

Ala Cys Leu Ala Ala Leu Cys Ile Cys Cys Thr Met Asp Met Leu Phe
            115                 120                 125

<210> SEQ ID NO 52
<211> LENGTH: 534
<212> TYPE: PRT
<213> ORGANISM: Saccharomyces cerevisiae

<400> SEQUENCE: 52

Met Ser Ser Asp Glu Glu Asp Phe Asn Asp Ile Tyr Gly Asp Asp Lys
 1               5                  10                  15

Pro Thr Thr Thr Glu Glu Val Lys Lys Glu Glu Glu Gln Asn Lys Ala
             20                  25                  30

Gly Ser Gly Thr Ser Gln Leu Asp Gln Leu Ala Ala Leu Gln Ala Leu
         35                  40                  45

Ser Ser Ser Leu Asn Lys Leu Asn Asn Pro Asn Ser Asn Asn Ser Ser
     50                  55                  60

Ser Asn Asn Ser Asn Gln Asp Thr Ser Ser Lys Gln Asp Gly Thr
 65                  70                  75                  80

Ala Asn Asp Lys Glu Gly Ser Asn Glu Asp Thr Lys Asn Glu Lys Lys
             85                  90                  95

Gln Glu Ser Ala Thr Ser Ala Asn Ala Asn Ala Asn Ala Ser Ser Ala
            100                 105                 110

Gly Pro Ser Gly Leu Pro Trp Glu Gln Leu Gln Gln Thr Met Ser Gln
            115                 120                 125

Phe Gln Gln Pro Ser Ser Gln Ser Pro Pro Gln Gln Val Thr Gln
    130                 135                 140

Thr Lys Glu Glu Arg Ser Lys Ala Asp Leu Ser Lys Glu Ser Cys Lys
145                 150                 155                 160

Met Phe Ile Gly Gly Leu Asn Trp Asp Thr Thr Glu Asp Asn Leu Arg
                165                 170                 175

Glu Tyr Phe Gly Lys Tyr Gly Thr Val Thr Asp Leu Lys Ile Met Lys
            180                 185                 190

Asp Pro Ala Thr Gly Arg Ser Arg Gly Phe Gly Phe Leu Ser Phe Glu
            195                 200                 205

Lys Pro Ser Ser Val Asp Glu Val Val Lys Thr Gln His Ile Leu Asp
    210                 215                 220

Gly Lys Val Ile Asp Pro Lys Arg Ala Ile Pro Arg Asp Glu Gln Asp
225                 230                 235                 240

Lys Thr Gly Lys Ile Phe Val Gly Gly Ile Gly Pro Asp Val Arg Pro
                245                 250                 255

Lys Glu Phe Glu Glu Phe Phe Ser Gln Trp Gly Thr Ile Ile Asp Ala
            260                 265                 270

Gln Leu Met Leu Asp Lys Asp Thr Gly Gln Ser Arg Gly Phe Gly Phe
            275                 280                 285
```

```
Val Thr Tyr Asp Ser Ala Asp Ala Val Asp Arg Val Cys Gln Asn Lys
    290                 295                 300

Phe Ile Asp Phe Lys Asp Arg Lys Ile Glu Ile Lys Arg Ala Glu Pro
305                 310                 315                 320

Arg His Met Gln Gln Lys Ser Ser Asn Asn Gly Gly Asn Asn Gly Gly
                325                 330                 335

Asn Asn Met Asn Arg Arg Gly Gly Asn Phe Gly Asn Gln Gly Asp Phe
            340                 345                 350

Asn Gln Met Tyr Gln Asn Pro Met Met Gly Gly Tyr Asn Pro Met Met
                355                 360                 365

Asn Pro Gln Ala Met Thr Asp Tyr Tyr Gln Lys Met Gln Glu Tyr Tyr
    370                 375                 380

Gln Gln Met Gln Lys Gln Thr Gly Met Asp Tyr Thr Gln Met Tyr Gln
385                 390                 395                 400

Gln Gln Met Gln Gln Met Ala Met Met Pro Gly Phe Ala Met Pro
                405                 410                 415

Pro Asn Ala Met Thr Leu Asn Gln Pro Gln Asp Ser Asn Ala Thr
            420                 425                 430

Gln Gly Ser Pro Ala Pro Ser Asp Ser Asp Asn Lys Ser Asn Asp
                435                 440                 445

Val Gln Thr Ile Gly Asn Thr Ser Asn Thr Asp Ser Gly Ser Pro Pro
    450                 455                 460

Leu Asn Leu Pro Asn Gly Pro Lys Gly Pro Ser Gln Tyr Asn Asp Asp
465                 470                 475                 480

His Asn Ser Gly Tyr Gly Tyr Asn Arg Asp Arg Gly Asp Arg Asp Arg
                485                 490                 495

Asn Asp Arg Asp Arg Asp Tyr Asn His Arg Ser Gly Gly Asn His Arg
            500                 505                 510

Arg Asn Gly Arg Gly Gly Arg Gly Gly Tyr Asn Arg Arg Asn Asn Gly
                515                 520                 525

Tyr His Pro Tyr Asn Arg
    530

<210> SEQ ID NO 53
<211> LENGTH: 34
<212> TYPE: DNA
<213> ORGANISM: Artificial sequence
<220> FEATURE:
<223> OTHER INFORMATION: Synthetic primer

<400> SEQUENCE: 53
ggaggatcca tggatacgga taagttaatc tcag                              34

<210> SEQ ID NO 54
<211> LENGTH: 36
<212> TYPE: DNA
<213> ORGANISM: Artificial sequence
<220> FEATURE:
<223> OTHER INFORMATION: Synthetic primer

<400> SEQUENCE: 54
ccaagctttc agtagcggtt ctgttgagaa aagttg                            36

<210> SEQ ID NO 55
<211> LENGTH: 20
<212> TYPE: DNA
<213> ORGANISM: Artificial sequence
<220> FEATURE:
<223> OTHER INFORMATION: Synthetic primer
```

<400> SEQUENCE: 55
ggtgtcttgg ccaattgccc    20

<210> SEQ ID NO 56
<211> LENGTH: 39
<212> TYPE: DNA
<213> ORGANISM: Artificial sequence
<220> FEATURE:
<223> OTHER INFORMATION: Synthetic primer

<400> SEQUENCE: 56
gtcgacctgc agcgtacgca tttcagatct tgctatac    39

<210> SEQ ID NO 57
<211> LENGTH: 40
<212> TYPE: DNA
<213> ORGANISM: Artificial sequence
<220> FEATURE:
<223> OTHER INFORMATION: Synthetic primer

<400> SEQUENCE: 57
cgagctcgaa ttcatcgatt gattcagttc gccttctatc    40

<210> SEQ ID NO 58
<211> LENGTH: 22
<212> TYPE: DNA
<213> ORGANISM: Artificial sequence
<220> FEATURE:
<223> OTHER INFORMATION: Synthetic primer

<400> SEQUENCE: 58
ctgttttgaa agggtccaca tg    22

<210> SEQ ID NO 59
<211> LENGTH: 34
<212> TYPE: DNA
<213> ORGANISM: Artificial sequence
<220> FEATURE:
<223> OTHER INFORMATION: Synthetic primer

<400> SEQUENCE: 59
ggaggatcca tggatacgga taagttaatc tcag    34

<210> SEQ ID NO 60
<211> LENGTH: 36
<212> TYPE: DNA
<213> ORGANISM: Artificial sequence
<220> FEATURE:
<223> OTHER INFORMATION: Synthetic primer

<400> SEQUENCE: 60
ggaccgcggg tagcggttct gttgagaaaa gttgcc    36

<210> SEQ ID NO 61
<211> LENGTH: 36
<212> TYPE: DNA
<213> ORGANISM: Artificial sequence
<220> FEATURE:
<223> OTHER INFORMATION: Synthetic primer

<400> SEQUENCE: 61
gaggatccat gcctgatgat gaggaagaag acgagg    36

<210> SEQ ID NO 62

```
<210> SEQ ID NO 62
<211> LENGTH: 26
<212> TYPE: DNA
<213> ORGANISM: Artificial sequence
<220> FEATURE:
<223> OTHER INFORMATION: Synthetic primer

<400> SEQUENCE: 62
cggaattcct cgagaagata tccatc                                         26

<210> SEQ ID NO 63
<211> LENGTH: 24
<212> TYPE: DNA
<213> ORGANISM: Artificial sequence
<220> FEATURE:
<223> OTHER INFORMATION: Synthetic primer

<400> SEQUENCE: 63
gggatcctgt tgctagtggg caga                                           24

<210> SEQ ID NO 64
<211> LENGTH: 34
<212> TYPE: DNA
<213> ORGANISM: Artificial sequence
<220> FEATURE:
<223> OTHER INFORMATION: Synthetic primer

<400> SEQUENCE: 64
gtaccgcgga tgtctttgaa cgactttcaa aagc                                34

<210> SEQ ID NO 65
<211> LENGTH: 35
<212> TYPE: DNA
<213> ORGANISM: Artificial sequence
<220> FEATURE:
<223> OTHER INFORMATION: Synthetic primer

<400> SEQUENCE: 65
gtggagctct tactcggcaa ttttaacaat tttac                               35

<210> SEQ ID NO 66
<211> LENGTH: 3153
<212> TYPE: DNA
<213> ORGANISM: Saccharomyces cerevisiae

<400> SEQUENCE: 66
atgtcggatt caaaccaagg caacaatcag caaaactacc agcaatacag ccagaacggt    60
aaccaacaac aaggtaacaa cagataccaa ggttatcaag cttacaatgc tcaagcccaa   120
cctgcaggtg gtactacca aaattaccaa ggttattctg gtaccaaca aggtggctat     180 caacagtaca atcccgacgc cggttaccag caacagtata atcctcaagg aggctatcaa   240
cagtacaatc ctcaaggcgg ttatcagcag caattcaatc cacaaggtgg ccgtggaaat   300
tacaaaaact tcaactacaa taacaatttg caaggatatc aagctggttt ccaaccacag   360
tctcaaggta tgtctttgaa cgactttcaa agcaacaaa agcaggccgc tcccaaacca   420
aagaagactt tgaagcttgt ctccagttcc ggtatcaagt tggccaatgc taccaagaag   480
gttggcacaa aacctgccga atctgataag aaagaggaag agaagtctgc tgaaaccaaa   540
gaaccaacta agagccaac aaaggtcgaa gaaccagtta aaaaggagga gaaaccagtc   600
cagactgaag aaaagacgga ggaaaaatcg gaacttccaa aggtagaaga ccttaaaatc   660
tctgaatcaa cacataatac caacaatgcc aatgttacca gtgctgatgc cttgatcaag   720
gaacaggaag aagaagtgga tgacgaagtt gttaacgatc cgcggatgga ctccaaagaa   780
```

```
tccttagctc cccctggtag agacgaagtc cctggcagtt tgcttggcca agggaggggg        840
agcgtaatgg acttttataa aagcctgagg ggaggagcta cagtcaaggt ttctgcatct        900
tcgccctcag tggctgctgc ttctcaggca gattccaagc agcagaggat tctccttgat        960
ttctcgaaag gctccacaag caatgtgcag cagcgacagc agcagcagca gcagcagcag       1020
cagcagcagc agcagcagca gcagcagcag cagccaggct tatccaaagc cgtttcactg       1080 tccatgggc tgtatatggg agagacagaa acaaaagtga tggggaatga cttgggctac        1140
ccacagcagg gccaacttgg cctttcctct ggggaaacag actttcggct tctggaagaa       1200
agcattgcaa acctcaatag gtcgaccagc gttccagaga accccaagag ttcaacgtct       1260
gcaactgggt gtgctacccc gacagagaag gagtttccca aaactcactc ggatgcatct       1320
tcagaacagc aaaatcgaaa aagccagacc ggcaccaacg gaggcagtgt gaaattgtat       1380
cccacagacc aaagcacctt tgacctcttg aaggatttgg agttttccgc tgggtcccca       1440
agtaaagaca caaacgagag tccctggaga tcagatctgt tgatagatga aaacttgctt       1500
tctcctttgg cgggagaaga tgatccattc cttctcgaag gaacacgaa tgaggattgt         1560 aagcctctta ttttaccgga cactaaacct aaaattaagg atactggaga tacaatctta       1620
tcaagtccca gcagtgtggc actaccccaa gtgaaaacag aaaaagatga tttcattgaa       1680 cttttgcaccc ccggggtaat taagcaagag aaactgggcc cagtttattg tcaggcaagc      1740
ttttctggga caaatataat tggtaataaa atgtctgcca tttctgttca tggtgtgagt       1800
acctctggag gacagatgta ccactatgac atgaatacag catccctttc tcagcagcag       1860
gatcagaagc ctgtttttaa tgtcattcca ccaattcctg ttggttctga aaactggaat       1920
aggtgccaag gctccggaga ggacagcctg acttccttgg gggctctgaa cttcccaggc       1980
cggtcagtgt tttctaatgg gtactcaagc cctggaatga gaccagatgt aagctctcct       2040
ccatccagct cgtcagcagc cacgggacca cctcccaagc tctgcctggt gtgctccgat       2100
gaagcttcag gatgtcatta cggggtgctg acatgtggaa gctgcaaagt attctttaaa       2160
agagcagtgg aaggacagca caattacctt tgtgctggaa gaaacgattg catcattgat       2220
aaaattcgaa ggaaaaactg cccagcatgc cgctatcgga aatgtcttca ggctggaatg       2280
aaccttgaag ctcgaaaaac aaagaaaaaa atcaaaggga ttcagcaagc cactgcagga       2340
gtctcacaag acacttcgga aaatcctaac aaaacaatag ttcctgcagc attaccacag       2400 ctcacccta ccttggtgtc actgctggag gtgattgaac ccgaggtgtt gtatgcagga        2460
tatgatagct ctgttccaga ttcagcatgg agaattatga ccacactcaa catgttaggt       2520
gggcgtcaag tgattgcagc agtgaaatgg gcaaaggcga tactaggctt gagaaactta       2580
cacctcgatg accaaatgac cctgctacag tactcatgga tgtttctcat ggcatttgcc       2640
ttgggttgga gatcatacag acaatcaagc ggaaacctgc tctgctttgc tcctgatctg       2700
attattaatg agcagagaat gtctctaccc tgcatgtatg accaatgtaa acacatgctg       2760
tttgtctcct ctgaattaca aagattgcag gtatcctatg aagagtatct ctgtatgaaa       2820
accttactgc ttctctcctc agttcctaag gaaggtctga gagccaaga gttatttgat        2880 gagattcgaa tgacttatat caaagagcta ggaaaagcca tcgtcaaaag ggaagggaac       2940
tccagtcaga actggcaacg gttttaccaa ctgacaaagc ttctggactc catgcatgag       3000
gtggttgaga atctccttac ctactgcttc cagacatttt tggataagac catgagtatt       3060
gaattcccag agatgttagc tgaaatcatc actaatcaga taccaaaata ttcaaatgga       3120
```
aatatcaaaa agcttctgtt tcatcaaaaa tga 3153

<210> SEQ ID NO 67
<211> LENGTH: 1052
<212> TYPE: PRT
<213> ORGANISM: Saccharomyces cerevisiae

<400> SEQUENCE: 67

```
Met Ser Asp Ser Asn Gln Gly Asn Asn Gln Asn Tyr Gln Gln Tyr
1               5                   10                  15

Ser Gln Asn Gly Asn Gln Gln Gly Asn Asn Arg Tyr Gln Gly Tyr
                20                  25                  30

Gln Ala Tyr Asn Ala Gln Ala Gln Pro Ala Gly Gly Tyr Tyr Gln Asn
            35                  40                  45

Tyr Gln Gly Tyr Ser Gly Tyr Gln Gly Gly Tyr Gln Gln Tyr Asn
50                  55                  60

Pro Asp Ala Gly Tyr Gln Gln Tyr Asn Pro Gln Gly Gly Tyr Gln
65                  70                  75                  80

Gln Tyr Asn Pro Gln Gly Gly Tyr Gln Gln Phe Asn Pro Gln Gly
                85                  90                  95

Gly Arg Gly Asn Tyr Lys Asn Phe Asn Tyr Asn Asn Asn Leu Gln Gly
            100                 105                 110

Tyr Gln Ala Gly Phe Gln Pro Gln Ser Gln Gly Met Ser Leu Asn Asp
            115                 120                 125

Phe Gln Lys Gln Gln Lys Gln Ala Ala Pro Lys Pro Lys Lys Thr Leu
130                 135                 140

Lys Leu Val Ser Ser Gly Ile Lys Leu Ala Asn Ala Thr Lys Lys
145                 150                 155                 160

Val Gly Thr Lys Pro Ala Glu Ser Asp Lys Glu Glu Glu Lys Ser
                165                 170                 175

Ala Glu Thr Lys Glu Pro Thr Lys Glu Pro Thr Lys Val Glu Pro
            180                 185                 190

Val Lys Lys Glu Glu Lys Pro Val Gln Thr Glu Glu Lys Thr Glu Glu
195                 200                 205

Lys Ser Glu Leu Pro Lys Val Glu Asp Leu Lys Ile Ser Glu Ser Thr
210                 215                 220

His Asn Thr Asn Asn Ala Asn Val Thr Ser Ala Asp Ala Leu Ile Lys
225                 230                 235                 240

Glu Gln Glu Glu Glu Val Asp Asp Glu Val Val Asn Asp Pro Arg Met
                245                 250                 255

Asp Ser Lys Glu Ser Leu Ala Pro Pro Gly Arg Asp Glu Val Pro Gly
            260                 265                 270

Ser Leu Leu Gly Gln Gly Arg Gly Ser Val Met Asp Phe Tyr Lys Ser
            275                 280                 285

Leu Arg Gly Gly Ala Thr Val Lys Val Ser Ala Ser Pro Ser Val
290                 295                 300

Ala Ala Ala Ser Gln Ala Asp Ser Lys Gln Gln Arg Ile Leu Leu Asp
305                 310                 315                 320

Phe Ser Lys Gly Ser Thr Ser Asn Val Gln Gln Arg Gln Gln Gln
                325                 330                 335

Gln Gln Gln Gln Gln Gln Gln Gln Gln Gln Gln Gln Gln Pro
            340                 345                 350

Gly Leu Ser Lys Ala Val Ser Leu Ser Met Gly Leu Tyr Met Gly Glu
            355                 360                 365
```

```
Thr Glu Thr Lys Val Met Gly Asn Asp Leu Gly Tyr Pro Gln Gln Gly
    370                 375                 380

Gln Leu Gly Leu Ser Ser Gly Glu Thr Asp Phe Arg Leu Leu Glu Glu
385                 390                 395                 400

Ser Ile Ala Asn Leu Asn Arg Ser Thr Ser Val Pro Glu Asn Pro Lys
                405                 410                 415

Ser Ser Thr Ser Ala Thr Gly Cys Ala Thr Pro Thr Glu Lys Glu Phe
            420                 425                 430

Pro Lys Thr His Ser Asp Ala Ser Ser Glu Gln Gln Asn Arg Lys Ser
        435                 440                 445

Gln Thr Gly Thr Asn Gly Gly Ser Val Lys Leu Tyr Pro Thr Asp Gln
    450                 455                 460

Ser Thr Phe Asp Leu Leu Lys Asp Leu Glu Phe Ser Ala Gly Ser Pro
465                 470                 475                 480

Ala Ser Lys Asp Thr Asn Glu Ser Pro Trp Arg Ser Asp Leu Leu Ile
                485                 490                 495

Asp Glu Asn Leu Leu Ser Pro Leu Ala Gly Glu Asp Asp Pro Phe Leu
            500                 505                 510

Leu Glu Gly Asn Thr Asn Glu Asp Cys Lys Pro Leu Ile Leu Pro Asp
        515                 520                 525

Thr Lys Pro Lys Ile Lys Asp Thr Gly Asp Thr Ile Leu Ser Ser Pro
    530                 535                 540

Ser Ser Val Ala Leu Pro Gln Val Lys Thr Glu Lys Asp Asp Phe Ile
545                 550                 555                 560

Glu Leu Cys Thr Pro Gly Val Ile Lys Gln Glu Lys Leu Gly Pro Val
                565                 570                 575

Tyr Cys Gln Ala Ser Phe Ser Gly Thr Asn Ile Ile Gly Asn Lys Met
            580                 585                 590

Ser Ala Ile Ser Val His Gly Val Ser Thr Ser Gly Gly Gln Met Tyr
        595                 600                 605

His Tyr Asp Met Asn Thr Ala Ser Leu Ser Gln Gln Gln Asp Gln Lys
    610                 615                 620

Pro Val Phe Asn Val Ile Pro Ile Pro Val Gly Ser Glu Asn Trp
625                 630                 635                 640

Asn Arg Cys Gln Gly Ser Gly Glu Asp Ser Leu Thr Ser Leu Gly Ala
                645                 650                 655

Leu Asn Phe Pro Gly Arg Ser Val Phe Ser Asn Gly Tyr Ser Ser Pro
            660                 665                 670

Gly Met Arg Pro Asp Val Ser Ser Pro Ser Ser Ser Ser Ala Ala
        675                 680                 685

Thr Gly Pro Pro Lys Leu Cys Leu Val Cys Ser Asp Glu Ala Ser
    690                 695                 700

Gly Cys His Tyr Gly Val Leu Thr Cys Gly Ser Cys Lys Val Phe Phe
705                 710                 715                 720

Lys Arg Ala Val Glu Gly Gln His Asn Tyr Leu Cys Ala Gly Arg Asn
                725                 730                 735

Asp Cys Ile Ile Asp Lys Ile Arg Arg Lys Asn Cys Pro Ala Cys Arg
            740                 745                 750

Tyr Arg Lys Cys Leu Gln Ala Gly Met Ala Asn Leu Glu Ala Arg Lys
        755                 760                 765

Thr Lys Lys Lys Ile Lys Gly Ile Gln Gln Ala Thr Ala Gly Val Ser
    770                 775                 780
```

```
Gln Asp Thr Ser Glu Asn Pro Asn Lys Thr Ile Val Pro Ala Ala Leu
785                 790                 795                 800

Pro Gln Leu Thr Pro Thr Leu Val Ser Leu Leu Glu Val Ile Glu Pro
                805                 810                 815

Glu Val Leu Tyr Ala Gly Tyr Asp Ser Val Pro Asp Ser Ala Trp
            820                 825                 830

Arg Ile Met Thr Thr Leu Asn Met Leu Gly Gly Arg Gln Val Ile Ala
            835                 840                 845

Ala Val Lys Trp Ala Lys Ala Ile Leu Gly Leu Arg Asn Leu His Leu
850                 855                 860

Asp Asp Gln Met Thr Leu Leu Gln Tyr Ser Trp Met Phe Leu Met Ala
865                 870                 875                 880

Phe Ala Leu Gly Trp Arg Ser Tyr Arg Gln Ser Ser Gly Asn Leu Leu
                885                 890                 895

Cys Phe Ala Pro Asp Leu Ile Ile Asn Glu Gln Arg Met Ser Leu Pro
            900                 905                 910

Cys Met Tyr Asp Gln Cys Lys His Met Leu Phe Val Ser Ser Glu Leu
            915                 920                 925

Gln Arg Leu Gln Val Ser Tyr Glu Glu Tyr Leu Cys Met Lys Thr Leu
            930                 935                 940

Leu Leu Leu Ser Ser Val Pro Lys Glu Gly Leu Lys Ser Gln Glu Leu
945                 950                 955                 960

Phe Asp Glu Ile Arg Met Thr Tyr Ile Lys Glu Leu Gly Lys Ala Ile
                965                 970                 975

Val Lys Arg Glu Gly Asn Ser Ser Gln Asn Trp Gln Arg Phe Tyr Gln
                980                 985                 990

Leu Thr Lys Leu Leu Asp Ser Met His Glu Val Val Glu Asn Leu Leu
                995                 1000                1005

Thr Tyr Cys Phe Gln Thr Phe  Leu Asp Lys Thr Met  Ser Ile Glu
            1010                1015                1020

Phe Pro  Glu Met Leu Ala Glu  Ile Ile Thr Asn Gln  Ile Pro Lys
            1025                1030                1035

Tyr Ser  Asn Gly Asn Ile Lys  Lys Leu Leu Phe His  Gln Lys
            1040                1045                1050

<210> SEQ ID NO 68
<211> LENGTH: 158
<212> TYPE: PRT
<213> ORGANISM: Saccharomyces cerevisiae

<400> SEQUENCE: 68

Met Ser Thr Val Pro Leu Val Tyr Ser Pro Val Asp Arg Glu Pro Leu
1               5                   10                  15

His Asp Asn Ser Ala Asn Ile Lys Arg Pro Leu Gly Ser Phe Val Thr
                20                  25                  30

Ser Ser Ala Ala Cys Phe Lys Pro Leu Thr Ile Pro Gly Pro Thr Thr
            35                  40                  45

Pro Cys Ala Phe Val Met Ser Ala His Ser Ala Ile Leu Tyr Thr Pro
50                  55                  60

Ala Glu Tyr Cys Asn Leu Thr Val Leu Pro Met Ser Ala Asn Phe Leu
65                  70                  75                  80

Ser Ser Lys Ser Lys Lys Leu Tyr Leu Ala Asp Asn Ala Phe Ser Gly
                85                  90                  95

Leu Thr Val Pro Ser Met Glu Lys Ser Val Lys Ile Ser Thr Cys Val
                100                 105                 110
```

Phe Ser Lys Gln Ile Leu Gly Pro Asn Ala Ser Thr Asn Ser Ser Asn
        115                 120                 125

Ser Leu Val Val Arg Thr Ser Asn Glu Ala His Lys Phe Val Cys Phe
    130                 135                 140

Ser Cys Met Ile Leu Asn Ser Leu Ala Ala Thr Gly Leu Gly
145                 150                 155

<210> SEQ ID NO 69
<211> LENGTH: 267
<212> TYPE: PRT
<213> ORGANISM: Saccharomyces cerevisiae

<400> SEQUENCE: 69

Met Ser Lys Ala Thr Tyr Lys Glu Arg Ala Ala Thr His Pro Ser Pro
1               5                   10                  15

Val Ala Ala Lys Leu Phe Asn Ile Met His Glu Lys Gln Thr Asn Leu
            20                  25                  30

Cys Ala Ser Leu Asp Val Arg Thr Thr Lys Glu Leu Leu Glu Leu Val
        35                  40                  45

Glu Ala Leu Gly Pro Lys Ile Cys Leu Leu Lys Thr His Val Asp Ile
    50                  55                  60

Leu Thr Asp Phe Ser Met Glu Gly Thr Val Lys Pro Leu Lys Ala Leu
65                  70                  75                  80

Ser Ala Lys Tyr Asn Phe Leu Leu Phe Glu Asp Arg Lys Phe Ala Asp
                85                  90                  95

Ile Gly Asn Thr Val Lys Leu Gln Tyr Ser Ala Gly Val Tyr Arg Ile
            100                 105                 110

Ala Glu Trp Ala Asp Ile Thr Asn Ala His Gly Val Val Gly Pro Gly
        115                 120                 125

Ile Val Ser Gly Leu Lys Gln Ala Ala Glu Glu Val Thr Lys Glu Pro
    130                 135                 140

Arg Gly Leu Leu Met Leu Ala Glu Leu Ser Cys Lys Gly Ser Leu Ser
145                 150                 155                 160

Thr Gly Glu Tyr Thr Lys Gly Thr Val Asp Ile Ala Lys Ser Asp Lys
                165                 170                 175

Asp Phe Val Ile Gly Phe Ile Ala Gln Arg Asp Met Gly Gly Arg Asp
            180                 185                 190

Glu Gly Tyr Asp Trp Leu Ile Met Thr Pro Gly Val Gly Leu Asp Asp
        195                 200                 205

Lys Gly Asp Ala Leu Gly Gln Gln Tyr Arg Thr Val Asp Asp Val Val
    210                 215                 220

Ser Thr Gly Ser Asp Ile Ile Ile Val Gly Arg Gly Leu Phe Ala Lys
225                 230                 235                 240

Gly Arg Asp Ala Lys Val Glu Gly Glu Arg Tyr Arg Lys Ala Gly Trp
                245                 250                 255

Glu Ala Tyr Leu Arg Arg Cys Gly Gln Gln Asn
            260                 265

<210> SEQ ID NO 70
<211> LENGTH: 286
<212> TYPE: PRT
<213> ORGANISM: Saccharomyces cerevisiae

<400> SEQUENCE: 70

Met Ser Ile Gln His Phe Arg Val Ala Leu Ile Pro Phe Phe Ala Ala
1               5                   10                  15

-continued

```
Phe Cys Leu Pro Val Phe Ala His Pro Glu Thr Leu Val Lys Val Lys
            20              25              30

Asp Ala Glu Asp Gln Leu Gly Ala Arg Val Gly Tyr Ile Glu Leu Asp
            35              40              45

Leu Asn Ser Gly Lys Ile Leu Glu Ser Phe Arg Pro Glu Glu Arg Phe
            50              55              60

Pro Met Met Ser Thr Phe Lys Val Leu Leu Cys Gly Ala Val Leu Ser
65              70              75              80

Arg Ile Asp Ala Gly Gln Glu Gln Leu Gly Arg Arg Ile His Tyr Ser
            85              90              95

Gln Asn Asp Leu Val Glu Tyr Ser Pro Val Thr Glu Lys His Leu Thr
            100             105             110

Asp Gly Met Thr Val Arg Glu Leu Cys Ser Ala Ala Ile Thr Met Ser
            115             120             125

Asp Asn Thr Ala Ala Asn Leu Leu Leu Thr Thr Ile Gly Gly Pro Lys
            130             135             140

Glu Leu Thr Ala Phe Leu His Asn Met Gly Asp His Val Thr Arg Leu
145             150             155             160

Asp Arg Trp Glu Pro Glu Leu Asn Glu Ala Ile Pro Asn Asp Glu Arg
            165             170             175

Asp Thr Thr Met Pro Val Ala Met Ala Thr Thr Leu Arg Lys Leu Leu
            180             185             190

Thr Gly Glu Leu Leu Thr Leu Ala Ser Arg Gln Gln Leu Ile Asp Trp
            195             200             205

Met Glu Ala Asp Lys Val Ala Gly Pro Leu Leu Arg Ser Ala Leu Pro
210             215             220

Ala Gly Trp Phe Ile Ala Asp Lys Ser Gly Ala Gly Glu Arg Gly Ser
225             230             235             240

Arg Gly Ile Ile Ala Ala Leu Gly Pro Asp Gly Lys Pro Ser Arg Ile
            245             250             255

Val Val Ile Tyr Thr Thr Gly Ser Gln Ala Thr Met Asp Glu Arg Asn
            260             265             270

Arg Gln Ile Ala Glu Ile Gly Ala Ser Leu Ile Lys His Trp
275             280             285
```

RECOMBINANT PRION-LIKE PROTEINS AND MATERIALS COMPRISING SAME

This application claims priority benefit of U.S. Provisional Application No. 60/138,833, filed Jun. 9, 1999, incorporated herein by reference.

ACKNOWLEDGMENT OF U.S. GOVERNMENT SUPPORT

This invention was made with U.S. Government support under Research Grant GM-25874 awarded by the National Institutes of Health. The U.S. Government has certain rights in this invention.

FIELD OF THE INVENTION

The present invention relates generally to the fields of genetics and cellular and molecular biology. More particularly, the invention relates to amyloid or fibril-forming proteins and the genes that encode them, and especially to prion-like proteins and protein domains and the genes that encode them.

DESCRIPTION OF RELATED ART

Prions (protein infectious particles) have been implicated in both human and animal spongiform encephalopathies, including Creutzfeldt-Jakob Disease, kuru, Gerstmann-Strassler-Scheinker Disease, and fatal familial insomnia in humans; the recently-publicized "mad cow disease" in bovines; "scrapie," which afflicts sheep and goats; transmissible mink encephalopathy; chronic wasting disease of mule, deer, and elk; and feline spongiform encephalopathy. See generally S. Prusiner et al., *Cell,* 93: 337-348 (1998); S. Prusiner, *Science,* 278:245-251 (1997); and A. Horwich and J. Weissman, *Cell,* 89: 499-510 (1997). A currently-accepted theory is that a prion protein (PrP) can exist in at least two conformational states: a normal, soluble cellular form ($PrP^C$) containing little β-sheet structure; and a "scrapie" form ($PrP^{Sc}$) characterized by significant β-sheet structure, insolubility, and resistance to proteases. Prion particles comprise multimers of the $PrP^{Sc}$ form. Prion formation has been compared and contrasted to amyloid fibril formation that has been observed in other disease states, such as Alzheimer's disease. See J. Harper & P. Lansbury, *Annu. Rev. Biochem,* 66: 385-407 (1997). More generally, the prion protein has been loosely classified (despite "some significant differences") as one of at least sixteen known human amyloidogenic proteins that, in an altered conformation, assemble into a fibril-like structure. See J. W. Kelly, *Curr. Opin. Struct. Biol.,* 6: 11-17 (1996), incorporated herein by reference.

There is growing patent and journal literature relating to scientists efforts to develop diagnostic, therapeutic, and prophylactic advances in the area of prion disease. For example, Fishleigh et al., U.S. Pat. No. 5,773,572 describes synthetic peptides that have at least one antigenic site of a prion protein, and suggest using such peptides to raise antibodies and to create vaccines. Prusiner et al., U.S. Pat. No. 5,750,361 describes prion protein peptides having at least one α-helical domain and forming a random coil conformation in aqueous medium, and suggests using such a peptide to assay for the scrapie form of prion protein ($PrP^{Sc}$).

Weiss et al., *J. Virology,* 69(8): 4776-83 (1995) state that isolation of $PrP^C$ from organisms has been a time-consuming and labor-intensive process. The authors purport to describe the synthesis of Syrian golden hamster prion protein as a fusion with glutathione S-transferase (GST) to enhance solubility and stability of $PrP^C$, and the release of $PrP^C$ from the fusion protein via thrombin cleavage. The authors report that only the cellular isoform $PrP^C$, and not the infectious $PrP^{Sc}$ isoform, was produced. [See also Volkel et al., *Eur. J. Biochem,* 251:462-471 (1998); Meeker et al., *Proteins: Structure, Function, and Genetics,* 30: 381-387 (1998) (Describing system to overexpress a fusion between the small, minimally soluble serum amyloid A protein and the bacterial enzyme Staphylococcal nuclease; and Zahn et al., *FEBS Lett.,* 417(3): 400-404 (1997) (reporting expression of human PrP proteins fused to a histidine tail to facilitate refolding).]

Prusiner et al., U.S. Pat. Nos. 5,792,901, 5,789,655, and 5,763,740 describe a transgenic mouse comprising a prion protein gene that includes codons from a PrP gene that is native to a different host organism, such as humans, and suggest uses of such mice for prion disease research. The '655 patent teaches to incorporate "a strong epitope tag" in the PrP nucleotide sequence to permit differentiation of PrP protein conformations using an antibody to the epitope. The patents describing these native mutated, and chimeric PrP gene and protein sequences are incorporated herein by reference. Mouthon et al., *Mol. Cell. Neurosci.,* 11(3):127-133 (1998) report using a fusion between a putative nuclear localization signal of PrP and a green fluorescent protein to study targeting of the protein to the nuclear compartment.

Weissmann et al., U.S. Pat. No. 5,698,763, describes a transgenic mouse in which the PrP gene has been disrupted by homologous recombination, allegedly rendering the mouse non-susceptible to spongiform encephalopathies. Use of PrP anti-sense oligonucleotides to treat non-transgenic animals suffering from an incipient spongiform encephalopathy also is suggested.

Cashman et al., International Publication No. WO 97/45746, purports to describe prion protein binding proteins and uses thereof, e.g., to detect and treat prion-related diseases or to decontaminate samples known to contain or suspected of containing prion proteins. The authors also purport to describe a fusion protein having a PrP portion and an alkaline phosphatase portion, for use as an affinity reagent for labeling, detection, identification, or quantitation of PrP binding proteins or $PrP^{Sc}$'s in a biological sample, or for use to facilitate the affinity purification of PRP binding proteins.

In addition, there has been significant research in recent years concerning the biology of prion-like elements in yeast. [See, e.g., V. Kushnirov and M. Ter-Avanesyan, *Cell,* 94: 13-16 (1998); S. Lindquist, *Cell,* 89: 495-498 (1997); DePace et al., Cell, 93: 1241-1252 (1998); and R. Wickner, *Annu. Rev. Genet.,* 30:109-139 (1996) (all incorporated herein by reference).] Although the two yeast prion-like elements that have been extensively studied do not spread from cell to cell (except during mating or from mother-to-daughter cell) and do not kill the cells harboring them, as has been observed in the case of mammalian PrP prion diseases, certain heritable yeast phenotypes exist that display a very "prion-like" character. The phenotypes appear to arise as the result of the ability of a "normal" yeast protein that has acquired an abnormal conformation to influence other proteins of the same type to adopt the same conformation. Such phenotypes include the [PSI⁺] phenotype, which enhances the suppression of nonsense codons, and the [URE3] phenotype, which interferes with the nitrogen-mediated repression of certain catabolic enzymes. Both phenotypes exhibit cytoplasmic inheritance by daughter cells from a mother cell and are passed to a mating partner of a [PSI⁺] or [URE3] cell.

Yeast organisms present, in many respects, far easier systems than mammals in which to study genotype and phenotype relationships, and the study of the [PSI⁺] and [URE3] phenotypes in yeast has provided significant valuable information regarding prion biology. Studies have implicated the Sup35 subunit of the yeast translation termination factor and the Ure2 protein that antagonizes the action of a nitrogen-regulated transcription activator in the [PSI⁺] and [URE3] phenotypes, respectively. In both of these proteins, the above-stated "normal" biological functions reside in the carboxy-terminal domains, whereas the dispensable, amino-terminal domains have unusual compositions rich in asparagine and glutamine residues.

It is the amino-terminal domains of these proteins (e.g., no more than about residues 2-113 of Sup35 and about residues 1-65 of Ure2) that have been implicated in conferring the [PSI⁺] and [URE3] phenotypes in a prion-like manner. King et al., *Proc. Natl. Acad Sci USA*, 94:6618-6622 (1997), purportedly expressed the N-terminal 114 residues of SUP35 (with a cleavable polyhistidine tag for purification) and reported that this peptide spontaneously aggregates to form thin filaments showing a β-sheet-type circular dichroism in vitro. Deletion of the amino termini of Sup35 and Ure2 in yeast eliminates the [PSI⁺] and [URE3] phenotypes, respectively. In contrast, over-expression of these proteins, or of their amino-terminal fragments, can induce the [PSI⁺] or [URE3] phenotype de novo. Once cells have acquired the [PSI⁺] or [URE3] phenotype in this manner, they continue to pass the trait to their progeny, even after the plasmid containing the over-expressed element is lost. [See Derkatch et al., *Genetics*, 144:1375-1386 (1996).]

Interestingly, the Sup35 protein contains similarities to mammalian PrP proteins in that Sup35 is soluble in [psi−] strains but prone to aggregate into insoluble, protease-resistant aggregates in [PSI⁺] strains. In experiments using a fusion between the Sup35 amino terminus and green fluorescent protein (GFP, a protein that fluoresces green on exposure to blue light), it has been shown that the fusion protein is freely distributed in [psi−] cells but aggregated in [PSI⁺] cells. See, e.g., Glover et al., *Cell*, 89: 811-819(1997); and Patino et al., *Science*, 273: 622-626(1997). Chaperone proteins or "heat shock proteins," such as the protein Hsp104 in yeast, have been implicated in the conformational conversion of Sup35 protein that is associated with the [PSI⁺] phenotype [see, e.g., J. Glover and S. Lindquist, *Cell*, 94: 73-82 (1998); V. Kushnirov and M. Ter-Avanesyan, *Cell*, 94:13-16 (1998); Y. O. Chernoff et al., *Science*, 268: 880-883 (1995)], and may be implicated in the conformational conversion of PrP. See, e.g., E. Schirmer and S. Lindquist, *Proc. Natl. Acad. Sci. USA*, 94: 13932-13937 (1997); S. DebBurman et al., *Proc. Natl. Acad. Sci. USA*, 94: 13938-13943 (1997).

As the foregoing discussion of literature indicates, there has been significant investigation into the biology of mammalian prions and prion-like yeast proteins for the purposes of developing a basic understanding of prion biology and developing effective measures for diagnosing, treating, and preventing mammalian prion diseases. Practical applications for prion and prion-like gene and proteins, in addition to the immediate medical implications of diagnosing, treating, and preventing spongiform encepalopathies and other amyloid diseases, is lacking.

SUMMARY OF THE INVENTION

The present invention is believed to be the first invention directed to employing unique features of prion biology in a practical context beyond fundamental prion research and applied research directed to the development of diagnostic, therapeutic, and prophylactic treatments of mammalian prion diseases (although aspects of the invention have utility in such contexts also). Likewise, the present invention is believed to be the first invention relating to the construction of novel prion-like elements that can change the phenotype of a cell in a beneficial way.

In one aspect, the invention provides a polynucleotide comprising a nucleotide sequence that encodes a chimeric polypeptide, the polynucleotide comprising: a nucleotide sequence encoding at least one SCHAG amino acid sequence fused in frame with a nucleotide sequence encoding at least one polypeptide of interest other than a marker protein, or a glutathione S-transferase (GST) protein, or a staphylococcal nuclease protein. In a preferred embodiment, the polynucleotide has been purified and isolated. In another preferred embodiment, the polynucleotide is stably transformed or transfected into a living cell.

By "chimeric polypeptide" is meant a polypeptide comprising at least two distinct polypeptide segments (domains) that do not naturally occur together as a single protein. In preferred embodiments, each domain contributes a distinct and useful property to the polypeptide. Polynucleotides that encode chimeric polypeptides can be constructed using conventional recombinant DNA technology to synthesize, amplify, and/or isolate polynucleotides encoding the at least two distinct segments, and to ligate them together. See, e.g., Sambrook et al., *Molecular Cloning—A Laboratory Manual*, Second Ed., Cold Spring Harbor Press (1989); and Ausubel et al., *Current Protocols in Molecular Biology*, John Wiley & Sons, Inc. (1998); both incorporated herein by reference.

The chimeric polypeptide comprises a SCHAG amino acid sequence as one of its polypeptide segments. By "SCHAG amino acid sequence" is meant any amino acid sequence which, when included as part or all of the amino acid sequence of a protein, can cause the protein to coalesce with like proteins into higher ordered aggregates commonly referred to in scientific literature by terms such as "amyloid," "amyloid fibers," "amyloid fibrils," "fibrils," or "prions." In this regard, the term SCHAG is an acronym for Self-Coalesces into Higher-ordered AGgregates. By "higher ordered" is meant an aggregate of at least 25 polypeptide subunits, and is meant to exclude the many proteins that are known to comprise polypeptide dimers, tetramers, or other small numbers of polypeptide subunits in an active complex. The term "higher-ordered aggregate" also is meant to exclude random agglomerations of denatured proteins that can form in non-physiological conditions. [From the term "self-coalesces," it will be understood that a SCHAG amino acid sequence may be expected to coalesce with identical polypeptides and also with polypeptides having high similarity (e.g., less than 10% sequence divergence) but less than complete identity in the SCHAG sequence.] It will be understood than many proteins that will self-coalesce into higher-ordered aggregates can exist in at least two conformational states, only one of which is typically found in the ordered aggregates or fibrils. The term "self-coalesces" refers to the property of the polypeptide to form ordered aggregates with polypeptides having an identical amino acid sequence under appropriate conditions as taught herein, and is not intended to imply that the coalescing will naturally occur under every concentration or every set of conditions. In fact, data exists suggesting that trans-acting factors, such as chaperone proteins, may be involved in the protein's conformational switching, in vivo.) Aggregates formed by SCHAG polypeptides typically are rich in β-sheet structure, as demonstrated by circular dichroism; bind Congo red dye and give a characteristic spectral shift in polarized light; and are insoluble in water or in solutions mimicking the physiological salt concentrations of the native cells in which the aggregates originate. In preferred embodiments the SCHAG polypeptides self-coalesce to form amyloid fibrils that typically are 5-20 nm in width and display a "cross-β" structure, in which the individual β strands of the component proteins are oriented perpendicular to the axis of the fibril. The SCHAG amino acid sequence may be said to constitute an "amyloidogenic domain" or "fibril-aggregation domain" of a protein because a SCHAG amino sequence confers this self-coalescing property to proteins which include it.

Exemplary SCHAG amino acid sequences include sequences of any naturally occurring protein that has the ability to aggregate into amyloid-type ordered aggregates under physiological conditions, such as inside of a cell. In one preferred embodiment, the SCHAG amino acid sequence includes the sequences of only that portion of the protein responsible for the aggregation behavior. Many such sequences have been identified in humans and other animals, including amyloid β protein (residues 1-40, 1-41, 1-42, or 1-43), associated with Alzheimer's disease; immunoglobulin light chain fragments, associated with primary systemic amyloidosis; serum amyloid A fragments, associated with secondary systemic amyloidosis; transthyretin and transthyretin fragments, associated with senile systemic amyloidosis and familial amyloid polyneuropathy I; cystatin C fragments, associated with hereditary cerebral amyloid angiopathy; $β_2$-microglobulin, associated with hemodialysis-related amyloidosis; apolipoprotein A-1 fragments, associated with familial amyloid polyneuropathy III; a 71 amino acid fragment of gelsolin, associated with Finnish hereditary systemic amyloidosis; islet amyloid polypeptide fragments, associated with Type II diabetes; calcitonin fragments, associated with medullary carcinoma of the thyroid; prion protein and fragments thereof, associated with spongiform encephalopathies; atrial natriuretic factor, associated with atrial amyloidosis; lysozyme and lysozyme fragments, associated with hereditary non-neuropathic systemic amyloidosis; insulin, associated with injection-localized amyloidosis; and fibrinogen fragments, associated with hereditary renal amyloidosis. See J. W. Kelly, *Curr. Op. Struct. Biol.*, 6:11-17 (1996), incorporated herein by reference. In addition, several other SCHAG amino acid sequences of yeast and fungal origin are described in detail below. Also, the Examples below set forth in detail how to use the SCHAG sequences specifically identified herein or elsewhere in the literature to screen databases or genomes for additional naturally occurring SCHAG amino acid sequences. The Examples also provide assays to screen candidate SCHAG sequences for prion-like properties. In addition, the Examples provide assays to rapidly screen random DNA fragments to determine whether they encode a SCHAG amino acid sequence. Such screening assays are themselves considered aspects of the invention.

In addition, SCHAG amino acid sequences include those sequences derived from naturally occurring SCHAG amino acid sequences by addition, deletion, or substitution of one or more amino acids from the naturally occurring SCHAG amino acid sequences. Detailed guidelines for modifying SCHAG amino acid sequences to produce synthetic SCHAG amino acid sequences are described below. Modifications that introduce conservative substitutions are specifically contemplated for creating SCHAG amino acid sequences that are equivalent to naturally occurring sequences. By "conservative amino acid substitution" is meant substitution of an amino acid with an amino acid having a side chain of a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine). Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm.C. Brown Publishers (1993).

Also contemplated are modifications to naturally occurring SCHAG amino acid sequences that result in addition or substitution of polar residues (especially glutamine and asparagine, but also serine and tyrosine) into the amino acid sequence. Certain naturally occurring SCHAG amino acid sequences are characterized by short, sometimes imperfect repeat sequences of, e.g., 5-12 residues. Modifications that result in substantial duplication of such repetitive oligomers are specifically contemplated for creating SCHAG amino acid sequences, too.

In another variation of the invention, the SCHAG amino acid sequence is encoded by a polynucleotide that hybridizes to any of the nucleotide sequences of the invention; or the non-coding strands complementary to these sequences, under the following exemplary moderately stringent hybridization conditions:

(a) hybridization for 16 hours at 42° C. in an aqueous hybridization solution comprising 50% formamide, 1% SDS, 1 M NaCl, 10% Dextran sulphate; and (b) washing 2 times for 30 minutes at 60° C. in an aqueous wash solution comprising 0.1% SSC, 1% SDS. Alternatively, highly stringent conditions include washes at 68° C.

Also provided are purified and isolated polynucleotide comprising a nucleotide sequence that encodes at least one SCHAG amino acid sequence, wherein the SCHAG-encoding portion of the polynucleotide is at least about 99%, at least about 98%, at least about 95%, at least about 90%, at least about 85%, at least about 80%, at least about 75%, or at least about 70% identical over its full length to one of the nucleotide sequences of the invention. Methods of screening for natural or artificial sequences for SCHAG properties are also described elsewhere herein.

A preferred category of SCHAG amino acid sequences are prion aggregation domains from prion proteins. The term "prion-aggregation domain" is intended to define a subset of SCHAG amino acid sequences that can exist in at least two conformational states, only one of which is typically found in the aggregated state. In one conformational state, proteins comprising the prion-aggregation domain or fused to the prion-aggregation domain perform their normal function in a cell, and in another conformational state, the native proteins form aggregates (prions) that phenotypically alter the cell, perhaps by sequestering the protein away from its normal site of subcellular activity, or by disrupting the conformation of an active domain of the protein, or by changing its activity state, or bay acquiring a new activity upon aggregation, or perhaps merely by virtue of a detrimental effect on the cell of the aggregate itself. A hallmark feature of prion-aggregation domains is that the phenotypic alteration that is associated with prion formation is heritable and/or transmissible: prions are passed from mother to daughter cell or to mating partners in organisms such as in the case of yeast Sup35, and Ure2 prions, perpetuating the [PSI+] or [URE3] prion phenotypes, or the prions are transmitted in an infectious manner in organisms such as in the case of PrP prions in mammals, leading to transmissible spongiform encephalopathies. This defining characteristic of prions is attributable, at least in part, to the fact that the aggregated prion protein is able to promote the rearrangement of unaggregated protein into the aggregated conformation (although chaperone-type proteins or other trans-acting factors in the cell may also assist with this conformational change). It is likewise a feature of prion-aggregation domains that over-production of proteins comprising these domains increases the frequency with which the prion conformation and phenotype spontaneously arises in cells.

Prion aggregation amino acid sequences comprising amino terminal sequences derived from yeast or fungal Sup35 proteins, Ure2 proteins, or the carboxy terminal sequences derived from yeast Rnq1 proteins are among those that are highly preferred. Referring to the *S. cerevisiae* Sup35 amino acid sequence set forth in SEQ ID NO: 2, experiments have shown that no more than amino acids 2-113 (the N domain) of that sequence are required to confer some prion aggregation properties to a protein, although inclusion of the charged "M" (middle) region immediately downstream of these residues, e.g., thru residue 253, is preferred in some embodiments. The N domain alone is very amyloidogenic and immediately aggregates into fibers, even in the presence of 2 M urea, a phenomenon that is desirable in embodiments of the invention where formation of stable fibrils of chimeric polypeptides is preferred. When the N domain is fused to the highly charged M domain, fiber formation proceeds in a slower, more orderly way. The M domain is postulated to shift the equilibrium to permit greater "switchability" between aggregated and soluble forms, and is preferably included where phenotypic switching is desirable. Referring to the *S. cereviciae* Ure2 amino acid sequence set forth in SEQ ID NO: 4, experiments have shown that no more than amino acids 2-65 of that sequence are required to confer prion aggregation activity to a protein. Referring to the *S. cereviciae* Rnq1 amino acid sequence set forth in SEQ ID NO: 50, experiments have shown that no more than amino acids 153-405 of that sequence are required to confer prion aggregation activity to a protein. Moreover, sequences differing from the native sequences by the addition, deletion, or substitution of 1, 2, 3, 4, 5, 6, 7, 8, 9, 10, 11, 12, 13, 14, 15, 16, 17, 18, 19, 20, or more amino acids, especially the addition or substitution of additional glutamine or asparagine residues, but which retain the properties of prion-aggregation domains as described in the preceding paragraph, are contemplated. Also, orthologs (corresponding proteins or prion aggregation domains thereof from different species) comprise an additional genus of preferred sequences (Kushinov et al., *Yeast* 6:461-472 (1990); Chernoff et al., *Mol Microbiol* 35:865-876 (2000); Santoso et al., *Cell* 100:277-288 (2000); and Kushinov et al, *EMBO J.* 19:324-31 (2000)). By way of example, Sup35 amino acid sequences from *Pichia pinus* and *Candida albicans* are set forth in Genbank Accession Nos. X56910 (SEQ ID NO: 46) and AF 020554 (SEQ ID NO: 47), respectively. Polypeptides of the invention include polypeptides that are encoded by polynucleotides that hybridize under stringent, preferably highly stringent conditions, to the polynucleotide sequences of the invention, or the non-coding strand thereof. Polypeptides of the invention also include polypeptides that are at least about 99%, at least about 98%, at least about 95%, at least about 90%, at least about 85%, at least about 80%, at least about 75%, or at least about 70% identical to one of SCHAG amino acid sequences of the invention.

As set forth above, in some aspects of the invention, the nucleotide sequence encoding the SCHAG amino acid sequence of the polypeptide is fused in frame with a nucleotide sequence encoding at least one polypeptide of interest. By "in frame" is meant that when the nucleotide is transformed into a host cell, the cell can transcribe and translate the nucleotide sequence into a single polypeptide comprising both the SCHAG amino acid sequence and the at least one polypeptide of interest. It is contemplated that the nucleotide sequences can be joined directly; or that the nucleotide sequences can be separated by additional codons. Such additional codons may encode an endopeptidase recognition sequence or a chemical recognition sequence or the like, to permit enzymatic or chemical cleavage of the SCHAG amino acid sequence from the polypeptide of interest, to permit isolation of the polypeptide of interest. Preferred recognition sequences are sequences that are not found in the polypeptide of interest, so that the polypeptide of interest is not internally cleaved during such isolation procedures. It will be understood that modification of the polypeptide of interest to eliminate internal recognition sequences may be desirable to facilitate subsequent cleavage from the SCHAG amino acid sequence. Suitable enzymatic cleavage sites include: the amino acid sequences $-(Asp)_n$-Lys-, wherein n signifies 2, 3 or 4, recognized by the protease enterokinase; -Ile-Glu-Gly-Arg-, recognized by coagulation factor $X_a$; an arginine residue or a lysine residue cleaved by trypsin; a lysine residue cleaved by lysyl endopeptidase; a glutamine residue cleaved by V8 protease, and a glu-asn-leu-tyr-phe-gln-gly site recognized by the tobacco etch virus (TEV) protease. Suitable chemical cleavage sites include tryptophan residues cleaved by 3-bromo-3-methyl-2-(2-nitrophenylmercapto)-3H-indole; cysteine residues cleaved by 2-nitroso-5-thiocyano benzoic acid; the dipeptides -Asp-Pro- or -Asn-Gly- which can be cleaved by acid and hydroxylamine, respectively; and a methionine residue which is specifically cleaved by cyanogen bromide (CNBr). In another variation, the additional codons comprise self-splicing intein sequences that can be activated, e.g., by adjustments to pH. See Chong et al., *Gene,* 192:27-281 (1997).

Additional codons also may be included between the sequence encoding the prion aggregation amino acid sequence and the sequence encoding the protein of interest to provide a linker amino acid sequence that serves to spatially separate the SCHAG amino acid sequence from the polypeptide of interest. Such linkers may facilitate the proper folding of the polypeptide of interest, to assure that it retains a desired biological activity even when the protein as a whole has formed aggregates with other proteins containing the SCHAG amino acid sequence. Also, additional codons may be included simply as a result of cloning techniques, such as ligations and restriction endonuclease digestions, and strategic introduction of restriction endonuclease recognition sequences into the polynucleotide.

In still another variation, the additional codons comprise a hydrophilic domain, such as the highly-charged M region of yeast Sup35 protein. While the N domain of Sup35 has proven sufficient in some cases to effect prion-like behavior, suggesting that the M region is not absolutely required in all cases, it is contemplated that the M region or a different peptide that includes hydrophilic amino acid side chains will in some cases be helpful for modulating prion-like character of chimeric peptides of the invention. Without intending to be limited to a particular theory, the highly charged M domain is thought to act as a "solublization" domain involved in modulating the equilibrium between the soluble and the aggregate forms of Sup35, and these properties may be advantageously adapted for other SCHAG sequences.

By "polypeptide of interest" is meant any polypeptide that is of commercial or practical interest and that comprises an amino acid sequence encodable by the codons of the universal genetic code. Exemplary polypeptides of interest include: enzymes that may have utility in chemical, food-processing (e.g., amylases), or other commercial applications; enzymes having utility in biotechnology applications, including DNA and RNA polymerases, endonucleases, exonucleases, peptidases, and other DNA and protein modifying enzymes; polypeptides that are capable of specifically binding to compositions of interest, such as polypeptides that act as intracellular or cell surface receptors for other polypeptides, for steroids, for carbohydrates, or for other biological molecules; polypeptides that comprise at least one antigen binding domain of an antibody, which are useful for isolating that antibody's antigen; polypeptides that comprise the ligand binding domain of a ligand binding protein (e.g., the ligand binding domain of a cell surface receptor); metal binding proteins (e.g., ferritin (apoferritin), metallothioneins, and other metalloproteins), which are useful for isolating/purifying metals from a solution containing them for metal recovery or for remediation of the solution; light-harvesting proteins (e.g., proteins used in photosynthesis that bind pigments); proteins that can spectrally alter light (e.g., proteins that absorb light at one wavelength and emit light at another wavelength); regulatory proteins, such as transcription factors and translation factors; and polypeptides of therapeutic value, such as chemokines, cytokines, interleukins, growth factors, interferons, antibiotics, immunopotentiators and immunosuppressors, and angiogenic or anti-angiogenic peptides.

However, specifically excluded from the scope of the invention are chimeric polynucleotides that have heretofore been described in the literature. For example, excluded from the scope of the invention are polynucleotides encoding a fusion consisting essentially of a SCHAG domain of a characterized protein fused in-frame to only: (1) a marker protein such as a fluorescing protein (e.g., green fluorescent protein or firefly luciferase), an antibiotic resistance-conferring protein, a protein involved in a nutrient metabolic pathway that has been used in the literature for selective growth on incomplete growth media, or a protein (e.g., β-galactosidase, an alkaline phosphatase, or a horseradish peroxidase) involved in a metabolic or enzymatic pathway of a chromogenic or luminescent substrate that results in the production of a detectable chromophore or light signal that has been used in the literature for identification, selection, or quantitation; or (2) a protein (e.g., glutathione S-transferase or Staphylococcal nuclease) that has been used in the literature as a fusion partner for the express purpose of facilitating expression or purification of other proteins. Notwithstanding this exclusion of certain products from the invention, the inventors contemplate novel uses of such specifically excluded products as aspects of the present invention. Moreover, polynucleotides that include a SCHAG sequence, and sequence encoding a polypeptide of interest, and a sequence encoding a marker protein such as green fluorescent protein are considered within the scope of the invention. Also, notwithstanding the above exclusion, polynucleotides that encode polypeptides whose SCHAG properties are described herein for the first time, fused to a marker protein, are considered within the scope of the invention. Also, purified fusion polypeptides that have been described in the literature and examined only in vivo, but never purified, are intended as aspects of the invention. For example, isolated fibers comprising polypeptides encoding a fusion protein consisting of essentially one or more SCHAG sequences fused to a marker protein, e.g., GFP are contemplated. Several such examples are provided in Example 5.

The encoding sequences of the polynucleotide may be in either order, i.e., the SCHAG amino acid encoding sequence may be upstream (5') or downstream (3') of the sequence, such that the SCHAG amino acid sequence of the resultant protein is disposed at an amino-terminal or carboxyl-terminal position relative to the protein of interest. In the case of SCHAG amino acid sequences identified or derived from sequences in nature, the encoding sequences preferably are ordered in a manner mimicking the order of the polypeptide from which the SCHAG amino acid sequence was derived. For example, the yeast Sup35 protein has an amino terminal SCHAG domain and a carboxy-terminal domain containing Sup35 translation termination activity. Thus, in embodiments of the invention where the SCHAG amino acid encoding sequence is derived from a Sup35 protein, this sequence preferably is disposed upstream (5') of the sequence encoding the at least one polypeptide of interest. In embodiments wherein the fibril-aggregation amino acid encoding sequence is derived from the sequence set forth in Genbank Accession No. p25367 (SEQ ID NO: 29) (where the prion-like domain is C-terminal), this sequence is preferably disposed downstream (3') of the sequence encoding the at least one polypeptide of interest. In an embodiment comprising sequences encoding two or more polypeptides of interest, the SCHAG encoding sequence may be disposed between the two polypeptides of interest.

To the extent that such sequences are not already inherent in the above-described polynucleotides, it will be understood that such polynucleotides preferably further comprise a translation initiation codon fused in frame and upstream (5') of the encoding sequences, and a translation stop codon fused in frame and downstream (3') of the encoding sequences. Also, it may be desirable in some embodiments to direct a host cell to secrete the chimeric polypeptide. Thus, it is contemplated that the polynucleotide may further comprise a nucleotide sequence encoding a translation initiation codon and a secretory signal peptide fused in frame and upstream of the encoding sequences.

In preferred embodiments, the polynucleotide of the invention further comprises additional sequences to facilitate and/or control expression in selected host cells. For example, the polynucleotide includes a promoter and/or an enhancer sequence operatively connected upstream (5') of the encoding sequences, to promoter expression of the encoding sequences in the selected host cell; and/or a polyadenylation signal sequence operatively connected downstream (3') of the encoding sequences. Since concentration is a factor that may influence the aggregation state of encoded chimeric polypeptides, regulatable (e.g., inducible and repressible) promoters are highly preferred.

To facilitate identification of cells that have been successfully transformed/transfected with the polynucleotide of the invention, the polynucleotide may further include a sequence encoding a selectable marker protein. The selectable marker may be a completely distinct open reading frame on the polynucleotide, such as an open reading frame encoding an antibiotic resistance protein or a protein that facilitates survival in a selective nutrient medium. The selectable marker also may itself be part of the chimeric polypeptide of the invention. In one embodiment, a visual marker such as a fluorescent protein (e.g., green fluorescent protein) is used that is distributed in the cell in a different manner when the protein is in the prion form than when the protein is in the non-prion form. In either case, cells comprising the selectable marker can be sorted, e.g., using techniques such as fluorescence activated cell sorting. Thus, this marker, in addition to permitting selection of transformed or transfected cells, also permits identification of the conformational state of the chimeric polypeptide. In another embodiment, the marker has two components: 1) a function that is changed when the protein is in a prion form and 2) a visual or selectable marker for that function. An example is the glucocorticoid receptor, GR and a reporter gene. GR is a transcription factor that binds to a specific DNA sequence to activate transcription. When this DNA sequence is fused to the coding sequence for an easily detected protein such as β-galactosidase or luciferase GR function can be easily assayed by the induction of the β-galactosidase or luciferase proteins.

Optionally, the polynucleotide of the invention further includes an epitope tag fused in frame with the encoding sequences, which tag is useful to facilitate detection in vivo or in vitro and to facilitate purification of the chimeric polypeptide or of the protein of interest after it has been cleaved from the SCHAG amino acid sequence of the chimeric polypeptide. (An epitope tag alone is not considered to constitute a polypeptide of interest.) A variety of natural or artificial heterologous epitopes are known in the art, including artificial epitopes such as FLAG, Strep, or poly-histidine peptides. FLAG peptides include the sequence Asp-Tyr-Lys-Asp-Asp-Asp-Asp-Lys (SEQ ID NO: 5) or Asp-Tyr-Lys-Asp-Glu-Asp-Asp-Lys (SEQ ID NO: 6). [See generally Brewer, *Bioprocess. Technol.*, 2: 239-266 (1991); Kunz, *J. Biol. Chem.*, 267: 9101-9106 (1992); Brizzard et al., *Biotechniques* 16: 730-735 (1-994); Schafer, *Biochem. Biophys. Res. Commun.*, 207: 708-714 (1995).] The Strep epitope has the sequence Ala-Trp-Arg-His-Pro-Gln-Phe-Gly-Gly (SEQ ID NO: 7). [See Schmidt, *J. Chromatography*, 676: 337-345 (1994).] Another commonly used artificial epitope is a poly-His sequence having six consecutive histidine residues. Commonly used naturally-occurring epitopes include the influenza virus hemagglutinin sequence Tyr-Pro-Tyr-Asp-Val-Pro-Asp-Tyr-Ala-Ile-Glu-Gly-Arg (SEQ ID NO: 8) and truncations thereof, which is recognized by the monoclonal antibody 12CA5 [Murray et al., *Anal. Biochem.*, 229: 170-179 (1995)] and the sequence (Glu-Gln-Lys-Leu-Leu-Ser-Glu-Glu-Asp-Leu-Asn) (SEQ ID NO: 9) from human c-myc, which is recognized by the monoclonal antibody 9E10 (Manstein et al., *Gene*, 162: 129-134 (1995)).

In another embodiment, the polynucleotide includes 5' and 3' flanking regions that have substantial sequence homology with a region of an organism's genome. Such sequences facilitate introduction of the chimeric gene into the organism's genome by homologous recombination techniques.

In yet another aspect, the invention provides a polynucleotide comprising a nucleotide sequence that encodes a chimeric polypeptide, the chimeric polypeptide comprising an amyloidogenic domain that causes the polypeptide to aggregate with polypeptides sharing an identical or nearly identical domain into ordered aggregates such as fibrils, fused to a domain comprising a polypeptide of interest; wherein the amyloidogenic domain comprises an amyloidogenic amino acid sequence of a naturally occurring protein and further includes a duplication of at least a portion of the naturally occurring amyloidogenic amino acid sequence, the duplication increasing the amyloidogenic affinity of the chimeric polypeptide relative to an identical chimeric polypeptide lacking the duplication. By way of example, if the naturally occurring protein comprises a Sup35 protein of *Saccharomyces cerevisiae* that is characterized by the partial amino acid sequence PQGGYQQYN (SEQ ID NO: 10), which sequence exists as multiple imperfect repeats, the duplication preferably includes the amino acid sequence PQGGYQQYN and/or an imperfect repeat thereof, such as a repeat wherein one or two residues has been added, deleted, or substituted. An exemplary sequence containing the NM regions of yeast Sup35, with two additional repeat segments, is set forth in SEQ ID NOs: 16 and 17.

In a related aspect, the invention provides a polynucleotide comprising a nucleotide sequence that encodes a chimeric polypeptide, the chimeric polypeptide comprising an amyloidogenic domain that causes the polypeptide to aggregate with identical polypeptides into fibrils, fused to a domain comprising a polypeptide of interest; wherein the amyloidogenic domain comprises amyloidogenic amino acid sequences of at least two naturally occurring amyloidogenic proteins.

In yet another related aspect, the invention provides a polynucleotide comprising a nucleotide sequence of the formula FPBT or FBPT, wherein: B comprises a nucleotide sequence encoding a polypeptide that is encoded by a portion of the genome of the cell; F and T comprise, respectively, 5' and 3' flanking sequences adjacent to the sequence encoding B in the genome of the cell; and P comprises a nucleotide sequence encoding a prion-aggregation amino acid sequence, wherein P is fused in frame to B. Using such polynucleotides and conventional homologous recombination techniques [see, e.g., Ausbel et al. (1998), Volume 3, supra], one can perform homologous recombination in a living cell to convert a protein-encoding gene of the cell to a prion gene of the cell, as described in greater detail below. Alternatively, strains can be constructed wherein the endogenous protein-encoding gene is deleted and a prion version of the gene is added back into the cell, either on a plasmid or by integration into the host genome.

The homologous recombination technique is itself intended as an aspect of the invention. For example, the invention provides a method of modifying a living cell to create an inducible and stable phenotypic alteration in the cell, comprising the steps of: transforming a living cell with the polynucleotide described in the preceding paragraph; culturing the cell under conditions that permit homologous recombination between the polynucleotide and the genome of the cell; and selecting a cell in which the polynucleotide has homologously recombined with the genome to create a genomic sequence comprising the formula PB or BP.

More generally, the invention provides a method of modifying a living cell to create an inducible and stable phenotypic alteration in the cell, such as a method comprising steps of: identifying a target polynucleotide sequence in the genome of the cell that encodes a polypeptide of interest; and transforming the cell to substitute for or modify the target sequence, wherein the substitution or modification produces a cell comprising a polynucleotide that encodes a chimeric polypeptide, wherein the chimeric polypeptide comprises a SCHAG amino acid sequence fused in frame with the polypeptide of interest. Such modifications can be performed in several ways, such as (1) homologous recombination as described in the preceding paragraphs; (2) knockout or inactivation of the target sequence followed by introduction of an exogenous chimeric sequence encoding the desired chimeric polypeptide; or (3) targeted introduction of a SCHAG-encoding polynucleotide sequence upstream and in-frame with the target sequence encoding the polypeptide of interest; (4) subsequent cloning or sexual reproduction of such cells; and/or other techniques developed by those in the art.

The foregoing aspects of the invention relate largely to polynucleotides. Also intended as part of the invention are vectors comprising the polynucleotides, and host cells comprising either the polynucleotides or comprising the vectors. Vectors are useful for amplifying the polynucleotides in host cells. Preferred vectors include expression vectors, which contain appropriate control sequences to permit expression of the encoded chimeric protein in a host cell that has been transformed or transfect with the vectors. Both prokaryotic and eukaryotic host cells are contemplated as aspects of the invention. The host cell may be from the same kingdom (prokaryotic, animal, plant, fungi, protista, etc.) as the organism from which the SCHAG amino acid sequence of the polynucleotide was derived, or from a different kingdom. In a preferred embodiment, the host cell is from the same species as the organism from which the SCHAG amino acid sequence of the polynucleotide was derived.

In yet another embodiment, the invention includes a host cell transformed or transfected with at least two polynucleotides encoding chimeric polypeptides according to the invention, wherein the at least two polynucleotides comprise compatible SCHAG amino acid sequences and distinct polypeptides of interest. Such host cells are capable of producing two chimeric polypeptides of the invention, which can be induced in vitro or in vivo to aggregate with each other into higher ordered aggregates. As explained in greater detail below, such aggregates can be advantageously employed in multi-step chemical reactions when the two or more polypeptides of interest each participate in a step of the reaction. Experiments using fluorescence resonance energy transfer (FRET) have demonstrated the efficacy of heterogeneous polypeptide aggregation into co-polymers.

In addition, the chimeric polypeptides encoded by any of the foregoing polynucleotides are intended as an aspect of the invention. Purified polypeptides are preferred, and are obtained using conventional polypeptide purification techniques. For example, the invention provides a chimeric polypeptide comprising: at least one SCHAG amino acid sequence and at least one polypeptide of interest other than a marker protein, a glutathione S-transferase (GST) protein, or a Staphylococcal nuclear protein. As described above, the SCHAG amino acid sequence may be directly linked (via a peptide bond) to the polypeptide of interest, or may be indirectly linked by virtue of the inclusion of an intermediate spacer region, a solubility domain, an epitope to facilitate recognition and purification, and so on.

As explained herein in detail, polypeptides of the invention are capable of existing in a conformation in which the polypeptide coalesces with similar polypeptides into ordered aggregates that may be referred to as "amyloid," "fibrils," "prions;" or "prion-like aggregates." Such ordered aggregates of polypeptides of the invention are intended as an additional aspect of the invention. Such ordered aggregates tend to be insoluble in water or under physiological conditions mimicking a host cell, and consequently can be purified and isolated using standard procedures, including but not limited to centrifugation or filtration. In a preferred embodiment, the SCHAG amino acid sequence is an amino acid sequence that will self-coalesce into ordered "cross-β" fibril structures that are filamentous in character, in which individual β-sheet strands of component chimeric proteins are oriented perpendicular to the axis of the fibril. In a highly preferred embodiment, the polypeptide of interest is disposed radiating away from the fibril core of SCHAG peptide sequences, and retains one or more characteristic biological activities (e.g., binding activities for polypeptides of interest that have specific binding partners; enzymatic activity for polypeptides of interest that are enzymes).

In still another embodiment, the invention provides a composition comprising an ordered aggregate of at least two chimeric polypeptides of the invention, wherein the at least two chimeric polypeptides have compatible SCHAG amino acid sequences and distinct polypeptides of interest. By "compatible" SCHAG amino acid sequences is meant SCHAG amino acid sequences that are either identical or sufficiently similar to permit co-aggregation with each other into higher ordered aggregates. In a preferred embodiment, the two or more polypeptides of interest retain their native biological activity (e.g., binding activity; enzymatic activity) in the ordered aggregate. Such aggregates can be advantageously employed in multi-step chemical reactions, as described in detail below.

The invention further includes methods of making and using polynucleotides and polypeptides of the invention.

For example, the invention provides a method comprising the steps of: transforming or transfecting a cell with a polynucleotide of the invention; and growing the cell under conditions which result in expression of the chimeric polypeptide that is encoded by the polynucleotide in the cell. In a preferred embodiment, the method further includes the step of isolating the chimeric polypeptide from the cell or from growth medium of the cell. In one variation, the method further comprises the step of detaching the SCHAG amino acid sequence of the protein from the polypeptide of interest. As described above in detail, the detachment may be effected with any appropriate means, including chemicals, proteolytic enzymes, self-splicing inteins, or the like. Optionally, the method further includes the step of isolating the protein of interest from the SCHAG amino acid sequence.

In a related embodiment, the invention provides a method of making a protein of interest, comprising the steps of: transforming or transfecting a cell with a polynucleotide, the polynucleotide comprising a nucleotide sequence that encodes a chimeric polypeptide, the chimeric polypeptide comprising an amyloidogenic domain that causes the polypeptide to aggregate with identical polypeptides into higher-ordered aggregates such as fibrils, fused to domain comprising a polypeptide of interest; growing the cell under conditions which result in expression of the chimeric polypeptide in the cell and aggregation of the chimeric polypeptide into fibrils; and isolating the chimeric polypeptide from the cell or from growth medium of the cell. In a preferred embodiment, the isolating step comprises the step of separating the fibrils from soluble proteins of the cell. In a highly preferred embodiment, the method further comprises the steps of proteolytically detaching the amyloidogenic domain of the chimeric protein from the polypeptide of interest; and isolating the polypeptide of interest. Preferably the detached polypeptide of interest maintains one or more of its biological functions, e.g., enzymatic activity, the ability to bind to its ligand, the ability to induce the production of antibodies in a suitable host system, etc.

In yet another aspect, the invention provides a method of modifying a living cell to create an inducible and stable phenotypic alteration in the cell. For example, such a method comprising the step of transforming or transfecting a living cell with a polynucleotide according to the invention, wherein the polynucleotide includes a promoter sequence to promote expression of the encoded chimeric polypeptide in the cell, the promoter being inducible to promote increased expression of the chimeric polypeptide to a level that induces aggregation of the chimeric polypeptide into higher-ordered aggregates such as fibrils. In one preferred embodiment, the method further comprises the step of growing the cell under conditions which induce the promoter, thereby causing increased expression of the polypeptide and inducing aggregation of the chimeric polypeptide into aggregates or fibrils in the cell. In a highly preferred embodiment, the host cell lacks any native protein that contains the same SCHAG amino acid sequence that might co-aggregate with the chimeric polypeptide. For example, the SCHAG amino acid sequence comprises an amino terminal domain of a Sup35 protein, and the host cell is a yeast cell that comprises a mutant Sup35 gene that expresses a Sup35 protein lacking an amino terminal domain capable of prion aggregation. In such host cells, the chimeric polypeptide can be expressed at a high level and induced to aggregate without concomitant precipitation of the host cell's Sup35 protein into the aggregates, which could be detrimental to host cell viability.

In yet another aspect, the invention provides methods for reverting the phenotype obtained according to the method described in the preceding paragraph. One such method comprises the step of overexpressing a chaperone protein in the cell to convert the polypeptide from a fibril-forming conformation into a soluble conformation. In a preferred embodiment, the chaperone protein comprises the Hsp 104 protein of yeast, or a related Hsp100-type protein from another species. Examples include the C1pB protein of *E. coli* and the At101 protein of *Arabidopsis*. [See generally Schirmer et al., *Trends in Biochemistry*, 21: 289-296 (1996), incorporated herein by reference.] The over-expression is achieved, e.g., by placing the gene encoding the chaperone-protein under the control of an inducible promoter and inducing the promoter.

Another such method for reverting the phenotype comprises the step of contacting the cell with a chemical denaturant at a concentration effective to convert the polypeptide from a fibril-forming conformation to a soluble conformation. Exemplary denaturants include guanidine HCl (preferably about 0.1 to 100 mM, more preferably 1-10 mM) and urea. In another variation, the cell is subjected to heat or osmotic shock for a period of time effective to convert the polypeptide's conformation. Both over-expression of Hsp104 and growth on guanidine-HCl containing medium have proven effective for inducing phenotypic reversion of chimeric NM-GR prion constructs described in the Examples herein.

In yet another aspect, the invention provides materials and methods for identifying novel SCHAG amino acid sequences. One such method comprises the steps of joining a candidate nucleotide sequence "X" to a nucleotide sequence encoding the carboxyl terminal domain of a Sup35 protein (CSup35), especially a yeast Sup35 protein, to create a chimeric polynucleotide of the formula 5'-XCSup35-3' or 5'-CSup35X-3'; transforming or transfecting a host cell with the chimeric polynucleotide; growing the host cell under conditions in which the host cell loses its native Sup35 gene, such that the chimeric polynucleotide becomes the only polynucleotide encoding CSup35; growing the resultant host cell under conditions selective for a nonsense suppressive phenotype; and selecting a host cell displaying the nonsense suppressive phenotype, wherein growth in the selective conditions is correlated with the candidate nucleotide sequence X encoding a SCHAG amino acid sequence. Additional methods steps and alternative methods are described in detail below in the Examples. In one variation, the Csup35 is substituted by a different protein domain for which selection on the basis of inactivation is possible.

Many of the foregoing aspects of the invention relate, at least in part, to embodiments that involve chimeric polynucleotides and polypeptides, wherein properties of SCHAG amino acid sequences are advantageously employed through attaching them to other sequences using recombinant molecular biological techniques. In another variation of the invention, the advantageous properties of SCHAG amino acid sequences are exploited by making SCHAG sequences with sites that are modifiable using organic chemistry or enzymatic techniques.

For example, in one embodiment, the invention provides a method of making a reactable SCHAG amino acid sequence comprising the steps of identifying a SCHAG amino acid sequence, wherein polypeptides comprising the SCHAG amino acid sequence are capable of forming ordered aggregates; analyzing the SCHAG amino acid sequence to identify at least one amino acid residue in the sequence having a side chain exposed to the environment in an ordered aggregate of polypeptides that comprise the SCHAG amino acid sequence; and modifying the SCHAG amino acid sequence by substituting an amino acid containing a reactive side chain for the amino acid identified as having a side chain exposed to the environment in an ordered aggregate of polypeptides that comprise the SCHAG amino acid sequence. By "reactive" side chain is meant an amino acid with a charged or polar side chain that can be used as a target for chemical modification using conventional organic chemistry procedures, preferably procedures that can be performed in an environment that will not permanently denature the protein. In preferred embodiments, the amino acid containing a reactive side chain is cysteine, lysine, tyrosine, glutamate, aspartate, and arginine. The identifying step entails any selection of a SCHAG amino acid sequence. For example, the identifying can simply entail selecting one of the SCHAG amino acid sequences described in detail herein; or can entail screening of genomes, proteins, or phenotypes of organisms to identify SCHAG sequences (e.g., using methodologies described herein); or can entail de novo design of SCHAG sequences based on the properties described herein.

Proteins comprising the SCHAG sequence are capable of coalescing into higher-ordered aggregates. The polypeptides of such aggregates have amino acids that are disposed internally (in close proximity only to other amino acids in the aggregate), and other amino acids whose side chains are exposed to the environment of the aggregate such that they contact molecules in the environment. In the method, the analyzing step entails a prediction or a determination of at least one amino acid within the SCHAG sequence that is exposed to the environment of an aggregate of the proteins, meaning that it is an amino acid that will likely contact chemical reagents that mixed with the aggregates. Amino acids in a SCHAG amino acid sequence having side chains exposed to the environment in ordered aggregates of polypeptides comprising the SCHAG amino acid sequence can be identified experimentally, for example, by structural analysis of mutants constructed using site-directed mutagenesis, e.g., high throughput cysteine scanning mutagenesis, as described in detail below in the Examples. Alternatively, specific amino acids in a SCHAG amino acid sequence can be predicted to have side chains that are exposed to the environment in ordered aggregates of polypeptides comprising the SCHAG amino acid sequence based on structural studies or computer modeling of the SCHAG amino acid sequence. The step of modifying the amino acid sequence entails changing the identity of an amino acid within the sequence. For the purposes of such a method, the act of inserting a reactive amino acid within the amino acid sequence, at a position essentially adjacent to the position of the identified amino acid, is considered the equivalent of substituting that amino acid for the identified amino acid. In other words, for the purposes of making a reactable SCHAG amino acid sequence, the term "substituting" should be understood to include inserting an amino acid within the amino acid sequence, at a position essentially adjacent to the position of the identified amino acid.

It is contemplated that some naturally-occurring SCHAG amino acid sequences will fortuitously include one or more reactive amino acids whose side chains are exposed to the environment in polypeptide aggregates. Use of such naturally occurring SCHAG reactive amino acids is contemplated as an additional aspect of the invention. Moreover, modification of naturally occurring SCHAG amino acid sequences that contain an undesirable number of reactive amino acids to eliminate one or more reactive amino acids is contemplated.

In a preferred embodiment, the method further comprises a step of making a polypeptide comprising the reactable SCHAG amino acid sequence. Substitution of such amino acids with amino acid residues containing reactive side chains can be carried out in the laboratory by, e.g., site-directed mutagenesis of a SCHAG-encoding polynucleotide or by peptide synthesis of the SCHAG amino acid sequence. In another preferred embodiment, the invention additionally comprises the step of making a polymer comprising an ordered aggregate of polypeptide monomers wherein at least one of the polypeptide monomers comprises a reactable SCHAG amino acid sequence. For example, polypeptide monomers comprising the reactable SCHAG amino acid sequence are seeded with an aggregate or otherwise subjected to an environment favorable to the formation of an ordered aggregate or "polymer" of the polypeptide monomers. In yet another preferred embodiment, the invention further comprises the step of contacting the reactive side chains with a chemical agent to attach a substituent to the reactive side chains. The substituent itself may be a linker molecule to facilitate attachment of one or more additional molecules. The substituent may be attached using a chemical agent. Attachment of a substituent depends on the nature of the substituent, as well as the identity of the reactive side chain, and can be accomplished by conventional organic chemistry procedures. Exemplary procedures for modifying the sulfhydryl group of a cysteine residue that has been introduced into a SCHAG amino acid sequence are described in greater detail below in the Examples. In preferred embodiments, the substituent is an enzyme, a metal atom, an affinity binding molecule having a specific affinity binding partner, a carbohydrate, a fluorescent dye, a chromatic dye, an antibody, a growth factor, a hormone, a cell adhesion molecule, a toxin, a detoxicant, a catalyst, or a light-harvesting or light altering substituent. In a preferred embodiment, the reactive amino acid that has been introduced into the SCHAG sequence will be substantially absent from the rest or the SCHAG amino acid sequence, or at least substantially absent from those portions of the sequence that are exposed to the environment in ordered aggregates of the polypeptide. This absence may be a natural feature, or may be the result of an additional modification step to substitute or delete other occurrences of the amino acid. Designing the reactable SCHAG amino acid sequence in this manner permits controlled chemical modification at the reactive sites that have been designed into the sequence, without modification of other residues.

In yet another embodiment of the invention, the invention further comprises the steps of contacting the polypeptides comprising the reactive side chains with a chemical agent to attach a substituent to the reactive side chains, thereby providing modified polypeptides, and making a polymer comprising an ordered aggregate of polypeptide monomers, wherein at least some of the polypeptide monomers comprise the modified polypeptides. Exemplary procedures for making a polymer comprising an ordered aggregate of modified polypeptide monomers are described in greater detail below in the Examples.

In yet another embodiment, the invention provides a method of making a reactable SCHAG amino acid sequence, wherein the SCHAG amino acid sequence is modified to contain exactly one, two, three, four, or some other specifically desired number of the reactive amino acids. An exemplary method comprises the steps of (a) identifying a SCHAG amino acid sequence, wherein polypeptides comprising the SCHAG amino acid sequence are capable of forming ordered aggregates; (b) analyzing the SCHAG amino acid sequence to identify at least one amino acid residue in the sequence having a side chain exposed to the environment in an ordered aggregate of polypeptides that comprise the SCHAG amino acid sequence; (c) modifying the SCHAG amino acid sequence by substituting an amino acid containing a reactive side chain for the amino acid identified as having a side chain exposed to the environment in an ordered aggregate of polypeptides that comprise the SCHAG amino acid sequence; (d) analyzing the SCHAG amino acid sequence to identify at least a second amino acid residue in the sequence having an amino acid side chain that is exposed to the environment in an ordered aggregate of polypeptides that comprise the SCHAG amino acid sequence; and (e) modifying the SCHAG amino acid sequence by substituting an amino acid containing a reactive side chain for at least one amino acid identified according to step (d), wherein the amino acid substituted in steps (c) and (d) differ, thereby making a reactable SCHAG amino acid sequence with at least two selectively reactable sites. This method can be further elaborated to create SCHAG amino acids sequences with more than two selectively reactable sites. By introducing two or more different reactive amino acids, a SCHAG sequence is created with two or more sites that can be separately reacted/modified. It will be appreciated that the method also can be performed to introduce the same reactive amino acid for each identified amino acid, to create two or more identical reactive sites in the SCHAG sequence.

In another embodiment of the invention, the invention provides polypeptides comprising a SCHAG amino acid sequence that has been modified by substituting at least one amino acid that is exposed to the environment in an ordered aggregate of the polypeptides with an amino acid containing a reactive side chain, as well as polynucleotides that encode the polypeptides. In a further embodiment, a substituent is attached to the reactive amino acid of the modified polypeptide of the invention or reactable SCHAG sequence. In a highly preferred embodiment, the SCHAG amino acid sequence is modified to contain exactly one, two, three, four, or some other specifically desired number of the reactive amino acids, thereby providing a SCHAG amino acid sequence which is modifiable at controlled, stoichiometric levels and positions. To achieve this goal, modifications to remove undesirable, native reactive amino acids from a naturally occurring SCHAG sequence are contemplated. Polypeptides comprising a naturally occurring SCHAG amino acid sequence characterized by one or more reactive amino acids, that have been modified by substituting or eliminating a natural reactive amino acid, are considered a further aspect of the invention, as are polynucleotides that encode the polypeptides.

The invention also provides polymers or fibers of ordered aggregates comprising polypeptide subunits wherein at least one of the polypeptide subunits comprises a reactable SCHAG amino acid sequence. By the term "fibril" or "fiber" is meant a filamentous structure composed of higher ordered aggregates. By "polymer" is meant a highly ordered aggregate that may or may not be filamentous. In another embodiment, the polymer or fiber is modified or substituted by attaching a substituent to the reactable SCHAG amino acid sequence of the polypeptide subunits. Also contemplated are polymers or fibers that comprise more than one type of substituent by attachment of different substituents to the reactable SCHAG amino acid sequence of the polypeptide subunits of the polymer or fiber. Attachment of the substituents to the reactive side chains contained in the reactable SCHAG amino acid sequence can occur either before or after coalescing of the polypeptides comprising the reactable SCHAG amino acid sequences into polymers comprising ordered aggregates of the polypeptides. Modification by attachment of specific substituents to such polymers or fibers can confer distinct functions to these molecules. Thus, polymers or fibers, wherein one or more discrete regions of the polymer or fiber are modified to enable a distinct function are contemplated. In another variation, different regions of a polymer or fiber are differentially modified to confer different functions. Also contemplated are polymers or fibers containing patterns of attachments, and consequently patterns of functionalities. The invention also provides polymers comprising fibers wherein at least one fiber has a distinct function different from that of another fiber in the polymer. Fibers comprising polypeptides subunits that are capable of emitting light or altering the wavelength of the light emitted in response to binding of a ligand to the fiber can be used as highly sensitive biosensors. Polymers comprising fibers wherein some of the fibers comprise polypeptide subunits capable of absorbing light of one wavelength and emitting light of second wavelength, and other fibers comprising polypeptide subunits capable of absorbing the light emitted by the first set of fibers and emitting light of a different wavelength are also contemplated.

In one preferred embodiment, the polymer or fiber is long and thin and contains no or few branches, except at positions defined by deliberate introduction of sites for interaction between the polypeptide subunits. Polymers or fibers in which the polypeptide subunits have been modified to enable directed interactions between the polypeptide subunits within a single polymer or fiber, or between two discrete polymers or fibers are contemplated. Polymers of fibers that have been modified to enable interactions to occur between separate polymers of fibers can be used to create a meshwork of polymers of fibers. In one variation, the meshwork can be generated reversibly by using interactions dependent on sulfhydryl groups present on the polypeptide subunits of the polymer of fiber. Such meshworks can be useful, for example, for filtration purposes. In another preferred embodiment, a fibril, ordered aggregate, polymer or fiber is attached to a solid support. For example, binding of a polymer of fiber to a solid support can be mediated by biotin-avidin interactions, wherein the biotin is attached to the polymers or fibers and avidin is bound to the solid support or vice versa.

In a related embodiment, the invention provides a method of making a polymer or fiber with a predetermined quantity of reactive sites for chemically modifying the polymer of fiber, comprising the steps of providing a first polypeptide comprising a first SCHAG amino acid sequence that is capable of forming ordered aggregates with polypeptides identical to the first polypeptide; providing a second polypeptide comprising a second SCHAG amino acid sequence that is capable of forming ordered aggregates with polypeptides identical to the first polypeptide or the second polypeptide, wherein the second SCHAG amino acid sequence includes at least one amino acid residue having a reactive amino acid side chain that is exposed to the environment and serves as a reactive site in ordered aggregates of the second polypeptide and; mixing the first and second polypeptides under conditions favorable to aggregation of the polypeptides into ordered aggregates, wherein the polypeptides are mixed in quantities or ratios selected to provide a predetermined quantity of second polypeptide reactive sites. In a preferred embodiment, the invention further comprises the step of reacting the reactive side chains to attach a substituent to the reactive amino acid side chains of the polymer of fiber. Alternatively, the step of reacting the reactive side chains to attach a substituent to the reactive amino acid side chains is performed prior to mixing of the polypeptides comprising reactable SCHAG amino acid sequences to from ordered aggregates. In yet another embodiment, the invention provides a method of making a polymer or fiber comprising a first polypeptide comprising a first SCHAG amino acid sequence and a second polypeptide comprising a second SCHAG amino acid sequence, wherein both the first and second SCHAG amino acid sequence includes at least one amino acid residue having a reactive amino acid side chain that is exposed to the environment and serves as a reactive site, and wherein the reactive amino acid side chains of the first and second SCHAG amino acid sequences that are exposed to the environment in ordered aggregates are not identical, thereby permitting selective reaction of the reactive amino acid side chain of the first SCHAG amino acid sequence without reacting the reactive amino acid side chain of the second SCHAG amino acid sequence.

In another embodiment, the invention provides a method of making a polymer comprising two or more regions with distinct function comprising the steps of (a) providing a first polypeptide comprising a SCHAG amino acid sequence and a first functional domain and a second polypeptide comprising a SCHAG amino acid domain and a second functional domain that differs from the first functional domain, wherein the SCHAG amino acid sequences of the polypeptides are capable of forming ordered aggregates with polypeptides identical to the first or second polypeptide; (b) aggregating the first polypeptide by subjecting a composition comprising the first polypeptide to conditions favorable to aggregation of the first polypeptide into ordered aggregates, thereby forming a polymer comprising a region containing polypeptides that include the first functional domain; and (c) mixing a composition comprising the second polypeptide with the polymer formed according to step (b), under conditions favorable to aggregation of the second polypeptide with the polymer of step (b), thereby forming a polymer comprising the first region containing polypeptides that include the first functional domain and a second region containing polypeptides that include the second functional domain. In one preferred embodiment, the SCHAG amino acid sequences of the first and second polypeptides are identical. In another preferred embodiment, at least one of the first and second functional domains comprises an amino acid that comprises a reactive amino acid side chain. In yet another preferred embodiment, at least one of the first and second functional domains comprises an amino acid sequence of a polypeptide of interest. In another variation, the method further comprises the step of mixing a composition comprising the first polypeptide with the polymer formed according to step (c), under conditions favorable to aggregation of the first polypeptide with the polymer of step (c), thereby forming a polymer comprising the first region containing polypeptides that include the first functional domain, the second region containing polypeptides that include the second functional domain, and a third region containing polypeptides that include the first functional domain. Alternatively, the invention provides a method of making a polymer comprising two or more regions with distinct function wherein the method further comprises the steps of providing a third polypeptide that comprises a SCHAG amino acid sequence and a third functional domain that differs from the first and second functional domains, wherein the SCHAG amino acid sequence of the third polypeptide is capable of forming ordered aggregates with polypeptides identical to the first polypeptide or the second polypeptide; and mixing a composition comprising the third polypeptide with the polymer formed according to step (c), under conditions favorable to aggregation of the third polypeptide with the polymer of step (c), thereby forming a polymer comprising the first region containing polypeptides that include the first functional domain, the second region containing polypeptides that include the second functional domain, and a third region containing polypeptides that include the third functional domain.

In still another variation, the invention provides various living cells with two or more customized, reversible phenotypes. For example, the invention provides a living cell that comprises: (a) a first polynucleotide comprising a nucleotide sequence encoding a polypeptide that comprises a prion aggregation domain and a domain having transcription or translation modulating activity, wherein the living cell is capable of existing in a first stable phenotypic state characterized by the polypeptide existing in an unaggregated state and exerting a transcription or translation modulating activity and a second phenotypic state characterized by the polypeptide existing in an aggregated state and exerting altered transcription or translation modulating activity; and (b) an exogenous polynucleotide comprising a nucleotide sequence that encodes a polypeptide of interest, with the proviso that the sequence encoding the polypeptide of interest includes a regulatory sequence causing differential expression of the polypeptide in the first phenotypic state compared to the second phenotypic state. Exemplary prion aggregation domains are described with respect to Sup35, Rnq1, and Ure2. The first polynucleotide may itself be an endogenous (native) polynucleotide of the cell, such as the native yeast Sup35 sequence in a yeast cell, which comprises a prion aggregation domain fused to a translation termination factor sequence. Alternatively, the first polynucleotide may be introduced into the cell (or a parent cell) using genetic engineering techniques. The term "exogenous polynucleotide" is meant to encompass any polynucleotide sequence that differs from a naturally occurring sequence in the cell as a result of human genetic manipulation. For example, an exogenous sequence may constitute an expression construct that has been introduced into a cell, such as a construct that contains a promoter, a foreign polypeptide-encoding sequence, a stop codon, and a polyadenylation signal sequence. Alternatively, an exogenous sequence may constitute an endogenous polypeptide-encoding sequence that has been modified only by the introduction of a promoter, an enhancer, or other regulatory sequence that is not naturally associated with the polypeptide-encoding sequence. Introduction of a regulatory sequence that is influenced by the aggregation state of the polypeptide encoded by the first polynucleotide is specifically contemplated. In one preferred variation, the cell further comprises a nucleotide sequence that encodes a polypeptide that modulates the expression level or conformational state of the polypeptide that comprises the prion aggregation domain. Such a polynucleotide facilitates manipulation of the cell to switch phenotypes. Polynucleotides encoding chaperone proteins that influence prion protein folding represent one example of this latter category of polynucleotide. In one specific variation, the invention provides a living cell according to claim 97, wherein the first polynucleotide comprises a nucleotide sequence encoding a polypeptide that comprises a prion aggregation domain fused in-frame to a nucleotide sequence encoding a translation termination factor polypeptide; and wherein the regulatory sequence comprises a stop codon that interrupts translation of the polypeptide of interest.

In another variation, the invention provides a living cell comprising: (a) a polynucleotide comprising a nucleotide sequence encoding a polypeptide that comprises a prion aggregation domain fused in-frame to a nucleotide sequence encoding a translation termination factor polypeptide; and (b) an exogenous polynucleotide comprising a nucleotide sequence that encodes a polypeptide of interest, with the proviso that the sequence encoding the polypeptide of interest includes at least one stop codon that interrupts translation of the polypeptide of interest; wherein the living cell is capable of existing in a first stable phenotypic state characterized by translational fidelity and substantial absence of synthesis of the polypeptide of interest and a second phenotypic state characterized by aggregation of the translation termination factor, reduced translational fidelity, and expression of the polypeptide of interest.

Additional features and variations of the invention will be apparent to those skilled in the art from the entirety of this application, including the drawing and detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWING

FIG. 1 depicts the DNA and deduced amino acid sequences (SEQ ID NOs: 66-67) of an NMSup35-GR chimeric gene described in Example 1.

FIG. 3 depicts the nucleotide sequence (SEQ ID NO: 49) of the plasmid of FIG. 2. As shown in FIG. 2, the NUre2-CSup35 chimeric gene is encoded on the strand complementary to the strand whose sequence is depicted in FIG. 3.

DETAILED DESCRIPTION OF THE INVENTION

Figure 2:
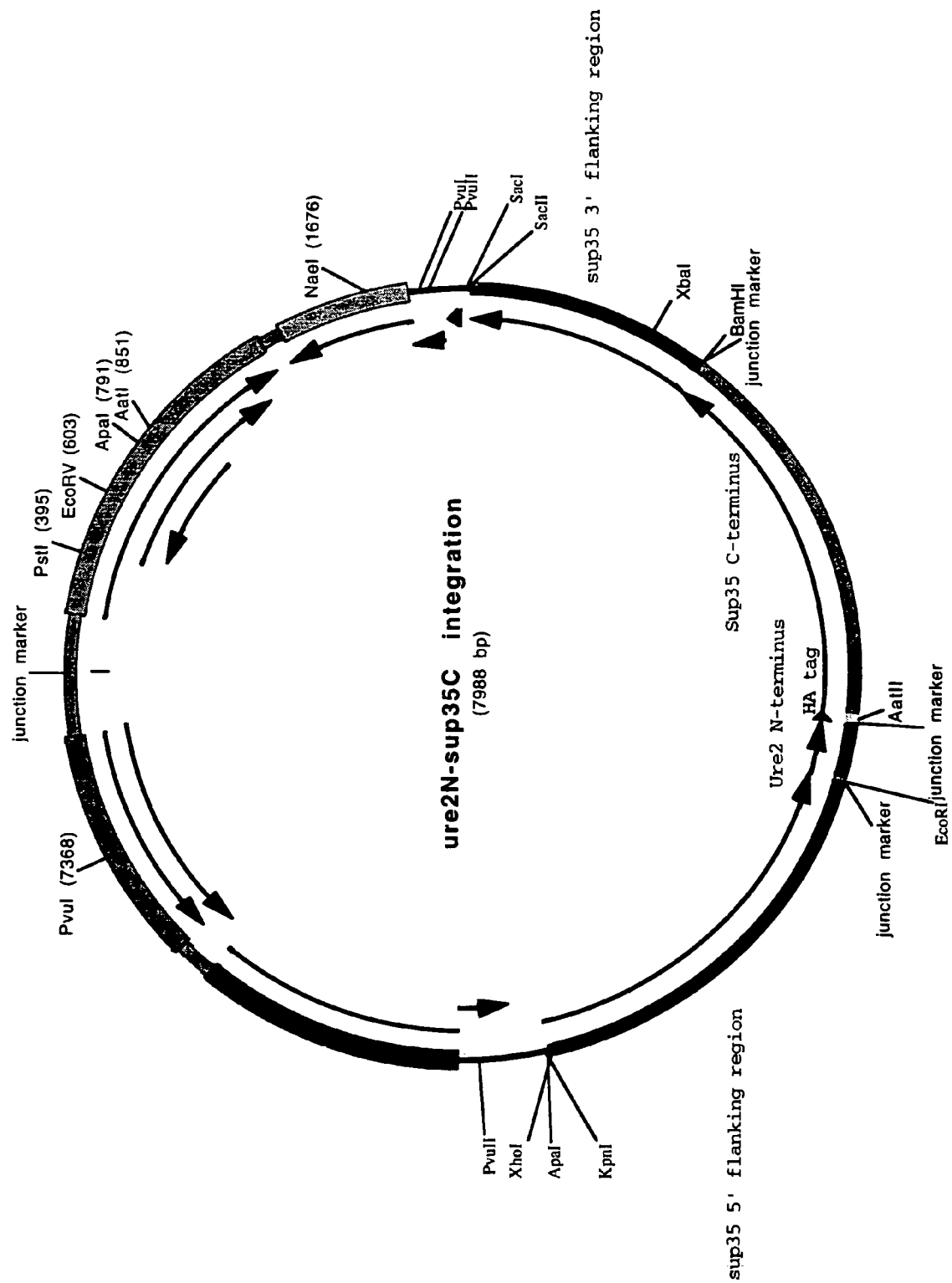
FIG. 2 depicts a map of an integration plasmid described in Example 2 which contains a chimeric gene comprising the amino-terminal domain of yeast Ure2 protein, a hemagglutinin tag sequence, and the carboxyl-terminal domain of yeast Sup35 protein.

The present invention expands the study of prion biology beyond the contexts where it has heretofore focused, namely fundamental research directed to developing a greater understanding of prion biology and medical research directed to developing diagnostic and therapeutic materials and methods for prion-associated disease states, and provides diverse and practical applications that advantageously employ certain unique properties of prions, including one or more of the following:

(1) prion genes and proteins afford the possibility of two stable, heritable phenotypes and the ability to effect at least one switch between such phenotypes;
(2) prions provide the ability to sequester a protein or protein-binding molecule into an ordered aggregate;
(3) prion protein aggregates are easily isolated from cells containing them; with at least some prions, the ordered aggregate is fibrillar in structure, stable and unreactive, a collection of properties that is exploited in certain embodiments of the invention;
(4) a protein of interest that is fused to a prion protein can potentially retain its normal biological activity even when the fusion has formed an ordered prion aggregate; and
(5) a protein of interest that is fused to a prion protein can switch from an active to an inactive state, and this change is reversible.

Prion proteins have been observed to exist in at least two stable conformations in cells that synthesize them. For example, the PrP protein in mammals has been observed in a soluble PrP$^C$ conformation in "normal" cells and in an aggregated, insoluble PrP$^{Sc}$ conformation in animals afflicted with transmissible spongiform encephalopathies. Similarly, the Sup35 protein in yeast has been observed in a "normal" non-aggregated conformation in which it forms a component of a translation termination factor, and also aggregated into fibril structures in [PSI⁺] yeast cells (characterized by suppression of normal translation termination activity). To the extent that scientific literature has ascribed any practical importance to these observations, the importance has focused on identifying materials and methods to modulate conformational switching, which might lead to treatments for prion-mediated diseases; or to detect the infectious PrP$^{Sc}$ form to protect the food supply; or to diagnose infection and prevent its spread. At least in the case of the yeast Sup35 prion, the [PSI⁺] phenotype can be eliminated by effecting an over-expression or under-expression of the heat shock protein Hsp104, and can be induced by effecting an over-expression of Sup35 or the Sup35 amino-terminal prion-aggregation domain.

The practical applications that arise from the ability to alter the phenotype of a cells or an entire organism by transforming/transfecting cells with a polynucleotide that encodes a non-native protein (and/or that integrates into the cell's genome to cause production of a non-native protein) are legion and underlie a major portion of the entire biotechnology industry. Such applications include medical/therapeutic applications (e.g., gene therapy to treat genetic disorders such as hemophilia; gene therapy to treat pathological conditions such as ischemia, inborn errors of metabolism, restenosis, or cancer); pharmacological applications (e.g., recombinant production of therapeutic polypeptides such as erythropoietin, human growth hormone, angiogenic and anti-angiogenic peptides, or cytokines for therapeutic administration); industrial applications (e.g., genetic engineering of microorganisms for bioremediation or frost prevention; or recombinant production of catalytic enzymes, vitamins, proteins, or other organic molecules for use in chemical and food processing); and agricultural applications (e.g., genetic engineering of plants and livestock to promote disease resistance, faster growth, better nutritional value, environmental durability, and other desirable properties); just to name a few. In such biotechnology applications, a cell typically is transformed/transfected with a single novel gene to introduce a single phenotypic alteration that persists as long as the gene is present. Means of controlling the new phenotype conventionally involve eliminating the new gene, or possibly placing the gene under the control of inducible or repressible promoter to control the level of gene expression. The present invention provides the realization that prion genes and proteins afford an additional, alternative means of biological control, because the introduction of a prion sequence into a protein introduces the possibility of two stable, heritable phenotypes and the ability to effect at least one switch between such phenotypes. Specifically, one can phenotypically alter a cell to produce a protein of interest by transforming/transfecting a cell with a gene encoding a prion-aggregation domain fused to a protein of interest. To reduce or eliminate the activity of this protein, one induces the protein to undergo a conformational alteration and adopt a prion-like aggregating phenotype, thereby sequestering the protein. To re-introduce the original recombinant phenotype, one induces the protein to undergo a conformational alteration and adopt the soluble phenotype.

By way of example, the phenotypic alteration potential of prion-like proteins can be harnessed to permit a species (plant, animal, microorganisms, fungi, etc.) to survive in a wider range of environmental conditions and/or quickly adopt to environmental changes. Species that thrive in one environment often have difficulty in another. For example, some photosynthetic organisms grow well under bright light because they produce pigments that protect the organism from potentially toxic effects of bright light, whereas others grow well under low light conditions because of other light-gathering pigment systems that efficiently harvest all available light. By placing the regulators for such systems under a prion control mechanism, prion conformational switching is advantageously harnessed for increased environmental adaptability.

A preferred prion system for harnessing environmental adaptation is a prion system such as the Sup35 or Ure2 yeast prions that undergo natural switching. In these systems, the yeast prion state and phenotype arises naturally (in a non-prion population) at a frequency of about one per million cells, and is lost at a similar frequency in a prion population. Thus, in any yeast culture of reasonable size, both phenotypes will be present. If the prion state imparts a growth advantage under some conditions and the non-prion state imparts a growth advantage under other conditions, the culture as a whole will survive and thrive under either set of conditions. Although one phenotype may be disfavored and selected against, it will nonetheless be present (due to natural switching behavior of the prion) and ready to "take over" the culture if conditions change to favor it. In this regard, also contemplated as an aspect of the invention is a cell culture comprising cells transformed or transfected with a polynucleotide according to the invention, wherein the cells express the chimeric polypeptide encoded by the polynucleotide, and wherein the cell culture includes cells wherein the chimeric polypeptide is present in an aggregated state and cells free of aggregated chimeric polypeptide.

The prion-mediated flexibility described in the preceding paragraph possesses a crucial advantage over traditional "switches" because it does not depend upon fortuitous genetic mutations and reversions. Each phenotype arises from the same genotype and each is available within the population, even under selective conditions. Thus, in a cultured photosynthetic organism as described above, transformation with one or more genes encoding an aggregating domain fused to pigment or protective proteins will provide an increased adaptability to varying light conditions.

This "natural switching" quality of prions has applicability to a wide variety of variable growth conditions that might be encountered by cultured cells or organisms, including varied levels of salinity, metals, carbon sources, and toxic metabolic byproducts. Adaptability to such environments is often mediated by one or a few proteins, such as metal-binding proteins and enzymes involved in the synthesis or breakdown of particular organic compounds. The advantages of prion natural switching are considered particularly well suited for fields of bioremediation, where multiple environmental conditions are expected to be encountered, and fermentation processes where nutrients are consumed and fermentation by products are created, changing an environment over time.

By way of another example, pigment genes for flowers, textile fibers (e.g., cotton), or animal fibers (e.g., wool) are placed under the control of prion-like aggregating elements. A plurality of colors and/or color patterns is achieved in a single plant by altering growing conditions to induce or cure the prion regulated pigment, or by subjecting portions of the plant to chemical agents that modulate conformation of the prion protein.

The present invention also provides practical applications stemming from the realization that prions provide the ability to sequester a protein of interest or the protein's binding partner into an ordered aggregate. This property is demonstrated herein by way of example involving the prion aggregation domain of the yeast Sup35 gene fused to a glucocorticoid receptor. When cells expressing this fusion are in a non-prion phenotype (i.e., the fusion protein is soluble), the cells are susceptible to hormonal induction through the glucocorticoid receptor, and one can induce the expression of a second gene that is operably fused to a glucocorticoid response element. However, when cells expressing the fusion are in a prion phenotype (i.e., the fusion protein is forming aggregates), the susceptibility to hormonal induction is reduced, because the glucocorticoid receptor that is sequestered into cytoplasmic aggregates is unable to effect its normal activity in the cell's nucleus.

This ability to a sequester protein or protein-binding partner has direct application in the recombinant production of biological molecules, especially where recombinant production is difficult using conventional techniques, e.g., because the molecule of interest appears to exert a toxic or growth-altering effect on the recombinant host cell. Such effects can be reduced, and production of the polypeptide of interest enhanced, by expressing the polypeptide of interest as fusion with a prion aggregation domain in a host cell that has, or is induced to have, a prion aggregation phenotype. In such host cells, the recombinant fusion protein forms ordered aggregates through its prion aggregation domain, thereby sequestering the protein of interest as part of the aggregate, and reducing its adverse effects on other cellular components or reactions. (If the molecule of interest is the binding partner of the non-prion domain of the fusion protein, the binding partner also will be sequestered by the aggregate, provided that the binding activity of this domain is retained in the aggregate.)

The present inventors also provide practical applications stemming from the fact that prion aggregates can be readily isolated from cells containing them. Because prions form insoluble aggregates in appropriate host cells, it is relatively easy to separate aggregated prion protein from most other proteinaceous and non-proteinaceous matter of a host cell, which is comparatively more soluble, using centrifugation techniques. When the prion protein is fused to a protein of interest, the protein of interest can likewise be separated from most other host cell impurities by centrifugation techniques. Thus, the present invention provides materials and methods useful for the purification of virtually any recombinant protein of interest. If a recognition sequence for chemical or enzymatic cleavage is included between the prion aggregation domain and the protein of interest, the protein of interest can be cleaved and separated from the insoluble prion aggregate in a second purification step. Such protein production techniques are considered an aspect of the invention. For example, the invention provides a method comprising the steps of: expressing a chimeric gene in a host cell, the chimeric gene comprising a nucleotide sequence encoding a SCHAG amino acid sequence fused in frame to a nucleotide sequence encoding a protein of interest; subjecting the host cell, or a lysate thereof, or a growth medium thereof to conditions wherein the chimeric protein encoded by the chimeric gene aggregates; and isolating the aggregates. In one variation, the method further includes the step of cleaving the protein of interest from the SCHAG amino acid sequence and isolating the protein of interest.

Moreover, the improved purification techniques are not limited to proteins fused to a prion domain. For example, a host cell expressing a prion aggregation domain fused to a protein of interest can be used in a like manner to purify a binding partner of the protein of interest. For example, if the protein of interest is a growth factor receptor, it can be used to sequester the growth factor itself by virtue of the receptor's affinity for the growth factor. In this way, the growth factor can be similarly purified, even though it is not itself expressed as a prion fusion protein. If the protein of interest comprises an antigen binding domain of an antibody, then the same techniques can be used to sequester and purify virtually any antigen (protein or non-protein) that is produced by the host cell or introduced into the host cell's environment. In this regard, it is well-known in the literature that relatively short variable (V) regions within antibodies are largely responsible for highly specific antigen-antibody immunoreactivity, and such antigen-binding regions occur within particular regions of an antibody's primary structure and are susceptible to isolation and cloning. (See, e.g., Morrison and Oi, *Adv. Immunol.*, 44:65-92 (1989). For example, the variable domains of antibodies may be cloned from the genomic DNA of a B-cell hybridoma or from cDNA generated from mRNA isolated from a hybridoma of interest. Likewise, it is known in the art how to isolate only those portions of the variable region gene fragments that encode antigen-binding complementarity determining regions ("CDR") of an antibody, and clone them into a different polypeptide backbone. [See, e.g., Jones et al.,

*Nature*, 321:522-525 (1986); Riechmann et al., *Nature*, 332: 323-327 (1988); Verhoeyen et al., *Science,* 239:1534-36 (1988); and Tempest et al., *Bio/Technology,* 9:266-71 (1991).] A polypeptide comprising an antigen binding domain of an antibody of interest might comprise only one or more CDR regions from an antibody, or one or more V regions from an antibody, or might comprise entire V region fragments linked to constant domains from the same or a different antibody, or might comprise V regions that have been cloned into a larger, non-antibody polypeptide in a way that preserves their antigen binding characteristics, or might comprise antibody fragments containing V regions, and so on. Also, it is known in the art to select and isolate polypeptides comprising antigen binding domains of antibodies using techniques such as phage display that obviate the need to immunize animals and work with native antibodies at all.

The present invention also provides practical applications stemming from the fact that at least some proteins of interest will retain their normal biological activity when expressed as a fusion with a prion aggregation domain, even when the fusion protein forms prion-like aggregates. This feature of the invention is demonstrated by way of example below using the *S. cerevisiae* Sup35 prion aggregation domain fused to a green fluorescent protein (GFP). Even in [PSI$^+$] cells or in other cells where aggregation of the fusion protein into fibrils has occurred, the GFP fluoresces green under blue light, indicating that the GFP portion of the fusion has retained a biologically active conformation.

When the example is repeated substituting a protein of interest for the GFP marker protein, ordered aggregates comprising a biologically active protein of interest are produced. In a preferred embodiment, the protein of interest is a protein that is capable of binding a composition of interest. For example, the protein of interest comprises an antigen binding domain of an antibody that specifically binds an antigen of interest; or it comprises a ligand binding domain of a receptor that binds a ligand of interest. Fibrils comprising such fusion proteins can be used as affinity matrices for purifying the composition of interest. Thus, aggregates of a chimeric protein comprising a SCHAG amino acid sequence fused to an amino acid sequence encoding a binding domain of a protein having a specific binding partner are intended as an aspect of the invention.

In another preferred embodiment, the polypeptide of interest is an enzyme, especially an enzyme considered to be of catalytic value in a chemical process. Fibrils comprising such fusion proteins can be used as a catalytic matrix for carrying out the chemical process. Thus, aggregates of a chimeric protein comprising a SCHAG amino acid sequence fused to an enzyme are intended as an aspect of the invention.

In another preferred embodiment, ordered aggregates are created comprising two or more enzymes, such as a first enzyme that catalyzes one step of a chemical process and a second enzyme that catalyzes a downstream step involving a "metabolic" product from the first enzymatic reaction. Such aggregates will generally increase the speed and/or efficiency of the chemical process due to the proximity of the first reaction products and the second catalyst enzyme. Aggregates comprising two or more proteins of interest can be produced in multiple ways, each of which is itself considered an aspect of the invention.

It may be advantageous to attach fibers to a solid support such as a bead (e.g., a Sepharose bead) or a surface to create a "chip" containing loci with biological or chemical function.

In one variation, each chimeric protein comprising an aggregation domain and a protein of interest is produced in a separate and distinct host cell system and recovered (purified and isolated). The proteins are either recovered in soluble form or are solubilized. (Complete purification is desirable but not essential for subsequent aggregation/polymerization.) Thereafter, a desired mixture of the two or more proteins is created and induced into polymerization, e.g., by "seeding" with a protein aggregate, by concentrating the mixture to increase molarity of the proteins, or by altering salinity, acidity, or other factors. The desired mixture may be 1:1 or may be at a ratio weighted in favor of one chimeric protein (e.g., weighted in favor of an enzyme that catalyzes a slower step in a chemical process). The different chimeric proteins co-polymerize with the seed and with each other because they comprise compatible aggregation (SCHAG) domains, and most preferably identical aggregation domains. In certain embodiments it may be desirable to include in the pre-aggregation mixture a polypeptide comprising the SCHAG domain only, without an attached enzyme, for the purpose of increasing the average space between individual enzyme molecules in the aggregate that is formed. The additional space may be desirable, for example, if the enzyme's substrate is a large molecule.

In another variation, the two distinct host cell systems are co-cultured, and the chimeric transgenes include signal peptides to induce the cells to secrete the chimeric proteins into the common culture medium. The proteins can be co-purified from the medium or induced to aggregate without prior purification.

In still another variation, the transgenes for two or more recombinant chimeric polypeptides are co-transfected into the same host cell, either on a single polynucleotide construct or multiple constructs. Such a host cell produces both recombinant polypeptides, which can be induced to polymerize in vivo in a prion phenotype host, or can be recovered in soluble form and induced to polymerize in vitro. The present invention also exploits the fact that at least certain prion proteins form aggregates that are fiber-like in shape; strong; and resistant to destruction by heat and many chemical environments. This collection of properties has tremendous industrial application that heretofore has not been exploited. Thus, in one embodiment, the invention provides polypeptides comprising SCHAG amino acid sequences which have been modified to comprise a discrete number of reactive sites at discrete locations. The polypeptides can be recombinantly produced and purified and aggregated into robust fibers resistant to destruction. The reactive sites permit modification of the polypeptides (or the fibers comprising the polypeptides) by attachment of virtually any chemical entity, such as pigments, light-gathering and light-emitting molecules for use as sensors, indicators, or energy harnessing and transduction; enzymes; metal atoms; organic and inorganic catalysts; and molecules possessing a selective binding affinity for other molecules. Electrical fields may be applied to fibers that are labeled with metal atoms, so that the fibers can be oriented in a specific direction. Because the fiber monomers are protein, conventional genetic engineering techniques can be used to introduce any number of desired reactive sites at precise locations, and the precise location of the reactive sites can be studied using conventional protein computer modeling as well as experimental techniques. Proteins and fibers of this type enjoy the utilities of the chimeric proteins described above (e.g., as chemical purification matrices, chemical reaction matrices, etc.) and additional utility due to the ability to bind a potentially infinite variety of non-protein molecules of interest to the reactive sites. The fibers can be grown or attached to solid supports to create devices comprising the fibers.

These and other aspects of the invention will be better understood by reference to the following examples. The examples are not intended to limit the scope of the invention, and variations will be apparent to the reader from the entirety of this document.

EXAMPLE 1

Construction and Assaying of a Chimeric, Prion-Like Gene and Protein With Yeast Sup35 Protein The following experiments were performed to demonstrate that a prion-determining domain of a prion-like protein can be fused to a polypeptide from a wholly different protein to construct a novel, chimeric gene and protein having prion-like properties. The relevance of these experiments to the present invention also is explained.

A. Construction of a NMSup35-GR Chimeric Gene

The yeast (*Saccharomyces cerevisiae*) Sup35 protein (SEQ ID NO: 2, 685 amino acids, Genbank Accession No. M21129) possesses the prion-like capacity to undergo a self-perpetuating conformational alteration that changes the functional state of Sup35 in a manner that creates a heritable change in phenotype. Experiments have demonstrated that it is the amino-terminal (N region, amino acids 1-123 of SEQ ID NO: 2) or the amino-terminal plus middle (M, amino acids 124-253 of SEQ ID NO: 2) regions of Sup35 that are responsible for this prion-like capacity. See Glover et al., *Cell*, 89: 811-819 (1997); see also King et al., *Proc. Naitl. Acad. Sci. USA*, 94:6618-6622 (1997) (N-terminal polypeptide fragment consisting of residues 2-114 of Sup35 spontaneously aggregates to form thin filaments in vitro.). The M domain is highly charged and therefore acts to maintain the protein in solution. This property causes the aggregation process to proceed more slowly, providing beneficial control to the system.

A chimeric polynucleotide FIG. 1 and (SEQ ID NO: 66) was constructed comprising a nucleotide sequence encoding the N and M domains of Sup35 (FIG. 1 and SEQ ID NO: 66, bases 1 to 759) fused in-frame to a nucleotide. sequence (derived from a cDNA) encoding the rat glucocorticoid receptor (GR) (Genbank Accession No. M14053, FIG. 1 and SEQ ID NO: 66, bases 766-3150), a hormone-responsive transcription factor, followed by a stop codon. This construct was inserted into the pRS316CG (ATCC Accession No. 77145, Genbank No. U03442) and pG1 (Guthrie & Sink, "Guide to Yeast Genetics and Molecular Biology" in *Methods of Enzymology*, Vol. 194, pp. 389-398 (1981)) plasmids under the control of either the CUP1 promoter (plasmid pCUP1-NMGR, inducible by adding copper to the growth medium) or the constitutive GPD promoter (plasmid pGDP-NMGR). The nucleotide sequences of CUP1 and GDP (Genbank Accession No. M13807) promoters are set forth in SEQ ID NOs: 11 and 48, respectively. The GR coding sequence without NM, in the same promoter and vector constructs (plasmids pCUP1-GR and pGDP-GR), served as a control. GR activity in transformed yeast was monitored with two reporter constructs containing a glucocorticoid response promoter element (GRE) [Schena & Yamamoto, *Science*, 241:965-967 (1988)] fused to either a β-galactosidase (Swiss-Prot. Accession No. P00722) or to a firefly luciferase (Genbank Accession No. M15077) coding sequence. When GR is activated by hormone, e.g., deoxycorticosterone (DOC), it normally binds to the GRE and promotes transcription of the reporter enzyme in either mammals or yeast. See M. Schena and K. Yamamoto, *Science* 241:965-967 (1988).

B. Construction of a NMSUP35-GFP Chimeric-Gene

A chimeric gene comprising the NM region of Sup35 fused to a green fluorescent protein (GFP) sequence and under the control of the CUP1 promoter was constructed essentially as described in Patino et al., *Science*, 273: 622-626 (1996) (construct NPD-GFP), incorporated by reference herein. (The use of GFPs as reporter molecules is reviewed in Kain et al., *Biotechniques*, 19:650-655 (1995); and Cubitt et al., *Trends Biochem. Sci.*, 20:448-455 (1995), incorporated by reference herein.) The resulting construct encodes the $NH_2$-terminal 253 residues of Sup35 (SEQ ID NO: 2) fused in-frame to GFP. The NM-Sup35-GFP encoding sequence was amplified by PCR and cloned into plasmid pCLUC [D. Thiele, *Mol. Cell. Biol.*, 8: 745 (1988)], which contains the CUP1 promoter for copper-inducible expression. A similar construct was created substituting the constitutive GDP promoter for the CUP1 promoter. An identical GFP construct lacking the NM fusion also was created.

C. Transformation and Phenotypic Analysis of [psi–] and [PSI+] Yeast

1. Constructs Regulated by the CUP1 Promoter

The GR and NM-GR constructs regulated by the CUP1 promoter on a low copy plasmid (ura selection) were transformed into [psi–] and [PSI+] yeast cells (strain 74D) along with a 2μ (high copy number) plasmid containing a GR-regulated β-galactosidasereporter gene with leucine selection. Transformants were selected by sc.-leu-ura and used to inoculate sc.-leu-ura medium. Cultures were grown overnight at 30° C., and induced by adding copper sulfate to the medium to a final 0-250 μM copper concentration.

After 4 to 24 hours of induction, both proteins were expressed at a similar level in [psi–] cells, and both the GR and NM-GR transformed [psi–] cells produced similar levels of reporter enzyme activity in response to hormone (DOC added to a final concentration of 10 μM at the time of copper sulfate induction). Virtually no reporter enzyme activity was detected without hormone. The fact that both GR and NM-GR constructs resulted in similar levels of activity indicates that the NM fusion does not intrinsically alter the ability of GR to function in hormone-activated transcription, demonstrating the utility of the NM domain as a fusion protein tag.

In contrast, when the same constructs were transformed into yeast cells that contain the heritable, conformationally-altered form of Sup35 [PSI+], GR activity was reduced in cells expressing the NM-GR fusion construct, compared to cells expressing GR. Thus, pre-existing prions (which comprise self-coalescing aggregates of NM-containing Sup35 protein) can interact with NM-GR. Similar results were obtained with NM-Green Fluorescent Protein (GFP) constructs: NM-GFP interacted with pre-existing [PSI+] elements, but GFP alone did not.

An important difference existed between the NM-GR and NM-GFP studies in the [PSI+] cells, however. Unlike the NM-GR fusion, the NM-GFP fusion retained similar GFP activity with the [PSI+] prion, i.e., the NM-GFP fusion still glowed green. This difference in activity is explained by the facts that, for biological activity, GR needs to be in the nucleus, bind to DNA, and interact in specific ways with other elements of the transcription machinery. When NM-GR is sequestered in [PSI+] cells by interacting (aggregating) with the Sup35 prion filaments, the GR function is diminished.

2. Constructs Regulated by the Constitutive GPD Promoter on a High Copy Plasmid.

A set of experiments demonstrated that plasmids that cause expression of NM at a high level can be successfully transformed into [psi–] yeast cells, but not into [PSI+] cells. Apparently, over-expressed NM causes excessive prion-like aggregation of endogenous Sup35 in cells that are already [PSI+], eliminating so much translation termination factor function that the yeast cells cannot survive.

When a high copy plasmid vector comprising the NM-GR open reading frame under the control of the constitutive GPD promoter was used to transform [psi−] or [PSI+] yeast, no [PSI+] transformants were obtained, whereas [psi−] transformants were readily obtained. The control GR construct in the same vector and under control of the same promoter transformed equally well into both [PSI+] and [psi−] cells.

When amino acids 22-69 in the N domain of Sup35 are deleted, the resultant protein fails to form ordered aggregates, and yeast comprising this Sup35 variant fail to adopt a [PSI+] phenotype. When these same amino acids were deleted from the high copy number NM-GR plasmid, the inability to transform [PSI+] cells was eliminated: transformants were obtained as readily in [PSI+] as [psi−] cells.

Both NM-GR and GR [psi−] transformants were used to inoculate sc.-leu-trp medium, and the cultures were grown at 30° C. overnight, diluted into fresh medium to achieve a cell density of 2–4×10$^6$ cells/ml, induced with DOC (10 µM final concentration), and grown for an additional period varying from 1 hour to overnight. Analysis of marker gene activity in the transformed [psi−] cells demonstrated that hormone responsive transcription was lower in NM-GR transformants than in GR transformants. Western blotting using an anti-GR monoclonal antibody (Affinity Bioreagents Inc., MA1-510) was used to examine the levels of NMGR and GR expression in these cells. Although cells carrying the NM-GR fusion had lower levels of GR activity, the NM-GR protein was actually expressed at a much higher level than the GR protein without the NM domain. Thus, the reduced levels of hormone-activated transcriptional activity were not due to an effect of NM on the accumulation of the transcription factor, but to an alteration in GR activity in the NM-GR-expressing cells. This reduced activity suggested that NM-GR is capable of undergoing a de novo, prion-like alteration in function when it is expressed at a sufficiently high level.

To confirm that NM-GR was forming prions de novo in the transformed [psi−] cells into which it had been introduced, such cells were induced with copper to express NM-GR and then were plated onto copper-free media lacking adenine, and therefor selective for the [PSI+] element/phenotype. See Chemoff et al., Science, 268: 880 (1995), and Cox et al., Yeast, 4(3): 159-178 (1988). A substantial fraction of the cells were able to grow on medium selective for [PSI+], suggesting that the highly expressed NM-GR was responsible for the formation of new prions putatively containing both NM-GR and Sup35 protein. Moreover, the number of colonies obtained varied with the level of copper induction prior to plating. This change in the growth properties of the cells was observed to be heritable and was maintained even under conditions where the NM-GR plasmid construct was lost by the host cells, indicating that NM-GR had induced the formation of a new Sup35-containing prion.

D. Analysis of NMGR-Induced Phenotype in Cells Carrying a Deletion of the NM Region of Sup35.

To further confirm that NM-GR was truly functioning as an independent, novel prion, experiments were conducted to determine whether an NM-GR prion was formed independently of both the yeast [PSI+] element and the endogenous Sup35 protein. Specifically, the GPD-regulated GR and NM-GR constructs were co-transformed with plasmid p5275 (containing GRE linked to a firefly luciferase reporter gene) into a yeast strain (ΔNMSUP35) carrying a deletion of the NM region of the SUP35 gerie. Three independent transformants of each construct (GR or NM-GR) were examined. Colonies were picked and grown overnight in SC selective media (-trp, -ura) at 30° C. Thereafter, deoxycorticosterone (DOC) was added to the growth medium to a final concentration of 10 µM. Luciferase activity was assayed in intact cells after 25 hours of DOC induction.

All three transformants expressing the NM-GR protein showed lower levels of GR activity (specific activities of about 4, 5, 4) than the three transformants expressing GR without the NM fusion (specific activities of about 23, 28, and 39). The differences in GR activity was observed after 1 hour of hormone induction and appeared to increase after 5.5 or after 25 hours of induction.

Western blotting was conducted to determine whether the differences in activity were the result of differences in protein concentration. Ethanol lysates were prepared from 3 ml yeast cultures expressing GR or NMGR twenty-five hours after the addition of DOC. About 50 µg total protein was analyzed by SDS/PAGE and immuoblot. The protein gel was transferred onto PVDF membranes and probed with a monoclonal antibody against GR (Bu-GR2, Affinity Bioreagents, Golden Colorado). The same membrane was later stained with Coomassie blue to semiquantitatively evaluate total protein. The Western studies again showed that the levels of NM-GR were higher than the levels of GR alone.

E. Effect of Guanidine Hydrochloride and Hsp 104 on NM-GR Prions.

When the yeast having [URE3] or [PSI+] phenotypes are passaged on medium containing low concentrations of guanidine hydrochloride (GdHCl), their prion determinants change ("cure") at a high frequency from the aggregated, inactive prion state into the active, unaggregated state, and such changes are heritable. These phenotypes also can be cured by over-expression of the chaperone Hsp104.

Another series of experiments were conducted to assay for such curative behavior in yeast harboring an NM GR construct. The natural GR protein contains a ligand-binding domain and hormone must be added to the medium to determine whether or not the protein is active. For this series of experiments, the hormone-binding domain was removed from the NM-GR construct, creating an NM-GR fusion that was constitutively active.

Yeast expressing the NM-GR chimeric construct and a glucocorticoid response element fused to a β-galactosidase marker exhibited different levels of prion-like behavior, manifested by different colony colors. In addition to white colonies (indicative of a prion-like state lacking β-gal induction) and blue colonies (indicative of soluble NM-GR and high levels of β-gal induction), medium blue and pale blue colonies also were observed. (Western blotting indicated that differently colored colonies contained comparable amounts of GR protein.) These differently colored colonies were replica-plated onto plates containing 5 mM GdHCl and then subsequently replica-plated again onto X-Gal indicator plates. In control cells expressing vector alone (no NM-GR insert), white colonies remained white. However, all of the NM-GR-expressing colonies produced blue colonies. The efficiency of curing varied with the NM-GR strain: medium blue colonies produced almost entirely blue colonies, whereas pale blue colonies produced a mixture of blue and white colonies.

To determine if the heritable loss of NM-GR activity is susceptible to Hsp104 curing, white colonies of cells expressing NM-GR were transformed with a GDP-HSP104 over-expression plasmid and streaked onto X-Gal indicator plates. Control cells transformed with empty vector remained white. In contrast, white cells transformed with the Hsp104 overexpression construct changed to blue. The blue cells remained blue upon-restreaking, indicating that transient over-expression of Hsp104 was sufficient to cure cells of the heritable reduction of NM-GR activity.

When the same NM-GR constructs were used to transform yeast containing a deletion mutation of Hsp104, white colonies were never produced. This finding is consistent with the observation that Hsp104 mutations are incompatible with the maintenance of the [PSI+] phenotype.

Together, the foregoing data indicate that the difference in GR activity observed when NM-GR is expressed at a high constitutive level is due to a heritable alteration in GR function, rather than to an alteration in GR expression.

Collectively, the foregoing experiments demonstrate that the amino-terminal domain of a prion-like yeast gene, Sup35, can be fused to a polypeptide from a wholly different protein to construct a novel, chimeric gene and protein having prion-like properties. Significantly, these results are believed to be the first demonstration that a SCHAG protein domain can be fused to a non-native protein domain to form a chimera, expressed in a host cell that fails to express the native SCHAG protein, and still behave in a prion-like manner. (Specifically, these results demonstrate that the NM domains of SUP35 will behave like a prion even when the C-terminal domain of the protein is not the native Sup35 C-terminus, and even when the host cell does not express an endogenous Sup35 protein containing an NM region.) The experiments also define exemplary assays for screening other putative prion-like peptides for their ability to confer a prion-like phenotype. (It will be apparent that the use of markers other than GFP, GR, luciferase, or β-galactosidase would work in such assays. The GFP marker is useful insofar as it provides an effective marker for localizing a fusion protein in vivo. The GR marker is additionally useful insofar as GR activity depends on GR localization in the nucleus, DNA binding, and interaction with transcription machinery; whereas GFP is active in the cytoplasm.) Exemplary prion-like peptides for screening in this manner are peptides identified according to assays described below in Example 5; mammalian PrP peptides responsible for prion-forming activity; and other known fibril-forming peptide sequences, such as human amyloid β (1-42) peptide.

In addition, the experiments demonstrate an improved procedure for recombinant production of certain proteins that might otherwise be difficult to recombinantly produce, e.g., due to the protein's detrimental effect on the growth or phenotype of the host cell. For example, DNA binding and DNA modifying enzymes that might locate to a cell's nucleus and detrimentally effect a host cell may be expressed as a fusion with a SCHAG-amino acid sequence from a prion-like protein. In host cells wherein the aggregate-forming phenotype is present, the recombinant protein is "sequestered" into higher order aggregates. By virtue of this sequestration, the biological activity of the resultant protein in the nucleus is reduced. The fusion protein is purified from the insoluble fraction of host cell lysates, and can be cleaved from the fibril core if an appropriate endopeptidase recognition sequence has been included in the fusion construct between the SCHAG amino acid sequence and the sequence of the protein of interest. (An appropriate endopeptidase recognition sequence is any recognition sequence that is not present in the protein of interest, such that the endopeptidase will cleave the protein of interest from the fibril structure without also cleaving within the protein of interest.)

EXAMPLE 2

Construction and Assaying of a Chimeric, Prion-Like Gene and Protein With Yeast Ure2 Protein The following experiments were performed to demonstrate that the prion-determining domain of yeast Ure2 protein also can be fused to a polypeptide other than the Ure2 functional domain to construct a novel, chimeric gene and protein having some prion-like properties. Two prion-like elements are known in yeast: [PSI+] and [URE3]. The underlying proteins, Sup35 and Ure2, each contain an amino-terminal domain (the N domain) that is not essential for normal function but is crucial for prion formation. The N domains of both Sup35 and Ure2 are unusually rich in the polar amino acids asparagine and glutamine.

A. Construction of a NUre2-CSup35 Chimeric Gene

Figure 3A:
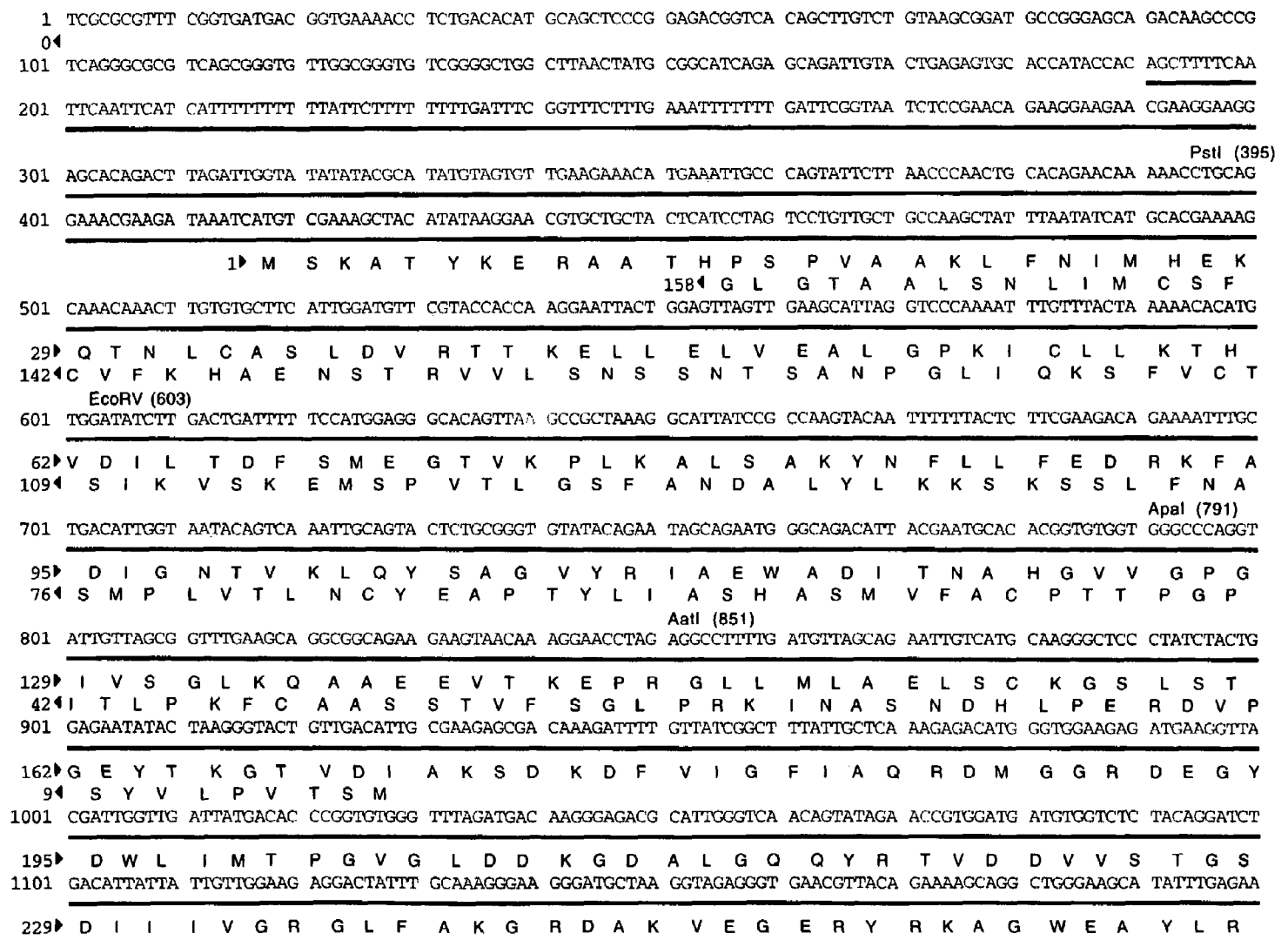
Figure 3C:
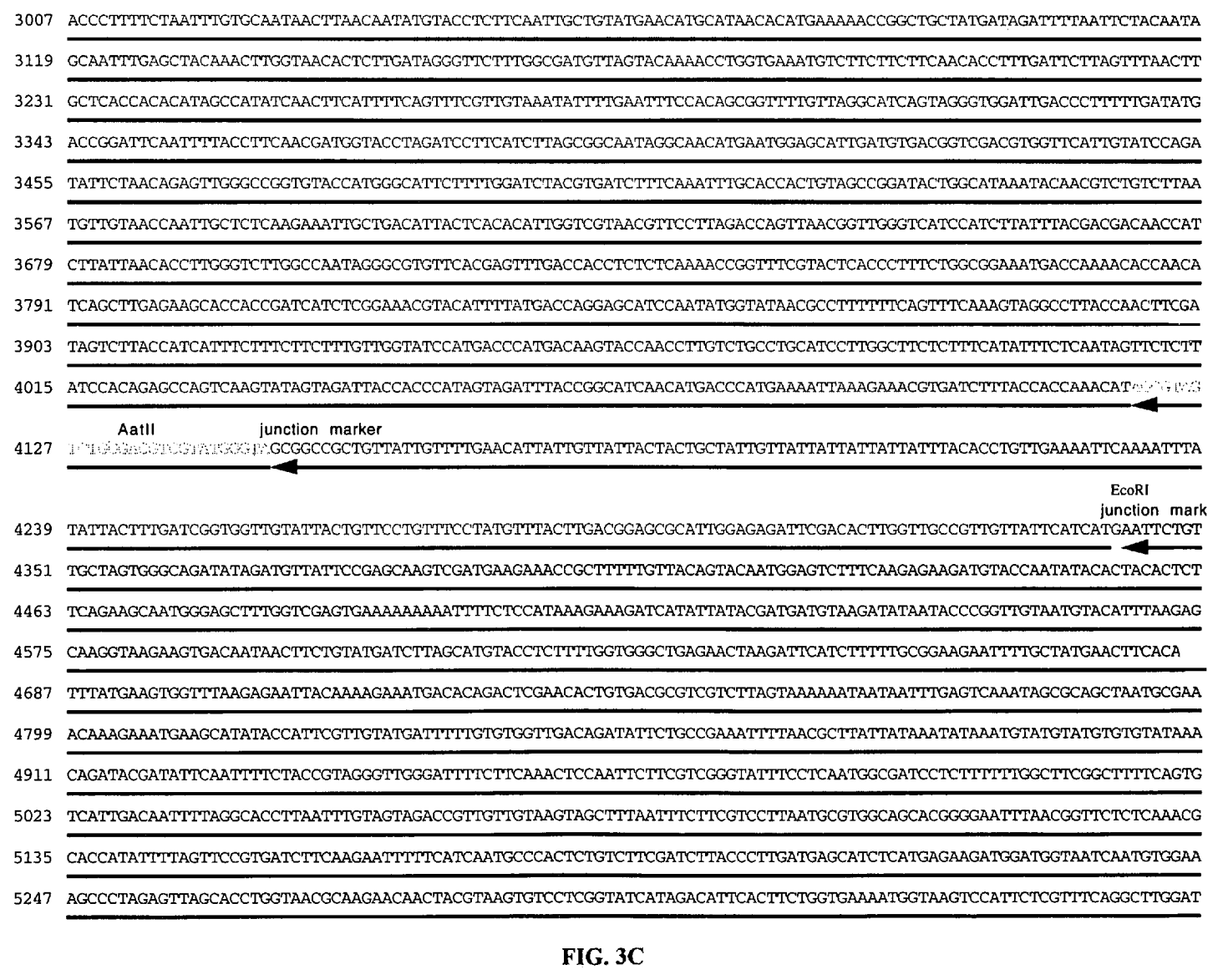
Figure 3D:
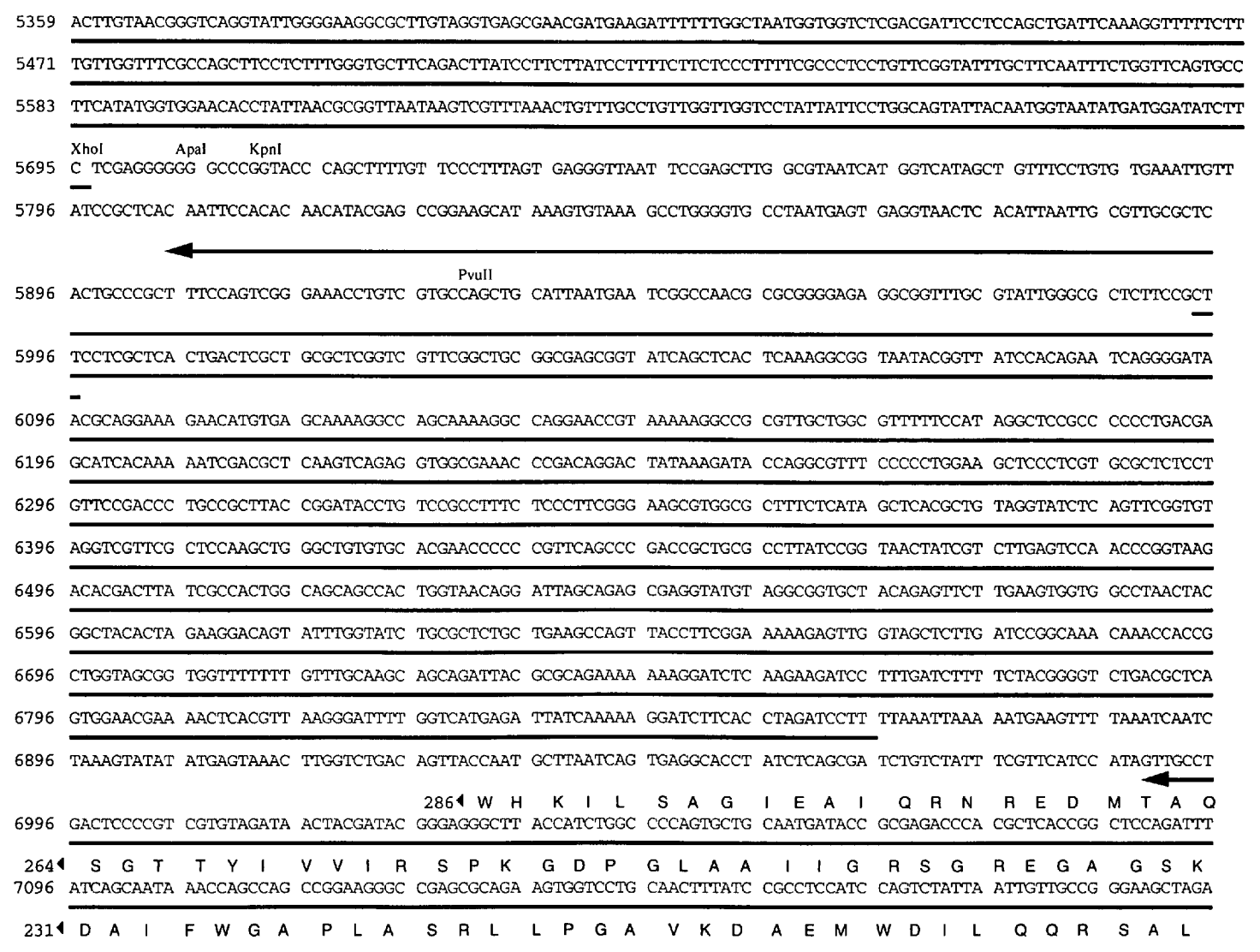

A chimeric polynucleotide (FIG. 3, SEQ ID NO: 49) was constructed comprising a nucleotide sequence encoding the N domain of yeast (*Saccharomyces cerevisiae*) Ure2 protein (Genbank Accession No. M35268, SEQ ID NO: 3, bases 182 to 376, encoding amino acids 1 to 65 (SEQ ID NO: 4) of Ure2 (NUre2)), fused in-frame to a nucleotide sequence encoding a hemagglutinin tag (SEQ ID NO: 13, TAC CCA TAC GAC GTC CCA GAC TAC GCT), fused in-frame to a nucleotide sequence encoding the C domain of yeast Sup35 (CSup35) protein that is responsible for translation-regulation activity of Sup35 (Genbank Accession No. M21129, SEQ ID NO: 1, bases 1498-2793, encoding amino acids 254 to 685 of Sup35 (SEQ ID NO: 2)). At the 5' and 3' ends of this construct were 5' and 3' flanking regions, respectively, of the yeast Sup35 genomic DNA. This construct was inserted into the pRS306 plasmid (available from the ATCC, Manassas, Va., USA, Accession No. 77141; see also Genbank Accession No. U03438) as shown in FIGS. 2 and 3, and used to transform yeast as described below.

B. Transformation and Phenotypic Analysis of Yeast

To replace the Sup35 gene with the NUre2-CSup35 chimeric gene, the first step was to integrate the gene fragment into the yeast genome. Freshly grown cells from overnight culture were collected and resuspended in 0.5 ml LiAc-PEG-TE solution (40% PEG4000, 100 mM Tris-HCL, pH7.5., 1 mM EDTA) in a 1.5 ml tube. 100 μg/10 μl carrier DNA (salmon testis DNA, boiled 10 minutes and chilled immediately on ice) and 1 μg/2 μl of transforming plasmid DNA were added and mixed. This transformation mixture was incubated overnight at room temperature and then heat shocked at 42° C. for 15 minutes. 100 μl of transformation mixture were then spread onto a uracil dropout plate. After transformation, selection for Ura+ results in an integration event, such that native and chimeric genes bracket the URA3-containing plasmid sequence. Transformants were picked and cells having the integrated chimeric gene were confirmed by genomic PCR and Western blot.

The second step of the replacement involved the excision or "popping out" of the wildtype Sup35 gene through homologous recombination between the native Sup35 and the chimeric sequence. Popout of the plasmid was monitored by screening for colonies that are ura- and therefore resistant to the drug 5-fluoroorotic acid (5-FOA). Cells with NUre2-CSup35 integrated were thus plated onto 5-FOA medium to select for those that have the plasmid sequence containing one copy of the Sup35 gene popped out. Clones in which the native Sup35 gene had been replaced with the chimeric gene were then screened by means of colony PCR and further confirmed by Western blot.

To screen for yeast strains that have gene integration and replacement, a Ure2 coding sequence N-terminal primer and a Sup35 coding sequence primer were used for PCR reactions. The NUre2-CSup35 DNA fragment can only be amplified from genomic DNA of cells containing the chimeric gene. To confirm that only the fusion protein of NUre2-CSup35 was expressed in those cells that have the gene replacement, yeast cells were lysed and the cell lysates were run on SDS-polyacrylamide gel and proteins were transferred to PVDF immunoblot. Since there is a hemagglutinin (HA) tag inserted between NUre2 and CSup35, Western blots were then probed with anti-HA antibody from Boehringer Mannheim. To confirm that NUre2-CSup35 is the only copy of Sup35 gene in yeast genome, Western blots were also probed with an antibody against the middle region of Sup35 protein. Loss of antibody signal verified that the NM region of Sup35 gene had been replaced with the N-terminus of Ure2. Thus, the transformed cells were characterized by a deleted native Sup35 gene that had been replaced by the NUre2-CSup35 chimeric gene.

Transformed colonies carrying the chimeric NUre2-CSup35 gene of interest were grown on rich medium (YPD) at 30° C. The resultant colonies were streaked onto [PSI$^+$] selective medium (SD-ADE) and incubated at 30° C. to determine whether some or all contained a [PSI$^+$] phenotype. Two different types of colonies were observed. Some showed normal translational termination characteristic of a [psi–] phenotype. Others showed the suppressor phenotype characteristic of [PSI$^+$] cells. Both phenotypes were very stable and were inherited from generation to generation of the transformed yeast cells.

To determine whether the observed difference in translational fidelity was due to a heritable change in protein conformation, cells were lysed and the lysates subjected to centrifugation at 12,000 or 100,000×g for 10 minutes. Supernatants and precipitate fractions were screened for the fusion protein using an anti-HA antibody (HA·11, Covance Research Products Inc.). The cells that showed reduced translational fidelity also showed aggregation of the NUre2-CSup35 fusion protein, whereas the fusion protein did not appear aggregated in cells having normal translation termination characteristics.

The foregoing experiments demonstrate that the amino-terminal domain of another prion-like yeast gene, Ure2, can be fused to a polypeptide derived from a wholly different protein to construct a novel, chimeric gene and protein having prion-like properties. These results represent the first such demonstration of this kind; [Compare Maison & Wickner, *Science*, 270: 93 (1995) (Ure2$_{1-65}$/β-gal fusion did not change the activity of the β-galactosidase enzyme) and Paushkin et al., *EMBO J.*, 15(12): 3127-3134 (1996) (GST-NSup35 chimeric construct did not allow native Sup35 to adopt an altered state.)]

Several factors are suggested for achieving prion-like behavior with chimeric genes that comprise SCHAG sequences. First, it is preferable to include the SCHAG sequence at a location in the chimeric gene (e.g., amino-terminus or carboxy-terminus) that corresponds to the location at which it is found in its native gene. For example, if NSup35 is selected as the SCHAG sequence, then the chimeric gene preferably is constructed with NSup35 at the amino-terminus, preceding the sequence encoding the polypeptide of interest. Second, it is preferable to include a spacer region of, e.g., at least 5, 10, 20, 30, 40, or 50 amino acids, and preferably at least 60, 70, 80, 90, 100, 120, 130, 140, or 150 amino acids, to separate the SCHAG domain from other domains and reduce the likelihood of steric hinderance caused by other domains. The length of spacer apparently can be quite large because a chimeric construct comprising whole Sup35 fused to Green Fluorescence Protein appears to act as a prion in preliminary experiments. Third, it is preferable if the protein of interest is a protein that does not itself naturally form multimers, because multimer formation of the protein of interest is apt to cause steric interference with the ordered aggregation of the SCHAG domain. (Maison & Wickner's research involved β-galactosidase, which forms a tetrameric functional unit.) The experiments also demonstrate an alternative assay system (i.e., CSup35 fusions) to the GFP and GR assay systems described in the preceding example to screen peptide sequences for their ability to confer prion-like phenotypic properties.

Also contemplated are fusion proteins comprising the M domain of Sup35, or portions of fragments thereof, fused to a different protein to generate a novel protein with prion-like activities. Likewise, fusion proteins displaying prion-like properties, comprising portions or fragments of the N domain, or comprising portions or fragments of the N and of the M domain are also contemplated.

EXAMPLE 3

Modulation of Propensity of Protein to Form Prion-Like Aggregates

The following experiments demonstrate that the propensity of novel chimeric proteins to aggregate into prion-like fibrils can be modulated by varying the number of oligopeptide repeats in the SCHAG portion of the chimeric protein. An increased propensity to form such fibrils is useful in instances where the fibrils themselves comprise a desirable end product to be harvested from cells, e.g., via lysis and centrifugation; and in instances where fibril formation in vivo is desired to phenotypically alter a cell, e.g., by sequestering a biologically active molecule in the cell away from the molecule's normal subcellular region of biological activity.

The yeast Sup35 protein contains an oligopeptide repeat sequence (PQGGYQQYN, SEQ ID NO: 2, residues 75 to 83; with imperfect repeats at residues 41 to 50; 56 to 64; 65 to 74; and 84 to 93). The following experiments demonstrated that an expansion of this oligopeptide repeat in the NM region of Sup35 increases the rate of appearance of new, heritable, [PSI$^+$]-like elements, whereas decreasing the number of repeats lessened the rate of appearance of such elements.

Three expression vectors were created for the experiment containing a chimeric gene comprising a CUP1 promoter sequence (SEQ ID NO: 11) operably linked to a sequence encoding a Sup35 NM region, fused in-frame with a "superglow" GFP encoding sequence (SEQ ID NO: 39). In the first construct (RΔ2-5), the Sup35 NM region had been modified by deleting four of the five oligopeptide repeats found in the native N region (SEQ ID NOs: 14 & 15). In the second construct (R2E2), the Sup35 NM region had been modified by twice expanding the second oligopeptide repeat found in the native N region, creating a total of seven oligopeptide repeats (SEQ ID NOs: 16 & 17). In the third construct, the native Sup35 NM region was employed (SEQ ID NO: 1, nucleotides 739 to 1506, encoding residues 1 to 256 of SEQ ID NO: 2). The CUP1 promoter permitted control of the expression of the chimeric proteins by manipulation of copper ion concentration in the growth medium. [See Thiele, D.

J., *Mol. Cell. Biol.*, 8: 2745-2752 (1988).] The attachment of GFP to NM permitted visualization of the mutant proteins in living cells.

Each of the three above-described NM-GFP constructs were introduced via homologous recombination at the site of the wild-type Sup35 gene into [psi–] yeast cells carrying a nonsense mutation in the ADE1 gene (strain 74-D694 [psi–]), and monitored for the frequency at which cells converted to a [PSI+] phenotype. Cell cultures in the log phase of growth at 30° C. were induced to express the GFP-fusion proteins by adding $CuSO_4$ to the cultures cells to a final concentration of 50 μM. For analysis via fluorescence microscopy, cells were fixed with 1% formaldehyde after four hours and twenty hours of culture. For analysis of [PSI+] induction, cells overexpressing the GFP fusion proteins were serially diluted and spotted onto YPD and SD-ADE media after four hours and twenty hours. Conversion was measured by the ability of cells to grow on medium without adenine (SD-ADE). The [PSI+] phenotype causes readthrough of nonsense mutations, producing sufficient protein to suppress the ADE1 mutation and allow growth without adenine.

Cells were induced with copper for 4 hours to promote expression of the chimeric gene and serially diluted, and then aliquots of each dilution were plated on SD-ADE, conditions that allowed loss of the plasmid. To demonstrate that the initial cultures contained similar numbers of cells, serial dilutions from each culture also were plated on rich medium (YPD) which allowed the growth of all cells in the culture. After incubating the plates for 48 hours at 30° C., colonies on each plate were counted.

Cells expressing the oligopeptide repeat expansion mutation converted to [PSI+] at a much higher frequency than cells expressing the native Sup35NM-GFP, which in turn converted to [PSI+] at a higher frequency than cells expressing the oligopeptide repeat deletion mutation. The observed conversion results were specifically attributable to the production of the chimeric proteins, because the conversion to [PSI+] did not occur in cells that were not induced with copper (control).

Figure 4:
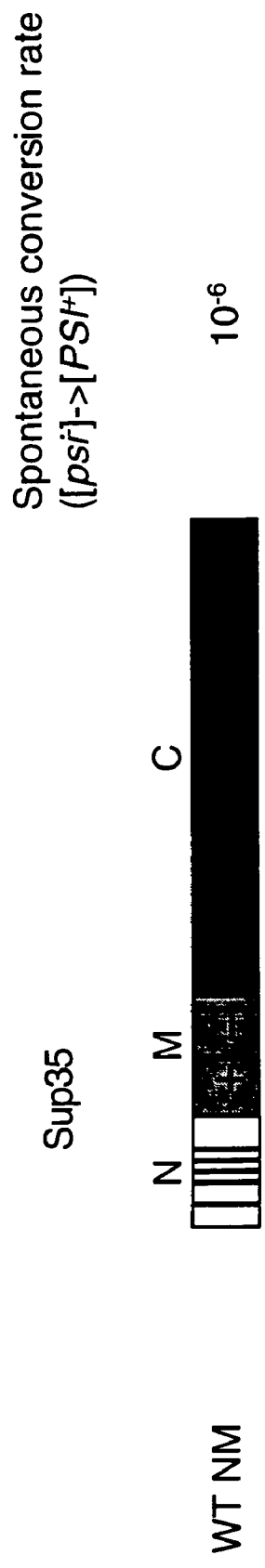
FIG. 4 schematically depicts that the structure of wild-type (WT) yeast Sup35 protein (Top), which contains an amino-terminal region characterized by five imperfect short repeats, a highly charged middle (M) region, and a carboxyl-terminal region involved in translation termination during protein synthesis; a Sup35 mutant designated RΔ2-5, characterized by deletion of four of the repeat sequences in the N region; and a Sup35 mutant designated R2E2 (bottom), into which two additional copies of the second repeat segment have been engineered into the N region. Also depicted is the frequency with which yeast strains carrying these various Sup35 constructs were observed to spontaneously convert from a [psi–] to a [PSI⁺] phenotype.

In a related experiment, the repeat expansion and repeat deletion mutations were introduced into a full-length Sup35 protein-encoding sequence to create constructs encoding the NM(R2E2) and NM(RΔ2-5) fused to the CSup35 domain. These constructs were introduced into the genome of [psi–] yeast strain 74-D694 with the wild-type Sup35 promoter, in each case replacing the native Sup35 gene. Transformants were selected on uracil-deficient medium and confirmed by genomic PCR. Recombinant excision events were selected on medium containing 5-fluoroorotic acid. [See Ausubel et al., *Current Protocols in Molecular Biology*, Green Publishing Associates and Wiley Interscience, New York (1991).] Strains in which wild-type Sup35 was replaced with the R2E2-CSup35 and RΔ2-5CSup35 variants were screened by PCR and confirmed by Western blotting. The cells were cultured on ypd or synthetic complete media at 25° C. for 24 hours, serially diluted, and plated on SD-ADE media to screen for [PSI+] conversions. As shown in FIG. 4, the spontaneous rate of appearance of [PSI+] colonies was increased about 5000-fold in cells carrying the repeat expansion (R2E2) compared to wild-type cells. The wild-type cells produced colonies on the selective medium at a frequency of about 1 per million cells plated. The RΔ2-5 cells produced such colonies at even lower frequency, and it appears that none of these were attributable to development of a [PSI+] phenotype, since they could not be cured by growth on medium containing 5 mM guanidine HCl. In contrast, growth of the wild-type and the R2E2 colonies on the selective medium could indeed be cured by the guanidine HCl treatment.

In additional experiments, the effects of the Sup35 repeat variants were examined when they were used to replace the wild-type Sup35 gene in [PSI+] cells. Cells with the R2E2 replacement remained [PSI+], whereas all cells carrying the RΔ2-5 replacement became [psi–]. Thus, maintenance of the [PSI+] phenotype requires a Sup35 gene having more than one of the oligopeptide repeats.

Still another series of tests examined the effects of the repeat variants on the structural transition of NM in vitro. When purified recombinant NM is denatured and diluted into aqueous buffers, it slowly changes from a random coil into a β-sheet rich structure and forms fibers that bind Congo red with the spectral shift characteristic of amyloid proteins. When deposited at high concentrations, the Congo red-stained fibers also show apple-green birefringence. To determine if the repeat variants alter the intrinsic capacity of the protein to fold in this form, the wild-type and two repeat variants were purified in fully denatured states and then diluted into a non-denaturing buffer. Structural changes were monitored by the binding of Congo red [Klunk et al., *J. Histochem. Cytochem.*, 37: 1293-1297 (1989)] and confirmed by circular dichroism and electron microscopy analysis. In these experiments, the R2E2 variant converted to a β-sheet rich structure about twice as quickly as the wild-type NM polypeptide, which in turn converted significantly faster than the RΔ2-5 variant. These differences were reproducibly obtained in both rotated and unrotated reactions, although the transition was slower in the unrotated reactions. This data indicates that alterations in the number of repeat units alters the propensity of Sup35 NM polypeptides to progress from an unfolded state into a β-sheet rich, higher-ordered structure.

The foregoing experiments demonstrate that the propensity of novel chimeric proteins to aggregate into prion-like fibrils can be modulated by alteration of the SCHAG amino acid sequence of the chimera. Modulation of any SCHAG amino acid sequence in this manner is specifically contemplated as an aspect of the invention, as are the resulting gene and protein products. In addition to alteration by adding or deleting oligopeptide repeat regions, alterations by adding or deleting larger regions is specifically contemplated as an aspect of the invention. By way of example, the entire N terminal region of Sup35 or Ure2 could be duplicated to increase the propensity of transformed cells to produce aggregated chimeric sequences.

EXAMPLE 4

Demonstration that a Prion can be Moved from One Organism to Another

The following experiments demonstrate that a prion protein from one organism will continue to behave in a prion-like manner when recombinantly expressed in another organism, and can even do so when expressed in a different cellular compartment than that in which the protein is produced in its native host.

Polynucleotides encoding mouse (SEQ ID Nos: 18 and 19) and Syrian Hamster (SEQ ID Nos: 20 and 21) PrP proteins were expressed in yeast cells under the control of the constitutive GPD promoter. The protein was produced in the yeast cytosol, without signal sequences that would normally guide it to the endoplasmic reticulum, and without the tail that is normally clipped off during maturation of these proteins in their native hosts. In other words, the PrP protein product in yeast was similar to the final mature product in mammalian neurons, except that it did not contain the sugar modification and GPI anchor. There has been considerable data suggesting that these sugar and GPI anchor characteristics are not required for prion formation.

The normal cellular form of PrP (PrP$^C$) is detergent soluble, but the conformationally changed-protein that is characteristic of neurodegenerative prion disease states (PrPsc) is insoluble in detergent such as 10% Triton. When PrP protein is expressed in yeast, is was insoluble in non-ionic detergents, suggesting that a PrP$^{sc}$ form was present.

PrP-transfected yeast cells were lysed in the presence of 10% Sarkosyl and centrifuged at 16,000×g over a 5% sucrose cushion for 30 minutes. Proteins in both the supernatant and pellet fractions were analyzed on SDS polyacrylamide gels. Coomassie blue staining revealed that most proteins were soluble under these conditions and were present in the supernatant fraction. When identical gels were blotted to membranes and reacted with antibodies against mammalian PrP, most of the PrP protein was found in the pellet fraction, further suggesting that a PrP$^{sc}$ form was present in the yeast.

Protease studies provide further evidence that the yeast PrP was adopting a PrP$^{sc}$ conformation. When PrP protein is expressed in yeast it displays the same highly specific pattern of protease digestion as does the disease form of the protein in mammals. The normal cellular form of PrP is very sensitive to protease digestion. In the disease form, the protein is resistant to protease digestion. This resistance is not observed across the entire protein, but rather, the N-terminal region from amino acids 23 to 90 is digested, while the remainder of the protein is resistant. As expected, when PrP was expressed in the yeast cytosol it was not glycosylated, and it migrated on an SDS gel as a protein of ~27 kD. After protease digestion, a resistant fragment of ~19-20 kD was detected, corresponding exactly to the size expected if the protein were being cleaved at the same site as the PrP$^{sc}$ form of the protein that can be recovered from diseased mammalian brains.

The foregoing data indicates that, when mammalian PrP is expressed in yeast, a species from an entirely different taxonomic kingdom, it be behaves unlike common yeast proteins, and very much like the disease form of PrP in mammals.

Besides the diseased form, a small portion of PrP protein expressed in yeast cytosol also behaves like the normal cellular form of PrP. Even after centrifugation at 180,000 g for 90 minutes, there is still some PrP protein detectable in the supernatant fraction. This part of PrP expressed in yeast, like normal cellular PrP, was soluble in non-ionic detergent, suggesting this small portion of PrP is present in the PrP$^c$ conformation.

EXAMPLE 5

Assays to Identify Novel Prion-Like Amyloidogenic Sequences

The following experiments demonstrate how to identify novel prion-like amyloidogenic sequences and confirm their ability to form prions in vivo. The experiments involve (A) identifying sequences suspected of having prion forming capability; and (B) screening the sequences to confirm prion forming ability.

A. Identifying Sequences Suspected of Having Prion Forming Capability

Known prion or prion-like amino acid sequences, or polynucleotides encoding such sequences, are used to probe sequence databases or genomic libraries for similar sequences. For example, in one embodiment, a prion or prion-like amino acid sequence (e.g., a mammalian PrP sequence; the N or NM regions from a yeast Sup35 sequence; or the N region from a yeast Ure2 sequence) is used to screen a protein database (e.g., Genbank or NCBI) using a standard search algorithm (e.g., BLAST 1.4.9.MP or more recent releases such as BLAST 2.0, and a default search matrix such as BLOSUM62 having a Gap existence cost of 11, a per-residue gap cost of 1, and a Lambda ratio of 0.85. See generally Altschul et al., *Nucleic Acids Res.,* 25(17): 3389-3402 (1997).). As an exemplary cutoff, database hits are selected having P(N) less than 4×10$^{-6}$, where P(N) represents the smallest sum probability of an accidental similarity. For database searching, polypeptide sequences are preferred, but it will be apparent that polynucleotides encoding the amino acid sequences also could be used to probe nucleotide sequence databases.

In an alternative embodiment, one or more polynucleotides encoding a prion or prion-like sequence is amplified and labeled and used as a hybridization probe to probe a polynucleotide library (e.g., a genomic library, or more preferably a cDNA library) or a Northern blot of purified RNA for sequences having sufficient similarity to hybridize to the probe. The hybridizing sequences are cloned and sequenced to determine if they encode a candidate amino acid sequence. Hybridization at temperatures below the melting point ($T_m$) of the probe/conjugate complex will allow pairing to non-identical, but highly homologous sequences. For example, a hybridization at 60° C. of a probe that has a $T_m$ of 70° C. will permit ~10% mismatch. Washing at room temperature will allow the annealed probes to remain bound to target DNA sequences. Hybridization at temperatures (e.g., just below the predicted $T_m$ of the probe/conjugate complex) will prevent mismatched DNA targets from being bound by the DNA probe. Washes at high temperature will further prevent imperfect probe/sequence binding. Exemplary hybridization conditions are as follows: hybridization overnight at 50° C. in APH solution [5×SSC (where 1×SSC is 150 mM NaCt, 15 mM sodium citrate, pH 7), 5×Denhardt's solution, 1% sodium dodecyl sulfate (SDS), 100 µg/ml single stranded DNA (salmon sperm DNA)] with 10 ng/ml probe, and washing twice at room temperature for ten minutes with a wash solution comprising 2×SSC and 0.1% SDS. Exemplary stringent hybridization conditions, useful for identifying interspecies prion counterpart sequences and intraspecies allelic variants, are as follows: hybridization overnight at 68° C. in APH solution with 10 ng/ml probe; washing once at room temperature for ten minutes in a wash solution comprising 2×SSC and 0.1% SDS; and washing twice for 15 minutes at 68° C. with a wash solution comprising 0.1×SSC and 0.1% SDS.

In another alternative embodiment, known prion sequences or other SCHAG amino acid sequences are modified, e.g., by addition, deletion, or substitution of individual amino acids; or by repeating or deleting motifs known or suspected of influencing fibril-forming propensity. To form novel prion sequences, modifications to increase the number of polar residues (glutamine, asparagine, serine, tyrosine) are specifically contemplated, with modifications that increase glutamine and asparagine content being highly preferred. [See Depace et al., *Cell,* 93:1241-1252 (1998), incorporated herein by reference.] In a preferred embodiment, the alterations are effected by site directed mutagenesis or de novo synthesis of encoding polynucleotides, followed by expression of the encoding polynucleotides.

In yet another alternative embodiment, antibodies are generated against the prion forming domain of a prion or prion-like protein, using standard techniques. See, e.g., Harlow and Lane, *Antibodies, A Laboratory Manual,* Cold Spring Harbor Laboratory, Cold Spring Harbor, N.Y. (1988). The antibodies are used to probe a Western blot of proteins for interspecies counterparts of the protein, or other proteins that possess highly conserved prion epitopes. Candidate proteins are purified and partially sequenced. The amino acid sequence information is used to generate probes for obtaining an encoding DNA or cDNA from a genomic or cDNA library using standard techniques.

Sequences identified by the foregoing techniques can be further evaluated for certain features that appear to be conserved in prion-like proteins, such as a region of 50 to 150 amino acids near the protein's amino-terminus or carboxyl-terminus that is rich in glycine, glutamine, and asparagine, and possibly the polar residues serine and tyrosine which region may contain several oligopeptide repeats and have a predicted high degree of flexibility (based on primary structure). In the case of Sup35, a highly charged domain separates the flexible N-terminal region having these properties from the functional C-terminal domain. Sequences possessing one or more of these features are ranked as preferred prion candidates for screening according to techniques described in the following section.

By way of example, the Genbank protein database (accessible via the worldwide web at www.ncbi.nlm.nih.gov) was screened using the Basic Local Alignment Search Tool (BLAST) program (version 1.4.9) using the standard (default) matrix and stringency parameters (BLOSUM62). The prion forming domains of Ure2 (Genbank Acc. No. M35268, SEQ ID NO: 4, amino acids 1-65) and Sup35 (Genbank Acc. No. M21129, SEQ ID NO: 2, amino acids 1-114) from *S. cerevisiae* were used as BLAST query sequences. Open reading frames (ORFs) from *S. cerevisiae* with high similarity scores [P(N) less than $4 \times 10^{-6}$] resulting from the initial search included the following Genbank database entries:

(1) residues 53-97 from Accession No. Z73582 (SEQ ID NO: 22), an uncharacterized open reading frame from *S. cerevisiae*;

(2) residues 1030-1071 from PID No. e236901, in Accession No. Z71255 (SEQ ID NO: 23), an uncharacterized open reading frame from *S. cerevisiae*;

(3) residues 4-58 from locus ybm6, Accession No. P38216 (SEQ ID NO: 24), an uncharacterized open reading frame from *S. cerevisiae*;

(4) residues 251-380 from locus hrp1, Accession No. U35737 (SEQ ID NO: 25), an RNA binding and transport protein having homology to hnRNP1 in humans.

(5) residues 28-126 from locus np13, Accession No. U33077 (SEQ ID NO: 26), an RNA binding and transport protein that functions genetically in the same pathway as Hrp1;

(6) residues 97-286 from locus mcm1, Accession No. X14187 (SEQ ID NO: 27), a DNA binding protein active in cell cycle regulation and mating-type specificity;

(7) residues 205-414 from locus nsr1, Accession No. P27476 (SEQ ID NO: 28), a protein that binds nuclear localization sequences and is active in mRNA processing;

(8) residues 153-405 from Accession No. P25367 (SEQ ID NO: 29), an uncharacterized open reading frame;

(9) residues 806-906 from Accession No. P40467 (SEQ ID NO: 30), an uncharacterized open reading frame;

(10) residues 605-677 from Accession No. S54522 (SEQ ID NO: 31), an uncharacterized open reading frame;

(11) residues 100-300 from locus yk76, Accession No. P36168 (SEQ ID NO: 32), an uncharacterized open reading frame;

(12) residues 1 to 250 from locus fps1, Accession No. S16712 (SEQ ID NO: 33), a membrane channel protein that controls passive efflux of glycerol;

(13) residues 334-388 from Accession No. p40002 (SEQ ID NO: 34), an uncharacterized open reading frame;

(14) residues 325-375 from locus mad1, Accession No. P40957 (SEQ ID NO: 35), an uncharacterized open reading frame; and

(15) residues 215-284 from locus kar1, Accession No. M15683 (SEQ ID NO: 36), an uncharacterized open reading frame.

The nuclear polyadenylated RNA-binding protein hrp1 (Genbank Accession No. U35737) is an especially promising prion candidate. It is the clear yeast homologue of a nematode protein previously cloned by cross-hybridization with the human PrP gene; it scored highly (p value 3.9 e-5) in a Genbank BLAST search for sequences having homology to the N-terminal domain of Sup35; and it contains a stretch of 130 amino acids at its C-terminus that is glyine- and asparagine-rich and contains repeat sequences similar to the oligomeric repeats in the N-terminal domain of Sup35; and is predicted by secondary structure programs to consist entirely of turns.

The sequence corresponding to residues 153-405 of SEQ ID NO: 29 comprises another promising prion candidate. This region is rich in glutamine and asparagine, and is part of a protein that is normally found in aggregates in yeast although it is not aggregated in some strains. When expressed as a fusion protein with green florescent protein, this sequence causes the GFP to aggregate. This aggregation is completely dependent upon Hsp104, much the same as Sup35 aggregation. When residues 153-405 of SEQ ID NO: 29 are substituted for the NM region of SUP35 and transformed into [psi−] yeast, the yeast exhibit a suppression phenotype analogous to [PSI+].

B. Screening Sequences to Confirm Prion-Forming Capability.

Sequences identified according to methods set forth in Section A are screened to determine if the sequences represent/encode proteins having the ability to aggregate in a prion-like manner.

1. Aggregation Assay Using Fusion Proteins

In a preferred screening technique, a polynucleotide encoding the ORF of interest is amplified from DNA or RNA from a host cell using polymerase chain reaction, or is synthesized using the well-known universal genetic code and using an automated synthesizer, or is isolated from the host cell of origin. The polynucleotide is ligated in-frame with a polynucleotide encoding a marker sequence, such as green fluorescent protein or firefly luciferase, to create a chimeric gene. In a preferred embodiment, the polynucleotide is ligated in frame with a polynucleotide encoding a fusion protein such as a Bleomycin/luciferase fusion, which would permit both selection for drug-resistance and quantification of soluble and insoluble proteins by enzymatic assay. See, e.g., Elgersma et al., *Genetics*, 135: 731-740 (1993).

The chimeric gene is then inserted into an expression vector, preferably a high-copy vector and/or a vector with a constitutive or inducible promoter to permit high expression of the ORF-marker fusion protein in a suitable host, e.g., yeast. The expression construct is transformed or transfected into the host, and transformants are grown under conditions that promote expression of the fusion protein. Depending on the marker, the cells may be analyzed for marker protein activity, wherein absence of marker protein activity despite the presence of the marker protein is correlated with a likelihood that the ORF has aggregated, causing loss of the marker activity. Alternatively, host cells or host cell lysates are analyzed to determine if the fusion protein in some or all of the cells has aggregated into aggregates such as fibril-like structures characteristic of prions. The analysis is conducted using one or more standard techniques including microscopic examination for fibril-like structures or for coalescence of marker protein activity; analysis for sensitivity or resistance to protease K; spectropolarimetric analysis for circular dichroism that is characteristic of amyloid proteins; and/or Congo Red dye binding.

A number of the candidates identified above were screened in this manner using a GFP fusion construct. To create the vector that was employed in these analyses, a copper inducible Cup1 promoter was amplified from a genomic library by standard polymerase chain reaction (PCR) methods using the primers 5'-GG GAATTCCCATTACCGACATTTGGGCGC-3' (SEQ ID NO: 37) and 5'-GG GGATCCTGATTGATTGATTGATTGTAC-3' (SEQ ID NO: 38), digested with the restriction enzymes EcoRI and BamHI, and ligated into the pRS316 vector that had digested with EcoRI and BamHI. The annealed vector, designated pRS316Cup1, was transformed into *E. Coli* strain AG-1, and transformants were selected using the ampicillin resistance marker of the vector. Correctly transformed bacteria were grown overnight to provide DNA for further vector construction.

Next, a sequence encoding superbright GFP (SEQ ID NOs: 39, 40) was inserted into the pRS316Cup1 vector. Superbright GFP was amplified from pPSGFP using the primers 5'-GACCGCGGATGGCTAGCAAAGGAGAAG-3' (SEQ ID NO: 41) and 5'-CCT GAGCTCTCATTTGTATAGTTCATCC-3' (SEQ ID NO: 42). The resultant PCR products were digested with SacI and SacII and inserted into PRS316Cup1 that also had been digested ed with SacI and SacII. This created a pRS316Cup1GFP plasmid into which a polynucleotide encoding a candidate open reading frame could be inserted for expression studies. In particular, it was contemplated that candidate open reading frames be amplified by PCR from genomic DNA or cDNA using primers engineered to contain BamHI and SacII restriction sites, to permit rapid cloning into the BamHI and SacII sites of the derived PRS316Cup1GFP vector. For example, in the case of open reading frame (ORF) P25367 the following primers were used: 5'-GGA GGATCCATGGATACGGATAAGTTAATCTCAG-3' (SEQ ID NO: 43, BamHI site underlined) and 5'-GGA CCGCGGGTAGCGGTTCTGTTGAGAAAAGTTGCC-3' (SEQ ID NO: 44, SacII site underlined). PCR products were digested with BamHI and SacII and inserted into the derived plasmid. This created a plasmid that can inducibly express a fusion of an open reading frame of interest fused to GFP. The sequence of pRS316-Cup1-p25367-GFP is set forth in SEQ iD NO: 45.

2. In Vitro Aggregation Assay Using Chaperone Protein

A polynucleotide encoding the ORF of interest is synthesized using the well-known universal genetic code and using an automated synthesizer, or is isolated from the host cell of origin, or is amplified using polymerase chain reaction from DNA or RNA from such a host cell. In a preferred embodiment, the polynucleotide further includes a sequence encoding a tag sequence, such as a polyhistidine tag, HA tag, or FLAG tag, to facilitate purification of the recombinant protein. The polynucleotide is inserted into an expression vector and expressed in a host cell compatible with the selected vector, and the resultant recombinant protein is purified.

Serial dilutions of the recombinant polypeptide (e.g., 100 mM, 10 mM, 1 mM, 0.1 mM, 0.01 mM final concentration) are mixed with 1 µg of a chaperone protein such as yeast Hsp104 protein [See Schirmer and Lindquist, *Meth. Enzymol.*, 290: 430-444 (1998)] in a low salt buffer (e.g., 10 mM MES, pH 6.5, 10 mM $MgSO_4$) containing 5 mM ATP in a 25 µl reaction volume. As controls, reactions are performed in parallel using buffer alone or using Sup35 protein. Reactions are incubated at 37° C. for eight minutes, and the ATPase activity of the chaperone protein is measured by determining released phosphate, e.g., using Malachite Green [Lanzetta et al., *Analyt. Biochem.*, 100: 95-97 (1979)]. In this assay, several fibril-aggregation proteins, including yeast Sup35, the yeast Sup35 N terminal domain, mammalian PrP protein, and β-amyloid (1-40) and (1-42) forms, were found to inhibit the ATPase activity of Hsp104; whereas control proteins (aldolase, BSA, apoferritin, and IgM) did not.

3. Assay Results

To determine if the proteins represented by the ORF's identified above in part A were aggregation prone, a hallmark of prions, polynucleotides encoding the specified residues of interest within the ORF's were amplified from *S. cerevisiae* genomic DNA via PCR and ligated in-frame to a sequence encoding superbright, as described above in section B.1.

These plasmids were transformed into the yeast strain 74D (a, his, met, leu, ura, ade). Transformant colonies were selected (ura+) and inoculated into liquid SD ura and grown to early log phase. Copper sulfate was added to the cultures (final concentration 50 µM copper) to induce protein expression. Cells were fixed after four hours of induction and intracellular GFP expression was visualized.

Examination of GFP fluorescence revealed that the sGFP tag had coalesced in transformants expressing six of the ORF's. This coalescence was similar to that observed with Sup35-GFP fusions in [PSI+] yeast and was considered to be indicative of an ORF having prion-like aggregate-forming ability. Two of the positive sequences represent uncharacterized open reading frames: Z73582 and ybm6. Four are known proteins: mcm1, fps1, p25367 and hrp1 as described above in section B.1. Aggregation of the MCM1-GFP fusion was relatively rare, and was not influenced by Hsp104 dosage in the cells. Of particular interest was the hrp1 construct, which aggregated into multiple cytoplasmic points in the transformed *S. cerevisiae*, and also in transformed *C. elegans*. Deletion of the Hsp104 gene was shown to eliminate the aggregation pattern of hrp1. Also of special interest was the aggregation pattern of the P25367 construct, because this aggregation was completely eliminated by overexpression of Hsp104.

The foregoing experiments demonstrate that searches with prion forming sequences will identify additional sequences with prion-like properties, which sequences can be used according to various aspects of the invention that are specifically exemplified herein with respect to Sup35 or URE2 sequences.

The ability of newly identified aggregating proteins to exist in both an aggregating and non-aggregating conformational state can be further examined, if desired, by studying aggregation phenomena in host cells expressing varying levels of the protein (a result achieved using an inducible promoter, for example), and in host cells having normal and over- or underexpressed chaperone protein levels. (The ability of Sup35 in yeast to enter a [PSI+] conformation depends on an appropriate intermediate level of the chaperone protein Hsp104; elimination of Hsp104 or over-expression of Hsp104 causes loss of [PSI+] and prevents de novo appearance of [PSI+]. See Chernoff et al., *Science*, 268: 880 (1995) and Patino et al.,

*Science*, 273: 622-626 (1996). Growth on a mildly denaturing media, as described elsewhere herein, provides another alternative assay.

The foregoing assays, chimeric constructs, and candidate SCHAG amino acid sequences are all intended as aspects of the invention.

EXAMPLE 6

Identification of Rnq1 as an Epigenetic Modifier of Protein Function in Yeast

The following experiments demonstrate that putative prions can be identified by searching for three attributes of the known yeast prion proteins: unusual amino-acid composition with a high concentration of the polar amino-acid residues glutamine and asparagine, constant expression levels through log and stationary phase growth, and a capacity to switch between distinct stable physical states (in this case, insoluble and soluble forms). One of the candidates isolated in this search, Rnq1, has both in vitro and in vivo characteristics of a prion. Rnq1, exists in distinct, heritable physical states, soluble and insoluble. The insoluble state is dominant and transmitted between cells through the cytoplasm. When the prion-like region of Rnq1 was substituted for the prion domain of Sup35, the protein determinant of the prion [PSI$^+$], the phenotypic and epigenetic behavior of [PSI$^+$] was fully recapitulated. These findings identify Rnq1 as a prion, demonstrate that prion domains are modular and transferable, and establish a paradigm for identifying and characterizing novel prions.

A. Identification of Prion Candidates

The characteristics of Sup35 and Ure2 suggested several criteria for identifying new prion candidates. Previous experiments have demonstrated that particular regions (residues 1-65 for Ure2 (Genbank Acc. No. M35268, SEQ ID NO: 4) and residues 1-123 for Sup35 (Qenbank Acc. No. M21129, SEQ DI NO: 2)) are critical for prion formation by these proteins. Over-expression of these regions is sufficient to induce the prion phenotype de novo. Deletion of these regions has no effect upon the normal cellular function of the proteins but prevents them from entering the prion state. These critical prion-determining domains have an unusually high concentration of the polar residues glutamine and asparagine and are predicted to have very little secondary structure. The domains are located at the ends of proteins that have an otherwise ordinary amino acid composition. We hypothesized that by searching for open reading frames with these characteristics we might find new prion proteins.

A BLAST search (1.4.9 MP version) of the NCBI database of non-redundant coding sequences was performed using the prion-determining domains of Ure2 and Sup35 (residues 1-65 of SEQ ID NO: 4 and residues 1-123 of SEQ ID NO: 2, respectively) as the query sequence with the following parameters: V=100, B=50, H=0, S=90, and P=4. This search revealed approximately twenty open reading frames that had prion-like domains appended to polypeptides with an otherwise normal amino acid composition. To restrict the number of likely candidates, we took advantage of recent global descriptions of mRNA expression patterns. In examining this data we noted that Sup35 and Ure2 are expressed at nearly constant levels as cells transit from the log to the stationary phase of growth. Large fluctuations in expression would be inconsistent with the stability of both their heritable prion and non-prion states. The open reading frames from the BLAST search whose expression varies by less than two-fold in the log phase transition were selected for further analysis. They were fused to the coding sequence of green fluorescent protein (GFP) using PCR and expressed in the yeast strain 74D-694 (ade1-14, trp1-289, his3Δ-200, ura3-52, leu2-3, lys2). Three of the proteins, RNQ1 (Genbank Acc. No. NP009902, SEQ ID NO: 50), YBR016w (Genbank Acc. No. NP009572, SEQ ID NO: 51), and HRP1 (Genbank Acc. No. NP014518, SEQ ID NO: 52), showed coalescence of GFP, as previously described for Sup35.

B. Rnq1 Exists in Distinct States Controllable by Hsp104

We next asked if expression of the fusion protein in a strain that lacked the chaperone Hsp104 eliminated the coalescence of GFP, as it does for Sup35-GFP fusions. This is not a necessary criterion for prion proteins (an interaction with Hsp104 has not been demonstrated for [URE3]) but interaction with the chaperone provides a useful tool for further analysis. In wild-type yeast, fluorescence from the Rnq1-GFP fusion was found in one or more small, intense, cytoplasmic foci. When the fusion protein was expressed in the isogenic Dhsp104 strain, fluorescence was diffuse. The C-terminal end of Rnq1 (amino acids 153-405 of SEQ ID NO: 50) contained the region rich in glutamine and asparagine residues. Fusion of this region alone to GFP gave an identical result to that seen with the full length Rnq1-GFP fusion. Since the effect of HSP104 deletion upon the coalescence of the Rnq1 fusion was the most dramatic, it was chosen for further analysis.

Differential centrifugation was employed to determine if the coalescence observed with Rnq1-GFP fusion proteins reflected the behavior of the endogenous Rnq1 protein. Log phase yeast were lysed using a bead beater (Biospec) into 75 mM Tris-Cl (pH7), 200 mM NaCl, 0.5 mM EDTA, 2.5% glycerol, 0.25 mM EDTA, 0.25% Na-deoxycholate, supplemented with protease inhibitors (Boehringer-Mannheim). Lysates were cleared of crude cellular debris by a 15 second 6000 RPM spin in a microcentrifuge (Eppendorf). Non-denatured total cellular lysates were fractionated by high-speed centrifugation into supernatant and pellet fractions using a TLA-100 rotor on an Optima TL ultracentrifuge (Beckman) at 280,000×g (85,000 RPM) for 30 minutes. Protein fractions were resolved by 10% SDS-PAGE and immunoblotted with an α-Rnq1 antibody. Rnq1 remained in the supernatant of a Δhsp104 strain, but pelleted in the wild-type. Thus, the GFP coalescence is not an artifact of the fusion; the Rnq1 protein itself is sequestered into an insoluble aggregate in an Hsp104-dependent fashion. We also examined the solubility of Rnq1 in several unrelated yeast strains. In four (S288c, YJM436, SK1 and W303) the protein fractionated in the pellet, in two (YJM128, YJM309) it partitioned between the pellet and supernatant fractions, and in two others (33G, 10B-H49) the protein was chiefly recovered in the supernatant fraction. Thus, Rnq1 naturally exists in distinct physical states in different strains.

C. The Insoluble State of Rnq1 is Transmitted by Cytoduction

The heritability of the known yeast prions is based upon the ability of protein in the prion state to influence other protein of the same sequence to adopt the same state. Because the protein is passed from cell to cell through the cytoplasm, the conformational conversion is heritable, dominant in crosses, and segregates in a non-Mendelian manner. To determine if the insoluble state of Rnq1 is transmissible in this way, we used cytoduction, a well-established tool for the analysis of the [PSI$^+$] and [URE3] prion. The karyogamy deficient (kar1-1) strain 10B-H49 (ρ° ade2-1, lys1-1, his3-11,15, leu2-3,112, kar1-1, ura3::KANR) can undergo normal conjugation between a and α cells but is unable to fuse its nucleus with its mating partner. Cytoplasmic proteins and organelles are mixed in fused cells, but the haploid progeny that bud from them contain nuclear information from only one of the two parents.

10B-H49 shows diffuse expression of Rnq1-GFP, and served as the recipient for the transfer of insoluble Rnq1 from W303 (Mata, his3-11,15, leu2-3,112, trp1-1, ura3-1, ade2-1), the donor. After cytoduction, colonies derived from haploid cells that contained the 10B-H49 nuclear genome but had undergone cytoplasmic mixing, as demonstrated by mitochondrial transfer, were selected. Cytoductants were selected after overnight mating on defined media lacking tryptophan that had glycerol as the sole carbon source. All showed single or multiple cytoplasmic aggregates of Rnq1-GFP—a pattern indistinguishable from that of the W303 parent. Furthermore, density-based centrifugation of protein extracts, performed as above, indicated that cytoduction caused the endogenous Rnq1 protein of the 10B-H49 strain to shift from the soluble to the insoluble fraction. Thus exposure of 10B-H49 cells to the cytoplasm of W303 is sufficient to cause a heritable change in the physical state of Rnq1. Because RNQ1 is a nuclear gene (not transmitted during cytoduction) the protein's insoluble state is not due to polymorphisms in its amino acid sequence, nor to any other trait carried by the W303 genome. Rather, like the Sup35 and Ure2 prions, its altered conformational state is "infectious", transmissible from one protein to another.

D. Purified Rnq1 Forms Fibers and Shows Seeded Polymerization

Both Sup35 and Ure2 have the capacity to form highly ordered amyloid fibers in vitro, as analyzed by the binding of amyloid specific dyes and by electron microscopy. To examine conformational transitions of Rnq1 in vitro, the protein was expressed in *E. coli* and studied as a purified protein. Rnq1 was cloned into pPROEX-HTb (GibcoBRL). The primers 5'-GGA GGA TCC ATG GAT ACG GAT AAG TTA ATC TCAG-3' (SEQ ID NO: 53) and 5'-CC AAG CTT TCA GTA GCG GTT CTG TTG AGA AAA GTTG-3' (SEQ ID NO: 54) were used for PCR in a solution containing 10 mM Tris (pH8.3), 50 mM KCl, 2.5 mM $MgCl_2$, 2 mM dNTPs, 1 µM of each primer and 2 U of Taq polymerase; and using genomic 74D DNA as template under the following conditions: incubation at 94° C. for 2 min, followed by 29 cycles of 94° C. for 30 sec, 50° C. for 30 sec, and 72° C. for 90 sec, followed by a final incubation at 72° C. for 10 minutes. The PCR product was then digested and ligated into the BamHI and HindIII sites of pPROEX-HTb (GibcoBRL). The plasmid was electroporated into BL21-DE3 lacIq cells. Transformed bacterial cultures were induced at $OD_{600}$=1 with 1 mM IPTG for four hours at 30° C. The cells were lysed in 8M urea (Rnq1 was purified under denaturing conditions (8M urea) because it had a tendency to form gels during purification in the absence of denaturant), 20 mM Tris-Cl pH8. Protein was purified over a Ni-NTA column (Qiagen) followed by Q-sepharose (Pharmacia). The $(His)_6$-tag from the vector was cleaved under native conditions (150 mM NaCl, 5 mM KPi) using TEV protease followed by passage of the protease product over a Ni-NTA column to remove uncleaved protein. Protein was methanol precipitated prior to use. Recombinant protein was resuspended in 4M urea, 150 mM NaCl, 5 mM KPi, pH 7.4 at a concentration of 10 µM. Seeded samples were created by sonication of 1/50 volume of a 10 µM solution of pre-formed fibers verified by electron microscopy. The protein samples were incubated at room temperature on a wheel rotating at 60 r.p.m.

To determine if Rnq1 forms amyloids we used Thioflavin T fluorescence. This dye exhibits an increase in fluorescence and a red-shift in the $\lambda_{max}$ of emission upon binding to multimeric fibrillar β-sheet structures characteristic of many amyloids, including transthyretin, insulin, β-2 microglobulin and Sup35. Fluorimeter samples were prepared as 3.3 µM Rnq1, 50 µM Thioflavin T in buffer. Samples were analyzed on a Jasco FP750 with the following settings: $\lambda_{exc}$=409 nm, $\lambda_{emi}$=484 nm, bandwidth 10 mm. The acquisition of Thioflavin T binding was sigmoidal (lag phase ~six) suggesting a self-seeded process of protein assembly. The addition of 2% preformed fibers to fresh solutions of Rnq1 reduced the lag time—from 6.4±0.2 hrs to 4.3±0.2 hrs (n=4).

The formation of higher ordered structures was confirmed by transmission electron microscopy. For electron microscopy analysis, 5 µl of a 10 µM protein solution was placed on a 400 mesh carbon coated EM grid (Ted Pella, Cat. 01822), and allowed to adsorb for 1 minute. The sample was negatively stained with 200 µl of 2% aqueous uranyl acetate, and wicked dry. Samples were observed in a Philips CM120 transmission electron microscope operating at 120 kV in low dose mode. Micrographs were recorded at a magnification of 45,000 on Kodak SO-163 film. The protein formed fibers with a diameter of 11.3±1.4 nm. This figure is comparable to the reported range for Ure2 (~20 nm) and Sup35 (~17 nm) fibers. The fibers appeared to be branching and the termini were unremarkable. The appearance of the fibers was coincident with the onset of rapid increases in Thioflavin T fluorescence.

E. Rnq1 Disruption

[URE3] and [PSI⁺] produce phenotypes that mimic loss-of-function mutations in their protein determinants. To determine the loss of function phenotype of Rnq1, the entire ORF was deleted by homologous recombination in a diploid 74D-694 strain using a kanamycin resistance gene. Strains deleted of the Rnq1 open reading frame were created using the long flanking homology PCR method. Primers 5'-GGT GTC TTG GCC AAT TGC CC-3' (SEQ ID NO: 55) and 5'-GTC GAC CTG CAG CGT ACG CAT TTC AGA TCT TTG CTA TAC-3' (SEQ ID NO: 56) or 5'-CGA GCT CGA ATT CAT CGA TTG ATT CAG TTC GCC TTC TATC-3' (SEQ ID NO: 57) and 5'-CTG TTT TGA AAG GGT CCA CATG-3' (SEQ ID NO: 58) were used to amplify genomic DNA. These PCR products were used as primers for a second round of PCR on plasmid pFA6a, which is described in Wach et al., Yeast 13:1065-75 (1994), digested with NotI. The product of the second PCR round was used to transform log-phase yeast cultures. Transformants were selected on YPD containing 200 mg/mL G418 (GibcoBRL). Upon sporulation each tetrad produced four viable colonies, two of which contained the Rnq1 disruption, confirmed by immunoblotting total cellular proteins with an α-Rnq1 antibody and PCR analysis of the genomic region. The Δrnq1 strain had a growth rate comparable to that of wild-type cells on a variety of carbon and nitrogen sources and was competent for mating and sporulation. The strain grew similarly to the wild-type in media with high and low osmolarity, and in assays testing sensitivity to various metals (cadmium, cobalt, copper).

F. Fusion of Rnq1 (153-405) to Sup35 (124-685)—Nonsense Suppression Phenotype

The lack of an obvious loss-of-function phenotype was not unexpected, as the two known yeast prions, [URE3] and [PSI⁺] only exhibit phenotypes under unusual selective conditions. However, the absence of a phenotype presented difficulties in determining whether Rnq1 could direct the epigenetic inheritance of a trait. To determine if the prion-like domain of Rnq1 could produce an epigenetic loss-of-function phenotype we asked if it could replace the prion-determining domain of Sup35. When the wild-type Sup35 translation termination factor enters the prion state the loss-of-function phenotype it produces is nonsense suppression—the readthrough of stop codons. This phenotype can be conveniently assayed in the strain 74D-694 because it contains a UGA stop codon in the ADE1 gene. In [psi⁻] 174D-694 cells, ribosomes efficiently terminate translation at this codon. Cells are therefore unable to grow on media lacking adenine (SD-ade), and colonies appear red on rich media due to the accumulation of a pigmented by-product. In [PSI⁺] strains, sufficient readthrough occurs to support growth on SD-ade and prevent accumulation of the pigment on rich media.

The coding region for amino acid residues 153-405 of Rnq1 (amino acid residues 153-405 of SEQ ID NO: 50) was substituted for 1-123 of Sup35 and the resulting fusion gene, RMC, was inserted into the genome in place of the endogenous SUP35 gene. RNQ1, SUP35 and its promoter were cloned by amplification of 74D-694 genomic DNA. The RNQ1 open reading frame was cloned using 5'-GGA GGA TCC ATG GAT ACG GAT AAG TTA ATC TCAG-3' (SEQ ID NO: 59) and (A) 5'-GGA CCG CGG GTA GCG GTT CTG TTG AGA AAA GTT GCC-3' (SEQ ID NO: 60). RNQ1 (153-405) was cloned using 5'-GA GGA TCC ATG CCT GAT GAT GAG GAA GAA GAC GAGG-3' (SEQ ID NO: 61) and (A). The SUP35 promoter was cloned using 5'-CG GAA TTC CTC GAG AAG ATA TCC ATC-3' (SEQ ID NO: 62) and 5'-G GGA TCC TGT TGC TAG TGG GCA GA-3' (SEQ ID NO: 63). SUP35 (124-685) was cloned using 5'-GTA CCG CGG ATG TCT TTG AAC GAC TTT CAA AAGC-3' (SEQ ID NO: 64) and 5'-GTG GAG CTC TTA CTC GGC AAT TTT AAC AAT TTT AC-3' (SEQ ID NO: 65) by PCR using the conditions described above in section D.

The RMC gene replacement was performed as described in Rothstein, 1991. To create the plasmid for pop-in/pop-out replacement in pRS306 (available from ATCC), the SUP35 promoter was ligated into the EcoRI-BamHI site, RNQ1 (153-405) was ligated into the BamHI-SacII site, and SUP35 (124-685) was ligated into the SacII-SacI site. To create the disrupting fragment, this plasmid was linearized with MluI and transformed. Pop-outs were selected on 5-FOA (Diagnostic Chemicals Ltd.) and verified by PCR. The resulting strain, RMC, had a growth rate similar to that of wild-type cells on YPD, although the accumulation of red pigment was not as intense as seen in [psi⁻] strains. RMC strains showed no growth on SD-ade even after 2 weeks of incubation). Thus, the protein encoded by the RMC gene (Rmc) fulfilled the essential translational termination function of Sup35.

At a low frequency, RMC variants appeared that were white on rich media and grew on SD-ade even more robustly than [PSI⁺] cells did. The frequency at which these variants appeared (~10⁻⁴) was far greater than expected for reversion of the UGA stop codon mutation in ade1-14, and subsequent analysis demonstrated that the allele had not reverted. The suppressor phenotype of these variants was comparable in stability to that of [PSI⁺]. Because Sup35 proteins that lack residues 1-123 are incapable of making such conversions, these observations suggest that the Rnq1 prion-like domain can direct a prion conversion in the Rmc fusion protein.

Transient over-expression of Sup35 can produce new [PSI⁺⁺] elements, because higher protein concentrations make it more likely that a prion conformation will be achieved. To test whether over-expression of Rmc can produce heritable suppressing variants, the original, non-suppressing RMC strain was transformed with an expression plasmid for RMC. These transformants showed a greatly elevated frequency of conversion to the suppressor state compared to control strains carrying the plasmid alone. Once a prion conformation is achieved it should be self-perpetuating and normal expression should then be sufficient for maintenance. When the RMC expression plasmid was lost all strains retained the suppressor phenotype. Thus, transient over-expression of Rmc produced a heritable change in the fidelity of translation termination.

G. Non-Mendelian Segregation of Rmc-Based Suppression Phenotype

To examine the genetic behavior of the suppressor phenotype in RMC strains, an isogenic α mating partner was created from a non-suppressing a RMC strain. When this strain was crossed to the original, non-suppressing, RMC strain, neither the diploids nor their haploid meiotic progeny exhibited the suppressor phenotype. However, when this strain was mated to RMC suppressor strains, the resulting diploids all displayed the suppressor phenotype, demonstrating that suppression is dominant. In fourteen tetrads dissected from two different diploids of this cross, all four haploid progeny showed inheritance of the suppression phenotype, instead of the 2:2 segregation expected for a phenotype encoded in the nuclear genome. Following convention, we henceforth refer to the dominant, non-Mendelian suppressor phenotype as [RPS⁺] (for Rnq1 [PSI⁺]-like Suppression) and the non-suppressed phenotype as [rps⁻].

To determine if the dominant, non-Mendelian [RPS⁺] phenotype arises from the ability of Rmc protein to form a prion, we tested it for two additional unusual genetic behaviors that are not expected for other non-Mendelian genetic elements, such as viruses or mitochondrial genomes. First, it should become recessive and Mendelian in crosses to strains carrying a wild-type Sup35 allele. This is because Sup35 lacks the Rnq1 sequences that would allow it to be incorporated into an [RPS⁺] prion. Wild-type Sup35, therefore, should cover the impaired translation-termination phenotype associated with the [RPS⁺] prion. However, even when this phenotype has disappeared, Rmc protein in the prion state should still convert new Rmc protein to the same state. Therefore, in haploid meiotic progeny of this diploid, the phenotype will reappear in segregants carrying the RMC gene, but not in segregants carrying the SUP35 gene (2:2 segregation).

Indeed, diploids of a cross between an [RPS⁺] strain and an isogenic strain with a wild-type SUP35 gene did not exhibit a suppressor phenotype. Upon sporulation, suppression reappeared in only two of the four progeny. By PCR genotyping, these strains had the RMC gene at the SUP35 locus. Thus the [RPS⁺] factor had been preserved in the diploid, even though the phenotype had become cryptic.

Second, maintenance of [RPS⁺] should depend upon continued expression of the Rmc protein. Although [RPS⁺] is maintained in a cryptic state in diploids with a wild-type Sup35 gene, it should not be maintained in their haploid progeny whose only source of translational termination factor is wild-type Sup35. To determine if these progeny harbored the [RPS⁺] element in a cryptic state, they were mated to an [rps⁻] RMC strain whose protein would be converted if [RPS⁺] were still present. When this diploid was sporulated, none of the progeny exhibited the suppressor phenotype. Thus, the [RPS⁺] element was not maintained in a cryptic state unless the Rmc protein was present.

H. Curing of [RPS⁺]

One of the hallmarks of yeast prions is that cells can be readily and reversibly cured of them. [PSI⁺] is curable by several means, including growth on media containing low concentrations of the protein denaturant guanidine hydrochloride and transient over-expression or deletion of the protein remodeling factor HSP104.

Strains carrying [RPS⁺] were passaged on medium containing 2.5 mM guanidine hydrochloride (GdnHCl) (Fluka) and then plated to YPD and to SD-ade to assay the suppressor phenotype. Cells passaged on GdnHCl no longer displayed the [RPS+] phenotype, while cells not treated with GdnHCl retained it. [RPS+] was also lost when the HSP104 gene was deleted by homologous recombination, performed using the same strategy as described above in section E, or when HSP104 was over expressed from a multicopy plasmid using the constitutive GPD promoter. Cells that had been cured of [RPS+] by over-expression of HSP104 were passaged on YPD medium to isolate strains that had lost the over-expression plasmid. These strains remained [rps−]. Thus transient over-expression of HSP104 is sufficient to heritably cure cells of [RPS+].

Finally, we asked if Hsp104-mediated curing was reversible. Cells cured by over-expression of HSP104 were re-transformed with a plasmid bearing a single copy of RMC. To create the single-copy RMC plasmid in pRS316 (available from ATCC) the ClaI-SacI fragment (includes promoter and RMC) from the plasmid used above for the RMC gene replacement was ligated into the ClaI-SacI site. Transformants were then plated onto SD-ade to assess the rate at which they converted to the [RPS+] suppressor phenotype. [RPS+] was regained at a rate comparable to that seen in the parental RMC strain, indicating that the transient over-expression of HSP104 caused no permanent alteration in susceptibility to [RPS+] conversion.

I. Effect of Endogenous Rnq1 Upon [RPS+]

To determine if [RPS+] can act as an independent genetic element, the gene encoding the endogenous Rnq1 protein was deleted in strains carrying the RMC replacement of SUP35 using methods described above. The deletion had no effect upon the maintenance of the [RPS+] suppression phenotype. Growth on SD-ade was equally robust in [RPS+] and [RPS+] Δrnq1 strains. This indicates that Rmc can behave as an independent prion and is not dependent upon pre-existing Rnq1 in an insoluble state.

J. Physical State of the Rmc Protein in [RPS+] and [rps−] Strains

Finally, we examined the localization of the Rmc fusion protein in the [RPS+] and [rps−] strains. Both strains were transformed with inducible plasmids that provided Rnq1 (153-405)-GFP expression that were constructed as described above in section A. Strains that lacked the endogenous Rnq1 gene were used to prevent the GFP marker from localizing to the endogenous Rnq1 aggregate. Short-term expression of the GFP-fusion protein prevented the formation of new [RPS+] elements in the [rps−] strain.

Two distinct patterns of Rmc protein localization were revealed by this assay and these correlated with the phenotypic differences between [RPS+] and [rps−] strains. In the non-suppressing [rps−] strains, the Rnq1(153-405)-GFP label was diffuse. In the suppressing [RPS+] strains, fluorescence was punctate, and was excluded from the nucleus. This punctate pattern was different from that observed with the endogenous Rnq1 aggregates, as Rmc aggregates are numerous and very small.

Collectively, the foregoing experiments demonstrate that Rnq1, which was identified based on sequence analysis, exhibits prion-like behaviour in numerous in vitro and in vivo assays. The search method used here shows that putative prions can be identified by a directed prion search rather than by the study of a pre-existing phenotype. In addition, this method will be applicable to the identification of prion proteins in many other organisms. Our demonstration that a new prion protein domain can substitute for that of another well-characterized prion, reproducing its phenotypic characteristics and epigenetic mode of inheritance, also provides a crucial tool in the analysis of uncharacterized candidates.

We have shown that Rnq1 exists in distinct physical states—soluble and insoluble—in unrelated yeast strains. The insoluble state can be transmitted through cytoduction, and once transmitted is stably inherited. When the N-terminal prion-determining region of SUP35 was replaced with the C-terminal domain of RNQ1, the hybrid Rmc protein provided translation termination activity, mimicking the phenotype of [psi−] strains. At a low spontaneous frequency, the strain acquired a stable heritable suppressor phenotype, [RPS+], which mimicked the phenotype of [PSI+] strains. Suppression was dominant and segregated to meiotic progeny in non-Mendelian ratios. The possibility that this phenotype is caused by an epigenetic factor unrelated to the fusion protein was ruled out by genetic crosses showing that the phenotype is not expressed and can not be transmitted in strains that do not produce the fusion protein. The relationship of the suppression phenotype to protein conformation was further demonstrated by fluorescence localization of the hybrid protein in isogenic [RPS+] and [rps−] strains. In [RPS+] strains, most of the protein is sequestered into small foci and is presumably inhibited in its function in translational termination. Transient over-expression of Rmc greatly increased the frequency of conversion to [RPS+].

It is highly unusual for over-expression of a protein to cause a loss-of-function phenotype. It is even more unusual for phenotypes produced by over-expression to be stable after over-expression has ceased. Yet these properties are shared by the two yeast prion determinants and, to our knowledge, have been uniquely shared by them until now. They are believed to derive from stabilization of an otherwise unstable protein conformation by protein-protein interactions. Proteins in the altered form then have the capacity to recruit new proteins of the same type to the same form. The phenotype associated with this change is, therefore, stably inherited from generation to generation and transferred to mating partners in crosses.

The ability of amino acid residues 153-405 of Rnq1 (SEQ ID NO: 50) to substitute for the N-terminal domain of Sup35 and recapitulate its prion behavior was by no means predictable. The C-terminal region of Rnq1 (residues 153-405) and the N-terminal region of Sup35 have no primary amino-acid sequence homology—only a similar enrichment in polar amino acids. Reconstituting the epigenetic behavior of a prion requires that the Rmc fusion protein achieve an unusual balance between solubility and aggregation. If the fusion protein is too likely to aggregate, the inactive state will be ubiquitous; if it is too likely to remain soluble, the inactive state will not be stable. To recapitulate the epigenetic behavior of [PSI+] the fusion protein must be able to switch from one state to the other and maintain either the inactive or the active state in a manner that is self perpetuating and highly stable from generation to generation. Even minor variations in the sequence of the N-terminal region of Sup35, including several single amino-acid substitutions and small deletions, can prevent maintenance of the inactive state. And a small internal duplication destabilizes maintenance of the active state. Therefore, the ability of the Rnq1 domain to substitute for the prion domain of Sup35 and to fully recapitulate its epigenetic behavior provides a rigorous test for its capacity to act as a prion and suggests that it has been honed through evolution to serve this function.

The fusion of prion-determining regions with different functional proteins could be used to create a variety of recombinant proteins whose functions can be switched on or off in a heritable manner, both by nature and by experimental design. The two regions that constitute a prion, a functional domain and an epigenetic modifier of function, are modular and transferable.

EXAMPLE 8

High-Throughput Assay to Identify Novel Prion-Like Amyloidogenic Sequences

The procedures described in Example 5 are particularly useful for identifying candidate prion-like sequences based on sequence characteristics and for screening these candidate sequences for useful prion-like properties. The following modification of those procedures provides a high-throughput genetic screen that is particularly useful for identifying sequences having prion-like properties from any set of clones, including a set of uncharacterized clones, such as cDNA or genomic libraries.

A library of short DNA fragments, such as genomic DNA fragments or cDNAs, is cloned in front of a sequence encoding the C-terminal domain of yeast Sup35 to create a library of CSup35 chimeric constructs of the formula 5'-X-CSup35-3', wherein X is the candidate DNA fragment. Optionally, the 3' end of the construct encodes both the M and C domains of Sup35. This library is transformed into a [psi–] strain of yeast that carries Sup35 as a Ura+plasmid (with its chromosomal Sup35 deleted). Transformants are plated onto FOA-containing medium, which will cure the Ura+ plasmid so that the only functioning copy of Sup35 will be a fusion construct from the chimeric library.

Viable transformants are transferred to a selective media to screen for transformants which can suppress nonsense codons in a [PSI$^+$]-like manner. For example, if the host cell is a yeast strain carrying a nonsense mutation in the ADE1 gene, the transformants are screened for cells that are viable on a SD-ADE media. Cells that can survive via suppression of nonsense codons are selected for further analysis (e.g., as described in preceding Examples), under the assumption that the library chimera has altered the function of Sup35. By using prion-specific tests such as histological examination for protein aggregates, curing, and Hsp104-dosage alteration, true aggregation-directing protein domains will be identified from original library of DNA constructs. The constructs which display prion-like properties can be used as described herein. Also, such constructs can be isolated and sequenced and used to identify and study the complete genes from which they were derived, to see if the original gene/protein possesses prion properties in its native host. The foregoing assay also is useful for rapidly identifying fragments and variants of known prion-like proteins (NMSup35, NUre2, PrP, and so on) that retain prion-like properties. The assay, as well as chimeric constructs of the formula 5'-X-CSup35-3' and expression vectors containing such constructs, are considered additional aspects of the present invention.

EXAMPLE 9

Fiber Assembly Mechanism of the Prion-Determining Region (NM) of Yeast Sup35p

The investigation of specific protein aggregation is gaining an increasing role in conjunction with increasing numbers of human diseases characterized by altered protein structures, including prion-based encephalopathies, noninfectious neurodegenerative diseases, and systemic amyloidoses. Amyloid protein aggregates are β-sheet rich structures that form fibers in vitro and bind dyes such as CongoRed and ThioflavinT. Strikingly, most amyloids can promote the propagation of their own altered conformations, which is thought to be the basis of protein-mediated infectivity in prion diseases. This feature of protein self-propagation in amyloids may also be critical to disease progression in noninfectious amyloid diseases such as Alzheimer's or Parkinson's disease. A powerful system to study the molecular mechanism of amyloid propagation and specificity is the prion-like phenomenon [PSI$^+$] of *Saccharomyces cerevisiae*. Formation of higher ordered Sup35p complexes and the propagation of [PSI$^+$] is caused by NM region of Sup35p. In vitro, both full-length Sup35p and NM form amyloid fibers with NM dictating the formation of the fiber axis while the C-terminal region of Sup35p is thought to be located on the periphery of the fibers. Detailed analysis by circular dichroism showed that NM adopts a mainly random coil structure in solution before it changes slowly to a structure that is β-sheet-rich. This conformational conversion was shown to occur simultaneously to the formation of amyloid fibrils.

In general, amyloid polymerization is considered to be a two-stage process initiated by the formation of a small nucleating seed or protofibril. Seed formation is thought to be oligomerization of soluble protein accompanied by a transition from a predominantly random coil to an amyloidogenic β-sheet conformation. Subsequent to nucleation, the seeds assemble with soluble protein to form the observed amyloid fibrils. The mechanisms for nucleation and fiber assembly are not well understood.

Strikingly, the secondary structure of all proteins that form amyloid fibrils under physiological conditions is partially random coil in aqueous solutions. Such structure is usually significant for partially unfolded protein as found in folding intermediates. It is possible that this unique "high-energy" structure in solution is the driving force for fiber assembly of such proteins. Thereby, the fibrous aggregates might present the lowest energy conformer of these proteins. As a consequence, interference with their structural state in solution should influence their fiber assembly ability. This has been shown for Alzheimer's β-amyloid peptide, islet amyloid polypeptide, and the artificial peptide DAR16-IV, where changes in the secondary structure dramatically altered the fiber assembly process.

The following experiments were performed to examine and characterize the folding and association pathway of soluble NM by starting with chemically denatured protein. Similar results were obtained with proteins isolated under non-denaturing conditions. These studies were facilitated by use of labeled cysteine-substituted NM mutants. A better understanding of the mechanisms of fiber assembly will facilitate manipulations of fiber growth under various conditions A. Materials and Methods Bacterial Strains and Culture Using pEMBL-Sup35p (an *E. coli* plasmid containing the Sup35 protein) as template, DNA encoding NM was amplified by PCR with Various Linkers for subcloning. For recombinant NM expression, the PCR products were subcloned as NdeI-BamHI fragments into pJC25. For GST-NM fusions, the PCR products were subcloned as BamHI-EcoRI fragments into pGEX-2T (Pharmacia). For site-directed mutagenesis the protocol by Howorka and Bayley, *Biotechniques*, 25:764-766 (1998), was used for a high throughput cysteine scanning mutagenesis. A non-mutagenic primer pair for the β-lactamase gene and a mutagenic primer pair for each respective mutant were employed. In addition to generating a unique NsiI site, we used SphI and NspI sites, which allows introduction of a cysteine codon in front of methionine and isoleucine or after alanine and threonine codons, to increase the number of mutants in our cysteine screen. The fidelity of each construct was confirmed by Sanger sequencing. Protein was expressed in *E. coli* BL21 [DE3] after inducing with 1 mM IPTG ($OD_{600}$ of 0.6) at 25° C. for 3 hours.

Yeast Strains and Culture

Using pJLI-Sup35pC-Sup35p as a template, DNA encoding each of the respective $NM_{cys}$ was amplified by PCR with two EcoRI sites for subcloning. To investigate the propagation and maintenance of [PSI$^+$] by each $NM^{cys}$ used, integrative constructs, constructed using the standard pRS series of vectors (available from ATCC), were digested with XbaI and transformed into 74-D694 [PSI$^+$] and [psi] strains. Transformants were selected on uracil-deficient (SD-Ura) medium and confirmed by genomic PCR followed by digestion with AatII, which cleaves the HA-tag between $NM^{CYS}$ and Sup35pC. Recombinant excision events were selected on medium containing 5-fluoro-orotic acid. Only cells that have lost remaining integrative plasmids are able to grow on medium containing 5-fluoro-orotic acid. Again, replacements were confirmed by PCR followed by digestion with AatII as described above.

Protein Purification

NM and each $NM^{CYS}$ were purified after recombinant expression in *E. coli* by chromatography using Q-Sepharose (Pharmacia), hydroxyapatite (BioRad), and Poros HQ (Boehringer Mannheim) as a final step. All purification steps for NM or $NM^{CYS}$ were performed in the presence of 8M urea. GST-NM was purified by chromatography using Glutathione-Sepharose (Boehringer Manheim), Poros HQ (Boehringer Mannheim), and S-Sepharose (Pharmacia) as a final step. All purification steps for GST-NM were performed in the presence of 50 mM Arginine-HCl. Protein concentrations were determined using the calculated extinction coefficient of 0.90 (NM, $NM^{CYS}$) or 1.23 (GST-NM) for a 1 mg/ml solution in a 1 cm cuvette at 280 nm.

Secondary Structure Prediction

Secondary structure of NM was predicted by using two independent prediction methods, GOR IV and Hierarchical Neural Network. Both methods were provided by Pôle Bio-Informatique Lyonnais.

Secondary Structure Analysis

CD spectra were obtained using a Jasco 715 spectropolarimeter equipped with a temperature control unit. All UV spectra were taken with a 0.1 cm pathlength quartz cuvette (Hellma) in 5 mM potassium phosphate (pH 7.4), 150 mM NaCl and respective additives such as osmolytes in certain experiments. Protein concentration varied from 0.5 µM to 65 µM. Folding of chemically denatured NM or $NM^{CYS}$ was monitored at 222 nm in time course experiments by diluting protein out of 8M Gdm*Cl (Guanidinium Hcl; final concentration 50 mM) in the respective phosphate buffer. Thermal transition of NM or $NM^{CYS}$ was performed with a heating/cooling increment of 0.5° C./min. Spectra were recorded between 200 nm and 250 nm (2 accumulations). In a separate measurement, time courses were recorded for 30 sec at single wavelengths (208 nm and 222 nm) for each temperature and the mean value of each time course was determined. Temperature jump experiments were performed by incubating the sample in a water bath with the respective starting temperature for 30 min. The cuvette was transferred to the spectropolarimeter already set to the final temperature and time courses were taken with a constant wavelength of 222 nm. Settings for wavelength scans: bandwidth, 5 nm; response time, 0.25 sec; speed, 20 nm/min; accumulations, 4. All spectra were buffer-corrected.

Fluorescent Labeling of $NM^{CYS}$

The thiol-reactive fluorescent labels acrylodan and IANBD amide (Molecular Probes) were incubated with $NM^{cys}$ for 2 hours at 25° C. according to the manufacturer's protocol. Remaining free label was removed by size exclusion chromatography using D-Salt Excellulose desalting columns (Pierce). The labeling efficiencies were determined by visible absorption using the extinction coefficients of $2 \times 10^4$ for acrylodan at 391 nm and $2.5 \times 10^4$ for LKNBD B. Construction and Analysis of NM Mutants To investigate the structural requirements for amyloid fiber assembly, we used yeast Sup35p's NM-region as a model protein. Until recently, fiber assembly kinetics of NM and other amyloid forming proteins have been monitored by binding of dyes such as CongoRed (CR) or ThioflavinT. To gain further insight into NM folding and fiber assembly, a more sensitive method for detecting structural changes, such as that provided by intrinsic fluorescence, was necessary. As NM naturally lacks tryptophan, the only native amino acid with a reasonable environmental-sensitive fluorescence, site-directed mutagenesis could have been employed to artificially introduce tryptophan in NM. However, to improve experimental flexibility we introduced single cysteine substitutions throughout NM. Since NM naturally lacks cysteine, such single point mutations would allow probing of NM folding and assembly in a specific, well defined manner after cross-linking of fluorescent probes to the sulfhydryl-groups of cysteines.

NM mutants with single cysteine replacements at amino acids throughout NM that were predicted to be in structured regions or that were likely involved in the fiber assembly process were constructed. These included the following fifteen mutants: $NM^{S2C}$, $NM^{Y35C}$, $NM^{Q38C}$, $NM^{Q40C}$, $NM^{G43C}$, $NM^{G68C}$, $NM^{M124C}$, $NM^{P138C}$, $NM^{L144C}$, $NM^{T158C}$, $NM^{E167C}$, $NM^{K184C}$, $NM^{E203C}$, $NM^{S234C}$, and $NM^{L238C}$. As indicated in table 1 below, three of the fifteen mutants, $NM^{Y35CS}$, $NM^{Q40C}$, and $NM^{M124C}$, were not stably expressed at a sufficiently high protein levels in *E. coli*. All other mutants were purified to homogeneity under denaturing conditions. To confirm that refolded NM attained a native protein structure, a GST-NM fusion protein was purified with thrombin, and GST was removed by binding to Glutathione-Sepharose. A structural comparison of refolded and native NM using far-UV circular dichroism (CD) showed no apparent-differences between the two proteins.

TABLE 1

| NM Protein | Expression in *E. coli* | Secondary Structure [$\theta_{222nm}$] | Fiber assembly (CR-binding) | Fiber morphology (EM) |
|---|---|---|---|---|
| wild-type (wt) NM | yes | −2950 | yes | smooth fibers up to 35 µm long |
| $NM^{S2C}$ | yes | as wt | as wt | as wt |
| $NM^{Y35C}$ | not detectable | — | — | — |
| $NM^{Q38C}$ | yes | as wt | as wt | as wt |

TABLE 1-continued

| NM Protein | Expression in E. coli | Secondary Structure [θ$_{222nm}$] | Fiber assembly (CR-binding) | Fiber morphology (EM) |
|---|---|---|---|---|
| NM$^{Q40C}$ | very low, not stable | — | — | — |
| NM$^{G43C}$ | yes | −6420 | slower assembly rate | short fibers, only few are longer than 1 μm |
| NM$^{G68C}$ | yes | −6250 | slower assembly rate | short fibers, only few are longer than 1 μm |
| NM$^{M124C}$ | very low, not stable | — | — | — |
| NM$^{P138C}$ | yes | −4570 | as wt | as wt |
| NM$^{L144C}$ | yes | −4198 | as wt | as wt |
| NM$^{T158C}$ | yes | as wt | as wt | as wt |
| NM$^{E167C}$ | yes | as wt | as wt | as wt |
| NM$^{K184C}$ | yes | −4400 | as wt | as wt |
| NM$^{E203C}$ | yes | −4000 | as wt | less smooth, many short fibers |
| NM$^{S234C}$ | yes | −6410 | slower assembly rate | many short fibers |
| NM$^{L238C}$ | yes | −3730 | no | no detectable fibers |

To determine the direct influence of individual cysteine replacements on the folding and assembly of NM in vitro, the secondary structure of each NM$^{cys}$ was compared to wild-type NM structure by far-UV CD after refolding. The results are summarized in table 1. Structurally, only NM$^{S2C}$, NM$^{Q38C}$, NM$^{T158C}$, and NM$^{E167C}$ were identical to wild-type NM. All other mutants contained a higher content of secondary structure as indicated by an increased mean residue ellipticity at [θ]$_{222nm}$. NM and all $^{Nmcys}$, with the exception of NM$^{L238C}$, had identical mean residue ellipticities at [θ]$_{208nm}$ of −9000 degree cm$^2$ dmol$^{−1}$. In contrast, NML$^{L238C}$ had a decreased mean residue ellipticity at [θ]$^{208nm}$ indicating that this mutant had an aberrant structure in comparison to wild-type NM than the other NM$^{cys}$.

Next, fiber assembly of each mutant was performed on a roller drum and compared to wild-type NM assembly kinetics by binding of CongoRed (CR), which shows a spectral shift after interacting with amyloid fibers. Results form these experiments are summarized in table 1. Only NM$^{L238C}$ did not bind CR under all conditions tested. NM$^{G43C}$, NM$^{G68C}$, and NM$^{S234C}$ showed slightly altered CR-binding kinetics suggesting slower fiber assembly rates in comparison to wild-type NM.

Electron microscopy (EM) was used to confirm that NM$^{cys}$ fibers were morphologically identical to wild-type fibers. As indicated in table 1, the electron micrographs showed no apparent differences in fiber density, fiber diameter, or other morphological features in comparison to wild-type NM for NM$^{S2C}$, NM$^{Q38C}$, NM$^{0138C}$, NM$^{L144C}$, NM$^{T158C}$, NM$^{E167C}$, and NM$^{K184C}$, NM$^{L238C}$, fibers were not detectable by EM, suggesting that the apparent lack of CR-binding of NM$^{L238C}$ was not due to structural differences in fibers that affected CR-binding. Results from CD (secondary structure), CR-binding (fiber assembly kinetics), and EM (fiber morphology) indicate that the NM$^{S2C}$, NM$^{Q38C}$, NM$^{T158C}$, and NM$^{E167C}$ mutants display no apparent differences to wild-type NM with respect to these parameters. To further confirm that the chosen cysteine mutants were not influencing the principal properties of NM, genomic wild-type NM could be replaced by Nm$^{cys}$.

C. Covalent Binding of Fluorescent Labels to NM$^{cys}$

Environmentally sensitive fluorescent probes, such as naphthalene derivatives or benzofurazans, are commonly used to detect conformational changes and assembly processes of proteins. Here, we made use of 6-acryloyl-2-dimethylaminonaphathlene (acrylodan) and N,N'-dimethyl-N (iodoacetyl)-N'-(7-nitrobenz-2-oxa-1,3-diazol-4-yl)ethylene diamine (IANBD amide) both of which react specifically with free thiol-groups on proteins. Whereas acrylodan is very sensitive to its structural environment, IANBD amide exhibits appreciable fluorescence when linked to buried or unsolvated thiols. Therefore, the latter fluorescence is highly sensitive to changes in the solvation level of the fluorophore as seen in folding events, whereas acrylodan is more powerful for investigating conformational changes of a protein. The specific labeling efficiencies of soluble NM$^{cys}$ were in the range of 0.40 to 0.78 (mol label/mol protein) with unspecific binding below 0.05 mol/mol for both fluorescent probes.

After covalent binding to NM$^{cys}$, the influence of the fluorescent labels on fiber assembly was investigated. No differences were found in fiber assembly for 7 mutants (see table 1) in the presence of fluorescent labels in comparison to non-labeled protein as detected by CR-binding. No gross structural changes in assembled fibers were visible by EM for NM$^{Q38C}$, NM$^{P138C}$, NM$^{L144C}$, NM$^{T158C}$, NM$^{E167C}$, and NM$^{K184C}$. In contrast, NM$^{S2C}$ fibers labeled with both acrylodan and IANBD amide appeared rougher with an overall shorter length, although these changes were subtle.

To determine the incorporation of labeled NM$^{cys}$ into fibers, equal amounts of labeled and non-labeled protein were mixed. The amount of label in the soluble protein fraction was detected over the course of fiber assembly. During the experiment, the label to protein ratio was constant indicating an equal incorporation of labeled and non-labeled protein into fibers. The resulting fibers were monitored for fluorescent emission of the respective label. Both measurements showed that fluorescent-labeled protein was sufficiently incorporated into amyloid fibers without influencing the assembly kinetics or the assembled state for NM$^{Q38C}$, NM$^{P138C}$, NM$^{L144C}$, NM$^{T158C}$, NM$^{E167C}$, and NM$^{K184C}$.

The foregoing experiments examined the folding process of NM using NM$^{cys}$ mutants that exhibited folding processes and structural characteristics similar to wild-type NM. These results provide a better understanding of the process of NM folding.

EXAMPLE 10

Bi-Directional Formation of Fibers Composed of the Prion-Determining Region (NM) of Yeast Sup35p The following experiments were performed to demonstrate that fibers composed of the NM region of Sup35p are capable of adding NM protein at both ends of the fiber. This was investigated using a mutant NM protein, in which the lysine residue at position 184 was substituted by cysteine, that was capable of forming fibers labeled with specifically modified gold colloids. Visualization of the gold-labeled fibers allowed determination of the directionality of fiber growth.

A. Determining the Accessibility of Cysteine Residues in Assembled Fibers

First, the accessibility of cysteine residues was assayed in fibers composed of cysteine-substituted mutant NM (NM$^{cys}$) proteins, each of which carried different single cysteine replacements at amino acid residues throughout the NM protein. All Nm$^{cys}$, described in Example 9 above, that formed fibers were examined. For fiber assembly, NM$^{cys}$ protein was diluted out of 4M Gdm*Cl 80-fold into 5 mM potassium phosphate (pH 7.4), 150 mM NaCl to yield a final NM$^{cys}$ protein concentration of 10 µM. To accelerate the rate of fiber assembly, all NM$^{cys}$ proteins were incubated on a roller drum (9 rpm) for 12 hours. The resulting fibers were sonicated with a Sonic Dismembrator Model 302 (Artek) using an intermediate tip for 15 seconds. Sonication resulted in small sized fibers that did not reassemble to larger fibers as determined by electron microscopy (EM). Seeding of fiber assembly was performed by addition of 1% (v/v) of the sonicated fibers to soluble NM$^{cys}$ protein.

To test the accessibility of cysteines in assembled fibers composed of NM$^{cys}$ proteins, EZ-link PEO-maleimide-conjugated biotin (Pierce, product number 21901) was added to the assembled fibers and the labeling efficiency of the biotin was assayed. EZ-link PEO-maleimide-conjugated biotin was covalently linked to assembled NM$^{cys}$ fibers for 2 hours at 25° C. according to the manufacturer's protocol (protocol number 0748). Remaining free biotin was removed by size exclusion chromatography using D-Salt Excellulose desalting columns (Pierce, product number 20450). Labeling efficiency was determined by competing for avidin binding between biotin and [2-(4'-hydroxybenzene)] benzoic acid (HABA). The binding of HABA to avidin results in a specific absorption band at 500 nm. Since biotin displaces the HABA dye due to higher affinity of biotin for avidin, as compared to that of HABA dye for avidin, the binding of HABA to avidin and thus the specific absorption at 500 nm decreases proportionately when biotin is added to the reaction. Results from this assay indicated that fibers composed of either NMCYS proteins in which the lysine residue at position 184 was substituted by a cysteine residue (K184C) or NM$^{cys}$ proteins in which the serine residue at position 2 was substituted by a cysteine residue (S2C), bound a detectable amount of biotin. S2C fibers had a labeling efficiency of 0.16 mol biotin/mol protein, and K184C fibers exhibited a labeling efficiency of 0.56 mol biotin/mol protein. Thus, the cysteine residue at position 184 is highly accessible and the cysteine residue at position 2 is partially accessible on the surface of assembled fibers.

B. Analysis of Fiber Growth Using EM

K184C sonicated fibers were tested for their ability to seed fiber assembly of soluble wild-type NM protein. Fiber assembly was performed as described above using sonicated K184C fibers as seeds to assemble soluble wild-type NM protein. The rate of fiber assembly was assayed by CongoRed binding (CR-binding) and fiber morphology was examined by EM. For EM studies, protein solutions were negatively stained as previously described in Spiess et al., 1987, *Electron Microscopy and Molecular Biology: A Practical Approach*, Oxford Press, p. 147-166. Images were obtained with a CM120 Transmission Electron Microscope (Phillips) with an LaB6 filament, operating at 120 V in low dose mode at a magnification of 4500× and recorded on Kodak SO163 film. Results from CR-binding and EM experiments show that K184C fibers are able to seed wild-type NM fiber assembly. The resulting mixed K184C/NM fibers showed no apparent differences in assembly rate or morphology to fibers seeded with sonicated wild-type NM fibers. Similar results were obtained when biotinylated K184C seeds were used fro fiber assembly.

The surface exposure of the cysteine at position 184 in assembled fibers composed of the K184C mutant protein allowed sufficient labeling of fibers with specifically modified gold colloids. Monomaleimido Nanogold™ (Nanoprobes, product number 2020A) with a particle diameter of 1.4 nm was covalently cross-linked to the sulfhydryl group of accessible cysteine residues in sonicated K184C fibers for 18 hours at 4° C. according to the manufacturer's protocol. Remaining free Nanogold™ was removed by a repeated size exclusion chromatography using D-Salt Excellulose desalting columns (Pierce, product number 20450). The extent of labeling was determined by UV/visible absorption using extinction coefficients for Nanogold™ of 2.25×10$^5$ at 280 nm and 1.12×10$^5$ at 420 nm. Ratios of optical densities at 280 nm and 420 nm allowed an approximation of the labeling efficiency. These gold-labeled fibers were employed to seed fiber growth of soluble wild-type NM protein.

To visualize the 104 nm Nanogold™ particles attached to the assembled mixed K184C/NM fibers, we used Goldenhance™ (Nanoprobes) according to the manufacturer's instructions. Briefly, equal volumes of enhancer (Solution A) and activator (Solution B) were combined and incubated for 15 min at room temperature. Initiator (Solution C) was then added at a volume equal to that of enhancer or activator, and the resulting mixture was diluted (1:2) with phosphate buffer (Solution D). The final solution acts as an enhancing reagent by selectively depositing gold onto Nanogold™ particles, thereby providing enlargement of Nanogold™ to give electron-dense enlarged Nanogold™ particles in the electron microscope. For negative staining of gold-labeled fibers, 6 µl of protein (8 µM, 1% (w/w) gold labeled seed) were applied to a 400 mesh carbon-coated copper grid (Ted Pella) for 45 seconds. After washing with 100 µl phosphate buffer, grids were incubated with the final Goldenhance™ enhancing reagent, prepared as described above, for 5 min. After washing with 200 µl glass-distilled water, negative staining was employed as in Spiess et al., 1987 *Electron Microscopy and Molecular Biology: A Practical Approach*, Oxford Press, p. 147-166. EM results revealed that the gold-labeled K184C regions are located in the middle of the assembled K184C/NM fibers indicating bi-directional fiber assembly with no apparent polarity in the seeds used.

The foregoing experiments show that fiber assembly of NM proteins occurs at both ends of the fibers. These analyses were performed using K184C, a NM$^{cys}$ mutant wherein the lysine residue at position 184 has been substituted with a cysteine residue. Experiments by biotin-labeling of the cysteine residues on assembled K184C fibers were carried out to determine accessibility of the cysteines. Since wild-type NM protein does not contain any cysteine residues, labeling can only occur at position 184. Results show that position 184 is highly accessible in assembled K184C fibers. The ability of specifically modified gold colloids to covalently cross-link the sulfhydryl group of cysteines enabled generation of gold-labeled fibers that can be visualized by EM. Examination of fiber assembly, by taking advantage of the ability of K184C to produce gold-labeled fibers, indicates that fiber growth occurs bi-directionally. It further indicates that fibers with specific modifications and attachments, a single fiber containing modified and unmodified regions, and mixtures of modified and unmodified fibers can be produced.

While the present invention has been described in terms of specific embodiments, it is understood that variations and modifications will occur to those in the art, all of which are intended as aspects of the present invention. Accordingly, only such limitations as appear in the claims should be placed on the invention.

What is claimed is:

1. A purified polypeptide comprising a SCHAG amino acid sequence that is at least 90% identical to amino acids 2 to 113 of SEQ ID NO: 2;
   wherein the polypeptide self-coalesces into higher ordered aggregates,
   wherein the SCHAG amino acid sequence comprises an amino acid with a reactable side chain selected from the group consisting of cysteine, lysine, glutamate, aspartate, and arginine substituted for the amino acid present at position 2 of SEQ ID NO: 2, and
   wherein the reactable side chain is exposed to the environment in the polypeptide aggregates.

2. A purified polypeptide comprising a SCHAG amino acid sequence that is at least 90% identical to amino acids 2 to 253 of SEQ ID NO: 2;
   wherein the polypeptide self-coalesces into higher ordered aggregates,
   wherein the SCHAG amino acid sequence comprises an amino acid with a reactable side chain selected from the group consisting of cysteine and arginine substituted for the amino acid present at position 184 of SEQ ID NO: 2; and
   wherein the reactable side chain is exposed to the environment in the polypeptide aggregates.

3. A polypeptide according to claim 1, wherein the SCHAG amino acid sequence comprises an amino acid with a reactable side chain selected from the group consisting of cysteine, lysine, glutamate, aspartate, and arginine substituted for the amino acid present at position 2 of SEQ ID NO: 2 and said amino acid substituted at position 2 of SEQ ID NO: 2 is the only occurrence of said amino acid in the SCHAG amino acid sequence.

4. A purified polypeptide according to claim 1, wherein the amino acid with a reactable side chain is a cysteine or a glutamate.

5. A polypeptide according to claim 1 comprising an amino acid sequence identical to amino acids 2 to 113 of SEQ ID NO: 2, except at the position in said amino acid sequence that corresponds to position 2 of SEQ ID NO: 2.

6. A polymer comprising polypeptide subunits coalesced into ordered aggregates, wherein at least one of the polypeptide subunits comprises a polypeptide according to claim 1 or 2.

7. A polymer according to claim 6 that has a fiber morphology.

8. A polymer according to claim 7 attached to a solid support.

9. A polymer comprising polypeptide subunits coalesced into ordered aggregates, wherein all of the polypeptide subunits comprise a polypeptide according to claim 1 or 2.

10. A polypeptide according to claim 2, wherein the SCHAG amino acid sequence comprises an amino acid with a reactable side chain selected from the group consisting of cysteine and arginine substituted for the amino acid present at position 184 of SEQ ID NO: 2, and said amino acid substituted at position 184 of SEQ ID NO: 2 is the only occurrence of said amino acid in the SCHAG amino acid sequence.

11. A purified polypeptide according to claim 2, wherein the amino acid with the reactable side chain is a cysteine.

12. A polypeptide according to claim 2 comprising an amino acid sequence identical to amino acids 2 to 253 of SEQ ID NO: 2, except at the position in said amino acid sequence that corresponds to position 184 of SEQ ID NO: 2.

13. An isolated filamentous polymer comprising polypeptide subunits coalesced into ordered aggregates, wherein each of the polypeptide subunits comprises a SCHAG amino acid sequence as set forth in claim 1 or claim 2, and
  wherein the reactive side chain of the substituted amino acid is exposed to the environment of the polymer and has a moiety selected from the group consisting of an enzyme, a metal atom, an affinity binding molecule having a specific affinity binding partner, a carbohydrate, a fluorescent dye, a chromatic dye, an antibody, a growth factor, a cell adhesion molecule, a toxin, a detoxicant, a catalyst, a light-harvesting moiety, and a light altering moiety attached thereto.

14. A purified fiber comprised of an ordered aggregate of polypeptides that comprise a SCHAG amino acid sequence as set forth in claim 1 or claim 2, and wherein the substituted amino acid is exposed to the environment in an ordered aggregate comprised of said polypeptides and has a moiety selected from the group consisting of an enzyme, a metal atom, an affinity binding molecule having a specific affinity binding partner, a carbohydrate, a fluorescent dye, a chromatic dye, an antibody, a growth factor, a hormone, a toxin, a detoxicant, a catalyst, a light-harvesting moiety, a cell adhesion molecule and a light altering moiety attached to its side chain.

15. A purified fiber according to claim 14, wherein the amino acid with the reactive amino acid side chain is selected from the group consisting of cysteine and arginine.

16. A purified fiber according to claim 14, wherein the polypeptides further include an epitope tag.

17. A fiber according to claim 14, wherein the polypeptides further include a polyhistidine tag.

18. A fiber according to claim 14, wherein the moiety is a metal atom.

19. A fiber according to claim 14, with the proviso that amino acid 184 of SEQ ID NO: 2 has been substituted for by cysteine.

20. A fiber according to claim 14, with the proviso that amino acid 2 of SEQ ID NO: 2 has been substituted for by cysteine.

21. A purified fiber according to claim 14, wherein the SCHAG amino acid sequence comprises an amino acid sequence at least 95% identical to amino acids 2-113 of SEQ ID NO: 2.

22. A purified fiber comprised of an ordered aggregate of polypeptides that comprise a SCHAG amino acid sequence as set forth in claim 1 or claim 2,
  wherein the polypeptides further include a moiety attached to the reactive amino acid side chain, wherein the moiety is selected from the group consisting of an enzyme, a metal atom, an affinity binding molecule having a specific affinity binding partner, a carbohydrate, an antibody, a growth factor, a hormone, a cell adhesion molecule, a toxin, a detoxicant, and a catalyst.

23. A purified fiber according to claim 14, wherein the SCHAG amino acid sequence comprises an amino acid sequence at least 95% identical to amino acids 2-253 of SEQ ID NO: 2.

24. A purified polypeptide comprising the SCHAG amino acid sequence of SEQ ID NO: 2, with the proviso that amino acid 184 of SEQ ID NO: 2 has been substituted for by a cysteine or glutamate, or comprising a sequence at least 90% identical to the SCHAG amino acid sequence of SEQ ID NO: 2 with the proviso that amino acid 184 of the sequence at least 90% identical to the SCHAG amino acid sequence of SEQ ID NO: 2 is a cysteine or glutamate, wherein the polypeptide self-coalesces to form higher ordered aggregates.

25. A purified polypeptide comprising the SCHAG amino acid sequence of SEQ ID NO: 2, with the proviso that amino acid 2 of SEQ ID NO: 2 has been substituted for by an amino acid selected from the group consisting of cysteine, lysine, tyrosine, glutamate, aspartate, and arginine, or comprising a sequence at least 90% identical to the SCHAG amino acid sequence of SEQ ID NO: 2 with the proviso that amino acid 2 of the sequence at least 90% identical to the SCHAG amino acid sequence of SEQ ID NO: 2 is selected from the group consisting of cysteine, lysine, tyrosine, glutamate, aspartate, and arginine, wherein the polypeptide self-coalesces to form higher ordered aggregates.

26. A polymer comprising polypeptide subunits coalesced into fibrous aggregates, wherein at least one of the polypeptide subunits comprises a polypeptide according to any one of claims 24-25.

27. A polymer according to claim 26, wherein the polymer is attached to a solid support.

28. A SCHAG polypeptide that comprises:
  an amino acid sequence selected from the group consisting of:
    (a) a SCHAG amino acid sequence that is at least 90% identical to amino acids 2-253 of SEQ ID NO: 2, wherein the SCHAG amino acid sequence comprises an amino acid with a reactable side chain selected from the group consisting of cysteine and arginine substituted for the amino acid present at position 184 of SEQ ID NO: 2; and
    (b) a SCHAG amino acid sequence that is at least 90% identical to amino acids 2-113 of SEQ ID NO: 2, wherein the SCHAG amino acid sequence comprises an amino acid with a reactable side chain selected from the group consisting of cysteine, lysine, glutamate, aspartate, and arginine substituted for the amino acid present at position 2 of SEQ ID NO: 2;
  wherein there is a moiety attached to a side chain of the SCHAG polypeptide, wherein the moiety is selected from the group consisting of an enzyme, a metal atom, an affinity binding molecule having a specific affinity binding partner, a carbohydrate, a fluorescent dye, a chromatic dye, an antibody, a growth factor, a hormone, a cell adhesion molecule, a toxin, a detoxicant, a catalyst, a light-harvesting moiety, and a light altering moiety, and wherein the side chain is one that is exposed to the environment when the SCHAG polypeptide self-coalesces to form an ordered aggregate.

29. A polypeptide according to claim 28, wherein the moiety is selected from the group consisting of an enzyme, a metal atom, an affinity binding molecule having a specific affinity binding partner, an antibody, a cell adhesion molecule, a toxin, a detoxicant, and a catalyst.

30. A polypeptide according to claim 29, wherein the amino acid substituted at position 2 of SEQ ID NO:2 is selected from the group consisting of cysteine and arginine.

31. A polypeptide according to claim 29, wherein the amino acid is cysteine.

32. A polypeptide according to claim 31, wherein the cysteine is substituted for the amino acid present at position 184 of SEQ ID NO: 2.

33. A polypeptide according to claim 28 that is attached to a solid support.

34. A polypeptide according to claim 33, wherein the moiety is selected from the group consisting of an enzyme, a metal atom, an affinity binding molecule having a specific affinity binding partner, an antibody, a cell adhesion molecule, a toxin, a detoxicant, and a catalyst.

35. A polypeptide according to claim 34, wherein the amino acid substituted at position 2 of SEQ ID NO:2 is selected from the group consisting of cysteine and arginine.

36. A polypeptide according to claim 35, wherein the amino acid is cysteine.

37. A polypeptide according to claim 36, wherein the cysteine is substituted for the amino acid present at position 184 of SEQ ID NO: 2.

38. A fiber comprised of:
SCHAG polypeptides as set forth in claim 28 coalesced into a fibrous ordered aggregate.

39. A fiber according to claim 38 that is attached to a solid support.

40. A polypeptide according to claim 28, wherein the polypeptide comprises at least two moieties attached to side chains of the polypeptide, wherein the moieties are different.

* * * * *